US008407013B2

(12) United States Patent
Rogan

(10) Patent No.: US 8,407,013 B2
(45) Date of Patent: Mar. 26, 2013

(54) AB INITIO GENERATION OF SINGLE COPY GENOMIC PROBES

(76) Inventor: Peter K. Rogan, London (CA)

( * ) Notice: Subject to any disclaimer, the term of this patent is extended or adjusted under 35 U.S.C. 154(b) by 0 days.

(21) Appl. No.: 13/469,531

(22) Filed: May 11, 2012

(65) Prior Publication Data

US 2012/0253689 A1  Oct. 4, 2012

Related U.S. Application Data

(63) Continuation of application No. 12/794,933, filed on Jun. 7, 2010, now Pat. No. 8,209,129, which is a continuation of application No. 11/324,102, filed on Dec. 30, 2005, now Pat. No. 7,734,424.

(60) Provisional application No. 60/687,945, filed on Jun. 7, 2005.

(51) Int. Cl.
 G06F 19/00 (2011.01)
 C12N 15/11 (2006.01)
 C12Q 1/68 (2006.01)
(52) U.S. Cl. .................. 702/20; 536/24.3; 435/6.11
(58) Field of Classification Search .................. None
 See application file for complete search history.

(56) References Cited

U.S. PATENT DOCUMENTS

| 6,150,160 | A  | 11/2000 | Kazazian, Jr. |
| 6,828,097 | B1 | 12/2004 | Knoll et al. |
| 7,014,997 | B2 | 3/2006  | Knoll et al. |
| 2003/0022204 | A1 | 1/2003 | Lansdorp |
| 2003/0044822 | A1 | 3/2003 | Fletcher et al. |
| 2003/0108943 | A1 | 6/2003 | Gray et al. |
| 2003/0194718 | A1 | 10/2003 | Tomita et al. |
| 2004/0161773 | A1 | 8/2004 | Rogan et al. |
| 2004/0241734 | A1 | 12/2004 | Davis |
| 2005/0064450 | A1 | 3/2005 | Lucas et al. |

FOREIGN PATENT DOCUMENTS

WO  0188089 A2  11/2001

OTHER PUBLICATIONS

Altschul, S.F., et al., "Basic Local Alignment Search Tool," J Mol Biol, 1990, 215/3:403-410.
Bardoni, et al., "Isolation and Characterization of a Family of Sequences Dispersed on the Human X Chromosome," Cytogenet and Cell Genet, Human Gene Mapping 9, Abstracts of Workshop Presentations, Paris Conference, 1987, p. 575.
Batzoglou, S., et al., "Human and Mouse Gene Structure: Comparative Analysis and Application to Exon Prediction," Genome Research, 2000, 10:950-958.
Buhler, J., "Efficient Large-Scale Sequence Comparison by Locality-Sensitive Hashing," Bioinformatics, 2001, 17/5:419-428.
Carrillo, H., et al., "The Multiple Sequence Alignment Problem in Biology," SIAM J Applied Math, 1988, 48/5:1073-1082.
Chang, P-C., et al., "Design and Assessment of Fast Algorithm for Identifying Specific Probes for Human and Mouse Genes," Bioinformatics, 2003, 19/11:1311-1317.
Claverie, J-M., "Computational Methods of the Identification of Genes in Vertebrate Genomic Sequences," Hum Molec Genet, 1997, 6/10:1735-1744.
Craig, J.M., et al., "Removal of Repetitive Sequences from FISH Probes Using PCR-Assisted Affinity Chromatography," Hum Genet, 1997, 100/3-4:472-476.
Delcher, A.L., et al., "Alignment of Whole Genomes," Nucl Acids Res, 1999, 27/11:2369-2376.
Devereux, J., et al., A Comprehensive Set of Sequence Analysis Programs for the VAX, Nucl Acids Res, 1984, 12/1:387-395.
Dover, G., et al., "Molecular Drive," Trends in Genetics, 2002, 18/11:587-589.
Edgar, R.C., et al., "PILER: Identification and Classification of Genomic Repeats," Bioinformatics, 2005, 21(S1):i152-i158.
Eisenbarth, I., et al., "Long-Range Sequence Composition Mirrors Linkage Disequilibrium Pattern in a 1.13 Mb Region of Human Chromosome 22," Human Molec Genet, 2001, 10/24:2833-2839.
Faranda, S., et al., "The Human Genes Encoding Renin-Binding Protein and Host Cell Factor are Closely Linked in Xq28 and Transcribed in the Same Direction," Gene, 1995, 155:237-239.
Healy, J., et al., "Annotating Large Genomes with Exact Word Matches," Genome Res, 2003, 13:2306-2315.
Howell, M.D., et al., "Rapid Identification of Hybridization Probes for Chromosomal Walking," Gene, 1987, 55:41-45.
Jareborg, N., et al., "Comparative Analysis of Noncoding Regions of 77 Orthologous Mouse and Human Gene Pairs," Genome Res, 1999, 9:815-824.
Jurka, J., "Repeats in Genomic DNA: Mining and Meaning," Curr Opin in Struct Biol, 1998, 8/3:333-337.
Jurka, J., et al., "Censor-A Program for Identification and Elimination of Repetitive Elements from DNA Sequences," Computers Chem, 1996, 20/1:119-121.
Kent, W.J., et al., "Conservation, Regulation, Synteny, and Introns in a Large-Scale C.briggsae-C. elegans Genomic Alignment," Genome Res, 2000, 10:115-1125.
Kent, W.J., "BLAT—The Blast-Like Alignment Tool," Genome Res., 2002, 12:656-664.
Li, Y-C., et al., "Microsatellites: Genomic Distribution, Putative Functions and Mutational Mechanisms: A Review," Molec Ecol, 2002, 11:2453-2465.
Lichter, P., et al., "Delineation of Individual Human Chromosomes in Metaphase and Interphase Cells by In Situ Suppression Hybridization Using Recombinant DNA Libraries," Hum Genet, 1988, 80/3:224-234.
Morgenstern, B., et al., "DIALIGN: Finding Local Similarities by Multiple Sequence Alignment," Bioinformatics, 1998, 14/3:290-294.
Mottez, E., et al., "Conservation in the 5' Region of the Long Interspersed Mouse L1 Repeat: Implication of Comparative Sequence Analysis," Nucl Acids Res, 1986, 14/7:3119-3136.
Nakamura, Y., et al., "Variable Number of Tandem Repeat (VNTR) Markers for Human Gene Mapping," Science, 1987, 235:1616-1622.

(Continued)

Primary Examiner — John S Brusca
(74) Attorney, Agent, or Firm — Tracy Jong Law Firm; Tracy P. Jong

(57) ABSTRACT

Single copy sequences suitable for use as DNA probes can be defined by computational analysis of genomic sequences. The present invention provides an ab initio method for identification of single copy sequences for use as probes which obviates the need to compare genomic sequences with existing catalogs of repetitive sequences. By dividing a target reference sequence into a series of shorter contiguous sequence windows and comparing these sequences with the reference genome sequence, one can identify single copy sequences in a genome. Probes can then be designed and produced from these single copy intervals.

24 Claims, 2 Drawing Sheets

OTHER PUBLICATIONS

Newkirk, H.L., et. al., "Distortion of Quantitative Genomic and Expression Hybridization by Cot-1 DNA: Mitigation of this Effect," Nucl Acids Res, 2005, 33/22:e191, 8 pages.

Newkirk, H.L., et al., "Determination of Genomic Copy Number with Quantitative Microsphere Hybridization," Human Mutation, 2006, 27/4:376-386.

Price, A.L., et al., "De Novo Identification of Repeat Families in Large Genomes," Bioinformatics, 2005, 21(S1):i1351-i1358.

Rogan, P.K., et al., L1 Repeat Elements in the Human ε-Gγ-Globin Gene Intergenic Region: Sequence Analysis and Concerted Evolution with this Family, Mol Biol, 1987, 4/4:327-342.

Schwartz, S., et al., "PipMaker-A Web Server for Aligning Two Genomic DNA Sequences," Genome Res, 2000, 10:577-586.

Smit, A.F.A., "The Origin of Interspersed Repeats in the Human Genome," Current Opin in Gen & Dev, 1996, 6/6:743-748.

Vermeesch, J.R., et al., "Interstitial Telomeric Sequences at the Junction Site of a Jumping Translocation," Human Genet, 1997, 99:735-737.

Vincens, P., et al., "A Strategy for Finding Regions of Similarity in Complete Genome Sequences," Bioinformatics, 1998, 14/8:715-725.

Zhang, Z., et al., "A Greedy Algorithm for Aligning DNA Sequences," J of Comp Biol, 2000, 7/1-2:203-214.

Gene Expression: vol. 2, Eukaryotic Chromosomes, 1983, Lewin, B., Ed., Wiley, p. 503, Wiley & Sons, Inc., New York City, New York.

AB INITIO GENERATION OF SINGLE COPY GENOMIC PROBES

CROSS REFERENCE TO RELATED APPLICATIONS

This continuation-in-part application claims the benefit of U.S. Ser. No. 60/687,945, filed Jun. 7, 2005, non-provisional application U.S. Ser. No. 11/324,102 filed on Dec. 30, 2005 and now U.S. Pat. No. 7,734,424 issued Jun. 8, 2010, and continuation application U.S. Ser. No. 12/794,933 filed on Jun. 7, 2010, also publication number US 2010-0240880A1. The contents each of these patent applications and publications, and Disclosure Document No. 576,582, filed May 3, 2005, are each hereby incorporated herein by reference.

REFERENCE TO SEQUENCE LISTING APPENDIX

Accompanying this application is an electronic EFS-web filing of a gene sequence listings in compliance with 37 CFR §1.52(e) and 37 CFR §1.821-1.825 in standard ASCII character and file formats. The file contains Appendixes A, B, C, D and E.

FIELD OF THE INVENTION

The present invention generally relates to ab initio methods of computationally determining the locations of single copy intervals in genomes for use as probes.

BACKGROUND

Conventional hybridization studies with genome-derived nucleic acid probes require unlabeled Cot-1 DNA fractions to block cross-hybridization of repetitive sequences contained within these probes in eukaryotic genomes. This is necessary, because to achieve the specificity needed to identify, detect or quantify unique sequences contained in nucleic acid probes, confounding hybridization from repetitive sequences must be eliminated. Repetitive sequences comprise at least 50% of the human genome and contain a diverse set of distinct families (Smit, Curr Opin Genet Dev. 1996, 6(6):743-8). Despite the lack of selection for their function and broad, often variable degrees of orthology, such sequences often display sequence conservation throughout mammalian evolution (Rogan et al. Mol Biot Evol. 1987, 4(4):327-42; Mottez et al. Nucleic Acids Res. 1986, 14(7):3119-36), principally because they have properties of semiautonomous transposable elements that promote frequent amplification during host organism evolution, originally termed molecular drive by Dover (Dover, Trends Genet. 2002, 18(11):587-9). It is desirable to remove such sequences in most clinical diagnostic applications; because of their ubiquity throughout the genome, their presence can interfere with the development of probes for unique regions of the genome that correspond to functional genes whose structures must be preserved because they are essential for normal development and health.

Repetitive sequences are often interspersed with unique or single copy genes, especially in eukaryotic genomes, and their removal from genomic probes is essential to ensure that diagnostic probes specifically recognize only a single location in the genome. These sequences can be eliminated by laboratory techniques designed to sequester them away from labeled probes containing both single copy and interspersed repetitive sequences (Lichter et al. Hum Genet. 1988, 80(3):224-34; Craig et al. Hum Genet 1997, 100:472-476), by blocking their hybridization, or by deducing the single copy sequences by comparisons of known genomic reference sequences with comprehensive databases of consensus sequences that are representative of established repetitive sequence families and subfamilies (Jurka, Curr Opin Struct Biol. 1998, 8(3):333-7).

Cot-1 DNA is often used to attempt to suppress cross-hybridization of repetitive sequences to probes. The problem with attempting to suppress repeat hybridization with Cot-1 DNA is that it can result in enhanced non-specific hybridization between probes and genomic targets. Specifically, it has been demonstrated that Cot-1 added to target DNA actually enhanced hybridization to genomic probes containing conserved repetitive elements (Newkirk, H. L. et al., Nuc. Acids Res. 2005, 33(22):e191). In addition to repetitive sequences, Cot-1 was also found to be enriched for linked single copy sequences (Newkirk, H. L. et al., Nuc. Acids Res. 2005, 33(22):e191). Adventitious association between these sequences and probes distorts quantitative measurements of the probes hybridized to desired genomic targets. This also affects the reproducibility of hybridization assays with sources of genomic DNA, in particular, and can also impact hybridization to mRNAs that contain repetitive sequences (typically found in the untranslated regions of transcripts). The increased non-specific hybridization that occurs when using Cot-1 to block repeat sequence hybridization has particularly adverse effects on microarray studies which depend on quantification of signals obtained by hybridization to the unblocked presumably single copy sequences.

The elimination of Cot-1 DNA, either by sequestering repeats or by blocking their hybridization, was accomplished by direct synthesis of probes lacking repeat sequences. Knoll et al., U.S. Pat. No. 6,828,097 (termed '097 patent), discloses a procedure for determining the locations of single copy intervals and design of probes for hybridization to their complementary locations in the human genome. It is disclosed that the procedure can be implemented for any genome in which a comprehensive catalog of repetitive sequences is available. Presumed single copy sequences containing repetitive elements will cross-hybridize to multiple locations in the genome. Where hybridization occurs in too many genomic locations, the lack of specificity adversely impacts the utility of the probes in diagnosing disease. Therefore, methods from which single copy sequences can be deduced without requiring a comparison of the genomic sequence with a comprehensive database of consensus repetitive sequence family members would represent an improvement over current in silico methods of identifying single copy intervals and the ensuing probes.

Methods have been developed which can align the sequences of different, related, or the same complete genomes from which the locations of individual repetitive sequences in the genome can be inferred. One such example is the maximal unique matching algorithm which builds suffix trees from all maximal length unique matches (MUM) between sequence strings (Delcher et al. Nuc. Acids Res. 1999, 27:2369-2376). Repeats can be detected in a genome because they are found in overlapping MUMs that are not necessarily contiguous in that genome. Once repeat sequence elements are identified through such comparisons, families of related repeat sequences can be identified through comparisons of individual family members with the genome sequence itself Another popular method, the BLAT algorithm (Kent et al. Genome Res. 2002, 12:656-64), is a rapid alignment method that uses a hash-index algorithm to quickly find sequences similar to a particular test sequence in a genome; it is not, however, an ab initio approach for single copy sequence identification. Other comparative alignment tools useful for detecting repeat sequences include ASSIRC (Vincens et al. Bioinformatics 1998, 14:715-725), DIALIGN (Morgenstern et al Bioinformatics. 1998, 14(3):290-4.), DBA (Jareborg et al. Genome Res. 1999, 9(9):815-24), GLASS (Batzoglou et al. Genome Res. 2000, 10(7):950-8), LSH-ALL-PAIRS (Buhler, Bioinformatics. 2001, 17(5):419-28), MEGABLAST (Zhang J Comput Biol. 2000, 7(1-2):203-14), PIPMaker (Schwartz et al. Genome Res. 2000, 10(4):577-86), SSAHA (www.sanger.ac.uk/Software/analysis/SSAHA), and WABA (Kent and Zahler Genome Res. 2000, 10(8):1115-25).

U.S. application Ser. No. 10/229,058 discloses that sequences can be screened for the presence of known repetitive sequence families (e.g., Alu elements); however the details of these screening procedures are not disclosed. U.S. application Ser. No. 10/132,002 discloses a procedure for detecting repetitive sequences experimentally, but does not disclose the identification of single copy sequences. U.S. application Ser. No. 10/833,954 discloses that in situ hybridization of a mixture of single copy and repetitive sequences can be performed in the absence of blocking nucleic acids that prevent cross hybridization of repetitive sequences. A formulation of a hybridization reagent and washing conditions that could mitigate such cross-hybridization are disclosed, but no information is provided regarding the location of single copy and repetitive sequences within the probe segment. U.S. Ser. No. 10/132,993 discloses laboratory chromatographic methods to remove repetitive sequences from genomic DNA to make probes that are substantially complementary to single copy intervals. In this application, the locations or the specific single copy sequences are not determined prior to experimentally removing the repeat sequences. A very similar approach is described in U.S. application Ser. No. 10/798,949, in which repetitive sequences are subtracted by hybridization, and single copy sequences are subsequently amplified using so called unique sequence primers. Subtraction hybridization is not a robust technique, because low- to middle-reiteration frequency repeats are not completely eliminated under the hybridization conditions typically used in these studies. Therefore, the selection of these primers could result in the production of probes that are contaminated with repetitive sequence elements. Similarly, in U.S. application Ser. No. 10/229,058, the repetitive sequences are fractionated by hybridization methods prior to library production and sequencing. Presumably, the single copy sequences would be revealed after library enrichment; however U.S. Ser. No. 10/229,058 does not teach how to identify the precise boundaries of these sequences in the genome, and it does not teach the method of determining how to identify single copy sequences for use as probes. U.S. Ser. No. 10/330,089 is the most recent of several continuation applications which infer the single copy nature of cloned sequences by their lack of hybridization to total genomic DNA, which is highly enriched in repetitive elements. The specific single copy sequences are not revealed by this approach. Furthermore, the present applicants have demonstrated that the single copy sequences produced according to this method are contaminated with repetitive sequences, since they are particularly insensitive to the detection of low- to moderate-abundance repetitive sequence family members. See U.S. Pat. No. 6,828,097, Prosecution History.

While several of these approaches can find locally similar repetitive sequences without comparison to a library of sequences (as in Knoll et al., U.S. Pat. No. 6,828,097), their objective is to identify repetitive sequences and multiple copies of related sequences found in the genomes of different individuals or species. These approaches do not involve the use of repetitive sequences to infer the presence of single copy sequence intervals (between adjacent repetitive sequences in the genome) for the development of useful single copy probes from the intervening regions between the deduced repetitive sequences. These algorithms therefore produce libraries similar to that used in the '097 patent, and the sequences contained in these libraries will be similar to those already known. These algorithms do not describe inferred single copy intervals, or in particular, the use of probes obtained from those deduced intervals.

SUMMARY OF THE INVENTION

The present invention relates to the computational design of nucleic acid probes that exclusively contain sequences found at a single location in a reference genome sequence.

A method is described to identify single copy regions in a target genome interval of known sequence and then preparing probes from these regions, principally for the detection of chromosomal and genomic abnormalities by nucleic acid hybridization. The method divides the target genome interval into consecutive sequence subintervals and compares each of the subintervals with the reference genome sequence. Those subintervals which are found once within the reference genome sequence, typically referred to as single copy intervals, serve as sequences that serve as a starting point for subsequent analysis. To more precisely localize the single copy sequences, i.e., the single copies of sequences that appear within a single copy interval, these subsequences may either be further resected into non-overlapping sub-subintervals or they may be modified by selecting windows that overlap the original single copy subintervals, but which are displaced by one or more nucleotides from the original genomic coordinates in either the telomeric or centromeric direction. Typically, as series of overlapping sub-subintervals are derived from the original sequence by extending the sub-interval at one end of the sub-subsequence and shortening the sub-subsequence by the same length at the other end. The directionality of the overlapping sub-subsequence set is dictated by the orientation of the single copy subsequence adjacent to the subsequence that contains one or more repeat elements. The overlapping sub-subsequences are selected so that their displacement moves toward the location of the single copy subsequence. The overlapping sub-subsequences are compared with the genome reference sequence and the procedure is iterated by progressively decreasing the degree of overlap until either the overlapped interval demonstrates multiple regions of similarity in the reference genome or the end of the chromosome is reached. The single copy sequences thus obtained are then used to prepare probes either by direct nucleic acid synthesis, amplification or by retrieval and purification of these sequences from recombinant clones or genomic DNA.

In the present application, the probes are labeled and then hybridized to chromosomes from patients or cell lines. However, those of skill in the art will appreciate that the probes can be fixed on a surface or matrix and hybridized with genomic DNA or cDNA from patients or control specimens that have been labeled by chemical, fluorescent, or radioactive modification. With the present invention, it is not necessary to suppress hybridization of repetitive sequences with unlabeled Cot-1 nucleic acids when annealing these probes to their unique chromosomal locations in the genomes of patient samples or cell line chromosomal DNA.

The ab initio methods described in the instant invention are capable of identifying both the same repeat families that have been previously catalogued in the art and new repeat sequence families that have not been previously recognized in the art.

Another advantage of the present invention is that such ab initio methods can be used to deduce single copy sequences in instances of biological species for which catalogs of repetitive sequences have not been previously derived.

PARTICULAR ADVANTAGES OF THE INVENTION

Co-pending application U.S. Ser. No. 12/794,933 claims a method to identify and produce a single copy sequence in a target reference complete genome sequence by successive division of the target reference genome sequence into subintervals and comparison of the subintervals to the target reference sequence using various claimed hybridization conditions. The invention claimed herein is a method of producing a hybridization probe of a target reference complete genome sequence where the probe is limited to probes containing single copy and at least one divergent repetitive sequence. The limitation of "identifying a single copy interval and at least one contiguous divergent repetitive interval of the target reference sequence wherein at least one subsequence in the target sequence contains a divergent repetitive element suitable for use as a probe that hybridizes to a single location in the target genome" is patentable distinct and an improvement over the prior art because it produces an entire category of probes that the prior art eliminated with the older techniques, expanding the repertoire of single copy probes in the genome. One particular advantage realized by the method claimed herein is the production of probes from within the boundaries of short oncogenes and tumor suppressor genes. No such probes are currently available commercially and could not be produced with the methods of the prior art. In particular, the closest known prior art is that of inventor and these previously patented methods would have produced produce individual probes that are too short (<1.5 kilobase pairs) to be used in FISH, since the density of fluorescent labels incorporated in such probes is insufficient for reliable and routine visualization by epifluorescence microscopy.

DETAILED DESCRIPTION OF THE INVENTION

Figure 1:
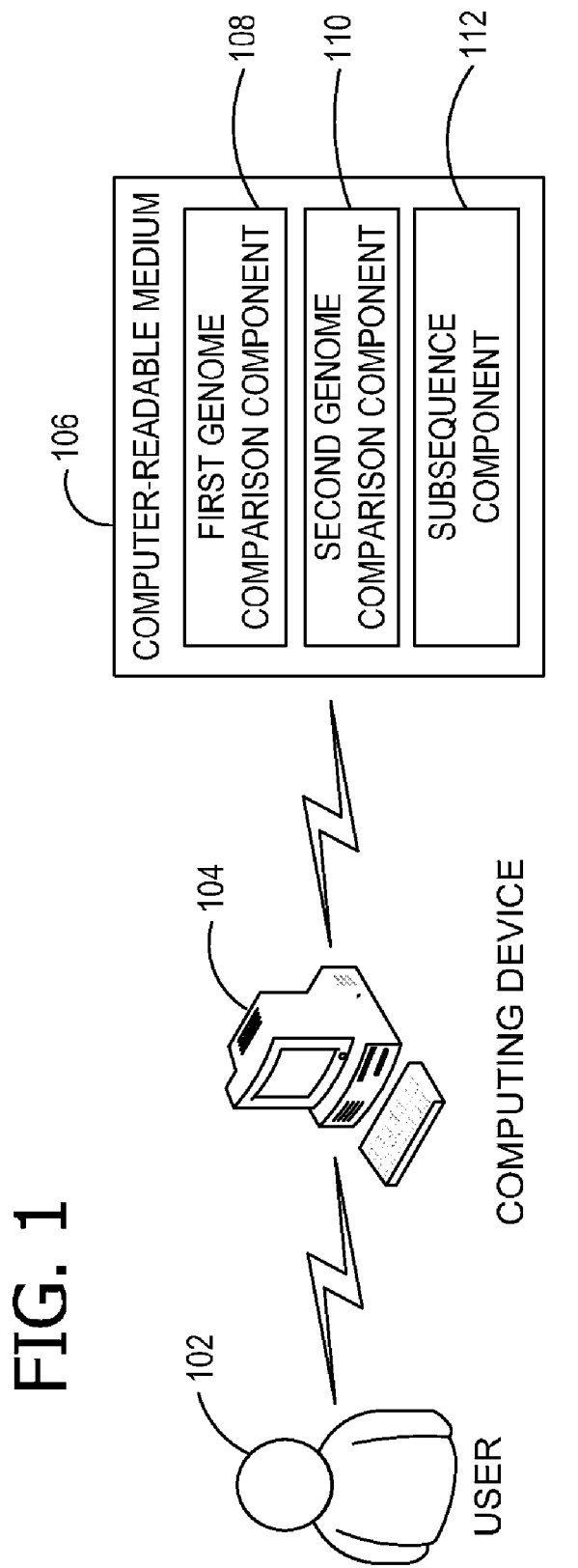
FIG. 1 is a block diagram illustrating a user interacting with a computing environment in one embodiment of the invention.

The present invention is concerned with nucleic acid (e.g., DNA or RNA) hybridization probes for detection of genetic or neoplastic disorders, such as for example Monosomy 1p36 syndrome, Wolf-Hirschorn Syndrome, Cri-du-Chat Syndrome, Williams Syndrome, Langer-Giedeon Syndrome, Chronic myelogenous leukemia, Acute lymphocytic leukemia, Aneuploidy for chromosome 13 (eg. Patau Syndrome), Prader-Willi Syndrome, Angelman Syndrome & Chromosome 15 duplication Syndrome, Acute Myelogenous leukemia—Type M4, Rubenstein-Taybi Syndrome, Smith-Magenis Syndrome, Charcot-Marie—Tooth Disease Type 1A, Miller-Dieker Syndrome, Alagille Syndrome, Down Syndrome, DiGeorge/Velocardiofacial Syndrome, Schizophrenia, Kallman Syndrome, Turner and Leri-Weill Syndromes, and subtelomeric chromosome rearrangements associated with idiopathic mental retardation, sex chromosome aneuploidy, and monosomy chromosome 22. See, for example, U.S. Ser. No. 09/854,867.

The probes are in the form of nucleic acid fragments or a collection of labeled nucleic acid fragments whose hybridization to a target sequence can be detected. The invention also pertains to methods of developing, generating and labeling or chemical modification of such probes, and to uses thereof. Chemical modifications of such probes can be used to permanently attach them to solid surfaces such as polystyrene microspheres or glass slides for subsequent hybridization to nucleic acids obtained, for example, from a patient for diagnosis of a genetic disorder, such as, for example, the syndromes described in U.S. Ser. No. 09/854,867, or of various cancers, such as, for example, breast cancer associated with amplification of the HER2/NEU gene, neuroblastoma associated with amplification of the N-myc gene, melanoma associated with chromosome deletions of p16/CDKN2A gene, chromosome translocations activating oncogenes associated with Chronic myelogenous leukemia (BCR/ABL1), Acute lymphocytic leukemia, B-cell lymphoma, prostate carcinoma, chromosome inversions such as that found in Acute Myelogenous leukemia—Type M4, and losses of heterozygosity for example, monosomies for chromosome 7q, 1p, 17p, and 8p. This list of chromosome abnormalities is provided for purposes of illustrating the types of abnormalities suitable for detection with probes of the art. There are many other art-recognized abnormalities which are diagnostic for neoplasia that involve gain or loss of copies of other genes and chromosomes, but result from the same or similar common mechanisms of chromosome rearrangement presented in these examples.

Various aspects of the present invention obviate the need to compare the sequence of the genomic interval from which single copy intervals and probes are derived with a database of existing repetitive sequences. Generally, a genomic subsequence is compared with the sequence of the complete haploid genome that contains that genomic subsequence. Assuming the subsequence is sufficiently long, there is a high probability that it will contain at least one repetitive element, sometimes also referred to as a repetitive or repeat sequence. Repetitive elements are detected by counting the number of times that the subsequence occurs in the genome. Typically, the presence of more than one copy of a sequence would exclude that sequence from being defined for use as an ab initio single copy probe; however, the presence of the same sequence tandemly repeated fewer than 10 times at a single location, preferably fewer than 8 times, more preferably fewer than 5 times, and still more preferably fewer than 3 times, in the genome may still be useful for detection of chromosome abnormalities if such internal tandem repetition does not display copy number polymorphism in populations. The locations of the repetitive elements are determined by aligning the subsequence with each of the genomic copies and determining the boundaries of the common multicopy sequence intervals. Single copy intervals will only align to a single genomic location. Accordingly, repetitive sequences, and therefore, single copy sequences as well, are deduced by ab initio methods rather than being derived from a preexisting repetitive sequence database.

One aspect of the invention, therefore, is probes that hybridize with the deduced single copy sequences. The probes hereof may be used with any nucleic acid target that contains the complementary single copy sequence as well as potentially repetitive sequences. These target sequences may include, but are not limited to chromosomal or purified nuclear DNA, heteronuclear RNA, cDNA or mRNA species that contain repetitive sequences as integral components of the transcript. In the ensuing detailed explanation, the usual case of a DNA target sequence and DNA probes is discussed; however, those skilled in the art will understand that the discussion is equally applicable (with art-recognized differences owing to the nature of the target sequences and probes) to other nucleic acid species.

One characteristic of the probes of the present invention is that they are made up of "single copy" or "unique" DNA sequences which are both complementary to at least a portion of the target DNA region of interest and essentially free of sequences complementary to repeat sequences within the genome of which the target region is a part. Accordingly, a probe made up of a single copy or unique sequence is complementary to essentially only one sequence in the corresponding genome. As used herein, a "repeat sequence" or "repetitive sequence" is a sequence which appears at least about twice in the genome of which the target DNA is a part. Typically, a repeat sequence will appear in a genome at least about 5 times, preferably about 50 times, more preferably about 200 times, and even more preferably about 1000 times. Factors affecting the number of times a repeat sequence appears in a genome include, for example, the size of the genome, evolutionary age of the repeat (degree of divergence from other related sequences), the mechanism(s) of copy number increase, and the relevance of pathogens which integrate into the host genome, horizontal genetic transfer (if any), and associative mating between individuals who are heterozygous for repetitive sequence copy number. A repeat sequence will generally have a sequence identity between repeats of at least about 60%, preferably at least about 70%, more preferably at least about 80%, still more preferably at least about 90%, even more preferably at least about 95%, and most preferably about 99%, and will be of sufficient length or have other qualities which would cause it to interfere with the desired specific hybridization of the probe to the target DNA, i.e., the probe would hybridize with one or more copies of the repeat sequence. Generally, a repetitive sequence appears at least about 5 times in the genome, preferably at least about 50 times, and most preferably at least about 200 times and has a length of at least about 20 nucleotides, preferably at least about 40 nucleotides, more preferably at least about 50 nucleotides, still more preferably at least about 75 nucleotides, and even more preferably at least about 100 nucleotides. Repeat sequences can be of any variety, including, for example, tandem, interspersed, palindromic or shared repetitive sequences (with some copies in the target region and some elsewhere in the genome), and can appear near the centromeres of chromosomes, distributed over a single chromosome, or throughout some or all chromosomes. This definition of a repeat includes closely related members of the same multigene family, since the utility of the probes is related to the unique locations on chromosomes. However, typically, repeat sequences are sufficiently degenerate such that most elements do not express physiologically useful proteins. Nevertheless, repeat sequences may exhibit length polymorphism such that they may be present in some individuals and absent in others. However when this is the case, complex repeats must be distinguished by copy number polymorphisms (which may contain multiple repeat elements and single copy sequences, and indeed, complete genes, in some cases). The instant invention utilizes the current assembly of a single or composite genome. One of skill in the art would recognize that polymorphisms that duplicate or delete repetitive sequence in different individuals will require that probes derived therefrom may not be present at a single location in the diploid genome. Therefore, as additional reference genome sequences from different individuals are publicly available, genomic probes of the art are compared with each reference genome to verify their single copy nature in each of the populations for which the probe is to be employed.

Repeat sequences occur in multiple copies in the haploid genome. The number of copies of any family of related repetitive sequences can range from ten to hundreds of thousands, depending on a number of factors, including, for example, mechanisms of slipped mispairing during DNA replication, amplification by unscheduled DNA replication, expansion or contraction through unequal or illegitimate crossover or gene conversion, transposition, transduction, or viral integration, or retrotransposition. The Alu family of repetitive DNA are exemplary of the latter numerous variety. The copies of a repeat may be clustered or interspersed throughout the genome. Repeats may be clustered in one or more locations in the genome, such as, for example, repetitive sequences occurring near the centromeres of each chromosome, and variable number tandem repeats (VNTRs; Nakamura et al, Science, 1987; 235: 1616); or the repeat sequences may be distributed over a single chromosome, such as, for example, repeats found only on the X chromosome as described by Bardoni et al., Cytogenet. Cell Genet., 46: 575 (1987); or the repeats may be distributed over all the chromosomes, such as, for example, the Alu (SINE), and L1 (LINE) families of repetitive sequences.

Simple repeats of low complexity can be found within genes but are more commonly found in non-coding genomic sequences. Such repeated elements consist of mono-, di-, tri-, tetra-, or penta-nucleotide core sequence elements arrayed in tandem units. Often the number of tandem units comprising these repeated sequences varies at the identical locations among genomes from different individuals. These repetitive elements can be found by searching for consecutive runs of the core sequence elements in genomic sequences.

As used herein, "sequence identity" refers to a relationship between two or more polynucleotide sequences, namely a reference genome sequence and a test sequence from a genomic region of interest, i.e. containing one or more potential probe sequence(s) to be compared with the reference sequence. Sequence identity is determined by comparing the test sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if, at that position, the nucleotides are identical. The total number of such position identities is then divided by the total number of nucleotides or residues in the reference sequence to give a percent sequence identity. Sequence identity can be readily calculated by known methods including, but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988). Preferred methods to determine sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403410 (1990). The BLASTX program is publicly available from NCBI and other sources (BLAST Manual, Altschul, S. et al., NCBI, NLM, NIH, Bethesda, Md. 20894, Altschul, S. F. et al., J. Molec. Biol., 215:403410 (1990)). These programs optimally align sequences using default gap weights in order to produce the highest level of sequence identity between the test and reference sequences. As an illustration, by a polynucleotide having a nucleotide sequence having at least, for example, 95% "sequence identity" to a reference nucleotide sequence, it is intended that the nucleotide sequence of the given polynucleotide is identical to the reference sequence except that the given polynucleotide sequence may include up to 5 differences per each 100 nucleotides of the reference nucleotide sequence. In other words, in a polynucleotide having a nucleotide sequence having at least 95% identity relative to the reference nucleotide sequence, up to 5% of the nucleotides in the reference sequence may be deleted, inserted, or substituted with another nucleotide, or a number of nucleotides up to 5% of the total nucleotides in the reference sequence may be inserted into the reference sequence. Inversions in either sequence are detected by these computer programs based on the similarity of the reference sequence to the antisense strand of the homologous test sequence. These variants of the reference sequence may occur at the 5' or 3' terminal positions of the reference nucleotide sequence or anywhere between those terminal positions, interspersed either individually among nucleotides in the reference sequence or in one or more contiguous groups within the reference sequence.

It should be understood that BLAST, BLAT, and similar heuristic algorithms do not provide the sequences of all of the matches (in the genome) above the specified expected value threshold; however, they tend to indicate the degree to which a sequence may be repetitive. Sequences which match numerous genomic locations (generally on the order of hundreds) tend to be quite abundant and well conserved. Sequences which match several genomic locations tend to be either less common or less well conserved between paralogs. Sequences which match a single location in the genome are expected to be single copy, since the stringency of recognizing pairwise matches with the WU-BLAST algorithm has been deliberately relaxed to detect weakly similar genomic copies of any input sequence.

The single copy probes of the invention preferably have a length of at least about 25 nucleotides, preferably at least about 40 nucleotides, more preferably at least about 50 nucleotides, still more preferably at least about 75 nucleotides, and even more preferably at least about 100 nucleotides. Probes of this length are sufficient for Southern blot analyses, bead suspension hybridization, and microarray hybridization. However, if other analyses such as fluorescence in situ hybridization (FISH) are employed, the probes should be somewhat longer, i.e., at least about 500 nucleotides, preferably at least about 1000 nucleotides, and even more preferably at least about 2000 nucleotides in length. Factors used in determining the length of the probes include, for example, the type of analysis or hybridization method to be used, sequence specificity (i.e. complexity of the probe), nucleotide content (which dictates the optimal annealing temperature of the probe), the amount of secondary structure that the probe may adopt (which can be predicted with available software programs), and replication timing (synchronous vs asynchronous) of the genomic target sequence. The probes can be used to detect virtually any type of chromosomal rearrangement, such as, for example, deletions, duplications, insertions, additions, markers, inversions or translocations.

In addition to FISH, computationally determined single copy genomic hybridization probes may be used in a quantitative microsphere suspension hybridization assay to determine copy number of a specific sequence relative to a reference sequence or standard curve (Newkirk et al, Human Mutation, in press (2006)). Those of skill in the art would also recognize that single copy probes used as probes for microarrays would have properties similar to microsphere hybridization, since in both platforms the probes are attached to a solid phase substrate and hybridized to either labeled genomic DNA or to cDNA. Single copy probes have been shown to be more accurate for copy number determination than probes containing repetitive sequences that utilize Cot-1 DNA for suppression of cross hybridization of repetitive elements (Newkirk et al., Nucleic Acids Research 2005, 33(22):e191). Sufficient accuracy is achieved to distinguish normal copy number which is generally two for autosomes from hemizygosity or from three or more alleles. This assay allows for the direct analysis of whole genomic DNA (or RNA) using flow cytometry and if necessary can follow routine cytogenetic analysis without requiring large patient sample quantities, additional blood draws, locus-specific amplifications, or time-consuming genomic purification methods. It is notable therefore that copy number determination at a single locus can be carried out within a complex background of sequences consisting of the complete genome. This exquisite level of discrimination achieved by computationally-defined single copy probes can also be used to determine copy number of rare transcripts against the background of the complete transcriptome, or for detection of extremely dilute or low concentrations of specific nucleic acid sequences within heterogeneous solutions of nucleic acids.

In order to develop probes in accordance with the invention, the sequence of the target DNA region must be known. The target region may be an entire chromosome or only portions thereof where rearrangements have been suspected or identified. With this sequence knowledge, the objective is to determine the boundaries of single copy or unique sequences within the target region. This is preferably accomplished by inference from the locations of repetitive sequences within the target region. An important distinction between the method of the instant invention and the other methods is that the target region sequences of the present invention are not compared with known repeat sequences from the corresponding genome, using available computer software. With the instant invention, a catalog of known repeat sequences is, therefore, not a prerequisite to computational recognition of single copy intervals with this software. Therefore, single copy sequences can be derived with the instant invention from any complete genome sequence, so long as a determination of that sequence is completed.

Initially, a genomic or mRNA sequence is identified from which one or more single copy intervals and probes are desired. This test sequence, sometimes also referred to as a target sequence, typically contains at least one repetitive element; however, it is not a requirement that the test sequence contain a repetitive sequence. In the latter instance, the method does not eliminate any sequence from consideration as a potential probe; it simply verifies that the entire test sequence is non-repetitive. This test sequence is subsequently compared with the reference sequence of the same genome from which the test sequence is derived. Using homology search algorithms common in the art, such as, for example, BLAST or BLAT (see details below), this approach will identify matches with at least 80% identity to genomic sequences. Often weaker orthologies with as little as 70% or 60% identity can also be detected, although this typically requires few or no gaps to be present in the sequence alignment. This level of sensitivity is more than adequate for detection of single copy sequences, since highly divergent repetitive elements form heterologous duplexes that are easily eliminated by hybridizing and washing the probe under high stringency conditions (e.g., 0.1×SSC, 42° C.). These comparisons identify at least one region of the genome that matches (or nearly matches, due to genomic polymorphism) that test sequence. The exact and similar matches to the test sequence are termed "hits." When multiple hits are obtained, the test sequence contains one or more members of a repetitive sequence family or one or more low-copy segmental duplicons. In principal, such intervals are not preferred for probe design since a probe designed using such intervals could potentially hybridize to more than a single genomic locus.

There are mitigating circumstances in which multiple hits may still be suitable for probe design, such as, for example, if the two hits occur at nearly contiguous locations on the chromosome. This can be deduced from the chromosomal coordinates of the sequences in the genome that are similar to the potential probe interval. For hybridization by FISH to metaphase chromosomes, these coordinates may be up to approximately 3 million nucleotides apart (it can be more or less than this quantity depending on the level of condensation of the particular genomic region), and the probe signals obtained by FISH will be coincident even at the highest power magnification. For either array-based or microsphere suspension hybridization, however, much higher levels of granularity, i.e., genomic resolution, may be required to precisely localize a genomic target in, for example, a patient specimen.

Typically, 100,000-400,000 by intervals are tested to design single copy probes in a reasonable length of time (i.e., within 1-2 CPU hours on a modern cluster computer), however it can be appreciated by those of skill in the art that this approach could be applied genome-wide, given sufficient computational power. An advantage of genome-wide pre-computation would be that subsequent probe development would only involve looking up relevant single copy intervals to identify the most appropriate primers for amplification of single copy probes using the polymerase chain reaction (PCR) (see U.S. Pat. No. 6,828,097 for details of the PCR reaction to amplify products from deduced single copy genomic intervals).

While it is possible to conduct an exhaustive genome search of every subsequence window in the test sequence, such that the windows overlap and differ by a single nucleotide, this procedure is slow and inefficient. Certain embodiments employ a more efficient approach. The genomic frequency of sequences with test genomic sequence region can be determined to establish optimal parameters of window sizes and displacements based on estimates of the local distribution of repetitive sequences in the test sequence interval. Initially, the test genomic sequence region is prescreened by comparison with the reference genome sequence in order to determine local density of repetitive sequences within the region. This density can vary considerably within local regions across the euchromatic genome and it is not adequate to assume an average density for any particular region. This density dictates the granularity of the overlapping sequence windows needed to comprehensively find all repetitive sequences in a particular region. A higher density of repetitive sequences necessitates that windows of less than this length be used in the subsequent step of defining the precise locations of the repeats. In a preferred embodiment, for a sequence with at least one repeat per kilobase pair in the test region, windows of 0.5 kb sequences are used to determine locations of repeats.

First, end-to-end window comparisons of about 500 by to about 1000 base pairs (bp) are performed across the entire test sequence. This is akin to a pre-screening function. The length utilized in this embodiment was selected because it is consistent with studies indicating the average distances between interspersed repetitive elements in the human genome. The optimal window lengths may be different for other genomes since they would be based on overall repetitive complement in those genomes (determined from kinetic reassociation studies) and the respective genome sizes. This information is available from published sources (Lewin, Eukaryotic Gene Expression, Wiley, 1983). Other factors affecting the selection of a window length include, for example, the degree of resolution desired to determine the boundaries of a single copy sequence, the efficiency (i.e., the amount of time) desired to determine the boundaries of a single copy sequence, the density of repetitive sequences in the genome sequence of interest (i.e. containing potential probe sequences) and the accuracy of sequences in this region of the genome. Accordingly, the test sequence may be divided into test segments (i.e., window lengths) of about 20 by to about 5000 bp, preferably about 100 by to about 2500 bp, more preferably from about 250 by to about 1500 bp, still more preferably about 500 by to about 1000 bp, and most preferably about 1000 bp.

Alternative faster ab initio approaches for detection of repeats have been described based on exact word-matching algorithms based on nucleotide sequences (for example, Healy et al. Genome Res. 13:2306-15, 2003). Here, words are defined as overlapping or non-overlapping sequences of a short uniform length. However such approaches are not comprehensive. It also stated in this paper that this is not sufficient to ensure that repetitive sequences are completely eliminated from the microarray. Follow up approximate homology searching is performed so that the algorithm is carried out on a single human genome reference sequence. Of course, the human genome is highly polymorphic and the word match algorithm does not consider words containing the polymorphic variants. Therefore, a genomic microarray based on this algorithm alone may fail to detect repetitive sequences that contain polymorphic words. Of course, some of the sequences in the patient DNA hybridizing to those oligonucleotides will be repetitive. This will result in incorrect (vastly increased) copy number measurements. Since this is the signature of what they are trying to detect, i.e., abnormalities, it would result in false-positive identification of copy number changes in these oligonucleotides. However, a low-stringency approximate homology search by conventional repeat masking will pick up these sequences. This is why the exact word match procedure must be followed up with conventional repeat-masking (as was done in Healy et al Genome Res. 13:2306-15, 2003; see U.S. Pat. No. 6,828,097) to ensure that single copy sequences are synthesized on the microarray chip.

There are three possible outcomes of the prescreen for repetitive sequences: (1) the subsequence can be entirely composed of repetitive sequence, (2) one or more portions of the subsequence may be repetitive, or (3) the subsequence may contain no detectable repetitive sequences. Efficient methods for comparison of test sequences with complete or near complete reference genomes are well known in the art (BLAST and BLAT). If the genome comparison reveals the presence of sequences with high percentages of similar consecutive nucleotides to the test sequence at multiple genomic loci, this indicates the presence of one or more repetitive sequences within the test sequence.

A detailed description of how the method handles each of these outcomes follows: (1) if the paralogous (related or similar) copies span the entire length of the subsequence, then this subsequence is eliminated as a potential hybridization probe. For this class of subsequences, the objective then is to determine how far upstream and downstream of the subsequence the paralogous repeats extend. The adjacent subsequences within the test sequences are then analyzed to determine whether these sequences are similar to multiple genomic loci within the genome over their entire length. The process of analyzing contiguous adjacent subsequences is iterated until, either (a) the adjacent subsequence is found at only a single genomic location, or (b) only a portion of the subsequence shows similarity to multiple genomic locations, that portion determining the boundary of the single copy and multilocus subsequences; (2) pursuant to (b), such partially repetitive subsequences are again analyzed to determine which portion is contiguous with the relevant adjacent single copy interval. Segments of the subsequence can either be sampled to and compared with the genome reference to determine the approximate locations of repetitive domains which are then fine mapped by additional short sequence comparisons, or a relative series of consecutive, short or overlapping sequence windows are progressively tested against the genome sequence until coordinates that match a single location in the haploid genome sequence are found; (3) subsequences that match only a single location in the genome are considered single copy sequences, however exceptions, for example, including non-polymorphic tandemly repeated sequences of no more than about 10 copies, preferably no more than about 8 copies, more preferably no more than about 3 copies, and still more preferably no more than about 5 copies found at a single location in the genome may be treated as single copy intervals especially in FISH studies, because of their consistent, unequivocal patterns of hybridization to the genome.

Fine mapping of the approximate repetitive sequence/single copy interval within a subsequence is performed on overlapping sequence intervals by iteratively and unidirectionally displacing the sequence window by a fixed, constant length of, for example, 1 to 20 nucleotides. The new sequence is compared with the reference genome sequence and the number of significant matches in the genome (based on length and percent of identity to the new sequence) is determined. After each comparison, the window is again displaced by this length, compared with the reference genome and this process is iterated until the end of the subsequence is reached.

If multiple hits are detected in the genome, then the range of coordinates within the subsequence that contains the repetitive sequence is then refined. This is done by performing a low stringency comparison of the genome and subsequence, preferably with the Smith-Waterman algorithm, however other algorithms may also be used such as BLAST or BLAT. The location of the matching terminal coordinate within the query is determined and this coordinate is recorded. The window is again shifted by 1-20 nucleotides. The length of the pairwise match may increase, remain the same, or decrease. If this length increases, the matching coordinate is again recorded and the window is shifted in the same direction. If it stays the same, the window is also again shifted in the same direction. If the length decreases, then the complete repeat has been found (both boundaries). The final coordinates of the centromeric and telomeric boundaries of the repetitive sequence are then recorded (and the prior intermediate coordinates are discarded).

An optional step that would reduce future computational expense is to bootstrap a catalog of repetitive elements derived from the ab initio procedure. Rather than discarding the sequences found to be present more than once per genome, the interface between single copy and repetitive sequence elements could be defined using the aforementioned procedure, which would determine the coordinates of the repeat, and the repeat sequence then catalogued. This could be accomplished by storing the sequences of the repetitive sequences detected in a separate database for subsequent searches. Similar repeats could then be sorted into families and subfamilies by multiple alignments. Subsequent searches will first compare a new sequence with the repeat sequence database, and then to the genome reference sequence as described above. Although this step is not required, it will significantly improve performance of the algorithm to detect single copy intervals, especially as the repeat catalog grows in size.

Repetitive sequence elements defined by the above method can then be deposited in an electronic database where they can be subsequently retrieved for comparisons with other potential sequences containing single copy and repetitive intervals. Since each matched segment contains an individual repetitive element, the element in most instances will not be identical to the consensus sequence of the corresponding repetitive sequence family representative found in, for example, Knoll et al.'s '097 patent, because consensus sequences are derivative sequences that are compiled by selecting the most common nucleotide at a particular position among a set of elements. Various embodiments can be used to screen sequences contained within current repeat libraries in order to ensure that a repetitive sequence is not misassigned as a single copy sequence. Finally, this procedure may identify repetitive sequences that are not otherwise recognized with the technology described in other approaches reliant upon an established repeat library because the newly identified sequences are not necessarily represented in existing databases.

Defining the boundary of the single copy interval can occur as follows. As the window moves, the repeat sequence boundary should shift by the length of the sequence displaced through each step. When sufficient steps in one direction have been performed so that there is no longer a match to a repeat sequence, this defines the other boundary of the repeat. Definition of the repeat sequence boundaries on both ends makes the repeat sequence eligible for optional deposition into a repeat sequence database.

The resolution of the single copy window is defined by the length of the smallest sequence displacement (i.e., the nucleotide word length) between iteration cycles used in the definition of the repeat/single copy boundary. The single copy interval sequence can be shortened by at least one word at the repeat boundary to ensure that the entirety of the region selected for probe development is single copy.

Single copy sequences defined by this approach can be used to detect chromosome rearrangements including deletions, insertions, additions, translocations, inversions and any combination of these chromosomal modifications by hybridization. Often, such rearrangements are diagnostic for the detection of genetic diseases and cancer.

Accordingly, among the various aspects of the present invention is a method to identify a single copy sequence in a target reference genomic sequence. The method comprises determining a number of matches between at least one subsequence of a first screened sequence and a target reference sequence, wherein the target reference sequence comprises the first screened sequence, the first screened sequence is divided into at least two subsequences, and a subsequence of the first screened sequence with a single match to the target reference sequence or a group of contiguous subsequences of the first screened sequence each with a single match to the target reference sequence is identified as a single copy interval of the first screened sequence; determining a number of matches between at least one subsequence of a second screened sequence and the target reference sequence, wherein the second screened sequence comprises a single copy interval of the first screened sequence; the second screened sequence overlaps the single copy interval of the first screened sequence; the subsequences of the first screened sequence are either (i) consecutive non-overlapping subintervals of the second screened sequence or (ii) overlapping non-identical subintervals of the second screened sequence, each containing one nucleotide homologous to the reference sequence that is not present in the adjacent subinterval; and a subsequence of the second screened sequence with a single match to the target reference sequence or a group of contiguous subsequences of the second screened sequence each with a single match to the target reference sequence is identified as a single copy interval of the second screened sequence; and identifying a single copy interval as a single copy sequence of the target reference sequence suitable for use as a single copy hybridization probe. In one embodiment, the subsequences may be at least about 100 consecutive non-overlapping nucleotides, at least about 200 consecutive non-overlapping nucleotides, at least about 400 consecutive non-overlapping nucleotides, at least about 600 consecutive non-overlapping nucleotides, at least about 800 consecutive non-overlapping nucleotides, or even at least about 1000 consecutive non-overlapping nucleotides.

In one embodiment of the invention, the method further comprises the step of determining a number of matches between at least one subsequence of a third screened sequence and the target reference sequence, wherein the third screened sequence comprises a single copy interval of the second screened sequence; the third screened sequence overlaps the single copy interval of the second screened sequence; the subsequences of the third screened sequence are either (i) consecutive non-overlapping subintervals or (ii) overlapping non-identical subintervals, each containing one nucleotide homologous to the reference sequence that is not present in the adjacent subinterval; and a subsequence of the third screened sequence with a single match to the target reference sequence or a group of contiguous subsequences of the third screened sequence each with a single match to the target reference sequence is identified as a single copy interval of the third screened sequence. In another embodiment, the method further comprises the step of determining a number of matches between at least one subsequence of a fourth screened sequence and the target reference sequence, wherein the fourth screened sequence comprises a single copy interval of the third screened sequence; the fourth screened sequence overlaps the single copy interval of the third screened sequence; the subsequences the of fourth screened sequence are either (i) consecutive non-overlapping subintervals or (ii) overlapping non-identical subintervals, each containing one nucleotide homologous to the reference sequence that is not present in the adjacent subinterval; and a subsequence of the fourth screened sequence with a single match to the target reference sequence or a group of contiguous subsequences of the fourth screened sequence each with a single match to the target reference sequence is identified as a single copy interval of the fourth screened sequence.

In still another embodiment, the method further comprises the step of identifying a subsequence of the screened sequence with at least two matches to the target reference sequence as a subsequence containing a repetitive element wherein the single copy sequence is located adjacent to the repetitive element. In another embodiment, the method further comprises the step of identifying a second, distinct subsequence of the screened sequence with at least two matches to the target reference sequence as a subsequence containing a different repetitive element, wherein the single copy interval is located between the first and the second subsequences containing the distinct repetitive elements.

Another aspect of the present invention is a single copy hybridization probe as described herein. Such probes may comprise at least one single copy interval or single copy sequence identified according to the methods disclosed herein. In one embodiment, the probes comprise at least two contiguous subsequences of a screened sequence, each having a single match to the target reference sequence.

Referring to FIG. 1, a block diagram illustrates a user 102 interacting with a computing environment in one embodiment of the invention. In the example of FIG. 1, the user 102 interacts with a computing device 104. The computing device 104 has access to one or more computer-readable media such as computer-readable medium 106. The computer-readable medium 106 stores one or more computer-executable components. In this example, the components include a first genome comparison component 108, a second genome comparison component 110, and a subsequence component 112. The first genome comparison component 108 determines a number of matches between at least one subsequence of a first screened sequence and a target reference sequence. The target reference sequence includes the first screened sequence which is divided into at least two subsequences. A subsequence of the first screened sequence with at least two matches (and preferably more than five matches) to the target reference sequence can be identified as containing a repetitive element. A subsequence of the first screened sequence with a single match to the target reference sequence or a group of contiguous subsequences of the first screened sequence, each with a single match to the target reference sequence is identified as a single copy interval of the first screened sequence.

The second genome comparison component 110 determines a number of matches between at least one subsequence of a second screened sequence and the target reference sequence. The second screened sequence includes a single copy interval of the first screened sequence. The second screened sequence overlaps the single copy interval of the first screened sequence. The subsequences are either (i) consecutive non-overlapping subintervals of the second screened sequence or (ii) overlapping non-identical subintervals of the second screened sequence, each containing one nucleotide homologous to the reference sequence that is not present in the adjacent subinterval. A subsequence of the second screened sequence with at least two matches (and preferably more than five matches) to the target reference sequence can be identified as containing a repetitive element. A subsequence of the second screened sequence with a single match to the target reference sequence or a group of contiguous subsequences of the second screened sequence each with a single match to the target reference sequence is identified as a single copy interval of the second screened sequence.

The subsequence component 112 identifies a single copy interval as a single copy sequence of the target reference sequence suitable for use as a single copy hybridization probe.

Hardware, software, firmware, computer-executable components, and/or computer-executable instructions such as the exemplary components/instructions illustrated in the figures constitute means for determining a number of matches between at least one subsequence of the first screened sequence and the target reference sequence, means for determining a number of matches between at least one subsequence of the second screened sequence and the target reference sequence, and means for identifying a single copy interval as a single copy sequence of the target reference sequence suitable for use as a single copy hybridization probe.

An exemplary operating environment for implementing aspects of the invention (e.g., the computer programs described herein) such as shown in FIG. 1 includes a general purpose computing device such as computing device 104 executing computer-executable instructions. The computing device 104 typically has at least some form of computer readable media. Computer readable media, which include both volatile and nonvolatile media, removable and non-removable media, may be any available medium that may be accessed by the general purpose computing device 104. By way of example and not limitation, computer readable media comprise computer storage media and communication media. Computer storage media include volatile and nonvolatile, removable and non-removable media implemented in any method or technology for storage of information such as computer readable instructions, data structures, program modules or other data. Communication media typically embody computer readable instructions, data structures, program modules, or other data in a modulated data signal such as a carrier wave or other transport mechanism and include any information delivery media. Those skilled in the art are familiar with the modulated data signal, which has one or more of its characteristics set or changed in such a manner as to encode information in the signal. Wired media, such as a wired network or direct-wired connection, and wireless media, such as acoustic, RF, infrared, and other wireless media, are examples of communication media. Combinations of any of the above are also included within the scope of computer readable media. The computing device 104 includes or has access to computer storage media in the form of removable and/or non-removable, volatile and/or nonvolatile memory. The user 102 may enter commands and information into the computing device 104 through input devices or user interface selection devices such as a keyboard and a pointing device (e.g., a mouse, trackball, pen, or touch pad). Other input devices (not shown) may be connected to the computing device 104. The computing device 104 may operate in a networked environment using logical connections to one or more remote computers.

Although described in connection with an exemplary computing system environment, aspects of the invention are operational with numerous other general purpose or special purpose computing system environments or configurations. The computing system environment is not intended to suggest any limitation as to the scope of use or functionality of aspects of the invention. Moreover, the computing system environment should not be interpreted as having any dependency or requirement relating to any one or combination of components illustrated in the exemplary operating environment. Examples of well known computing systems, environments, and/or configurations that may be suitable for use in embodiments of the invention include, but are not limited to, personal computers, server computers, hand-held or laptop devices, multiprocessor systems, microprocessor-based systems, set top boxes, programmable consumer electronics, mobile telephones, network PCs, minicomputers, mainframe computers, distributed computing environments that include any of the above systems or devices, and the like.

Embodiments of the invention may be described in the general context of computer-executable instructions, such as program modules, executed by one or more computers or other devices. Generally, program modules include, but are not limited to, routines, programs, objects, components, and data structures that perform particular tasks or implement particular abstract data types. The computer-executable instructions may be embodied in any computer programming language or scripting language including, but not limited to, C, C++. C#, and Perl. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

Aspects of the invention may also be practiced in distributed computing environments where tasks are performed by remote processing devices that are linked through a communications network. In a distributed computing environment, program modules may be located in both local and remote computer storage media including memory storage devices. In operation, the computing device 104 executes computer-executable instructions such as those illustrated in the figures to implement embodiments of the invention.

Figure 2:
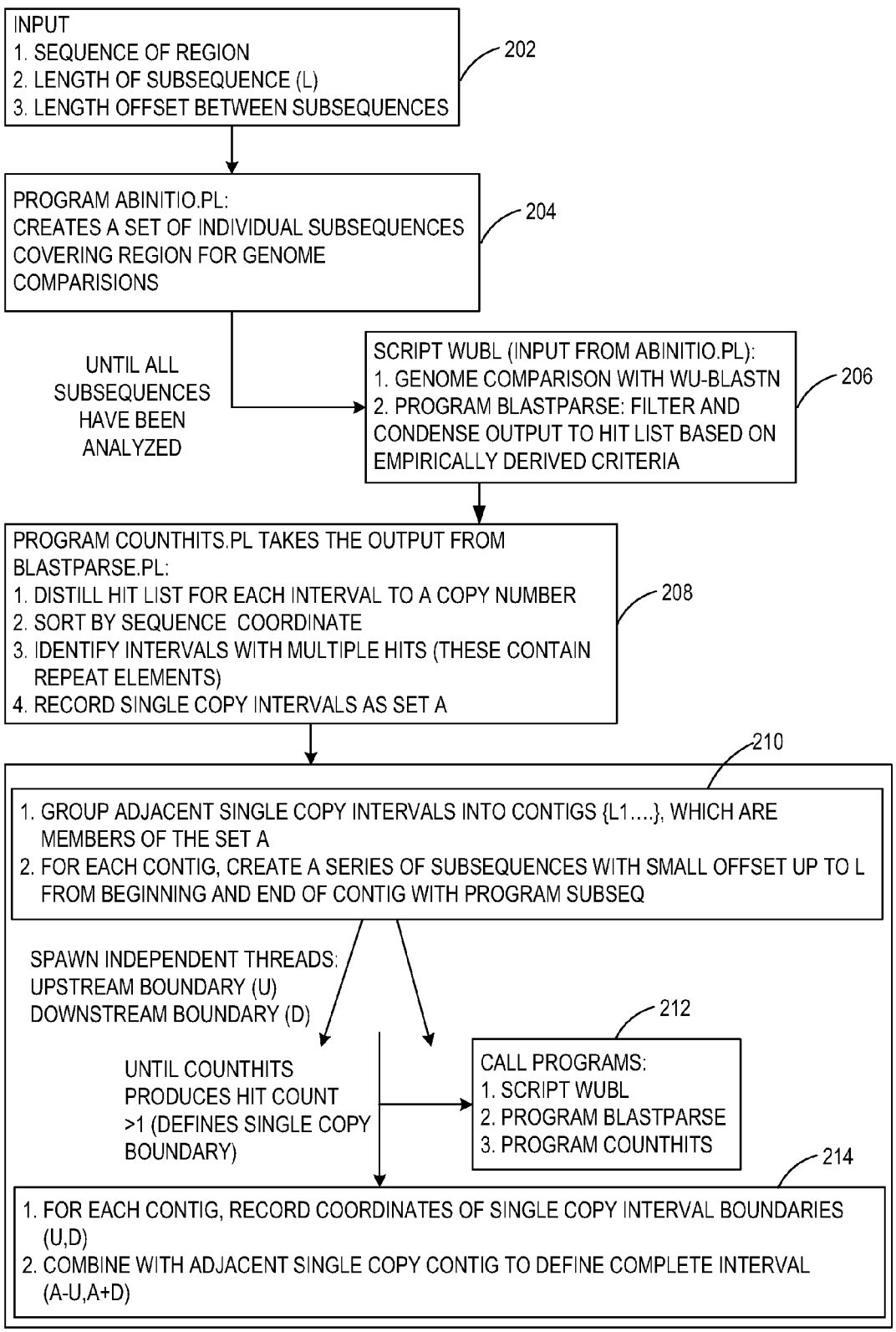
FIG. 2 is a flow chart depicting exemplary operations for deriving the locations of single copy intervals used in probe production.

Referring next to FIG. 2, a flow chart depicts exemplary operations for deriving the locations of single copy intervals used in probe production. FIG. 2 illustrates one exemplary implementation of aspects of the invention using computer-executable instructions. Other implementations are within the scope of embodiments of the invention. For example, the operations illustrated in FIG. 2 may be organized into other components or application programs.

In FIG. 2, an ABINITIO.PL script creates a set of individual subsequences covering a region for genome comparisons. The script takes as input the following at 202: a genomic sequence file, a length of subsequence, a length of window offset between subsequences, a minimum length of match to genomic repeats or paralogs (e.g., for filtering results of genomic comparisons), and a minimum percentage of match to genomic repeats or paralogs. If the length of window offset is smaller than the length of subsequence, the script produces overlapping windows. If the length of window offset is larger than the length of subsequence, the script produces subsequences separated by gaps having a length equal to the length of subsequence minus the length of window offset. If the length of window offset is equal to the length of subsequence, the script produces consecutive windows.

The ABINITIO.PL script outputs at 204 a set of individual subsequences (e.g., files named by subsequence boundaries) to a WUBL script (e.g., a BLAST script) to perform genome comparisons. The WUBL script performs the genome comparisons at 206 on a cluster computer (e.g., a separate parallel job is run simultaneously on a different node). Files indicating the results of the WUBL genome comparisons are filtered by a BLASTPARSE.PL script and condensed to a hit list based on user-provided or empirically-derived criteria. The BLASTPARSE.PL script produces files of filtered output.

The user 102 may confirm that the comparisons with the genome sequence have been completed using an application program, such as qstat, which is a Sun-Grid Engine utility to monitor processor status. In another embodiment, this confirmation operation is automated and the user 102 is notified when the comparisons have been completed.

The files of filtered output from the BLASTPARSE.PL script are input into a COUNTHITS.PL script for summarizing. The COUNTHITS.PL script distills at 208 the hit list from the BLASTPARSE.PL script for each interval to a copy number and sorts by sequence coordinate. The COUNTHITS.PL script identifies intervals with multiple hits as these contain repeat elements and records single copy intervals as, for example, Set A.

One output of COUNTHITS.PL is a count which contains the quantity of hits in the genome found with each subsequence interval. If the quantity of hits exceeds one, the sequence is not single copy based on the parameter definitions that are acceptable by one of skill in the art. These definitions aim to prevent cross hybridization between a single copy probe and other genomic locations that are partially paralogous to the entire potential probe sequence or a portion thereof.

The single copy intervals in Set A are grouped at 210 into contigs {L1 . . . } which are members of the Set A. For each contig, a SUBSEQ program creates a series of subsequences with small offset up to the length of subsequence from the beginning and end of the contig.

Independent threads are spawned with the series of subsequences having an upstream boundary (U) and a downstream boundary (D). The WUBL script, BLASPARSE program, and COUNTHITS.PL script are executed at 212 until the COUNTHITS.PL script produces a hit count greater than one (e.g., defining a single copy boundary). For each contig, the coordinates of single copy interval boundaries (U, D) are recorded and combined with adjacent single copy contigs to define a complete interval (A-U, A+D) at 214.

Appendix A includes an example of the ABINITIO.PL script. Appendix B includes an example of the WUBL script. Appendix C includes an example of the BLASTPARSE.PL script. Appendix D includes an example of the COUNTHITS.PL script. Appendix E includes an example of the SUBSEQ.PL script.

In another embodiment, the operations for deducing single copy intervals use a single program set to analyze a larger sequence and produce a single table that gives the genomic copy number of each consecutive or overlapping subsequence. Via this table, the system automatically detects the transitions between repetitive and single copy intervals. The boundaries may be refined in increasingly higher resolution using a programmable iterative procedure.

The order of execution or performance of the operations illustrated and described herein is not essential, unless otherwise specified. That is, the operations may be performed in any order, unless otherwise specified, and the operations may include more or less elements than those disclosed herein. For example, it is contemplated that executing or performing a particular operation or element before, contemporaneously with, or after another operation or element is within the scope of an embodiment of the invention.

Having described the invention in detail, it will be apparent that modifications and variations are possible without departing from the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

The following example illustrates how the probes designed using the instant invention produce similar results to the repeat-free probes described in U.S. Pat. No. 6,828,097. Here we rederive the single copy intervals shown in Example 1 of that patent with the present invention. First we determined the locations of the repetitive sequences in the human HIRA gene and flanking regions (SEQ ID NO: 1) and subsequently inferred the locations of the single copy intervals therefrom.

TABLE 1

Results obtained using the method described in U.S. Pat. No. 6,828,097

| POSITION IN REFERENCE SEQUENCE | | REPEAT FAMILY | POSITION IN REPEAT CONSENSUS SEQUENCE* | |
|---|---|---|---|---|
| Begin Coord | End Coord | | Begin Coord | End Coord |
| 633 | 653 | GC_rich | 1 | 21 |
| 695 | 859 | (CCG)n | 3 | 172 |
| 987 | 1008 | GC_rich | 1 | 22 |
| 647 | 1061 | MLT2A1 | 436 | 1 |
| 2913 | 3014 | MER58B | 239 | 340 |
| 3053 | 3397 | L1M4 | 2884 | 3209 |
| 3398 | 3698 | AluJb | 303 | 2 |
| 3699 | 3935 | L1M4 | 3209 | 3451 |
| 4002 | 4465 | L1M4c | 1469 | 1003 |
| 4466 | 4766 | AluY | 300 | 1 |
| 4767 | 4861 | L1M4c | 1004 | 910 |
| 4865 | 5081 | AluJo | 5 | 220 |
| 5082 | 5137 | AluSq/x | 86 | 141 |
| 5138 | 5211 | AluS | 76 | 2 |
| 5214 | 5713 | L1MEc | 2392 | 1876 |
| 5740 | 6031 | AluSx | 295 | 6 |
| 6077 | 6206 | L1 | 5015 | 4879 |
| 6291 | 6557 | L1 | 4686 | 4399 |
| 6560 | 6600 | L1M4c | 1457 | 1497 |
| 6602 | 6663 | MLT1E1 | 231 | 293 |
| 6677 | 6743 | MLT1E1 | 417 | 481 |
| 6774 | 6897 | L1PB2 | 91 | 210 |
| 6878 | 7534 | L1PB2 | 1113 | 1767 |
| 7577 | 7655 | Alu | 312 | 234 |
| 7656 | 8290 | L1PB2 | 1771 | 2376 |
| 8291 | 8583 | AluSx | 293 | 1 |
| 8584 | 9844 | L1PB2 | 2376 | 3758 |
| 9845 | 10143 | AluSx | 1 | 298 |
| 10144 | 11262 | L1PB2 | 3983 | 5142 |
| 11263 | 11282 | (TAAAA)n | 3 | 22 |
| 11283 | 11525 | L1PB2 | 5142 | 5378 |
| 11526 | 11659 | AluJb | 1 | 134 |
| 11661 | 11964 | AluJb | 1 | 306 |
| 11965 | 12896 | L1PB2 | 5365 | 6313 |
| 12897 | 13179 | AluSx | 282 | 1 |
| 13180 | 13675 | L1PB2 | 6313 | 6805 |
| 13762 | 14060 | AluJb | 1 | 288 |
| 14136 | 14364 | AluJb | 1 | 229 |
| 14387 | 14502 | FLAM_C | 117 | 2 |
| 14528 | 14584 | L1 | 2931 | 2987 |
| 14586 | 15758 | L1 | 3041 | 4281 |
| 15989 | 16191 | MER1B | 337 | 127 |
| 16191 | 16223 | MER1B | 33 | 1 |
| 16449 | 16582 | L1M | 5265 | 5393 |
| 16728 | 16858 | FLAM_C | 2 | 143 |
| 18149 | 18455 | AluSx | 1 | 307 |

TABLE 1-continued

Results obtained using the method described in U.S. Pat. No. 6,828,097

| POSITION IN REFERENCE SEQUENCE | | REPEAT FAMILY | POSITION IN REPEAT CONSENSUS SEQUENCE* | |
|---|---|---|---|---|
| Begin Coord | End Coord | | Begin Coord | End Coord |
| 18677 | 18964 | L1MCa | 895 | 1178 |
| 18993 | 19286 | AluSg | 293 | 1 |
| 19287 | 19575 | AluSq | 302 | 1 |
| 19586 | 19893 | AluSx | 309 | 2 |
| 20067 | 20241 | HAL1 | 1469 | 1634 |
| 20261 | 20453 | L2 | 2798 | 3023 |
| 20469 | 20569 | AluY | 310 | 210 |
| 20570 | 20852 | L2 | 3043 | 3313 |
| 20994 | 21151 | L2 | 2489 | 2646 |
| 21945 | 22025 | A-rich | 6 | 86 |
| 25263 | 25558 | AluJo | 297 | 2 |
| 28496 | 28708 | AluSg/x | 294 | 82 |
| 29588 | 29670 | MIR | 105 | 191 |
| 30298 | 30367 | MIR | 107 | 34 |
| 32436 | 33041 | L1MCa | 1529 | 2328 |
| 33042 | 33352 | AluSq | 311 | 1 |
| 33353 | 33440 | L1MCa | 2328 | 2416 |
| 33444 | 33753 | AluSc | 1 | 308 |
| 33768 | 33788 | AT_rich | 1 | 21 |
| 33821 | 33945 | FLAM_A | 4 | 128 |
| 33976 | 34107 | L1MC1 | 5912 | 6056 |
| 34108 | 34410 | AluSx | 1 | 295 |
| 34411 | 34513 | L1MC1 | 6056 | 6154 |
| 34523 | 34658 | L1MC1 | 6197 | 6332 |
| 34668 | 34835 | L1MCa | 2559 | 2728 |
| 34843 | 36256 | Tigger1 | 1 | 1358 |
| 36257 | 36551 | 7SLRNA | 19 | 312 |
| 36552 | 36572 | Tigger1 | 1358 | 1377 |
| 36573 | 36868 | AluY | 1 | 296 |
| 36869 | 37248 | Tigger1 | 1377 | 1889 |
| 37253 | 37554 | AluSx | 300 | 1 |
| 37726 | 37860 | MER2 | 1 | 137 |
| 37861 | 38163 | AluSx | 298 | 1 |
| 38164 | 38378 | MER2 | 137 | 344 |
| 38914 | 38938 | AT_rich | 1 | 25 |
| 40144 | 40447 | AluSx | 1 | 309 |
| 40464 | 40735 | AluSx | 312 | 1 |
| 40738 | 41039 | AluSx | 303 | 1 |
| 41814 | 41920 | L1MEd | 1000 | 895 |
| 41961 | 42592 | L1MB6 | 6172 | 5522 |
| 42728 | 43063 | L1MB6 | 5502 | 5156 |
| 43064 | 43363 | AluSq | 301 | 1 |
| 43371 | 43496 | AluJo | 136 | 2 |
| 43497 | 43694 | L1MB6 | 5168 | 4972 |
| 43817 | 44531 | L1MEd | 823 | 59 |
| 44543 | 44777 | AluSq | 1 | 234 |
| 44780 | 44945 | AluJo | 170 | 1 |
| 47718 | 47829 | L2 | 3141 | 3256 |
| 48724 | 48880 | MER104 | 180 | 1 |
| 49052 | 49217 | MIR | 28 | 218 |
| 49281 | 49513 | L1MC/D | 5655 | 5434 |
| 49514 | 49803 | AluY | 306 | 1 |
| 49804 | 49836 | L1MC/D | 5434 | 5404 |
| 49837 | 50139 | AluSg | 1 | 301 |
| 50140 | 50254 | L1MC/D | 5404 | 5256 |
| 50311 | 50596 | AluSc | 288 | 3 |
| 50716 | 50756 | AT_rich | 1 | 41 |
| 51099 | 51415 | AluSx | 306 | 1 |
| 51696 | 51914 | L1 | 4329 | 4067 |
| 51952 | 52256 | L1M4 | 3980 | 3658 |
| 53254 | 53280 | (T)n | 1 | 27 |
| 53417 | 53495 | L1ME4A | 5612 | 5692 |
| 53641 | 53782 | L1ME4A | 5968 | 6125 |
| 54265 | 54528 | L1MA10 | 6182 | 5922 |
| 54529 | 54835 | AluSc | 1 | 300 |
| 54836 | 54877 | L1MA10 | 5922 | 5881 |
| 55140 | 55445 | AluSx | 307 | 1 |
| 57716 | 57845 | MIR | 110 | 250 |
| 60803 | 61122 | AluSx | 1 | 311 |
| 61247 | 61490 | L1ME | 5680 | 5448 |
| 61472 | 61955 | L1ME2 | 5628 | 6132 |
| 61964 | 62271 | AluY | 309 | 1 |
| 63775 | 63814 | AT_rich | 1 | 40 |
| 63849 | 64147 | AluSg | 299 | 1 |
| 66128 | 66369 | L2 | 3031 | 3263 |
| 66726 | 67033 | AluSq | 1 | 308 |
| 69187 | 69478 | AluJb | 1 | 300 |
| 69502 | 69575 | MIR | 157 | 237 |
| 69646 | 69699 | L2 | 3187 | 3240 |
| 70252 | 70300 | AT_rich | 1 | 49 |
| 71084 | 71533 | L2 | 510 | 1029 |
| 71589 | 71784 | L2 | 1815 | 2014 |
| 71790 | 71871 | FLAM | 132 | 48 |
| 71986 | 72419 | L2 | 2275 | 2777 |
| 72700 | 72741 | L2 | 3217 | 3258 |
| 73316 | 73622 | AluJo | 1 | 311 |
| 73820 | 74122 | AluY | 1 | 300 |
| 76503 | 76829 | L1ME4A | 5747 | 6111 |
| 79310 | 79501 | MIR3 | 10 | 186 |
| 79772 | 80074 | AluSx | 304 | 1 |
| 82071 | 82145 | L2 | 3185 | 3266 |
| 82529 | 82563 | Tigger4 (Zombi) | 2730 | 2696 |
| 82555 | 82950 | MLT1G1 | 101 | 587 |
| 82960 | 83036 | MLT1K | 509 | 586 |
| 83328 | 83392 | L2 | 3281 | 3216 |
| 83428 | 83581 | L2 | 3081 | 2907 |
| 83877 | 83905 | (TTTTA)n | 2 | 31 |
| 84088 | 84406 | AluY | 315 | 1 |
| 85204 | 85399 | AluJo | 117 | 305 |
| 85429 | 85604 | AluSg/x | 309 | 134 |
| 85605 | 85643 | Alu | 40 | 2 |
| 85644 | 85998 | L1MB6 | 4209 | 4547 |
| 85999 | 86291 | AluSp | 1 | 293 |
| 86292 | 86804 | L1MB6 | 4547 | 5036 |
| 86805 | 87130 | AluJb | 311 | 1 |
| 87131 | 87414 | L1MB6 | 5036 | 5306 |
| 87415 | 87719 | AluSx | 6 | 310 |
| 87720 | 87833 | L1MB6 | 5306 | 5414 |
| 87834 | 88134 | AluSc | 1 | 301 |
| 88135 | 88725 | L1MB6 | 5414 | 6154 |
| 88771 | 88791 | AT_rich | 1 | 21 |
| 88794 | 88834 | L1MD1 | 5987 | 6024 |
| 88835 | 89139 | AluY | 1 | 301 |
| 89140 | 89415 | L1MD1 | 6024 | 6258 |
| 89418 | 89444 | (CA)n | 2 | 28 |
| 89656 | 89751 | L2 | 2313 | 2413 |
| 89911 | 90214 | L2 | 2995 | 3302 |
| 90533 | 90562 | (TG)n | 1 | 30 |
| 90672 | 90973 | AluJb | 5 | 301 |
| 90982 | 91007 | (CAAA)n | 2 | 28 |
| 91112 | 91213 | FRAM | 52 | 154 |
| 91214 | 91333 | L1PB3 | 6022 | 6140 |
| 91508 | 91808 | AluSq | 1 | 300 |
| 92080 | 92126 | L2 | 2383 | 2429 |
| 92181 | 92463 | AluSx | 283 | 1 |
| 92524 | 92635 | L1ME2 | 6022 | 6134 |
| 92657 | 92747 | (CATATA)n | 5 | 96 |
| 92793 | 93203 | L2 | 2545 | 3016 |
| 93225 | 93631 | LTR16A | 23 | 431 |
| 93945 | 94017 | (CA)n | 2 | 74 |
| 94573 | 94684 | L2 | 3310 | 3194 |
| 95304 | 95379 | MLT1L | 549 | 471 |
| 95504 | 95590 | MLT1L | 267 | 180 |
| 96194 | 96524 | AluSx | 1 | 299 |
| 97576 | 97749 | MER20 | 219 | 46 |
| 98589 | 98690 | MIR | 124 | 14 |
| 98733 | 98965 | MER20 | 2 | 218 |
| 99158 | 99286 | FLAM_A | 1 | 127 |
| 99626 | 99927 | AluSc | 304 | 1 |
| 100587 | 100676 | L2 | 3304 | 3210 |

The present invention is now shown to provide similar results to the above comparison of a sequence region with a predetermined library of repetitive sequences. The following results were obtained using one embodiment of the present invention.

Initially, the 103 kb HIRA sequence was divided into consecutive non-overlapping intervals of 1000 by in length to determine the density of repetitive sequences across this genomic region. The sequences of each of these intervals were compared with the May, 2004 human genome reference sequence using the WU-BLAST blastn program. The parameters for these comparisons were modified from default values to pick up the weakest similarities in the genome in order to ensure that even poorly conserved repetitive sequences would be detected. The parameters of the search were: −d human, span2, cpus=2 (number of threads), lcmask, and hspmax=100. Each comparison required approximately 5.8 seconds.

The 103 comparisons of 1 kb each required approximately 6 minutes on an 8 node dual CPU cluster computer, which is comparable or faster than the method described by Knoll et al. in the '097 patent.

After filtering the output with a Blast parsing routine (called from the Bioperl implementation of the Perl language; at www.bioperl.org), and counting the number of significant hits detected for each of the 1000 consecutive sub-intervals of SEQ ID NO: 1, the results are summarized in the Table 2. Regarding filtering, we have tested several minimum thresholds for repeat sequence detection in human genomic sequences have and each gives similar results. The preferred minimum thresholds for detection are a pairwise match between the test sequence and its genomic counterpart of at least 100 nucleotides in length and 70 percent identity. Equivalent results were obtained, for example, using criteria of at least a 50 nucleotide length match with at least 65 percent identity, since these filters eliminated all but the actual genomic location of the probe. One of skill in the art could appreciate that these criteria are of sufficiently low stringency so as to identify even the weakest members of a potential cross hybridizing repetitive sequence.

TABLE 2

Results of ab initio repeat detection for HIRA gene region from U.S. Pat. No. 6,828,097

| Begin coordinate SEQ ID No. 1 | End coordinate | Number hits/genome |
|---|---|---|
| 1 | 1000 | 7535 |
| 1001 | 2000 | 20 |
| 2001 | 3000 | 1 |
| 3001 | 4000 | 51045 |
| 5001 | 6000 | 27018 |
| 6001 | 7000 | 901 |
| 7001 | 8000 | 6853 |
| 8001 | 9000 | 5504 |
| 9001 | 10000 | 8337 |
| 10001 | 11000 | 17347 |
| 11001 | 12000 | 20284 |
| 12001 | 13000 | 21380 |
| 13001 | 14000 | 14891 |
| 14001 | 15000 | 30794 |
| 18001 | 19000 | 23772 |
| 19001 | 20000 | 23741 |
| 20001 | 21000 | 19360 |
| 21001 | 22000 | 5 |
| 22001 | 23000 | 1 |
| 23001 | 24000 | 1 |
| 24001 | 25000 | 1 |
| 25001 | 26000 | 17420 |
| 26001 | 27000 | 1 |

TABLE 2-continued

Results of ab initio repeat detection for HIRA gene region from U.S. Pat. No. 6,828,097

| Begin coordinate SEQ ID No. 1 | End coordinate | Number hits/genome |
|---|---|---|
| 27001 | 28000 | 1 |
| 28001 | 29000 | 15799 |
| 30001 | 31000 | 1 |
| 31001 | 32000 | 1 |
| 32001 | 33000 | 277 |
| 34001 | 35000 | 47220 |
| 35001 | 36000 | 5639 |
| 37001 | 38000 | 21053 |
| 38001 | 39000 | 42981 |
| 39001 | 40000 | 3 |
| 40001 | 41000 | 23551 |
| 41001 | 42000 | 7546 |
| 42001 | 43000 | 1789 |
| 43001 | 44000 | 22258 |
| 44001 | 45000 | 23320 |
| 45001 | 46000 | 1 |
| 46001 | 47000 | 1 |
| 47001 | 48000 | 1 |
| 48001 | 49000 | 1 |
| 49001 | 50000 | 21609 |
| 50001 | 51000 | 15465 |
| 51001 | 52000 | 12501 |
| 52001 | 53000 | 2 |
| 53001 | 54000 | 2 |
| 54001 | 55000 | 22837 |
| 55001 | 56000 | 23436 |
| 58001 | 59000 | 1 |
| 59001 | 60000 | 1 |
| 61001 | 62000 | 35227 |
| 62001 | 63000 | 23960 |
| 63001 | 64000 | 23119 |
| 64001 | 65000 | 22933 |
| 65001 | 66000 | 1 |
| 66001 | 67000 | 23787 |
| 67001 | 68000 | 6095 |
| 69001 | 70000 | 18850 |
| 70001 | 71000 | 1 |
| 71001 | 72000 | 611 |
| 72001 | 73000 | 2 |
| 73001 | 74000 | 20364 |
| 74001 | 75000 | 19815 |
| 75001 | 76000 | 1 |
| 76001 | 77000 | 3 |
| 77001 | 78000 | 1 |
| 78001 | 79000 | 1 |
| 79001 | 80000 | 23902 |
| 80001 | 81000 | 7712 |
| 81001 | 82000 | 1 |
| 82001 | 83000 | 5 |
| 83001 | 84000 | 1 |
| 84001 | 85000 | 23677 |
| 85001 | 86000 | 23474 |
| 86001 | 87000 | 22801 |
| 87001 | 88000 | 21328 |
| 88001 | 89000 | 21216 |
| 89001 | 90000 | 21128 |
| 90001 | 91000 | 22559 |
| 91001 | 92000 | 44018 |
| 93001 | 94000 | 270 |
| 95001 | 96000 | 1 |
| 96001 | 97000 | 22715 |
| 97001 | 98000 | 129 |
| 98001 | 99000 | 154 |
| 99001 | 100000 | 21398 |
| 100001 | 101000 | 1 |
| 101001 | 102000 | |

Consider, for example, the first single copy interval identified with the present invention—from positions 2001 to 3000. The method of the '097 patent shows that the interval between positions 1062 and 2913 are free of repetitive sequences. The following demonstrates that the method of the present invention confirms this result and independently can identify a single copy intervals delimited by similar coordinates.

The present invention shows that there are sequences with multilocus representation within the flanking subsegments. Within the subsequence defined by the coordinates 1000-2000 there is a match to at least 20 other genomic segments and within the sequence defined by 3000-4000 matches at least 51,045 other genomic sequences. The latter interval contains numerous highly conserved SINE and LINE repetitive elements. The short region containing a small portion of a MER58B repeat (2914-3000) contained within the corresponding single copy interval of the present invention is a highly divergent ember (24.8% of the sequence differs from a consensus MER58B subfamily repeat) that only includes a small portion of the total repeat element (from positions 239 to 340). Hence for all practical purposes, the 86 nucleotide region that is considered to be repetitive will not cross hybridize with other MER58B repeats in the genome, if the hybridization conditions of the probe designed using the instant technology are set to be stringent (final hybridization wash should be 0.1×SSC, at least 42° C.). Similarly, positions 22001-28000 are found to occur once in the haploid reference genome sequence using the method of the present invention.

To precisely define the boundaries of the single copy domain in this region, we then rerun the analysis of the subsegment defined by coordinates 1000 to 4000 of the initial 103 kb HIRA sequence at much higher resolution. This is carried out either by comparing shorter consecutive subsegments or overlapping subsegments from this region of the HIRA gene. The following table indicates a comparison of consecutive subsegments of 200 nucleotides with the genome reference sequence. The criteria for detecting a repeat was that the minimum length match is at least 60 nucleotides and at least 65% of the nucleotides matched.

TABLE 3

Hits in consecutive subsegments in coordinates 1000-4000

| Begin | End | Number hits/genome |
|---|---|---|
| 1001 | 1200 | 50 |
| 1201 | 1400 | 1 |
| 1401 | 1600 | 1 |
| 1601 | 1800 | 1 |
| 1801 | 2000 | 1 |
| 2001 | 2200 | 1 |
| 2201 | 2400 | 1 |
| 2401 | 2600 | 1 |
| 2601 | 2800 | 1 |
| 2801 | 3000 | 456 |
| 3001 | 3200 | 6 |
| 3201 | 3400 | 136 |
| 3601 | 3800 | 1059 |

This analysis indicates that the interval from 1201 through 2800 (a length of 1599 nucleotides) was composed of a single copy sequence (because each of the subsegments in this interval were found to be present once per haploid genome). The centromeric and telomeric boundaries of the single copy interval breaks were within the 1001-1200 and 2801-3000 nucleotide intervals. These results are consistent with the initial analysis of the density of repetitive sequences indicating that positions 1000-2000 and 3000-4000 were partially repetitive.

As an example, we illustrate how the boundary of the repetitive sequence within coordinates 1001-2000 can be even more precisely defined by comparing the sequences of overlapping windows within this region with the genome reference sequence. This is a computationally efficient approach for delineating repetitive sequence boundaries (Vincens et al. Bioinformatics 2002; 18:446-451). The 1 kb subsequences analyzed in the previous step were used to produce a series of subsets, each sequence 200 nucleotides in length, and each beginning 20 nucleotides downstream of the previous sequence (adjacent members contain 160 nucleotides in common). The minimum length pairwise match was 70 nucleotides and paralogous sequences were required to be at least 65% identical. Each of these sequences was compared with that of the reference genome in Table 4. The first two intervals (positions 1001-1200 and 1021-1220) contain one or more members of one or more repetitive sequence families, because these subsegments detect significant length matches to (at least) 50 and at least 118 different genomic locations, respectively. By shifting the centromeric end of the subsequence a further 20 nucleotides in the telomeric direction, the interval defined by positions 1041-1240 of the sequence matches a single genomic location with 100% identity (Query=1041_1240_HIRAcg; Min length of match=70; Min percent identity=65; Number of total hits=3; Number of qualified hits=1; Hit=ref|NC_000022.7|NC_000022, Length=200, Percent_id=100, Start_hit=17692626, End_hit=17692825). This indicates that the single copy interval is expected to begin approximately at this position and this finding is confirmed based on the method of the '097 patent (Table 1; see below). The degree of error in specifying the precise coordinate of the single copy interval is dictated by the amount of nucleotide displacement of each window, which in this case, is 20 nucleotides. It will be evident to those of the art that the coordinates of the 3' or telomeric boundary of this single copy interval can be refined using precisely the same procedure as was used to define the 5' or centromeric end of this interval at 200 nucleotide resolution.

TABLE 4

Detailed refinement of 5' centromeric boundary of a single copy interval in the HIRA gene

| Begin | End | Number hits in genome |
|---|---|---|
| 1001 | 1200 | 50 |
| 1021 | 1220 | 118 |
| 1041 | 1240 | 1 |
| 1061 | 1260 | 1 |
| 1081 | 1280 | 1 |
| 1101 | 1300 | 1 |
| 1121 | 1320 | 1 |
| 1141 | 1340 | 1 |
| 1161 | 1360 | 1 |
| 1181 | 1380 | 1 |
| 1201 | 1400 | 1 |
| 1221 | 1420 | 1 |
| 1241 | 1440 | 1 |
| 1261 | 1460 | 1 |
| 1281 | 1480 | 1 |
| 1301 | 1500 | 1 |
| 1321 | 1520 | 1 |
| 1341 | 1540 | 1 |
| 1361 | 1560 | 1 |
| 1381 | 1580 | 1 |
| 1401 | 1600 | 1 |
| 1421 | 1620 | 1 |
| 1441 | 1640 | 1 |
| 1461 | 1660 | 1 |
| 1481 | 1680 | 1 |
| 1501 | 1700 | 1 |
| 1521 | 1720 | 1 |
| 1541 | 1740 | 1 |
| 1561 | 1760 | 1 |

TABLE 4-continued

Detailed refinement of 5' centromeric boundary
of a single copy interval in the HIRA gene

| Begin | End | Number hits in genome |
|---|---|---|
| 1581 | 1780 | 1 |
| 1601 | 1800 | 1 |
| 1621 | 1820 | 1 |
| 1661 | 1860 | 1 |
| 1681 | 1880 | 1 |
| 1721 | 1920 | 1 |
| 1761 | 1960 | 1 |
| 1781 | 1980 | 1 |

TABLE 5

Analysis of Intermediate subsequence (minimum 50 nucleotides, 65% identity)

| Begin | End | Number_hits |
|---|---|---|
| 2001 | 2100 | 1 |
| 2101 | 2200 | 1 |
| 2201 | 2300 | 1 |
| 2301 | 2400 | 1 |
| 2401 | 2500 | 1 |
| 2501 | 2600 | 1 |
| 2601 | 2700 | 1 |
| 2701 | 2800 | 1 |
| 2801 | 2900 | 1 |
| 2901 | 3000 | 1 |

This moderate resolution (i.e. 100 nts) subsequence analysis at low stringency of the interval containing positions 2001-3000 confirms that the entire region is composed of single copy sequence. We then proceed to analyze the next 1 kb subsequence at moderate (Table 6), and then finally at high (Table 7) resolution.

TABLE 6

Definition of telomeric breakpoint at moderate resolution

| Begin | End | Number_hits |
|---|---|---|
| 3001 | 3100 | 1 |
| 3101 | 3200 | 1 |
| 3201 | 3300 | 1 |
| 3301 | 3400 | 1 |
| 3401 | 3500 | 2081 |
| 3501 | 3600 | 529 |
| 3601 | 3700 | 1 |
| 3701 | 3800 | 1 |
| 3801 | 3900 | 163 |
| 3901 | 4000 | 1 |

The results shown in Table 5 suggest that the telomeric boundary of the single copy sequence interval resides between coordinates 3400 and 3500.

TABLE 7

Detailed refinement of the 3' telomeric boundary
of the single copy interval in the HIRA gene using overlapping
windows (same interval as that analyzed in Table 4)

| Begin | End | Number hits |
|---|---|---|
| 3001 | 3100 | 1 |
| 3021 | 3120 | 2 |
| 3041 | 3140 | 7 |
| 3061 | 3160 | 4 |
| 3081 | 3180 | 2 |
| 3101 | 3200 | 1 |
| 3121 | 3220 | 1 |
| 3141 | 3240 | 1 |
| 3161 | 3260 | 1 |
| 3181 | 3280 | 2 |
| 3201 | 3300 | 6 |
| 3221 | 3320 | 11 |
| 3241 | 3340 | 67 |
| 3261 | 3360 | 63 |
| 3281 | 3380 | 20 |
| 3301 | 3400 | 39 |
| 3321 | 3420 | 36 |
| 3341 | 3440 | 150 |
| 3361 | 3460 | 610 |
| 3381 | 3480 | 1936 |
| 3401 | 3500 | 2081 |
| 3421 | 3520 | 2987 |
| 3441 | 3540 | 3626 |
| 3461 | 3560 | 330 |
| 3481 | 3580 | 3479 |
| 3501 | 3600 | 529 |
| 3521 | 3620 | 3473 |
| 3561 | 3660 | 819 |
| 3581 | 3680 | 1406 |
| 3601 | 3700 | 2044 |
| 3601 | 3700 | 2351 |
| 3641 | 3740 | 1281 |
| 3661 | 3760 | 1610 |
| 3701 | 3800 | 22 |
| 3721 | 3820 | 57 |
| 3741 | 3840 | 140 |
| 3761 | 3860 | 19 |
| 3781 | 3880 | 8 |
| 3801 | 3900 | 157 |
| 3801 | 3900 | 163 |
| 3821 | 3920 | 709 |
| 3881 | 3980 | 19 |

The results of the detailed analysis of the subsequence covered by the positions 3001-4000 subsequence indicate that the end of the first repetitive sequence can be found between positions 3100 and 3120 (positions 3021-3120 was present in 2 copies, whereas 3001-3100 is found only once per genome). Comparing with the results obtained in Table 1, we find that the telomeric boundary determined with the instant invention overlap highly divergent members of the MER58B and L1M4 subfamilies. The element contained in the HIRA derived subsequence respectively 24.5% and 22.8% (with 13.2% insertion/deletion) different from prototypic members of these families. Because of the level of divergence from the consensus elements in the genome, and the limited length of the match to these elements (101 and 47 nucleotides, respectively), probes containing these sequences should not cross hybridize with other genomic locations.

In this example, we have shown that the instant invention enables the definition of a particular single copy interval spanning coordinates 1041 through 3100 within the 103 kb HIRA complete genomic sequence. A probe prepared from this interval would be of adequate length and suitable for use as a genomic probe (for FISH, microsphere, microarray, MAPH, or Southern hybridization) using the method described in U.S. Pat. No. 6,828,097.

Although the non-homologous genomic location is still a very divergent copy, it nevertheless meets our minimum criteria for a repetitive sequence (65 nucleotides in length, and at least a 70% identity). Such a stringent criterion is necessary in order to eliminate the possibility of spurious cross hybridization with divergent repetitive sequences in the genome. This potential sequence similarly may not pose a problem of cross hybridization in actual laboratory experiments, however due to the cost and labor associated with carrying out those experiments, it is recommended that this sequence not be included in the probe. The match to the non-homologous sequence is indicated below:

search interval are dependent on characteristics of the specific repeat sequences that are being detected. There are many eukaryotic species with genomes with families of repetitive sequences that are highly heterogeneous and contain short repetitive elements (e.g., SINE elements in the canine genome, which are often polymorphic in terms of their presence or absence in different animals). The alternative strategy of using precise word matching methods to identify repetitive

```
>ref|NC_000017.8|NC_000017 Homo sapiens chromosome 17, complete sequence
Length = 81,860,266

Plus Strand HSPs:

Score = 189 (34.4 bits), Expect = 0.54, P = 0.42
Identities = 63/87 (72%), Positives = 63/87 (72%), Strand = Plus/Plus
Query:          12  CTAACTAAAATAATTG-AGTAAAACTCATAGGTCAAAGGGGAATTCTAATTAAGTGAAAT         70  (SEQ ID NO: 4)
                    ||||  |||  ||| ||   || |  |||  ||||||||||||||  ||| || ||  ||||||||||
Sbjct:    19011641  CTAAATAACATACTTTTAG-ATAACCCATAGGTCAAAGAAGAAGTC-AA--AAGTGAAAT   19011696  (SEQ ID NO: 5)
Query:          71  TAAAAATGACTTGCAAGAGAATGGTAA         97  (SEQ ID NO: 6)
                    ||||||    | ||   ||      ||||     ||
Sbjct:    19011697  TAAAAAGTATTTAGAACCAAATGAAAA   19011723  (SEQ ID NO: 7)
Score = 171 (31.7 bits), Expect = 3.5, P = 0.97
Identities = 63/87 (72%), Positives = 63/87 (72%), Strand = Plus/Plus
Query:          13  TAACTAAAATAATTGAGTAAAACTCATAGGTCAAAGGGGAATTCTAATTAAGTGAAATTA         72  (SEQ ID NO: 8)
                    |||  ||| ||||  ||  |||    | ||||||||||  ||||  |   |||  ||||||||
Sbjct:    12941025  TAAGTAATATAAGTAAATAAT-C-CATAGGTCAAAGAGGAAAT-T--TTATGGGAAATTA   12941079  (SEQ ID NO: 9)
Query:          73  AAAA--TGACTTGCAAGAGAATGGTAA         97  (SEQ ID NO: 10)
                    ||||   ||    |||  ||    |||||     ||
Sbjct:    12941080  AAAACATGTTTTG-AACTGAATGAAAA   12941105  (SEQ ID NO: 11)
```

Note that there are limitations to this precision of the breakpoints that can be defined by this method. In order to detect repetitive sequence elements that are highly degenerate, it is not appropriate to continue to reduce the length of the search sequence to extremely short segments because the algorithms used to detect repetitive sequences are sensitive to the lengths and composition of divergent genomic copies of such sequences. Repetitive sequences in the human genome often differ significantly both in homology and length from one another and consensus sequences derived from these repeat families, and this degree of sequence divergence challenges the sensitivity of most algorithms to detect repetitive sequence. Sequence comparisons between short test sequences and the genome using most of the common alignment methods can fail to detect shorter intervals (e.g., 50-75 nucleotides) containing members of repeat sequence families that are divergent from the majority of family members and thus the performance of the instant invention can be compromised by comparison of short subsets of sequences. The degree of similarity between a test sequence and other related sequences in the genome can vary widely across the length of the test sequence. Particular subintervals with low percentage identities can falsely indicate that a sequence is present once per genome, even though the overall subsequence (which contains this interval) is actually present multiple times in the genome.

To demonstrate this phenomenon, we attempted to divide the 1000 nucleotide subsegments from HIRA into consecutive, non-overlapping sequences as short as 50 nucleotides and search these sequences with the human genome. Most of these 50 nucleotide sequence were found by both BLAST and BLAT only one in the human genome reference, despite evidence showing that these sequences were subsets of known repetitive family methods. Thus, it might not be obvious to one of ordinary skill in the art that short contiguous sequences cannot be used to search the genome with high efficiency, since recognition of limitations on the length of the sequences are themselves insensitive to weak homologies between related family members and that lack of sensitivity is only amplified when the sequence being search is particularly short.

Based on the results in Table 1, the boundaries of cataloged repetitive sequence family members flanking this interval at the centromeric and telomeric ends occur at positions 1061 and at 2913, which are completely consistent with the findings indicated in Tables 3 and 4. The minimum length of this single copy interval, i.e., 1599 nucleotides, would be quite useful for probe production for a variety of applications including fluorescence in situ hybridization, microarray hybridization, Southern analysis, and microsphere suspension array hybridization.

This same procedure was then repeated for each 1000 by subsegment that was found to be present in single copy in the initial screen that determined the overall density of repetitive sequences across the HIRA gene region. These presumed single copy subsegments and the immediately flanking subsegments which contain repeat sequences are again selected for more detailed delineation of the boundaries of the single copy intervals. These regions would include intervals defined by positions 21001-26000, 25001-29000, 28001-33000, 44001-50000, 55001-62000, 64001-67000, 69001-72000, 74001-77000, 76001-80000, 80001-83000, 82001-85000, 93001-97000, and 100001-102000 (intervals derived from Table 2).

Upon identification of the single copy intervals with the present technology, DNA products derived from these intervals are then amplified, extracted or purified from genomic DNA or from recombinant DNA clones known to contain these sequences. The derivation of such products and their hybridization to other nucleic acids (from patients with chromosome abnormalities, for example) by either Southern analysis, fluorescence in situ hybridization, attachment to microsphere suspensions, microarrays or other solid phase surfaces are entirely conventional and well known by those of skill in the art. Examples and procedures for synthesis of such probes that have been developed from computationally defined sequences of single copy intervals and hybridization applications of the instant invention have been carried out by the inventor in the '097 patent.

Example 2

HIRA Gene

The same approximate 103 kilobase pair length interval comprising the 100,836 by HIRA gene and flanking sequences (SEQ ID NO: 1) was extracted from Genbank accession NT_001039. Position 1 of this interval corresponds to position 798,334 of NT_001039. This approximate 103 kb interval was analyzed using the method of the instant invention. The following indicates a comparison of results obtained for design of single copy probes using the method of U.S. Pat. No. 6,828,097 versus the ab initio method of the instant invention. The coordinates provided correspond to the 103 kb interval from which probes were previously derived.

Unless otherwise noted, initially the sequence region to be tested for repetitive and single copy sequences was separated into consecutive 1000 by intervals, each of which were tested for similarity for other sequences in the genome using WU-BLAST as described in Example 1. These were divided into 100 nucleotide (nt) intervals usually overlapping one another by 10-50 nucleotides and each tested for repeats by determining the number of genomic copies of each 100 nt subsequence with matches >70 nts in length and >=70% identity.

Previously determined single copy interval boundaries in U.S. Pat. No. 6,828,097: positions 55445-60803

The initial low (1 kb) resolution survey of the 103 kb region defined a single copy domain by positions 56,001-60,000 is present in single copy in the genome. The repetitive sequences adjacent to this interval were identified as follows: Centromeric boundary: $1^{st}$ iteration localized to positions 55001-56000; $2^{nd}$ iteration to 55393-55484 (because 55442-55541 is single copy and 55393-55492 is present in 1086 copies per haploid genome); $3^{rd}$ iteration to 55,424-55,434. This single copy interval boundary is within 11 nucleotides of the boundary determined with the method of U.S. Pat. No. 6,828,097.

Telomeric boundary: Boundary iteratively defined with increasingly narrower intervals. Intermediate resolution ($1^{st}$): positions 60,001-61,000; Higher resolution analysis ($2^{nd}$): we find that the interval from 60,687 to 60,786 is unique in the genome (1 copy) and the interval from 60,786-60,884 is repetitive (33 copies); Highest resolution ($3^{rd}$): positions 60,767-60,777. This single copy boundary is within 26 nucleotides of the boundary determined by the method of U.S. Pat. No. 6,828,097.

Previously determined single copy interval boundaries in U.S. Pat. No. 6,828,097: positions 44937-48722

Centromeric boundary: $1^{st}$: Intermediate resolution analysis shows that the 5' most repeat ends between positions 44991 and 45000. $2^{nd}$ Fine resolution analysis shows that the boundary is between 44911 and 44921. The interval downstream of 44937 (boundary within an AluJo repeat defined by method of U.S. Pat. No. 6,828,097) is single copy. The ab initio boundary is within 16 nucleotides of the '097 boundary.

Telomeric boundary: An L2 repetitive element was shown to begin at 47718, the boundary of the single copy interval defined by the '097 patent. With the instant invention: the intermediate resolution (1st) analysis shows that a repeat begins in the interval defined by positions 47601-47700. Fine (2nd) resolution analysis shows that a repetitive sequence (with 80% identity) present four times per genome beginning in the interval defined by 47651-47661. This boundary is 58 nucleotides upstream of the boundary disclosed in U.S. Pat. No. 6,828,097.

Previously determined single copy interval boundaries in U.S. Pat. No. 6,828,097: 76829-79310

Centromeric boundary: Intermediate resolution analysis (1st) delineates single copy boundary between positions 76801-76850. Fine resolution (2nd) analysis of nucleotides 76701-76900 indicates that the boundary of a repetitive sequence occurs between 76880 and 76900.

In other words, the ab initio detects a low copy divergent repeat (30% of the nucleotides are discordant) within the interval between positions 76829 and 76880 that is not found by the method of the U.S. Pat. No. 6,828,097. While this indicates that in some instances, the ab initio method may be more sensitive for detecting single copy intervals than the previous approach, one of skill in the art would recognize that divergent repetitive sequences with this level of sequence divergence do not usually produce cross-hybridization to other genomic locations under typical laboratory hybridization conditions.

Telomeric boundary: Intermediate resolution (1st) analysis (using a threshold of detecting repetitive sequences of 65% nucleotide identity) indicates boundary between positions 79400 and 79450. Fine resolution analysis (2nd) narrows this interval to between 79400 and 79410, which is 90 nucleotides from the boundary detected using the method of the '097 patent. The ab initio approach fails to detect a portion of an extremely divergent MER3 repeat element which begins at position 79310 and ends at 79501 (which is found using the method of the '097 patent). This element differs by 33% from the consensus MER3 sequence and contains insertions and deletions comprising 13% of that sequence. Because of the weak similarity to other related elements, divergent repetitive sequences of this type would not cross-hybridize to other genomic locations under typical laboratory conditions. Therefore single copy probes containing such sequences would still hybridize to a single location in the human genome under moderately stringent post-hybridization wash conditions.

Previously determined single copy interval boundaries in U.S. Pat. No. 6,828,097: positions 21423-25270

Centromeric boundary: At intermediate resolution, the ab initio method finds the boundary between a centromeric repeat and the adjacent single copy sequence within the interval defined by positions 21101 through 21149. At high resolution, the boundary is more precisely delineated between positions 21119 and 21139 using the default conditions for repeat detection. However, using a lower threshold of detecting repetitive sequences of 65% nucleotide identity, a weak, highly divergent repetitive sequence (with 67% identity to one other element in the genome) is detected within positions 21301-21399. Under typical hybridization conditions, this unlinked repetitive element would not cross-hybridize with a probe derived from this genomic interval. Application of the method used in the '097 patent indicates that the repetitive sequence at the single copy boundary is an L2 element which ends at 21151. The single copy boundary found by the ab initio method is thus 12 nucleotides from the boundary demonstrated in the '097 patent.

Telomeric boundary: At intermediate resolution (1st), the boundary found with the ab initio method between single copy and repetitive sequences falls between 25199 and 25297. The high resolution (2nd), this boundary occurs within the interval delineated between positions 25280 and 25300, which is 10 nucleotides away from the interval boundary determined in the '097 patent (position 25270).

CDC2L1 Gene

The previously determined boundaries of single copy interval based on the method of the '097 patent used to develop probes are positions 8145-17744 of GenBank accession AL03182 (SEQ ID NO: 3).

Ab initio analysis of consecutive 1 kb intervals in AL03182 (SEQ ID NO: 3) shows that positions 9001-17000 are single copy in the human genome. The sequences adjacent to this interval each contain repetitive sequences. Sequences from positions 8001-9000 are present in 117 copies per genome and sequences from 17001-18000 are present in 1672 copies.

To more precisely define the boundaries of the repetitive sequences centromeric and telomeric to the single copy interval, each of the flanking regions were further analyzed by comparing overlapping genomic intervals with increasingly shorter displacement.

Centromeric boundary: The 1st analysis localized this boundary to positions 8151-8200; the 2nd analysis to 8170-8180. The minimum distance between the boundary of the single copy interval determined with the ab initio method and the boundary determined by '097 patent is 25 nucleotides.

Telomeric boundary: The 1st analysis localized this boundary to positions 17651-17749; the 2nd analysis to positions 17662-17672. The minimum distance between the boundary of the single copy interval determined with the ab initio method and the boundary determined by '097 patent is 72 nucleotides.

This 9.5 kilobase interval was divided into two overlapping single copy intervals in order to develop probes that could be easily amplified for hybridization. As in the '097 patent, the interval sequences were used as templates for essentially conventional PCR primer selection methods, as described in the '097 patent. The resulting probes from these two intervals substantially overlapped the sequences comprising the probes of the '097 patent and when labeled by nick translation, produce an identical genomic hybridization patterns previously obtained with FISH. Differences between results produced by the current invention and the '097 patent only occur for short probes (~100 nt) whose sequences fall at or close to the deduced boundary between the single copy and repetitive sequences (for example, for single copy probes of 100 nt typically used In microsphere hybridization assays). Probe design should avoid using probes comprised of deduced single copy sequences that are located close to the position of the single copy-repetitive sequence transition.

NDN (NECDIN) Gene

Three single copy probe intervals were derived from Genbank accession number: AC006596 (SEQ ID NO: 2) from the NECDIN gene on chromosome 15.

Previously determined single copy interval boundaries in U.S. Pat. No. 6,828,097: positions 68031-75948

For the first interval in the NECDIN gene region, the previously determined single copy interval boundaries (given in U.S. Pat. No. 6,828,097; amplified by PCR primers corresponding to SEQ ID NOS: 437 and 438 of the '097 patent) are bounded on the centromeric end by position 68031 and at the telomeric end at position 75948 of AC006596 (SEQ ID NO: 2). Sequences between these coordinates are considered single copy and are not similar to known families of repetitive sequences.

At 1 kilobase pair resolution, sequences between 69001 and 75000 were found to be present at only this location on chromosome 15 as a single copy sequence in the genome. The adjacent intervals consisting of positions 68001-69000 and 75001-76000 contained repetitive sequences based on initial copy number analysis of these sequences. Using the method of the instant invention, we first localized the centromeric boundary at intermediate resolution between positions 68051 and 68101. This interval was then refined to between positions 68051 and 68061, which is within 20 nucleotides of the previously determined centromeric single copy repetitive sequence boundary (in the '097 patent). The telomeric boundary was first determined to occur between 75949 and 75999 and subsequently refined to the interval between positions 75971 and 75981 using the ab initio method, which is within 23 nucleotides of the previously determined boundary using the method of the '097 patent.

Previously determined single copy interval boundaries in U.S. Pat. No. 6,828,097: positions 76241-78441

The second interval in the NECDIN gene region (corresponding to sequences for PCR amplification (SEQ ID NOS: 441 and 442 of the '097 patent)) has a centromeric bound at position 76249 and a telomeric bound at 79221 of the same Genbank accession number. Applying the ab initio method iteratively as shown in the previous examples, these intervals were found to occur between positions 76241-76251 at the centrometric end and between 78431-78441 at the telomeric end. Thus, the 10 nucleotide window containing the centromeric bound of the repetitive sequence defined by the ab initio method contains the boundary determined using the method of '097 patent, i.e., they are essentially coincident. The ab initio method locates a highly divergent repetitive sequence (70% sequence identity) that was not detected using the method of the '097 patent, which accounts for the 800 nucleotide difference between the respective boundary coordinates. This divergent repeat would not cause cross-hybridization under the laboratory conditions used for probe hybridization. In any case, the interval defined by the ab initio method is more conservative than the one found using the method of the '097 patent. Using typical laboratory chromosomal hybridization conditions (described in the '097 patent), one of skill in the art will understand that probes derived from this interval will produce hybridization to a single genomic location.

Previously determined single copy interval boundaries in U.S. Pat. No. 6,828,097: positions 94498-99152

The third interval in the NECDIN gene region (region (corresponding to sequences for PCR amplification (SEQ ID NOS: 439 and 440 of the '097 patent)) has a centromeric bound at position 94498 and a telomeric bound at 99152 of the Genbank AC006596. Applying the ab initio method iteratively as shown in the previous examples, these intervals were found to occur between positions 94661-94671 at the centrometric end and between 97691-97701 at the telomeric end.

The probe interval obtained using the ab initio method is more conservatively determined than the single copy interval defined by the method of the '097 patent, suggesting that the ab initio method identifies unrecognized repetitive sequences not detected with the '097 method. Indeed the instant invention detects a previously unrecognized highly divergent repetitive sequence which is present 23 times in the genome and shows an average 71% identity with the interval 97651-97750 in the Necdin gene region. This divergent repeat would not cause cross-hybridization under the laboratory conditions used for probe hybridization. Using typical laboratory chromosomal hybridization conditions (described in the '097 patent), one of skill in the art will understand that probes derived from this interval will produce hybridization to a single genomic location. At the telomeric end of this interval, the ab initio method detects several contiguous simple repetitive sequence composed of imperfect runs of polynucleotides (GO or polydinucleotides ($[TG]_n$). These are detected as well by the methods of the '097 patent; however because these sequences are relatively short interrupted runs of imperfect homopolymers, they will not cause cross-hybridization under the laboratory conditions used for probe hybridization and can therefore incorporated in most probes developed using the '097 invention. Nevertheless, the ab initio method does recognize even these short, divergent sequences as repetitive sequences.

As demonstrated above, the ab initio method of probe design can recapitulate in most cases the single copy probe intervals deduced using the method of the '097 patent. In those instances where the two methods differ, in nearly all cases, the ab initio approach is more sensitive detecting even weaker similarities (of less than 70% identity) to known repetitive elements in the genome than that found with the prior method. The ab initio method may in some cases produce purer single copy sequence compositions than the methods of the '097 patent. In the laboratory however, these weak sequences similarities are not relevant, since under even moderate stringency post-hybridization wash conditions, any duplexes formed with such sequences will be disrupted and eliminated, thus preventing cross hybridization between these highly divergent repeats at other genomic locations and the designed probes.

All references cited above are hereby incorporated herein by reference.

Appendix A

The following script is an example of the ABINITIO.PL script.

```perl
#!/usr/bin/perl
# gets subsequences of defined length and increment from input
sequence P Rogan 2005

use Bio::SeqIO;
use Bio::SeqIO::fasta;
use Bio::PrimarySeqI;
use Bio::SeqFeature::Generic;
# command line arguments:
# (1) Name of genomic sequence
# (2) Length of subsequence
# (3) Length of window increment
# (4) Minimum Length of Match to repeats
# (5) Minimum Percentage Match to repeat
system("date");
system("pwd");
#   get name of sequence
$ARGV = shift @ARGV;
chomp $ARGV;
if (-s $ARGV) {
print "processing $ARGV ...\n";
} else {
print "Params: (1) Name of genomic seq, (2) Length of subsequence, (3) Length of increment, \n(4) Min length of match and (5) Min percent match to repeats\n";
exit; }
$seqin = Bio::SeqIO->new('-file'=>$ARGV,
'-format' => 'Fasta');
#initialization of subsequence extraction
$begin = 1;
$end = shift @ARGV;
chomp $end;
if($end<2) {die "subsequence too short"};
$incr = shift @ARGV;
chomp $incr;
if ($incr < 1) {die "beginning and ending nucleotides of subsequence are identical"};
$minlen = shift @ARGV; chomp $minlen;
$minperc = shift @ARGV; chomp $minperc;
#   $seqout = Bio::SeqIO->new('-format'=>'Fasta', '-file'=>'>
#   output.fa');
#   print $ARGV," ", $end, " ", $incr;
while(( my $seqobj=$seqin->next_seq( ))) {
#length of full sequence
my $len = $seqobj->length;
#print "length ", $len;
while( $len > $end ) {
#    print "seen sequence ",seqobj->display_id( ),",start of seq",
#                             substr($seqobj->seq,1,10),"\n";
if($seqobj->alphabet eq 'dna'){
$subseqin = $seqobj->subseq($begin,$end);
$id = $seqobj->display_id( );
$idsub = $begin . "_" . $end . "_" . $id;
$nameseg = $begin . "_" . $end;
open (OUT, ">$nameseg");
print OUT ">",$idsub, "\n", $subseqin, "\n";
print ">",$idsub, "\n", $subseqin, "\n";
# insert system call for qsub of wublast job here
#   job runs the wubl script and then a perl program that has blast parser for each blast run. Results are
#   appended to a table
$fpresults = "~/Documents/" . $nameseg . "_results";
system("qsub -cwd -o $fpresults -e /dev/null ~/Documents/wubl ~/Documents/$nameseg $minlen $minperc");
#   for example: qsub -o ~/Documents/test wubl
   ~/Documents/101_200
close (OUT);
$begin = $begin + $incr;
$end = $end + $incr;
}
}}
$seqout->write_seq($subseqin)
$date=system("date");
print $date;
```

Appendix B

The following script is an example of the WUBL script.

```
if [ "$#" -ne 3 ]
then
   echo "form: wubl sequence_file min_length_match min_percent_match"
   echo "sequence name (fasta format): "$1
   echo "Minimum length of match to repeat: "$2
   echo "Minimum percent match to repeat: "$3
blastn -d "human" -span2 -i $1 -cpus 2 -lcmask -hspmax 100 -warnings -errors -o $1_results
   blaspars.pl $1_results $2 $3 >> blastparse
```

Appendix C

The following script is an example of the BLAST-PARSE.PL script.

```perl
#!/usr/bin/perl
use Bio::SearchIO;
use Bio::Tools::BPlite;
# this program is called within the wubl script

# command line parameters : name of blast result file, min length of match, min percent identity
$minlen = 100;
$minperc = 70;
$ARGV = shift @ARGV;
chomp $ARGV;
$minlen = shift @ARGV;
chomp $minlen;
$minperc = shift @ARGV;
chomp $minperc;
my $in = new Bio::SearchIO(-format => 'blast',
   -file  => $ARGV);
print $ARGV " \n";
while( my $result = $in->next_result ) {
print "\nQuery = ", $result->query_name, "\n";
print "Min length of match = ", $minlen, " Min percent identity = ", $minperc;
print "Number of hits = ", $result->num_hits, "\n";
while( my $hit = $result->next_hit ) {
while( my $hsp = $hit->next_hsp ) {
if( $hsp->length('total') > $minlen ) {
```

```
if ( $hsp->percent_identity >= $minperc ) {
print "Hit= ",    $hit->name,
",Length=",    $hsp->length('total'),
",Percent_id=", $hsp->percent_identity,
",Start_hit=", $hsp->start('hit'),
",End_hit=",  $hsp->end('hit'), "\n";
}
}
}
}
}
```

Appendix D
The following script is an example of the COUNTHITS.PL script.

```
#!/usr/bin/perl
#counts number of qualified hits along a windowed sequence
# 1 commandline argument: name of blastparse output file
# parameters
#min length of match
$minlen = 100;
#min percent identity
$minperc = 70;
$ARGV = shift @ARGV;
chomp $ARGV;
open (BLASTSUM, $ARGV);
open (COUNT, ">count");
$num=0;
print "Begin    End    Number hits\n";
print COUNT "Begin    End    Number hits\n";
while (<BLASTSUM>) {
chomp;
if (/Hit*/) {
$num++;
$coords[3]=$num; }
if (/Query*/) {
# count the number of lines with hits
#print out the number of hits for the previous query:
if ($num>0) {
print $coords[1],"\t", $coords[2], "\t", $coords[3], "\n";
print COUNT $coords[1],"\t", $coords[2], "\t", $coords[3], "\n";
}
s/Query = /_/;
@coords = split(/_/,$_);
$coords[3]= 0;
$num=0;
}
}
```

Appendix E
The following script is an example of the SUBSEQ script.

```
#!/usr/bin/perl
# gets subsequences of defined length and increment from input
sequence P Rogan 2005

use Bio::SeqIO;
use Bio::SeqIO::fasta;
use Bio::PrimarySeqI;
use Bio::SeqFeature::Generic;
# command line arguments:
# (1) Name of genomic sequence
# (2) Length of subsequence
# (3) Length of window increment
# (4) Minimum Length of Match to repeats
# (5) Minimum Percentage Match to repeat
system("date");
system("pwd");
#   get name of sequence
$ARGV = shift @ARGV;
chomp $ARGV;
if (-s $ARGV) {
print "processing $ARGV ...\n";
} else {
print "Params: (1) Name of genomic seq, (2) Length of
subsequence, (3) Length of increment, \n(4) Min length of match and (5)
Min percent match to repeats\n";
exit; }
$seqin = Bio::SeqIO->new('-file'=>$ARGV,
'-format' => 'Fasta');
#initialization of subsequence extraction
$begin = 1;
$end = shift @ARGV;
chomp $end;
if($end<2) {die "subsequence too short"};
$incr = shift @ARGV;
chomp $incr;
if ($incr < 1) {die "beginning and ending nucleotides of
subsequence are identical"};
$minlen = shift @ARGV; chomp $minlen;
$minperc = shift @ARGV; chomp $minperc;
#            $seqout = Bio::SeqIO->new('-format'=>'Fasta',
#'-file'=>'>output.fa');
#   print $ARGV," ", $end, " ", $incr;
while(( my $seqobj=$seqin->next_seq( ))) {
#length of full sequence
my $len = $seqobj->length;
#print "length ", $len;
while( $len > $end ) {
#             print "seen sequence ",
seqobj->display_id( ),",start of seq",
#                       substr($seqobj->seq,1,10),"\n";
if($seqobj->alphabet eq 'dna'){
$subseqin = $seqobj->subseq($begin,$end);
$id = $seqobj->display_id( );
$idsub = $begin . "_" . $end . "_" . $id;
$nameseg = $begin . "_" . $end;
open (OUT, ">$nameseg");
print OUT ">",$idsub, "\n", $subseqin, "\n";
print ">",$idsub, "\n", $subseqin, "\n";
# insert system call for qsub of wublast job here
#   job runs the wubl script and then a perl program that has blast
parser for each blast run. Results are
#   appended to a table
$fpresults = "~/Documents/" . $nameseg . "_results";
system("qsub -cwd -o $fpresults -e /dev/null ~/Documents/wubl
~/Documents/$nameseg $minlen $minperc");
#              this works: qsub -o ~/Documents/test wubl
~/Documents/101_200
close (OUT);
$begin = $begin + $incr;
$end = $end + $incr;
}
}}
$seqout->write_seq($subseqin)
$date=system("date");
print $date;
```

What is claimed is:

1. A computer implemented method of producing a hybridization probe of a target reference complete genome sequence, wherein a single copy sequence is identified by a method of successive division of the target reference genome sequence into subintervals and comparison of the subintervals to the target reference sequence, said method comprising:

using a computer to determine a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence comprises at least two subsequences, and a single copy interval of the first screened sequence is identified as (i) a subsequence of the first screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence;

using a computer to determine a count of the number of times a subsequence of a second screened sequence occurs in the target reference genome sequence, said screened sequence being at least one subinterval of the target reference genome sequence, wherein the second screened sequence comprises a single copy interval of the first screened sequence;

the second screened sequence overlaps the single copy interval of the first screened sequence;

the subsequences of the second screened sequence are either (i) consecutive non-overlapping subintervals of the second screened sequence or (ii) overlapping non-identical subintervals of the second screened sequence; and a single copy interval of the second screened sequence is identified as (i) a subsequence of the second screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence; and using a computer to identify a single copy interval and at least one contiguous divergent repetitive interval of the target reference sequence wherein at least one subsequence in the target sequence contains a divergent repetitive element suitable for use as a probe that hybridizes to a single location in the target genome, wherein said divergent repetitive element is washed under conditions that eliminate cross-hybridization to other target sequences in the genome.

2. The method of claim 1, wherein the computer implemented method further comprises a step of using a computer to determine a count of the number of times a subsequence of a third screened sequence occurs in the target reference sequence, wherein (A) the third screened sequence comprises a single copy interval of the second screened sequence; (B) the third screened sequence overlaps the single copy interval of the second screened sequence; (C) the subsequences of the third screened sequence are either (i) consecutive non-overlapping subintervals or (ii) overlapping non-identical subintervals; and (D) a single copy interval of the third screened sequence is identified as (i) a subsequence of the third screened sequence with a single subsequence occurrence in the target reference sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the third screened sequence, each member being a single subsequence occurrence in the target reference sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence.

3. The computer implemented method of claim 1, wherein the method further comprises a step of using a computer to determine a count of the number of times a subsequence of a fourth screened sequence occurs in the target reference sequence, wherein (A) the fourth screened sequence comprises a single copy interval of the third screened sequence; (B) the fourth screened sequence overlaps the single copy interval of the third screened sequence; (C) the subsequences of the fourth screened sequence are either (i) consecutive non-overlapping subintervals or (ii) overlapping non-identical subintervals; and (D) a single copy interval of the fourth screened sequence is identified as (i) a subsequence of the fourth screened sequence with a single subsequence occurrence in the target reference sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the fourth screened sequence, each member being a single subsequence occurrence in the target reference sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence.

4. The computer implemented method of claim 1, wherein said method further comprises a step of using a computer to identify a subsequence of the first or second screened sequences with at least two occurrences in the target reference sequence as a subsequence containing a repetitive element wherein the single copy interval is located adjacent to the repetitive element.

5. The computer implemented method of claim 4, wherein said method further comprises a step of using a computer to identify a second, distinct subsequence of the first or second screened sequences with at least two occurrences in the target reference sequence as a subsequence containing a different repetitive element, wherein the single copy interval is located between the first and the second subsequences containing the differing repetitive elements.

6. The computer implemented method of claim 3, wherein the second, third, or fourth screened sequence comprises (i) a centromeric end that overlaps the single copy interval of the first, second, or third screened sequence, respectively; (ii) a telomeric end that overlaps the single copy interval of the first, second, or third screened sequence, respectively; or (iii) a centromeric and telomeric end that both overlap the single copy interval of the first, second, or third screened sequence, respectively.

7. The computer implemented method of claim 6, wherein said method further comprises a step of using a computer to determine whether an extended test sequence extends in the direction toward the centromere of the chromosomal arm containing the subsequence.

8. The computer implemented method of claim 3, wherein a subsequence is (i) at least about 100 consecutive non-overlapping nucleotides; (ii) at least about 200 consecutive non-overlapping nucleotides; (iii) at least about 400 consecutive non-overlapping nucleotides; (iv) at least about 600 consecutive non-overlapping nucleotides; (v) at least about 800 consecutive non-overlapping nucleotides; or (vi) at least about 1000 consecutive non-overlapping nucleotides.

9. The computer implemented method of claim 1, wherein the target reference sequence is about 100,000 nucleotides to about 400,000 nucleotides.

10. The computer implemented method of claim 1, wherein the target reference sequence is a sequenced genome of an organism.

11. The computer implemented method of claim 10, wherein the target reference sequence is a sequenced genome of a human.

12. The computer implemented method of claim 1, wherein the overlapping subintervals of the screened sequence are displaced by at least about 20 nucleotides from adjacent subintervals.

13. The computer implemented method of claim 1, wherein the probe comprises at least two contiguous subsequences of a screened sequence, each of the contiguous subsequences having a single occurrence in the target reference complete genome.

14. The computer implemented method of claim 1, wherein the sequence of said divergent repetitive element exhibits less than or equal to 70% identity with the sequence of another member of the same repetitive sequence family.

15. The computer implemented method of claim 1 where the post-hybridization wash is a solution of 0.1×SSC at a temperature exceeding 42 degrees Celsius and the solution comprises 15 mM NaCl and 1.5 mM sodium citrate ($Na_3C_6H_5O_7$).

16. The computer implemented method of claim 1 where the post-hybridization wash is a solution of 0.2×SSC at a temperature exceeding 37 degrees Celsius and the solution comprises 30 mM NaCl and 3 mM sodium citrate ($Na_3C_6H_5O7$).

17. A computer implemented method of producing a hybridization probe of a target reference complete genome sequence, wherein a single copy sequence is identified by a method of successive division of the target reference genome sequence into subintervals and comparison of the subintervals to the target reference sequence, said method comprising:

using a computer to determine a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence comprises at least two subsequences, and a single copy interval of the first screened sequence is identified as (i) a subsequence of the first screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence;

using a computer to determine a count of the number of times a subsequence of a second screened sequence occurs in the target reference genome sequence, said screened sequence being at least one subinterval of the target reference genome sequence, wherein the second screened sequence comprises a single copy interval of the first screened sequence;

the second screened sequence overlaps the single copy interval of the first screened sequence;

the subsequences of the second screened sequence are either (i) consecutive non-overlapping subintervals of the second screened sequence or (ii) overlapping non-identical subintervals of the second screened sequence; and a single copy interval of the second screened sequence is identified as (i) a subsequence of the second screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence; and using a computer to determine a single copy interval and at least one contiguous divergent repetitive interval of the target reference sequence wherein at least one subsequence in the target sequence contains a divergent repetitive element suitable for use as a probe that hybridizes to a single location in the target genome, wherein said divergent repetitive element is washed under conditions that eliminate cross-hybridization to other target sequences in the genome, where such conditions comprise washing the hybridized probe in a solution of 0.1× SSC (15 mM NaCl and 1.5 mM $Na_3C_6H_5O_7$) at a temperature exceeding 42 degrees Celsius.

18. A computer implemented method of producing a hybridization probe of a target reference complete genome sequence, wherein a single copy sequence is identified by a method of successive division of the target reference genome sequence into subintervals and comparison of the subintervals to the target reference sequence, said method comprising:

using a computer to determine a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence comprises at least two subsequences, and a single copy interval of the first screened sequence is identified as (i) a subsequence of the first screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence;

using a computer to determine a count of the number of times a subsequence of a second screened sequence occurs in the target reference genome sequence, said screened sequence being at least one subinterval of the target reference genome sequence, wherein the second screened sequence comprises a single copy interval of the first screened sequence;

the second screened sequence overlaps the single copy interval of the first screened sequence;

the subsequences of the second screened sequence are either (i) consecutive non-overlapping subintervals of the second screened sequence or (ii) overlapping non-identical subintervals of the second screened sequence; and a single copy interval of the second screened sequence is identified as (i) a subsequence of the second screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence; and using a computer to determine a single copy interval and at least one contiguous divergent repetitive interval of the target reference sequence wherein at least one subsequence in the target sequence contains a divergent repetitive element suitable for use as a probe that hybridizes to a single location in the target genome, wherein said divergent repetitive element is washed under conditions that eliminate cross-hybridization to other target sequences in the genome, where such conditions comprise washing the hybridized probe in a solution of 0.2× SSC (30 mM NaCl and 3 mM $Na_3C_6H_5O_7$) at a temperature exceeding 37 degrees Celsius.

19. A method of designing and producing sequence content of hybridization probes of a target reference complete genome sequence, wherein a single copy sequence is identified by a method of successive division of the target reference genome sequence into subintervals and comparison of the subintervals to the target reference sequence, said method comprising:

determining a count of the number of times a subsequence of a first screened sequence occurs in the target reference genome sequence, said screened sequence being at least one subinterval of the target reference genome sequence obtained by division of the target reference genome sequence, wherein the target reference genome sequence comprises the first screened sequence, the first screened sequence comprises at least two subsequences, and a single copy interval of the first screened sequence is identified as (i) a subsequence of the first screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the first screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence;

determining a count of the number of times a subsequence of a second screened sequence occurs in the target reference genome sequence, said screened sequence being at least one subinterval of the target reference genome sequence, wherein the second screened sequence comprises a single copy interval of the first screened sequence;

the second screened sequence overlaps the single copy interval of the first screened sequence;

the subsequences of the second screened sequence are either (i) consecutive non-overlapping subintervals of the second screened sequence or (ii) overlapping non-identical subintervals of the second screened sequence; and a single copy interval of the second screened sequence is identified as (i) a subsequence of the second screened sequence with a single subsequence occurrence in the target reference genome sequence, wherein an occurrence is defined by at least about 50 consecutive nucleotides of the subsequence having (i) at least about 60% homology to the target reference sequence; (ii) at least about 70% homology to the target reference sequence; or (iii) at least about 80% homology to the target reference sequence, or (ii) a group of contiguous subsequences of the second screened sequence, each member being a single subsequence occurrence in the target reference genome sequence, wherein an occurrence is defined by at least about 50 consecutive nucleotides of the group of contiguous subsequences having (i) at least about 60% homology to the target reference sequence; (ii) at least about 70% homology to the target reference sequence; or (iii) at least about 80% homology to the target reference sequence;

identifying a single copy interval and at least one contiguous divergent repetitive interval of the target reference sequence wherein at least one subsequence in the target sequence contains a divergent repetitive element suitable for use as a probe that hybridizes to a single location in the target genome, wherein said divergent repetitive element is washed under conditions that eliminate cross-hybridization to other target sequences in the genome: and synthesizing a nucleic acid hybridization probe having at least one contiguous divergent repetitive interval of the target reference sequence.

20. The method of claim 19, further comprising the step of labelling or chemically modifying the nucleic acid hybridization probe.

21. The method of claim 20, wherein the labelled or chemically modified nucleic acid probe is hybridized to a complementary target sequence using either fluorescence in situ hybridization, Southern blot hybridization, or bead suspension hybridization.

22. The method of claim 20, wherein the labelled or chemically modified nucleic acid probes are hybridized to a complementary target sequence with a microarray, wherein said microarrays are comprised of hybridization probes composed of either fixed or cleavable oligonucleotides.

23. The method of claim 19, wherein the step of identifying a single copy interval and at least one contiguous divergent repetitive interval of the target reference sequence further comprises washing said hybridized probe comprising a divergent repetitive element under conditions that eliminate cross-hybridization to other target sequences in the genome, where such conditions comprise washing the hybridized probe in a solution of 0.2×SSC (30 mM NaCl and 3 mM $Na_3C_6H_5O_7$) at a temperature exceeding 37 degrees Celsius.

24. The method of claim 19, wherein the step of identifying a single copy interval and at least one contiguous divergent repetitive interval of the target reference sequence further comprises washing said hybridized probe comprising a divergent repetitive element under conditions that eliminate cross-hybridization to other target sequences in the genome, where such conditions comprise washing the hybridized probe in a solution of 0.1×SSC (15 mM NaCl and 1.5 mM $Na_3C_6H_5O_7$) at a temperature exceeding 42 degrees Celsius.

* * * * *

SEQUENCE LISTING

<160> NUMBER OF SEQ ID NOS: 11

<210> SEQ ID NO 1
<211> LENGTH: 102780
<212> TYPE: DNA

<213> ORGANISM: Homo sapiens

<400> SEQUENCE: 1

```
gctgcctcac ctgcacagca agtctctggc tcttcattcc ttaagagtcc cacttgcagc      60
ctggcttttt atgtgtacac acacacacac tcacacaaac tatcctggct ttatttggca     120
tgaacacatg cctgggtctc atccagccac ttgacatccg agtgagacat ggagtggaat     180
ggctgctagg ccagagatca gtggtcagtt accccggcct ctgactccaa gtccaaggct     240
ccttctccag gctcagaccc acacactggg tggtggtgac aaagatcagg acccaggagt     300
gggtggtact cagccctcac tgtgcttaaa gattctgtga ttctgttttct tctcctgtag     360
atcaacgtct ggatcacttt ctaataaaat ccaactttg ctgataattc tccaatatac     420
ccaagactgt aaatactgat ttcctttcat gaaattgtcc aaacagctgc agcccttggt     480
gcacagtatg atctggacct ggggcacagc aagaccagaa ccatgaacca ccatgaacca     540
tgactcctca cttgtgagat gacgtgtgca aggtgaccta tggtgcttca tgaccacaga     600
agtgaccact ctacactgtg aaatgaattt ctgcatgggg ggtatattag ggttctctac     660
agggacagaa ctaatagata tatatgaaag tttattaagt attaacttac acaatcacaa     720
ggtcccacaa taggccatct gcaagctgag gagcaaggag agccagttcg agtcccaaaa     780
ttgaagaact tgggagtccg atgtttgagg gcaggaagca tccagcacgg gagaaagatg     840
taggctggga ggctaagcaa gtctcatctc ttcacatttt tctgcctgct ttatattcgt     900
tggcagctga ttagatggtg cccacctgat taagagtggg tctgccttcc ccagcctgac     960
tcaaatgtta atctcctttg gcaacaccct cacagacaca tccaggatca atattgcatc    1020
cttcaatcca atcaagttga cacgcagtat taaccatgac aggggggaat gagatgacac    1080
aaaggatccc ttctggctct catgttctgt caccatctac ttcaggagag atgcactg      1140
tgtgggagg atgaaagtta gaaggaaaag gcaagagaaa tcaggagggt ttggtattca    1200
atgcgtgttc atttattta cacttacaaa agaaatcgcc cacccctttg ccccattccc     1260
ccaaaacagt ctctttttac aaacatttaa aaattaaaac caaatgaaga tagacaagtt    1320
aatttcagta caattatttt tcagtgtagc tgtcataatt agagtttaaa tttcctacaa    1380
gtgaccaatg tccaagtgac ttatagggaa atcctgatta tcggccaaag gaaattcaat    1440
attacaagtt agcaaattct agtacaaaaa tagtccgtgt gttggaacag cttttccttt    1500
acataggtct taggtcagtc tgctgtaata cctaacgctt ccggattctc tctcacaaat    1560
ggctcaatcg tcactgctga agcagcatgg tgcctgcagc agcaggggct agtgtccacc    1620
ttggggccgt gctggagacg gcaggcctgg gactgccttg ctggccccag gcacctggg     1680
cagagctcca gccctagctc cgcatcgggg gcttggaggg agggatgagc ttccccctcc    1740
tgaggcaatg tcagacccag gacacagggc acatctgccc agggagctgg gctggcgctg    1800
gtgcaggaca gcacatctcc tgccagtgtc tcctcccccct acagcctggt caggtgagag    1860
gcggtcctgc atgtcatcag cggcgagagt gtggccctgc ccttgctgca gccagggcag    1920
gctggggcag gctacttgtc cctcaggatg tcgagctgtt cctgacactc ggtgaagagg    1980
cgctggaatc ggaggttctg cccgatgact ggtagcagct ccttcagcag ctccctcttc    2040
cgcagaccct gtggacacag agtgacagct gagtgcaagt gtcagtgaag agacctagat    2100
tgtggggact ttcctggcct ggcagagaac cttgtgtctg ctcacgggag aaggaaagaa    2160
caattcctct gcaggtgaga aactgtgaga gagctgtggg gcaaatgtgc aggatgaagt    2220
ggcaggtgga atgggagcaa cacagtgtgg ggataaagga ggatgaggcc aatgcagggt    2280
```

```
ctgctcctcc atccgtgggc acagccactg ctgaccttat agtgactgag cagttccctg    2340
accatccagg gcaggatgag agtagaacaa ggctgagggt caggtggctg gccattcagg    2400
aggggctgtt ccctcatgct gatgtttgcc aggggtttga ggtcaagccc cagggcaagg    2460
atgcacctgg ggggcagtga ctggctttag ttttccagca acacaaatga ggtgccagta    2520
tcccctgatg tggaggatgt tcggatgctg accaaactat gcttagttgc ctaaacatcc    2580
tccacgtcag gtcatattgg caccacagtc tgaaacaagc attgccagtt ggggtctctg    2640
ctgcacagac caaaagagca gactcctgag cagtacggct gctccaaagg gaaaactacc    2700
agccagacaa ctttaaacact ggacgagaag gtctaagatc ttgaattaac ggtgacagat    2760
atacctgcaa caagtctaga agtgacagta aagaataagt gtaactatta ggtttgagta    2820
acacagaagt tgttagagat gggataagca ggagaatggc tgctgttggc gaccaagttt    2880
gatggaggag cagcccacac tccaacaggg aggctctgac accagagtgc catagtcaga    2940
acagagatgt tatggatttg caaaggctga atgtttact atctggtcct ttacagaaaa    3000
gtttgtcaac tcctaaaata gatcatgttt tctaactaaa ataattgagt aaaactcata    3060
ggtcaaaggg gaattctaat taagtgaaat taaaaatgac ttgcaagaga atggtaaaaa    3120
aaaaaaacca acacaaaata ctccaaaagt ggtaagattc agcaaaagtg ggcactttag    3180
aggcatttag aaacaacagc ttatactgta ttagagaaca tgaaagaatg acaagccaag    3240 actccaaccct aaagccatca ggggaaagga aaaaaaaaaa gactaaagaa aaaaaggaca    3300
tgagaaaaaa acatttttttt taaaaaaagg agataataaa aattgaaata ataaaaatag    3360
aaaacaaaga tttaatagag aagatttaga aaaacaattt tattttatat attttttttga    3420 gacagggtct agctctgttg cccaggctgg agcgtagtgg tgcaatcaca gctcgctgca    3480
gcctcaacct cccaggctca agtgatcctc ctgcctcagt tacccgagta gctgggacta    3540
taggtgtgtg ccaccatgtc tggctaattt ttatatattt agtagagcgg ggtttcacct    3600
tgttggccag gctgatctca aactcctgag ctcaagtgat cttcctgcct tgttctccca    3660
aagtgctggg attaaaggcg tgagccacta tgcctggcaa aagtcatttc ttgaaaagac    3720
taatggacaa acgtctggca ggattaatca agaaagagag agaaagctta aagaaataat    3780
attagaaata aaaagagaca taactacaga tatagaagaa agaaaagat atgattacta    3840 tcaactttat gctaagaaat ttgaacattt agagaaatg gagaaattcc tagaaaaata    3900
taatttatca aaactagctc aaaaagaaat agaaaggaaa agttaattat taccataaag    3960
aaaacatcag gaatactatt ttaaaactga catcaaggat gagattttct ttgtcttttcc    4020 tttcccacag tttgactaat gtgtctcagt gcaggttcct ttgggatttt cctacttaga    4080
gttcactgag gctcttgtat tagtagaccc ccgtctttcc tcaaatttgg aaaatttccg    4140
ccagtatttc ttcaaataag ctctctactc cttctctct cttacacttc tagaactccc    4200
attatggatt catgggtata cttggatggt gtctggtaag tctcttagac tctgtttgct    4260
tttcttcatt ctattttctt tttgctcctc atacttgata atttcaaatg acctgttttc    4320
aagtttgctg attacccctt ttgtctattc gagtctgctg ttgaacccctt ctagtgaact    4380 tttcaattca gttattgtat ttttaaactc cagatttctg tttagctctt tttttggaat    4440
ttctatctcc ttgttgatac tctcattttc tttttttttt tcttgagatg gagcctcgat    4500
ctgtcgccca ggctggagtg cagtggtgtg atctcggctc actgcaagct ccgcctcctg    4560
ggttcacacc attctcctgc ctcagcctcc cgagtagctg ggactacagg cgccggccag    4620
cacgcctggc taatttttttt gtattttttag tagagatggg gttccaccat gttagcaagg    4680
```

-continued

```
atggtctcga tctcctgacc ttgtgatccg cccgccttgg cctcccaaag tgctgggatt    4740
acaggcatga gccactgcac ccggccctca ttttcttcat atatagtttt cctgattttg    4800
tttagttgtc tgtattctcc ttgagcattt tttaagacat ttattttaaa gtcttatgtc    4860
tgatgggcac agtggctcat gcctgtaatc tcagcacttt gggaggccaa ggcgggcaga    4920
tcgcttgagg ccaggagttc gagaccagtc tggccaacat ggcgaaaccc catctccact    4980
aaaaatacaa aaattaggcc aggcgcgtg gctcacgcct ataatcccag cactttggga    5040
ggctgaggcg gctggatcac ttgaggtcag gagttcgaga ccagtctggc caacatggcg    5100 aaacccatc tccactaaaa atactaaaat tagccagtcc tgacctcagg tgatccacct    5160
gccttggcct cccaaagtgc tgggattaag gcatgaacca acgcacccgg cagtccttt    5220 acttttaagc cattgtgtta ttacatgtaa gctgggtttc ttataagcag catacagctg    5280
gttgttatta attctaatct gataatctat gccttttaga cctatattta atgattattg    5340
atatattagg gtttaaatct accatccat gtatgttttt ctgccttctt ttgaatgaat    5400
gtattatttt ctatcattca attttatcta tttgttagtt ttttagctac gattcttttt    5460
actgctttgg gatttgtatg tgtatgtgca tgagttttat ttttttggttt tggtggttgc    5520 tctagggcat ataacataca gtatatgcct ttacttatca tagtctgtct tcaagtatta    5580
tatcactttg cataatgtgt aaaaatcttt taatggtata ctttcatatc cccactcctg    5640
gcgtctgtga tactgctgtc atgccacttc acttctacat atgttataat tacaaactac    5700
attttcatta tttggcttaa aaaggcagaa cttttgact ttttttttt ttgagacagg    5760 gtcttgcgct ctgttgccca ggctggagtg cagtggcgtg atcttggctc actgcaacct    5820
ctgcctctca ggttcaagca attcttgtgt cttcgcctcc tgagtagctg ggactacagg    5880
catgtgccac cacacccggc taattttgt atttctagta gagatggggt ttcgccacgt    5940
tggccaggct ggtcttgaac tcctggcctc aagtgatctg tccacctcgg cctcccaaag    6000
tgctgggatt acaggcgtga gccaccgcgc cgaacgagaa cttttttaca ttttgacatt    6060
tagatgaaca cttttgacat ttaattctta acccttggga ggtatatttt tatgaactga    6120
agatctgctt ttacttagtt acatataaat aaccagtttc ctaaactcca tttattgaat    6180 agcccccct atttttccca ctgtatctgt tttgtcttct ctctcatata gcaaagtatc    6240
taaattactc cggcttcata ataaacccaa atatctggta gcatagtgaa tgtcttaact    6300
attcttggct ttttactgct ccatataaat tgttgaatta gcttgtcaag tttcattgaa    6360
acctctagtg ggcatttgat tagagaggca ttgagtcagt aggtctgttt agaaacggtt    6420
ggcgtctttt actgtactgc actttctcat cgtttgtcca ggttttcttt aatgacttta    6480
agtaaacgtt tataattctt agcatatagg ctatgtacat cctttgttag atttattctt    6540
agatacttta taattctcaa aagagacaat cttgaaagtg caaaaaaaa agtgactcat    6600 gagagggatt tgaagtttgt gaagaactac acgcacaatt gctggcttaa agatggagga    6660
ggcaggtgga aagctaacaa ggaaatgaat tctgctattc caataacgac tgagcttgga    6720
agaggaccct tgaaccctagg tgatctcatc tggccagtaa tttgagtaga gaattcagga    6780
accactgcaa aagcacacca ggaagaccga agaaatcac agatcctttg aaagaagtgg    6840
caggctgctg caaattccac aagacaggtg aaaaactctg gtgctctctc aaaagtgcca    6900
tctcctggct ggaggccaat taactcagga cattacagca attcataaca gaacaaccct    6960
gctccaagga aggagaaaaa caacagctaa ttccactgcc tgcaacatcc tttctaacca    7020
gtggtcctga gtgtgtccac atgatgactt cactggtagc ataaccagca tttgagaaag    7080
```

```
cctgcacact aaacatatct acaaacaagg actctcacag agtctacgcc attccctgg    7140
caccaccacc acagcaggtg ctggtatcca cagctgggag atctgaagat ggatcacatc   7200
accgggttct ttgcagacgt tccccagcat gggcccagag cctggtagcc ccactgggtg   7260
gctagaccca gaagggcaat aataatcacc gcagtctggc tcataggaat ctccatccct   7320
aggggaaggg gaagtgcacc aaatcaaggg atcaccctgt gggacaaaat aatctcaaca   7380
gcagcctctg agttccagat ttttccactg aactagtcta cccaaatgag aagtaatcag   7440
aaaagtaatt ctggcaataa tgacaaaaca aggttctata atacctccaa aagaccacac   7500
tagctcctca gcaatggatc caaaccaaga ataattacaa agtacatttt cattatttgg   7560
cttaaaaagg cagaactttt tggcttttc tttttcttt tttttgaga cagggtctcg     7620
ctctgttgtc caggctggag tgcagtggcg tgatctctga attgccaaag aattcagaag   7680
gctgattatt aagctactca aggagatacc aaaggtgaaa atcaacttca agaaattta    7740
aaaaatatat aggatatgga tgaaaaatgc tccagagaaa tcggtatcat aaagaaaaaa   7800
tcaaaaaatc aaaaatcaaa acttctggaa ataaaagaca cacttagaga aatacaaaat   7860
gcactagaaa gtttcaacaa tagaatcaaa gaagtagaag agagaacttc agaattcaaa   7920
gacaagactt tgaatcagac aaaaacaaag aaaaaataat tttttaaaaa aatgaacaaa   7980
gcctccaaga aatttgggat tatgttaaat ggccaaacct aagagtaaga ataaatggtg   8040
ttcctaagaa gagaaatcta aaagtctgaa aaacgtattt gtggggatag ttgaggaaag   8100
cttccctgac cttgctagag atctagacat ccaaatacaa gaagctcaaa gaacacctgg   8160
gaaatttatc acaaaaagat catcacccag gtacacagtc atcaggttat ctaaagtcaa   8220
gacaaaggaa agaatcttaa gagctgtaag gcaaaagcat caggtaacct atacacgaaa   8280
gcctatcgga ttttttttt tgagacagag tcttgctttg tcatccaggc tggagtgcag   8340
tggtgcaatc ttggctcact gcaatctctg ccgcccggt tcacgcaatt ctcctgcctc    8400
agcctcccaa gtagctggga ctacaggccc ctgccaccag gcctggataa tttttgtatt   8460
tttattagag gtggggtttc accgtgttgg ccaggctggt cttgaactcc tgaccttaaa   8520
tgatccaccc accttggcct ccctaagtgt tgggattaca cgaatgagcc actgcgcctg   8580
gccagaatac ctatcagatt aacagcagat ttctcagcag ataccctaca agccagaagg   8640
gtttgggttc ctatttttag cttcctcaaa caaactaact gccagccaag aatttagtat   8700
ccagcaaaat taagtgtcat atatgaagga ggcataaagt ctttttcaga caaatgctga   8760
gagaatttgc caccaccaag ccagcactac aagaaatgct aaaaggagtt ctaaatcttg   8820
aaacaaaacc ttgaaataca ccaaaataga acttccttaa agcataaaac tcacagggtc   8880
tataaaacaa taacaaaatg aaaaaaaaaa aaccaacaaa aaagaaggt attcaggtaa     8940
aaacaagcat ggtaaataaa acagtacctc acatctcgat actaacattg aatgtaaata   9000
gtctaaatgc tccacttaaa agatacagaa tggcagaatg gatacaaatc caccaaccaa   9060
atatctgcta acacatatgg actcacataa gttgagggta aagggtgaa aaaagatatt     9120
ccatgcaaat acaaaccaaa agcgagcaga aatagctatt cttatatcag acaaaacaga   9180
ctttaaagca acaatagttg aaaaagacaa aagggacat tacataatga taaaaggatc     9240
agtccaacag gaaaatatca caatcctaaa tatatatgca cctagcacgg agctcccaa     9300
atttataaaa caattagtac tcaacgtaag aaatgagata cacagcaaca cagtaacagc   9360
ggggacttca acactagaca ggtcatcaag acagaaaagc aacaaagaaa caatggactt   9420
acactatacc ctagaacaaa tggacttaac acatatttac agaacattct acccaacaac   9480
```

```
tgcagaatat acattctttt catcagcaca tggaacattc tccaagaaag accatatgat   9540
aggccacaaa acaactctca ataaacttaa gaaaatcgaa attatatcaa gtaccctctt   9600
agaccacagt aaaataaaat tggaaattaa ctccaaaagg aaccctcaaa actatacaaa   9660
tacatggaaa ttaaaaaata tgctcctgaa tgatctttgg gtaaacaatg aaatcaagat   9720
ggaaattaaa aagttttatg aactgaataa tgacacagct tatcaaaacc tctgggacac   9780
agcaaaagtg gtgctaagag gaaagttgat agcattaaat gcttacatca aaagtatga   9840 aagaggccaa gcacggtggc tcgtgtctgt aatcccagca ttttggagg ccaaggcagg   9900 aggatcactt gaggtcagga gttcaagacc agcctggcca aaatgccaaa accccgtctc   9960
tatcaaaaat agaaaaaaat tagctgggtg tggtgacgca tgcctgtagt cccagctact  10020
tgggaggctg aggcctgaga attgcttgaa cctggggaggc agaggttgta gtgagccgag  10080
atgcaccact gcactccagc ctgggcgaca gagcgagact ccgtctcaaa aaaaaaaaa  10140 aaagatccaa ttaagctaaa ttagaaacaa atgaaagat attcaactg ataccacaga  10200 aatagaaaag atcattcaag actactatga acacctttat gcacacaaac tagaaaatct  10260
agaggaaatg gataaattcc tggaaatata taaccctcct agattcattc aggaaaaaat  10320
agaaactttg aacagaccaa taataagtag caagactgaa acagtaattt aaaaattgcc  10380
aacaaaaaaa cagtctggga ccagatggat tcacagctga attctattga acattcaaag  10440
aagaatttgt accaatctta ctgaagctat acaaaagac agagaagag ggaatctccc  10500 taaatcactc tatgaagcca gtatcaccct aataccaaaa ccaggaaagg cataacaaa  10560 aaatgaaatc tacagaccaa tatccctggt gaacatagat gcaaaatcc tcaacaaaat  10620 actacctaat cgaatcaaat ggtgtatcaa aaagataata caccatgatc aagtgggttt  10680
cataccaggg atacagggaa gacttaacgt acacatgtca ataaatgaga tacatcacat  10740
aaacagaatt aaaaacaaaa tcatatgatc atctcaatag atgccgaaaa agcatctgac  10800
aaaatctagc atgccttcga ttaaagccct caggaaaacc gtcatagaat ggaaatacct  10860
caaggtaata aaagccacta tgacaaactc acagttgact ttataccgaa aagggaaaag  10920
ataaaagggt tcccctgag aactctaaca gacaaggatg cccactgtca ccactgctat  10980
tcaacattgt actggaagtc ctagccagag caaacagaca agagaaagaa ataaagggca  11040
tccaaatatg taaaggggaa gtcaaaatat cgctgtttgc caatgatatg atcgtatacc  11100
tagaaaaccc taaagactca tccaaaaagc tcctagatct aataaatgaa ttccgtaaac  11160
tttcagggta caaatcaat gtacacaaat cagtaacact gctgtatacc aacaatgacc  11220
aagctgagaa tcaaatcaag aacctcttgt acaatagct gcaaataaaa taaaataaaa  11280
tacttcggaa tatacctaac caaggatgtg aaagatctct acaagaaaaa ctgaaaaact  11340
gattgctgaa agaaatcata gacaacacaa ataaatggaa acacatctaa agctcatggt  11400
aggtaaaatt aaaaatgacc atactgctaa gagcaatcta cagattcaat gcaattccca  11460
tcaaactacc atgattattc ttcacagaac tagaaaaaac aaccctaaaa ttcacaagaa  11520
accacagcag ggtgtggtgg ctcacgcctg taattccagc actttgggag gctaaggtag  11580
gcagatcact tgagcccagg agttcgaaac cagtctgggc aacatggcga aactctgtct  11640
ctacaaaata tacaaaaatc agctgggtgt ggtggctcac gtctgtaatc ccagcacttt  11700
gggaggctaa aatgggcaga tcacttgagc ccaggagttc gagaccagcc tagacaacat  11760
ggtgaaaccc tatctttaca aaacatacaa aaattagccg ggtgtgctgg cacatgctgt  11820
agtcccagct actcaggagg ctgaggtgca ggatcacttg agccttggag gcagagtttg  11880
```

```
ccatgagccg agattgtgcc actgcactcc aacctgggtg acagagtggg accctgtttc   11940
aaaaaaaaaa aaaaaaaaa aaaatcatat ggaacaaaag agcccaaata gccaaagcaa    12000
gataaagctg gaggcatcac attacccgac atcaaactat actacaagga tatagttacc   12060 accaaaaacag catggtactg gtataaaaat aggcaaacag accaatggaa cagaatagag   12120
aacccagaaa taaagccaaa tacttacagc aacagatct  tcaacaaagc aaacaaaaat    12180
acagagtggg gaacaaacac cctattcaac aagtggtgct gggataactg gcaagccaca   12240
tatagaagaa tgaagctgga tcctcatctc tcatcttata caaatatcaa ttcaagatgg    12300
atcaaagact taaatctacg atctgaaacc acaacaattc tagaagataa catcggaaaa    12360
actcttctag acattggctt aggcaaatag ttcatgacta cgaacccaaa agcaaatgca   12420
acaaaaacaa ggataaagag atggcaccta attaaactta aaagcttctg cacagcaaaa    12480 gaataatca gcagagtaaa cagacaaccc acagagtggg agaaaatatt tgcaaactat    12540
gcatctgaca aaggactaat atctggaatc tacaaggaac tcaaacaaat cagcaagata   12600 aaacaaata accccattaa aaagtggaca aagaacatga atagacaatt ctcaaaagaa     12660
gatatacaaa tgaccaacaa acatatgaaa aaatgctca acatcactaa ttatcaggga    12720
aatgcaaatc aaaaccacaa tgacatacca ccttactcct gcaagaatgg ccataattaa    12780
aaaataaaaa aaatagatat tagcatggag gtggtgaaaa gggaacactt ttacactgct    12840
ggtgggaatg taaactagta caaccaccgt ggaaaacagt atggggactc gttctggaga    12900
tggagtctca ctctgtcacc caggctgaa tgcagtggca cgatctcggc tcactgaac      12960 ctctgcctcc tgggttcaag tgattctcct gcctcagcct cctgagtagc tgggactata    13020
ggcatgcgcc accatggttg ctaattttt tgtattttta gtagagacag gtttcacca     13080 tgttggctgt gctggtcttg aactcctgac ctcaggtgat ctttccgcct cagcctccca    13140
aagtgctggg attacaggca tgagccactg cacctggcca gagattcctt aaagaactaa    13200
aagtagaact accatttgat ccagcaatcc cactactgtg tatctaccca gaggaaaaga    13260
agtcattatg tgaacaatac acttgtacac acgtttatag cagcaccatt tgcaactgca    13320
aaaatacgga accagtctaa atgcccatca accaatgagt ggataaagaa aatgtggtat    13380
atatacacca tggaatacta ctcagcctta aaaggaatg  aaataatggc attcacagca    13440
acctggatgg agttggagac cattattcta agtgaagtaa ctcaggaatg gaaaccaaa     13500 cattatatgt tctcacttat aagtaggagc taacctatga ggatgcaaag gtataacaat    13560
gatgtaatga acttgtggga ctcaggggga agggtgaaga gggtgagtga taaaagacta    13620
cacattgggt acagtgtaca ctgctcaggt gatgggtgca ctaaaatgtc aaaaaaagaa    13680 aaaagcaac  tcatgtaaat aggatattca ataagattat cagcatagtc agtgggatga    13740
catattcaaa agaaagaaag aggccaggtg cagtggctca cacctgtaat cccagcactt    13800
tgggaggctg aggtaggtgg attgcttgag ctcaggagtt tgggaccagc ctgggcaaca    13860
cagcaaaatc ccacctctac caagaaaaaa aataaaaata aaaatttgc  caggcatggt    13920 ggcgcacatc tgtggtccca gctactcagg aggctgaggt ggggaggccca cttgagcctg   13980 ggaggtggag gttgaagtaa gtcgagatta caccaatgta ctccagcctg ggtggcagag    14040
tcagactctg tctccaaaaa tctacaacat cgtggaagtt ggaaaacaca ctgttatttt    14100
aaatttcatg tatttttata aaaacagatg gagttggttg ggtgtggtgg cttacacctg    14160
taatcccaac actttgggag cctgagacgg gtggattgat tgagcctagg aatttgagac    14220
cagcctgggc aacatggaga aaaccccatc tctacaaaag atacaacaat tagttgggtg    14280
```

```
tggtggtgca cgcctgtaat cccagctact cgggaggcag aggcaggagg attgattgag    14340
ccagaaggtt gaggccacag tgaggggaaa aaaaaaaaag agagagagag agagagtctt    14400
gctatgttgc tcaggctggt ctcgaattcc tgacctcaag tgatcttccc acctcagctt    14460
cccaaagtgc tgggattaca ggtgtgagcc accacgcctg gctgaaaaaa cacactatta    14520
aacaaagtga gacaaatgaa atgaaaata caacatacca aaacttacag tatgcagtga    14580
aagctgatct caaatcaata atctaacatt acaccttaag gaactagaaa aagaactata    14640
cctaaagcta gcagaagaaa ataataaaga taatgggaca agataaatgg aaaataatag    14700
agataatcaa tgaaaccaaa agttgattct ttgaaaagat gaacaaaatt gacaaacttt    14760
tagctagact acataataaa aagagagaca agatccaaat aatgaaaatc aaaaatgaaa    14820
gcagggacat tacaaccaat gccacaaaaa taaaaaagat tataaataag agaacagcat    14880
gaacaactat atgacaataa atctgataac ctacataaaa tggaaacaac ttaccaagac    14940
tggctcataa agaaattaaa aatctggacg gatctctaat gagcaagaaa actgaatcaa    15000
taaaacaaac cctctcataa agaaaagcct aggatcatat agcttctctg atgtattcta    15060
ccaaacactt agagaattaa caccaatcct ccttccaaaa taggtaggaa cacttcctat    15120
ttcattctat gaggacagca ttaccctgac aaagctagac aaagatacta caagaaaact    15180
attagatcaa tatcctttgt aaacagtgac ccaaaaatcc tcaacaaaat gccagcaaac    15240
agaattccaa agtacattaa agaattata caccatgacc aagtgggatt tattccttga    15300
atgcaagaat ggtttaacat atgaaaacca atcactgtaa tacatcacat taatgaaata    15360
aaagaaaatt ttaaaatgac acgatcatct taatgcagaa aaagcatctg agaaaatgca    15420
acattctttc ttgataaaag cactcaacaa actaggaatg gaagaaaact atctcgacat    15480
agtaaagacc ataaataaaa agcccacagc taacatcgta cttaatggta aaagactaaa    15540
agcttttcct ttaatatcag gaacaagaga aggatgcctg cttccagcac taatatttaa    15600
cgtagtatta agagtcctag acagatcaat taggcaagga gaagaaataa aaggcaacca    15660
aattgggaaa aaagaagtaa aattatttct gttcacagat gacatgatct tatatatgga    15720
aaaccctaaa gattcagcga aaaactacta taaacaaagc aaaacattct gcctgcctgt    15780
ggtactagga agaagctgca agaggacttg ccctctggcc tgaaggcaat gtaaagagca    15840
gccaagtatt attgatattt cctcacccct cggctctcag taaaggatgg ttttttccact    15900 cttccaggat gcgatgtata gctctttgta cagcctgcaa cacacaactt aatcaccacc    15960
tctctggcca ctgccacagg tcttacagca gcagtcccca accttttcgg cacccaggac    16020
tggttttttt ttatggacca gtgggggagg ggaagacggt tcaggataa aactgttcca    16080 cctcagatca tcaggcatta gattctcata aggagcacac aacctagatc tctcatatgt    16140
gaagttcaca atagggtttg tgctcctatg agaattaat gttgctgctg actggtctgt    16200
ggcccagagg ttggggaccc ctgtcttaca ctgaagacca cagcaaaggg aggcttccta    16260
agaacagggc ctggctgggg aggctggagc cagaacaaag cccaggaacc tgaaaggtgt    16320
ttgcttagtg ccccaacctt ctgcttctca ttttcctccc atgcacactg aaccatgcaa    16380
aggatccttg aagttgaaag aaatctgaac ctttggtgtc cctgtggtgc actggcagct    16440
caaatcagag tatataaaga gctcctataa tatacataga gttcctacaa accattgaga    16500
aaaacaaatg gcaacaagta tttcaataga tagttcaaaa aagggaaaca caagcggctc    16560
ttaagcatgt gaaatgatgc tctcctaaca agccttcttg ggagggctgc tgagtcagca    16620
tggctggttg gaagtccacc ctccaaccac agctatattt tcccagttat ttgaaggatc    16680
```

```
agttccactt gaatgaccaa ttctcaccat aaatgttgat aaataaggcc aggcacggtg   16740
gctcacgcct gtaatcccag cactttggga ggctgaggtg ggccactgca ttccacactc   16800
cagcctgggt gacagagaga gacttcgtct caaataaaca cataaataaa ataaaagagt   16860
gttgataaat aaacccaaga agagcacaga aggctcatgc tcactcatct cctctgcccc   16920
aacatctaga tgaaaagaca gtaaacatac agaaaaaaag gaacaaattc agaatagtgt   16980
tgagatcagg agaggacctg gcagaagaca ctgggattgg ctatgtctac gtctgctcta   17040
aatcctcttc tcttacatat tctttgtaca gagggagaaa acctgctcat tttcccagcc   17100
tcccttgcag cagaggtggg tgcccaagtg atttaatggt tgcctgtgag gcacagacta   17160
gtttctggga gagcgtttct tttctgatga gagggtgaat gttgctgttg ccagatttct   17220
cctgttctct ctccttccct gatcttggac atggaagcca ccttgtaacc atgagggaag   17280
ggctaggaga ccttttacaga gggtggtaag cgggtggtac atactgacag gtgactctgg   17340
gaggggaacc acagattctc ttaggcagag cctcagtgaa gtgtcctgtt tggagttggt   17400
aagaataatc agcaggaagg aggggagaag aagaaatcat ggccatcaaa tggtagcctg   17460
tttgtggctc cttctgtcta taccaccacg gcccagagtg cttactttca ggctgagaaa   17520
gagaactact atggtgagct ttggcgggca tcttgggcta aggctgacag aatgaagctc   17580
cacaacctgc ccatgagggg gactcactgg gcaggtttct gcctgcctcc cactctagta   17640
gatggctcat cggcctgtcc tggaggtgag atgtgctaag ctgtgctaag cgaacagctg   17700
tactcttgaa aaggaaacct gaggccacta tcaatctggg ttcttcactt gtaactacaa   17760
cctgataacc aaggatttcc acatagggta aaatgtcctc aagtaaagac cgcaatgaac   17820
aaatcaaaga ttgaacccag aaaagccaga taattcaggg aacaaattat tttagaaaat   17880
gttagcatct gcagctgata tctgagaaga tatcacaagc ctttccttcc attaatagac   17940
catgcaattc agaacagcct tcctcactga caacaaagaa aaaaaggtgg acaaatagca   18000
gcaaacttct gagagctaat gtgttaatga taaatgactg agccatgctg tggggaagac   18060
agagatccaa agagggatgc ctttgctttg gaaatatttta tccatgagga agaagctagg   18120
cagaacttct accaaacttg agggcctggg ttggagcgg tggctcatgt ctataatccc   18180
agcacttcgg gaggctgagg tgggtagatc acctgaggtc aggagtttga ccagcctg   18240 gtcaacatgg tgaaacccg cctctactaa aaaataaaa attagctggg tgtagtggtg   18300
tgtgcctgta attccagcta cttgggaggc tgaggcagga gaattgcttg aacccaggag   18360
gcagaggtta cagtgagctg atattgtgcc actgtactcc agcccgggtg acagagcgag   18420
actccgtctc aaaataaaca aacaaaacaa acaacaact gagggccta gggggaccat   18480 agcaggggct agggccctgt taacttaccc ctcctttgtc ctggtattcc aaaggtacgc   18540
aacctagaat aagcgtcaac tggaagtaaa ctagcctcta taccagctgg cacccagctt   18600
tgagttccag gcagcctaga aaacctcagt ccctgaacgg gatcatggag tccctacagt   18660
gctactccca agaagttggc agaagcaaat agaagtgttc tgtagaagaa gataacatca   18720
tcttaggcct caaactattt ctacaataaa tttttcaaat actatgtcca ccagatagta   18780
aaaaataacc aggtacataa ggagataaga caatctgaat gagaaacagc agaaatattt   18840
ataggcaacg gaaatagatc tgcaaaggct cctgatacta gaattatcag acataaaact   18900
ttaaaataac taagattatt atgctaaagt agataaaagc ctaaattaaa aatctggtga   18960
agaattgaaa gcatgaaaaa tgatacagct gattttttttt tttttgagac agagtctcac   19020
cctgtcgcct gggctggtgt gcaatggcgc gatctcggct cactgcaacc tccgcctcct   19080
```

```
gggttcaagt gattctcctg cctcagcctc ccaagtagct gggattacag gtgcccgcca   19140
ccatgcctgg ctaatttttt gtattttag tagagatggg gtttcactaa gttggccagg    19200
ctggtctcaa actcctgacc tcatgatccg accccttgg cctcccaaag tgctggaatt    19260
acaggagtga gccaccacgc ttggcctttt tattttttat ttttgagat ggagtttcgc    19320
tcttgtcgcc caggctggag tacaatggcg tgatcttggc tctgcctcct aggttcaagc   19380
gattctcctg cctcagcctc ccgagtagct gggattacag gcacatgtca ccaagcccag   19440
ctaattttt tttttagtag agtcggggtt tcaccatgtt ggctgggttg gtctcaaact    19500
cctgacctca ggtgatccgc ccatcttggc ctcccaaaag gctgggatta taggcatgag   19560
ccaccacgcc tggcctgata cttgatttta cttttttta aattttcctt ttcttgagac   19620
ggagttttgc tctgtctccc aggatggagt gcagtggtgt gatcttggct cactgcagcc   19680
tcctcctccc ggttcaagcg attctcctgc ctcagcctcc ccagtagctg ggattacagg   19740
agtgtgccac cacccagc taattttat ttttagtaga cgggatttt cagcatgttg       19800
gccgggcagg tcttgaactc ctgacctcag gtgatccacc catctcggtt tcccaaagtg   19860
ctgggattac aggcatgagc cactgtgccc ggcgatacag ctgattttaa aaagagagga   19920
tattcatct ctcagatgat ggggaaaatg aaagggaaga aataatcaaa taggaaaacc    19980
gaagaaaatc actggtctct gtctctgttt ctacagaatg aatgagcttt ctgaatcttc   20040
aaaacaccaa gataggatcc caagtactt acaaagcaat ggaaattaga tttacaatag    20100
attttttag caataacact ggatgcaaag tctatggaac aatgccttca gggacttaag    20160
gggatttgac tttgaaccca ggattcaaag tacctagtca attaaggtac accacagtca   20220
aatttaagaa tggaataaaa aattaggcct ctgtacacac caaggcctgt gagggctgac   20280
cctctggcct tttgatgtca actcctttca cccttctgct accatcccgt tgggctgttc   20340
cttttaaact ccaagctctc ccacctcagg cctttgcact ttccctctgc ctggatgttc   20400
ttctcccaaa tatatgcatg gtttcatccc tcacctttc tggtctctgc ttatctgttt    20460
gtttggcctt tccttttct ttctttttt tttttgag acggagtctc gctctattgc       20520
ccagactgga gtgcagtggc gcgatcttgg ctcactgaaa gcttagcctg ccttttctta   20580
attgccagc atgaaatagc agcctgccag tattctatat ctccctgccc ttttaatttt   20640
tttcccatgg catccatcac cactcaagac actacagata cctcttctca tttgcttagt   20700
ctgtctctct ccataagaaa gcagatccat gaatgcaggg actcagtctg ccttattcac   20760
tgctgcctgc cccattcact gctgcctgcc ctatgcctat aacatgcctg ccaggggag    20820
gtgccccatc agtaattgct caatgattga atgaagctgt gagctaactc ttagatccat   20880
accttctccc atccccacc aacctgttac cttcttgatt taatgaatgg ttctggcatc    20940
cattttttgc agctgaacct ggaggtgcca catgttcatt atgctttc cttccacatc     21000
caaccaccca tcaaatctta ttggttctgc ctccaaaata catcttgaat ctgtctcctt   21060
tcccctctcc atggccacca cactgatcca agtcaccttc atctcttcct gggactgtta   21120
cagaagatac tccctgactg ttttctatt ttagttcatg acacctctgt gccaactctg    21180
ccaagaagaa aacgctagct cctgtaaagg tctctgtggt ccacctcctg cctcatttca   21240
caccaccctc tccttttgcc ttctatgtgc cagccacagt ggctccaaac agatcaagca   21300
ctccttgctt ttactctcac ttctactagg aaacactttc tccaggtctc tgtatggctg   21360
tctcactctt ctccttgggt ttcatccgca gtgtcctctc acaaggcctt cctggtcact   21420
ccttcccagg cactctcatc tgaagaccct gcttacttcc ttcttagtct gaatctagtc   21480
```

```
tgaaaatatt ttgttgacct aactgcctcc ctgtttatgt gtgcatccct accagaccga   21540
gctccacgaa ggcagggaag taccttccgt cttttgtctt cacaaccaag cccagagccc   21600
ctgcaggcag cctccctcag cacaggcacg tggcggagca ctccgtggct cctgatgtcc   21660
agggcccagc tcctgccagg ttgtggaggg ccgtcggcat gtcaccctct cactgatgct   21720
gggacctgag gctgggtgct ggagaagtct aacgggacac aatttcaaag cactttggct   21780
tatttaaaaa atctccacct tcatgtttca agaaagaatt cttgcagcaa caatgaaaga   21840
agcacctacc actactgttg actcccactg gcttccagtg gagtagtgaa ccggacccag   21900
taagtccttg catatttctc gaagtcggta ttcaaaccct aattacgaaa aaacaaacaa   21960
acaacaacaa caaaaaacaa aacagaaata ggaacacatt acaaaaagaa ataaaatcaa   22020
gaatatgttg ttgtgtctat caaatcagaa taaacacatg cgtattttat tgcctactat   22080
gggcaagacg ccctgcatg tctctcagcg gggggcactg agacccataa tcacagattt    22140
tcactcactt gctcactccc ctgacatctg tagtgcctcc tctgtgtgtt gggcccagag   22200
gaaaaacgag atatggccag ttctgtgata aactccttaa ggtgatggga agatatggga   22260
aattgtgggc tggtgagatc tgtctttgag aagatgcgct ggcagctggt gttgagggga   22320
ggtcaggagg gtgggacggc cagcccgcag gaggtaagag atggcaaagg catgactgaa   22380
gagggcaac tgagtggagg gggcataggt ccattaactc aagggttatg ggcaccaccc    22440
agtagggctg ctagaaaggc tggaggtaga gtgtcgggt ttgtcagcac ttggggcagc    22500
taaagcaata gggaatggat taaactgtcc aaagaaaagg gtggagtaag agagatgaaa   22560
ctggaatctg aggaattttg gaagtgaatg gggtccactt ttatactaga ttcctccttt   22620
tacagccaag gaaacaaggg acagaatgga gggtgggtaa ctggtgtatg gacactagaa   22680
caggcaggtg gaagatggag aaagagaagc aagcagcaga agtcatccca agatgggtgg   22740
cggggcggag aggaggtggg gacttgatgc agggcatcag agcaagtccc agtcaacacc   22800
caggatgaag caaaccagag tggagtaaga ggaggggctc ccagggaaga cgtgactaga   22860
gcaccacagg agaggtatga gagcctggga aggctgagta ttcagaaaag ctggggacca   22920
cacataatgg caaccacata gacctggtgg gaagagtaaa catcaaattc atcatcgtgg   22980
tctgcaggga gggaggggag gcttcaagtt gatcagtaat atttgctgtc gtttacaagt   23040
gtatgtacac acacacacac atacactcgt atttacacag ccagaggcac atgtgacatg   23100
ttagttctgg gaattacatc cgtgaaggtc tgattatgat tttctctgtc ttttctgtac   23160
ttaaattttt ttctaaatta taatcaaaat ggggagggtg atgacaaaaa taaagcaaaa   23220
agcccaggaa gctgcacaga gagagctctg ggagggcctg ccccatgccg caccctgaag   23280
gctgcactca agtgggagga aaagttggta aggctattgg agtcactgtg aggacagtgc   23340
agccacctct tccagcacac ctggctttct gcaagggagg cagcagagtg agagctctgg   23400
cgggaagtgc cagaaatgga gggcctcagt aagtgcagga catcaggcaa gcctgtccag   23460
ggcaggaagg gctgggagga ggaagagaac cactgctaca agatgccctc actgattagc   23520
agcactgcca agtgtggtg cagggcagga gccagaacat agaatctgct ccttcagacc    23580
atgtctttcc acccaggcat ctattcctcc gtcctgctgc ctgtcctgct gcttctctgc   23640
gggaacaccc tcagggtcac tctattcaga gcctcagagc ctataagggg ctgggtgcct   23700
gctgagctgc cttgactgca gctcaggctg ggaggtagag gctgctgggc catcacatct   23760
tttccctgat ttcacaggga ctaagtgagg cctgggagga tggaggggca gaaggagaag   23820
gctgctcagg gctgccagga gcctcacctt cgtttacgag gtaccgtgcg tagacgagga   23880
```

```
gccaatggcg gtactcgtgg ctggactgca gggtgagtgc tgctgccacc tggttctcta    23940
ggtaggccag ggtggtctct tgctgcacca catgaggcac ggagaagagc cgggcagcct    24000
gccttcccga gctgcagaga ccaggagagt ttccatgatg gggcagcagg cactacacag    24060
agtcaggaac tgcccccgtg tgcaacaggc aaggagctgg caggaggcag gcaccagggc    24120
tgccaaggcc tcccgtccac tagccagtct gttggcagat gccagatctg ttgtctgccc    24180
atccccacgc cccagccatg tgcctcctgg caccccttggg gtatctcacc cagcacctgc    24240
catctgggcc cctgaagtga cagggccagt gattgctgcc cccaaccccca agatattacc    24300 tgatgcagga ccactaccct cagcacccct agtccgtcct gcccagcctg cctgtgctga    24360
ccagcacctg gggcacaggg gaagggcagg tggagaccag gcctgggcag ggactgtgcg    24420
tgcactgacc caggcacttc cccagggcag gactaaggac agtggccatg gcattcaggt    24480
cacgtacttg gaggtgcggc cctggattat ggctaacggt cctgagcaca gcatggcgtc    24540
ctgggatggg aggctgctcc taaagtctgc acactgagcc agtgagtcct gcttgtcaga    24600
aaccaggttc ctggggaggc aaaggcagga gcagagctca ggaaaaccaa gagatctggt    24660
tggcctcttt gccaaccaga gaaggctggc aaagaggcca cagagaagca gcccctgccg    24720
acacagaaag ccagtagagg ctgagcgccc ctgcacttcc gcacaggcgc ctatcactga    24780
caggtttcat ggtaatgggt ctgatagatc actgttccaa aggaaaaatg agtgaagtga    24840
aggctgtgga tagggccctt gctgggaaca cttcagctcc atatgttggt tcctgatgac    24900
tgcaggcctc tgtgtgcagt gtgctctgat gctcagctca aacactgcca tggtctgccc    24960
acagggccac atggcctggg ccctgtagct agcgagcaat gccaggcctc tacctgcctg    25020
tatttctaca actatcccag actggcagtc cttccacctt ctctggaccc ttctcatcct    25080
tgtgaagaag actcttcaca cacttttaga acagctagat gtctttgtaa atgtgtccaa    25140
aatacaaaga tgcctacaga gagtcaatat ttctcttctt aaataatcag cttatttcca    25200
ttattacagc aatcatatat aatagacaac attttgcaat ttgggggagc aggcagtgga    25260 gattttttt ttcctttgag acagggtctt actctgctgc ccaggctgaa gtgcagtagt    25320
gtgattacag ctcactgcag cctcgacctc ctgggctcaa gggatctcct gcttcagctt    25380
cccaaggagc tgggactaca gatgtgtgcc actgcacctg gcttatttaa aattttttt    25440 ttttggtaga gacagggtct cactatgttg cccaagctgg tctcaaactc atgggatcaa    25500
gcaatcctct cagcctccca cagcgctggg attacaggtg tgagccatcg cacccagcag    25560
attttttttt tccaaattca agaaagaagt ctcagtgtga atgtagactt ctgcatggca    25620
gttcttaaca gaaaaggggc taggaggtag caagctttgg ttcttaagga ccaaaggtat    25680
agacagaaga aaagaacttg gagtggctgg aacacaacgt acataattca cgtgtctggg    25740
ttaagagctc tgatgtataa attattttgc aagtacaaaa aagggctcca aattcctgag    25800
tggacagagg aaaagtacag accatcatgc ctgggtaagt ggataagcat ccttactaat    25860
tcactgagga agtctgaagt gcttactaag ctcacagaaa ttgactagtc ctgttaaggc    25920
tcctgtaaag cccactaacc tatgctcatg gtggctaagg gggccacagc aaaaaccata    25980
aaaattttgg ggcttttttca aaaagtgcct cctgaaaata atgcaggagg acagtgctcc    26040
tgcacacagg ctctgagggc agaggccata ggctgcagtg tcctgctggg acaggggagc    26100
atgcacagat agtcaatgca gcctgcactc cagggcctga ctctcaggaa aagcagggct    26160
aggcagccct gtaggccacg acccttttgct ctgctgtcta gagcagacag acactcttcc    26220
agggaatagg actgggggtc agcttgctta ccatgtggaa agtgacggat taaagcagta    26280
```

-continued

```
cgccttccca tcggacaggt tcattactgg gattccatgc tgcgtcagca agatctgtga    26340
taccgtcata tcacttcctg aggacagcat gggaatgagt tctgggtgtg ctctgatcag    26400
caagtgtttt caaacatatc aaaggagaaa tctgtactct aggctcccac agtcccagca    26460
gcaaatgcat caacactgcc ttggcaaata gggagggcaa gccattctcc ttgccacaca    26520
ccaggctttt gtcacctctt ggggacccat tcaaacatgc ccccaaaaag tgtgtgtctc    26580
ctgcagcgta accacacctc ctgcctcact gagagccctg ggctgaggcc agagcctggc    26640
tctctgagcg gggcccttct gcagcatcag acatgaactt gggcccccaa aagagtaggg    26700
acagcctgtt gcctgcatta cctgccagga tggagtgtag agactcttct ttcaccacaa    26760
ccacctgtct gtgaacatcc ctaggaggga dacagggaac agtttactca ccaacccagg    26820
taaacacatc agagtgtgcc ttggctgctc agacaccctg gccctactgc atgcgaccct    26880
aaccctggcc tctcctagtg agaggggctc tgggctacga gtggcttctg ctctccatgt    26940
gccactacac tccctctgca ttaaggctgc agcacaaagc ccaggcaaca gagccatggg    27000
gaaccctcag cgcccacacc actttggggg aagccaggcc acagcagcca catcaggaac    27060
atggccacat tctgccagct aagactccat ttctgatgaa tcttgcatag gaccctggca    27120
gtgcaactgg tcgcatgggc tgctccagta aggaaataat cgagcaggca agctgcctcc    27180 atccccttg cacactaccc ctcagccctc agcctaccca gggcacccaa cacaagcaat    27240
atcactaact gctcagggcc tcttctgggg cctgatggcc agccttgtcc actgccttcc    27300
ctgcccctgc agtgaggtgg ggcctacaca gccctgtcct gccctggctg aagcccaccc    27360
caccctgtgc ctgcctctca ccagacagag agtgtggctg cagcggtgag cgccatgacg    27420
taggagcctg tgcaatgcaa agtagagatc ggggatggca ggaggatggg agagaggaga    27480
cggcgaccac aggtggagaa cactgacagc atccttttt cacaggcgac acacaccacg    27540
tcactgagaa ggcagagtgg gggcaggtgt catgggggct gagtgctgca gccaagacag    27600
tagccctgga agtgtgggcc ttccctctgc ctgggcccaa caagggcctc ccctgagcag    27660
gtacagccag aagggaaggt ggattgggtc agggtagggc tggtggggct gttggagcct    27720
ccctgagatc ttggatgaaa gaggcttctg tcctatttcc acaggctgcc tgcgctttcc    27780
tgagctcatg ctgatgctga ccaaggggtg tgggggcttt ggagagccaa tgcctctgat    27840
gatcacccag gaaacatgcc ttgctcatca gataaggcca catagtaccc acaggacagt    27900
ctcctggctg caactagtca gaccagtcct gagaaggtct ctaacaaggc aggctaagag    27960
aagtatggga atgacagcat gcacctctgt gtccaggggg ctgtctggct ggcgtgggag    28020
atgtgtgtcg ctcccaaaca aggagtgcgt tacagaacag tctggacact gtccagcttc    28080
tcccgagtga ccaccaggcc cctgggtggg ccctgcacga gcaggctgct gccttcccag    28140
acagagcccc ctaaggcaca gccacaggcc cagggtgagg ctggagctca gacgcaggca    28200
ggggtagcag atgtacagcc agtacagtga gatcctggcc acagtaggcc acccagagcc    28260
ctgctttgtg tcacttctat cctggtgagc cagtcactcc agcaggctca aggaggtcag    28320
ttaaggaagg agctctgcca actgccttcc taatgagcca ctattgctac tggctccaaa    28380
aagggagagg caagtgagat gcttttgttt acaaatgttt acttggagag tatgaatcag    28440
agaacactct aagcagcacg ggcaacaagg agctctctgc agtgctgtga ctgaattctt    28500
attttttctg agacagagtc tcggtctgtc gcccaggctg gagtgtagtg gcgtgatctc    28560
ggctcactgc aacctccgcc tcccagttc aagcgattct cctaccttag cctcccgagt    28620
agctgggatt acaggcacat gctaccacgc ctggctaatt tttgtatttt tggtagagat    28680
```

```
ggggtttcaa tatgttggcc aggctggtac tgtgactgaa ttctatctgc ccatctctgg   28740
tggtcagagc ctggctcaag ccagcccact gcaaagaaag ccatcatttt tgggctgtaa   28800
cactggggaa caggtctgca ggctgggcct gaactgggca ggactaagca ggaggagagg   28860
tcccacgtgg tccagcaggc ttgccccaca gctgccatgt cactgtggga gaggctgtgc   28920
cgacacccct tagccctcag ctgggcaagc cacctgcctt gaggggaggg acagagagtg   28980
ggagcctgtg gaagcatctg atacacaggt gcctgggact gggaatttaa atggctcatc   29040
tggaggggga atttgaggga ggaacagaac aaacagtggg gtccctagg cctaaaaaca    29100 caaaactcac tcagggccca cgagaattgt ggtctaagac ctaaggccat gtgctttgac   29160
acaagtaaaa gcatttacat gggacctcat ggcagatgat taagggtgta attatgatga   29220
ctgtatctgg tcctgactgg gatgctacat cagacaggaa cctgaggaga acattggtt    29280 cccctccac attgaacaca ggtagggaca gggctcacgt acagttctag aacccaggg     29340 gaagatactg ggtgactaat cactgaatca aggtccccct cacagtgcag aatctggcat   29400
gggctgggat ggggacttca gggacagtca gaaatccatc ctgaccaact tggatggaaa   29460
tctgggatcc aaaaaaggaa ccagcccagg tcaaggtgag ccaggcacac ctcagtgtgg   29520
aattcgagac tttggggatc tggctggaca agggaatcag gccatcaggt tcaaagcttg   29580
gcctgggtaa ccctcaaggg ctcagttccc ccatctgtaa cacggggata ctgatgctga   29640
ccttgctggg tgctgcaggg actgagatga caagcacata tgcttggcct ggagtgaagc   29700
ctggtgtgag tctctgtggg agctggtgct cccagggtca tgcacctccc ctagacaggc   29760
ccaggcccag aatgatggca tgtgtgcctg tgtcacctgg gccggctaag gacctgccca   29820
cccttaccag ctgcccgcag cagtgaggat ccggctggtg agtaccgtct cccactcctt   29880
cccttcccgg ttgcacttca ggcggctcag cttcacgccc ccaccactg tcacttcatt    29940 ctccacctca atgtacatgg aaggatcgga gctgacctgg atgaagtaaa cacacgggtc   30000
tgctcagaca agggccgcag cccaggtgac atgctccaag gctctgtagc ctggggcccc   30060
aaggcagcag caggatacag aggcagactg gctggccaag agaggagagg gagggcaggt   30120
agggcaaagg ggctgagcgg gaggcccaga gggccagaca tgtggccccc aaggcaggga   30180
gaatgctggg agctggtttc taccctgtca tttgtgtagt tgaacagcca gagaagagaa   30240
gcagtgccag ggttaaagac cccaaagtct cccaaccctg ccacttcatc tcacaaggga   30300
gtaacgtgcc caaaagcaca ctgcaaagga ccgagctggg agtgagactt gggtttctag   30360
cctcctactt gaagaatctt caaagatggc agtgtttggc aagattagag accatgtcag   30420
tgcttggagg gaatgtttag aaaaccccca aggggctctc ccagttcctg tggtggtgag   30480
acttggtctg ctcaactgag actaaactgg caggggtgtt tatggcacag catgtatgaa   30540
aagcacctaa ttcagtgtct ggcaccaaat gggctcagcc acacgcgtgt gtggggagct   30600
gaccaacaga ttttccctgt ggtaaaatag gcagaaccac caaacagtct gtgcttgtgt   30660
ggccactcaa gtgggtgagc tgggccgagg gctgactgcc cccttcacag acccagaaat   30720
gacagtccca agcagtgctt ggagggcaag atgcctaggg gaagggctgg aggagtttgg   30780
gagagttctg tgctgagaag cagggcaccc aggagggaac ctaagtcaga acacctctga   30840
gtgcaagagc acgtctgaac gctgctgacc actggagggc ccctgcctcc gttcacacca   30900
gcaataagaa caaaccctat gggttcctac cctttggctt cctgcttca ttcctctgca    30960 ctgtggccca gaaggaccta tggtaggaag ggctgacgcc tgctctctgg tgccctgtga   31020
ggaccaacct gggctcagag cagtgtgtag ccagtgggaa gtgacccgca agcagggtcc   31080
```

```
aagaaggctg ctcgaggaca cgcacctgag ctgaggtaca agggtatgca gagaggcagc  31140
agtgtgtgtg acggcaccat ggcaggagag gcctagatac tatgctgggc caagtgacca  31200
ggagggctct gggtataaag gattatttac tccagaattg tgttttggat aaccacatgc  31260
ttacaagctt ccattccaag agctcaaaca actctgatga ttgactgtgc cagacactga  31320
gaagacaaag ctagcaggat ggttgggaga tagattatga ccacacattc ccacagacac  31380
caagcctgag gctgcccagg gctgtgtgtg gaggtggagg tggcttccag ccaggacacc  31440
tgagaggagt cctgaagagc accagaacat gtggtggtaa tggcagcccc agcagctgga  31500
atcccaaggg caaagccaga cagaggctat gggtgagtga gagtggaggc tggcaatttc  31560
gctaagagtt ggtgggtacc ccgatctgct atgacttctc ccagaaggtg atggagagcc  31620
actggaaacc aatctccaag gaagtgacaa gataggattt gtatgcagta ggggacagag  31680
aatgtctggg tgtgcctgag ggagaactgg cagggtccta gaacttacct ggagggtgaa  31740
tgctctctgg gggcttggaa ttggcagctt cagtgcaagt gctggtgcag acagacacat  31800
ggcctccttc tctgcggtta gggcagctgg agactggaag agccagaaac gttcctgagc  31860
cttgctctaa cactacgggg tagcatttgg taaaggcagg tcacccagaa gtgaggctga  31920
gcctgcgacc agagcatttc caccctggga gggaggaagc agaggggaat gctacaagga  31980
tcctaacctc atggacaagc cagttgatgc cagggaacct gctcaagggc cctgggtgag  32040
tcaagggcac atctgaggga gagcgtggcc tccatgctac attccagggg ctgcatgtct  32100
aagccagctg gttcccaagg tgacccaccc agctgaggct taccatgcac acagggcctt  32160
caagctctaa gtacagaaag gtgggctaaa gaaggcagga tgggcccact ggcctcacct  32220
ggacagacag agacacaggc atgagacgag agtccttccg aggccgccct ttcttcttct  32280
tctctactgt ctctacctca agctcaagtt ttcgcttgga cagtgaggaa gccttagcca  32340
aagggacttt ctcatcgctg tcactgctgc tctccaggag gtctcgggc ctcagctctt  32400 tcacaaggtt ctgctctttt aacctgcaca aaaacattac atcacacttc ccttcagaaa  32460
ccattcatgc aagaaagagt gaagtgaaat atttaaagtg cttaaacaaa cctcttgcca  32520
acctagaatt ctgtgtccag tgaaattatg cctcaaaagt aaaggagaaa taatgacttt  32580
gtcagacaaa aataaacaaa gagacaccgg aatctgttgc cagaagacct gccttgcaag  32640
aaatgttaaa agtcttttcag agagaagata atgatgcag gccagaaact cacatctgca  32700
tgaagaaagg aagagtgatg ttagagaaaa aaaacaatga acataaaata gaatctttg  32760 tatttcatat tcccaactga tctgagagac aactttctgt tcaaacaaat aacagccacc  32820
atgtcttgaa ttactatagt ttatgaatga gtgaaataag tggtaccaat gtcataggggc  32880 atggaaggaa agagtgggga actctttcta ctacccatga agtggtataa tattatttga  32940
aagtagagtt aggttatataa tgtttattgt aaactctaga gcaatcacta aaaaaaattt  33000
tttaaagcat aattaataat gctgagagga gagaaaattt atttttattt tattatcatt  33060 tttttttgg agatggattt tcactcttct cgcccagcct ggaatgcaat ggtgtgatct  33120
tggctcactg caacatccac ctactgggt caagtgattc tcctgcctca gtctcccaag  33180
tagctgggat tacaggtgtg tgccaccacg cctggttaat ttttgtatta ttagtagaga  33240
cagggtttca tcatgttggc caggccagtc ttgaactcct gacctcaggt gacctacccg  33300
cctcagcctc ccaaagtgtt gggattatgg tcgtgagcca ccatgcctgg ctgagaaaac  33360
tgaatcatat aaaatactca gctaaaacca gagaaggcag aaaaagaaga taaaagaag  33420 tgaagattaa aaaaaagaa taaggccggg cacggtggct cacgcctgta atcccagcac  33480
```

```
tttgggaggc tgaggtgggt gaatcacctg aggtcaggag attgagaccg tcctggccaa    33540
cacggtgaaa ccctgtctct actaaaatac aaaaaattag ccgggtgtgg tggcgtgtgc    33600
ctgtagtccc agctactcgg caggctgagg cagggcaatt gcttgaaccc aggaggcaga    33660
ggttgcaggg agtcaagatc gtgccactgc actccagcct ggtgacaaag tgagattccg    33720
tctcaaaaaa aaaacaaaa aaaacaaaaa aagaaatgg gtttatgttt ttaaaaattt      33780
aattttaact acaaaagaca aagacagatt aatagtaggt ggacacagtg gctcatgcct    33840
gtagtcccag ctacttggta ggctgaggca ggaggactgc tcgagcccag aggcttgaga    33900
gcagcctggg caaaataatg agaccccatc tctaagaaca aaaataagt aaataaataa     33960 atacaagaaa aggggtgatt ctaactatat gacaacctgg aacaggcaaa accatggaga    34020
caataaaaag atcagtggtt tccaggggtt ggggaaagga aggtaactat atgaagcaca    34080 gaattttaa ggcattgaaa ctattctggc tgggtgtggt ggctcttttcc tgtaattcct     34140 acactttggg aggccaaggt gggcagatca cttgaggtca ggagtttgag actggcctgg    34200
ccaacatggt gagaccccat ctctactaaa aatacaaaaa ttagccacgt gtggtggcat    34260
acacatgtaa tcccagctac tgggaggct gaggtaggag aattgcttga acctgggagg     34320
cggaggttgc agtgagccga gatgcgactg tgccaccgca ctccagcctg gcaatagag     34380 cgagactctg tctcgaaaaa acccaaaaaa ctattctgta agatatataa tgatgaatat    34440
atgtcattat acattggtta aacccgtaaa acgtacaaca tcaagagtag acccaaatgt    34500
aaactttggg tgacggtgtg ccccactctg gtggggatg ctgaaagtgg gggatgctat     34560
gggtatgttg gggaggcggg catgtgggaa ctctttgtat ttcctgttca atttagctgt    34620
gaacctaaac tgctctaaca aataaagtct attaaaaaaa aaaagcgagg actggagaaa    34680
gacatgccat gataacacta atcaaaaaaa ggtggtgtag ttacgtaagc aaagcaggca    34740
tcagagacag taaagttatc aaggataaag agggacatta cacagtgata aagatgaagg    34800
agtcaattct tcaagaagac agaacaattc tgaataagta cacaggcata ccttgtgtta    34860
ttgtgcttta cttcactgtg cttcgcagag actatgtttt ttttacaagt tgaaggtttg    34920
tggcaaccct gcatcaagca agtctattgg cgccatttcc ccaacagcag gtgctcattt    34980
cgtgtctctg tgtcacattt tgataattct cacaatattt caaacatttt cattcttatt    35040
gtatctgttt tggtgatctg ccattagtga tctttcatgt tagtattata actgttttgg    35100
ggcactgtga accacaccca tgtaagatgc tgaacttaat caataaatgg cgtttatgtt    35160
ctgactgctc caccaactgg ttgttctcct gtctcccttc ctctccccag gcctccctat    35220
tatctgagac aaaacaatat tgaaattagg ccaatcgata accctataat ggcctctaag    35280
taagtgttaa accaaaagct aaaaatgatt aagcttaaag aggaaggcac attgaaagct    35340
gagacaggcc aaaagctata cctttttgcac cagttagcca aggtgtgaat gcaatggaaa    35400
agctcttaaa ggaagttaaa agtgctactc cagtgaacac atgttttgaaa agaaagcaaa   35460 acagccttat tgctaatatg gagaaagttt tagtgctctg gatagaagat caaaccagcc    35520
acaacactcc cttaatccac agcctaatcc aaagcaaggc tctaactatt ttcatttcta    35580
tgaaggctga gagaggtgag gaagctggag aagaaagtct gaagctagca gaggttggct    35640
catgaagttt aaggaaagaa gctgcctcta aacataaaa cggcaaggtg aagcagcaag     35700
tgctaatgta gaagttgcag caaggtatta gaacatctag ctaagatcat ggatgaaggt    35760
ggtaacacta acaacagat tgtcagtgta ggtaaaacag ccttctatca gaagaagatg     35820
tcatctagga cttccctagc tagagaaggg aagtcaatgc ctggcttcaa agtttcagaa    35880
```

-continued

```
gacaggctgg ttatcttatt gaagtgaatg cagctggtga ttttaggtgg aagtcaatac    35940
tcattaacta ttccaaaaat cctagggccc ttaagaatta ttctaaatct ataaatgcaa    36000
caagaaagcc tagatgacag cacatctgtt tagagcatgg tttactgaat atttgaagcc    36060
caatgttgac acctactgct tggaaaaaaa gattcctttc aaaagattgc tgctgactgg    36120
caatgcactt ggtcaaccaa gagctctgac agagatgaat gttgttttca taccaactaa    36180
cacaacacac attctgcagc ccatgaacaa ggagcatttt catctttcaa gtttcattat    36240
ttaagaggta cattttttgcc tgtggtccca gctacctgga ggctgaggca ggaggactgt    36300
ttaagtccag aagttctgag ttatagtgcg ctatgccaat tgggtgtcca cactaagttt    36360
ggcatcagta tagtgacctt ctgagagcaa gagaccacac caggttgcct aaggagaggt    36420
gaactgccca gtttggaaac agagcaggta aaaactcttg tgttgataag tagtggtact    36480
gtgcctgtga ataacactgc actccagcct gggcaacata gcaagacact atctcttaaa    36540
taaattaaaa ataataatta aaaaatttg tgggccaggt gtggtggttc ccgcctgtaa    36600
tcccagcact ttgggaggct gaggcaggca gatcacaagg tcaggagacc gagaccatcc    36660
tggataacac ggtaaaaccc cgtctctact aaaaatacaa aaaattagcc aggtgtggtg    36720
gggggcgcct gtagtcccag ctacttggga ggctgaggca ggagaatggc gtgaacccgg    36780
gaggtggagc ttgcagtgag ccgagaccgc accactgcac tccagcctgg gcgacagagc    36840
gagactccgt ctcaaaaaaa caaaaaaaca ttttgtaagc tatatcagat tcctctggca    36900
gatctgggca aagtaatctg gaaagtattc accattctag atgtcattaa gaacatcagt    36960
gattcatggg atgtcaaaat atcaacctta acaagagttt ggaagaagcg gattccaacc    37020
ctcatgaatg actttgaggg gttcaagact tcagtggaaa aagtcattac acatgtggtg    37080
gaaacagtaa gagaactaga agtaaagcct gaagatggga ctaaattgct gcaatctcat    37140
aaaaaacttg aacaaatgag gaggtgctag ttagggaaga gcaaagaaag tagtttctta    37200
agatggaatc tcctggtgaa gatgctgtgc atattgttga aataataagg gatttatttta    37260 tttttatttt gagacagatt tcattctgt tgcccaggct ggagtacagt ggcacaatct    37320
cagctcgctg caacctccgc ctcctgggct caagggattc tcatacctca gcctccccga    37380
gtagctagga ctacaggcat gcaccgtgac aaccggctaa ttttttgtat ttttaataga    37440
gatgggtttt caccatgttg gccaagctgg tcttgagctc ctgacctcag atgaaccacc    37500
cacctcggcc tcccaaagtg ttgggattac aggtgtgagc cactgcacct ggcctttatt    37560
ggcatacatt gaaatatcat gccatcgaaa tccttttgt aaggttggta ctaatgcctc    37620
ctttcatttc tgattgtatt tatttatata ctaatcatac tttaatacaa ctgtatgtcg    37680
ggcttttttc aaataacatt ccatctgaac tatttttcca tagtacagtc atcctttggt    37740
atctgcatgg ggattgattc caggacccc aggagatatc aaaatccaag gatgctcaag    37800
tcccgtatat aaaatgattt agtatttgca tataatgtag gcacagcttc caatgtacca    37860
tttttttttt ttttttgaga cggagtctca ctctgttgct caggctggaa tgcagtggtg    37920
tgatcttgga tcactgcaac ctctgcctcc caggttcaag tgactctcct gcctcagcct    37980
cccaagtagc tgagattaca ggcacgcacc accacgcccc gctaattttt gtattttac    38040 tagagacgaa gttttgccat gttggccagg gtggtctcga attcctgacc tcaggtgatc    38100
tgcctgcctt ggcttcccaa agtgctgaga ttacaggtat gagccactga gctgagcccg    38160
gccagcctcc tatatacttt aaataatctc tagatcacgt atacatagta caatgcctaa    38220
aaataacttc atttgcatgg attcaaagta gtacttggca tgtagcaaat tcagtttttg    38280
```

```
cttttttggaa ctctgtggaa tttcttttcc caaatatttt tgatccatag ttggctgaat    38340
ccatagatgt ggaacccatg gatacagagg ggcgcctgta ctttggtcct tataaacatt    38400
aaagagaggc acaacataat gaatagctta cttcctcaac acctctcttt tgaagaagtt    38460
ggtaaatgtt tctcataatg ctgtgttaaa catctctaaa tatgacagac tccctggatc    38520
acaggtgcta tcactgatct tatttcctca aggagttcac catgagtgaa ctcctgtcta    38580
gtatccaaga gccctcatcc ctgcctgcct tcccactgct aaccagcctc tggcctgtta    38640
gcccctcctc tgggcactgt cttcagctgt tttccctgct agtcacctgg gtcaaagaaa    38700
tgtgggcaga tacacacacc agcgtgtaga atcctggatt cttttcattt gtatccatgt    38760
gaaaaactgg gaagacaaga ggcccatgac gctgctctgt gaaactgaag tgtctgttcc    38820
cctttcttct aatgtcctac aacagggcaa agcatccatc tgtgggtgta gcttaatatt    38880
ctggaagtcc tgagtcagtg ctcctcaaaa tcctttaaaa attttttttt ttttaaatgt    38940
cagacatttg cctcttcaaa gagcttgttt tactatgttg taaaaatcag atcatgtaca    39000
ttttcatatt aaattttttg ttaaataagc ttttggaaca gtcaaaaatg ctttctctca    39060
gatgttctga atatggaaat ggaatattag cttgttctaa tttttttctaa catgaatttt    39120
cctggttcag actgatctga aagggtttca tgtattaaaa tgagagaatc ctattgtgaa    39180
acatggaaaa aaagtcagac ttttatgtaa ctatcgtttt gtaaaataca gcgagaatgt    39240
cacagcaacg tccaactatc atctaagttt ctaaggcggg cggtggcttc ctgagctcac    39300
cacagcactg gccatgaca tacacttgct tggcactgcc gagctccagc tgctccaccc    39360
tctctggttg ggacccctga gagcccttag gagtctcccc acctcctgcc tctgccagat    39420
gccccattca gggactctgg ggccagtggc ccactgggaa ctgcacctcc ccagcctgca    39480
tgtgggcttg tatcagttgt tacaatatcc ctggagcac caggtaaatc gatctacagc    39540
agttgcccaa tggtctaga catctgtgaa gcaagagcac agctggccag ggctgccccc    39600
cttacaaatg ggctccatcc taggttctgt ctgctcaggc ctacttgccc tgtagtcact    39660
tacctcaggt ccctacgtgc ttctgcctga cacctggcct taggagaggg tggagcagaa    39720
gacccacagt ttcacccagg gctgctaccc tgtacctggg atgctagcat ttggctccca    39780
atccacctga ggctcttggc taggaagtgc cagtcaggtt gcaggggtct cactgcccaa    39840
ccactgtgac gcacaatgaa ggaacaacag caggagctga catgtgctgc tcaccgtgag    39900
gcaaggacca agatacggct ttacaggcct aaggttaagg gatacctcct atgaggagag    39960
ttttcctggg aggtccattc tgcctgagag gagatggact cagaaagacc atgtgtctca    40020
agattatccc tcctccctct ctgaggaagt gggggacctg gcctaacctt gcaaggtgta    40080
ttactttgcg caccacccct aaccactgca tgacactgtg cctcaaagaa aatctccact    40140
gaaggccagg tgcggtggct cacacctgta atcccaacac tgggaggccg aggtgggcgc    40200
atcacttgag gtcaggagtt caagaccagc ctggccaaca tggtgaaacc ccatctgtac    40260
taaaaataca aaaattagcc gggcgtcatg gcatacacct gtaatcccag ctactaggga    40320
ggctgaggca gaattgcttg agcctgggag acagaggttg cagtaagcca agactgcgcc    40380
actgcactcc agcctgggcg acacagcgag actctgtctc aaaaaacaaa caaacaaaca    40440
aagaaaatct ccactgatgg gtgtttctct gtttcgtttt gttttgttt tttgagacaa    40500
gtcttgttca ggctggagtg caatggtaca atctcggctc actgcaatct ctgcctcctg    40560
ggttcaagcg attctcctgc ctcagcctct cgccactaca cttggctaat ttttgtattt    40620
ttatagtaga gacggggttt caccatgttg gccaggctgg tctccaactc ctaacctcag    40680
```

```
gtgatctgcc cacctcggcc tcccaaatta caggcatgag ccaccacgcc tggcctgttt    40740
tgtttttatt cttgttttga gacagggtct cactctgttg cccaggctgc agtggagtga    40800
tttctgctta ctgcaacctc tgcttcctgc gtttaaggaa ttctgctgcc tcagcctcct    40860
gagtagctgg gactacaggc acgcaccacc atgcccagct aattttttgta ttttcagcag    40920 agatggggtt tcaccatgat gaccaagctg gtctcaaact cccggactca agtgatccac    40980
ctgcctcggc ctcccagaat gctaggattg actacaggca tgagccactg caccaggcct    41040
ccagtgatgg gtgttttaaa gggctcctcc tggttttcat tgagaatcaa tacaagaaaa    41100
cagccacatc aagaaagtat ctgcattttc tgtaaggcct tgttaaaga tactgggact     41160 tgttttattt cattttcctc atataaggat ccaacccaac ctgagaattc agcaccaggc    41220
tcctagaagc tcactatact cattctggct ggaaagcagg aagctcagcc ccaagtgaat    41280
gctcactcac tgccactttc aagtgagaaa ctgaggatga caaatgtgat ggtggcccct    41340
tattatacag atcttgctac agctgtattt atggctggac ggtcttgtga gaccctgtgg    41400
acatagctgc tgaggaacca acccttgtgg caccaggacc caggatatac agtcaagatt    41460
ctgtctccag aagccaatct aagggctatc ctcctggctt tcattcagg gtatgcacta     41520 catgagagat aagggccaca gaaagccaca aagcaaacat gagtgtcttc ctcaataagc    41580
aggactgtct gtggcacact gtagtttctc tcaggtgggg aattcattt atttattttg     41640 ttcagaactt gctccatttc aaaatctgag gtttcttcac cttctggtaa gcctcttaac    41700
tccctcttga caactacccc gcagcacatc ctcctggggg gactcctctc tattgccctg    41760
tcttcagctc cacctcctca cctctgtgcc actctggcca attttgtaga ctgaatgttc    41820
ttttcagctg gttctgatct gctctctgaa atgcttgttg acttttaaac tgcaatgatt    41880 attattttc ttttctaaaa gtatttttt tggttcattt ccaaatctgg ttttttttg       41940 atagtgtatt attctttaa tttttattga gatatatata tcataaactt cgccacttta    42000
aagtatagaa tcattagctt ttagcatatt cataaggtta agcaaccatc atcactatct    42060
aatgccagaa cattttcata attccaaaaa caaactctgt acccattggt actcactcct    42120
tatcctccct ccctcagacc ctggcaacca ctgttactct actttcttta tggattttcc    42180
attctggaca tttcctatca atggaatcat acaacctatg atcctttgtg actggcttct    42240
ttctcttagc ataatgtctt taaggtttat cgttattgta gcacatgtaa gcattccatt    42300
cctctttatt gttgaataat attctattgt atgggtaaac catattttgt ttattcatca    42360
cctgatggac ttttgggcta tttccacttt ttggttatta tgtacagatg tgaacattca    42420
tgtatgagtt attgcatgga tatatgtttt caattctcct gggtatgtat ctaggtgtgg    42480
gaactgctag gtcagatgat aactctatat tttaccattt gaggaacttc cagactgttt    42540
tccaaaggtg ctaaaagact ttacattcct accagcatgt atatgagggt tcccttagaa    42600 gctaatttt gttacagaa tagagtatta atctttcctc acattttgtt ttagctttca     42660
tgtccttcaa gacttaagca tactttatag tgccatctga caattctatg atcacaggtt    42720
tataggacca acacttatta tctgactatc tgatctttta attacagacc tccaaatggg    42780
tatgaagtat ttcattgaag ttttgctttg tatttccctg atggctaatg atgttgattg    42840 aattttatg tacctgtgct ttgtatatat tctctgcagt ttctcttcag atcttttgct     42900 cattttaag ctgtgttatt cgtctttta ttgttgaatt gtaaagtta tttatataat       42960 ttaaattctg gactttaatt agatgggatt tgcaaatatt ttctcccatt ctgtaggttg    43020
tctttcaatt ctgatagtgc tttggaagca aaaaagcttt taattttttt ttttttttt    43080
```

```
tgagatggag ttttgctctt tgcccaggc tggagtgaag tggcgtgatc tctgctcact    43140
gcaacctctg tcccccgagt ttaagtgatt ctcttgtctc agcctactga gtagctggga    43200
ttataggcgc ctgccaccat gcctggctca ttttttgtatt tttagtagag atggggtttc   43260
gccatgttgg ccaggctggt cttgaactcc tgacctcagg tgatccaccc acctcagcct   43320
cccaaagtgc taggattaca ggcgtgagcc accgtgcctg gccaagcttt taatttttaa   43380
catggttttg taaagatgag gtcttgccat gttgctcagg ctggtctgaa ttactgggcc   43440
ttctgtctcg ggcttccaaa gtgctaagat tataagcatg agccattgtg tccagccaaa   43500
agttttaaat tttgatgaag tccaatttat cgattccttc ctttagttgt ttgtgcatta   43560
ggtgtcatat ctaagaaaca gttgcctaat ccaaggtcac atagatttct atctatattt   43620
tcttctaaga gttttatagt ttttgctctt acatttagtt ctttgttccc ttttgagtta   43680
attttttgtt atagaataca gtattaatct ttcctcattt tgttttagct tttgttccaa   43740
ttttgtttta gctttcatgt cttttcaaaat ttgttccaat tttgttttag ctttcatgtc   43800
tttcaagact taagcatatt ttatagtgcc atctgacaat tctatgatca caggtttata   43860
gaaacctaag tctcccagta agtatgtctc ctgacatttg tgcatgacag gctctttctt   43920
cttgtgactg tggattttat gatcatctaa acagtgcttt atcagtggta atgctgtaca   43980
ccctggccca aggaatgtca ctgcatggtg gatacgcatc tctgccaagt gcctctgaac   44040
gtcaattaga ccaggatttc gtttgtgttc atttctcggc ttggcgattt ctatacaaca   44100
caagtagtat taaactggcc ctgaatccac atgagggcag acctgtggtt acacagtctc   44160
aagggaagac tgttatccca acccaaaaac aggctgagac attccaactt ctctgctagt   44220
tcttgtgctg tcagttgggt tttcccaggt ctgcctcagt cctttttttaa gcagcttgac   44280
tttatgctgg tgacttaatt ccaactccta catggcttag accccaggcc ttgtctcaag   44340
tcgatgtggt cattaaaact caaggtcctc agtcaagacc cctagccttg cacccatggt   44400
gcagttctgc tcactgctct ggctttttg ttcactctta gattttagac tctgggtact   44460
gctctttcct gtgaactagt tattcatttt agggacgagg gttgcattta atccagcatt   44520
tcaaagtatt tagaagcatg gagaccgcgc gcggtggctc acgcctgtaa tcccagcact   44580
ttaggaggct gaggcgggtg gatcacctga ggtcaggagt ttgagaccag cgtggccaac   44640
atggtgaaac cccatctcta ctaaaattac caaaaattag ccaggtgttg tggcaggcgc   44700
cagtaatccc agctacttgg gaggctgaag caggggaatc aatcaaacct gggaggcgga   44760
ggttgcagtg agcagagtgg ctaggacaat agacataagc cacaacacct ggataatttt   44820
tctggtagag atacgggtct cactatgttg cccaggctgg tctcaaactc ctggcctcaa   44880
gcgatcctcc tgtcttggcc tcccaaagca tttgggatta caggcatgag ctatcgcatg   44940
tggcctgcat tgagttaatt atgaaacaag catgattaga ttacagagca gactacaaga   45000
ttccacacca agtttataga tacagcatca aacttgcaga aagggtcctc ccatgctagc   45060
ttccaggaac tgttttccaa ggagaataaa tcctgtccag acatgcagtt ctggacaggg   45120
cttttcataa gcaaagcccc agaggtagca tgctgtggct ttagctccaa atcaccatct   45180
actgcaagga caggtcacat acaaatgctc ctttcattgg gcacctgctg gctgtgtggc   45240
tactgcaagt ttctgaccag tgtccttgta cttggctgat ggtggcacag gctagggtgt   45300
gtctgcccag ggctgctgag ccctataaac ctcgcagtgg ggtgcaactc ttaagggaca   45360
gctcttaagc ccccaaagtc cagcccacat ctgcctctcc tctcctaggc tctgactcac   45420
tgggatgtga acttagctcc ttgtcaagct aggcttggag ggaggggccc tctcaggagg   45480
```

```
cagagaactt cagtgccaat ggcagaggct gcagacattc gctctggcca cctcaggagg   45540
atgcactact gcaaaactcc aagaaataaa gaactacaac ctgcgtgatg tcacagctgt   45600
gtttgagggg agacccagag aatggataag cagcatagtg tccacaagag ctcagaagcc   45660
aatctgactt gacaaagacc tcacttacat cattttttatt gcagctctct acctctggtc   45720
agtttctgag tggaaggccg tcacttccat gatgtatcaa tatcagagtc ttccacctct   45780
ccaactaatc tcatgctctc ttccgtgcaa actctgggct ccatccaaac accattattc   45840
tcagttcagc ctctgcactg accaatcctt gtgcctttga ccttgtggtt cttttgccgc   45900
gtcctccccc atgactcctt ccagccacct tcccacttca aggaaccacc tctttctcct   45960
ggtggctcac taagggctct gcagtcttgc tcccatgtat tgagtggcta gagtcttttc   46020
cccaacagga aggcaggttg cttggtggga acactgccac tgtgctgttg acccatgcct   46080
gcaccctgcc tggtccttca gggtcctgca gctaccacct acctttccac agctgtcgga   46140
gtcatgctgg tcagggcagg agcacctggt gtggctttgg accgctctgt gaaccgggag   46200
tcaaacgctt tcatgggttc gatcttggac ggggtcgtta acacagaagg tgacaatgca   46260
gcaggagtag aggtagcatt catactgggg tgaagaagag gggaggcatg tcaagcgcaa   46320
tcctgaaagg atctggaggt ctagtatttg cattatttgg agcctactaa aaaaggcaca   46380
aatatcaaac ttccataaac acaaaaaatg tcaagataca atctactact cccatttctt   46440
taaaattttc atgtgtcaaa attatggaca cctagaaggt tgtgagcaaa tgcattcaca   46500 tttcccccctt tgcactgttc tgagagcttt tgcgggtaga atgaggccta gaacatggtt   46560
cttacaaccc ttttctctag tcacactgcc ctatctccac aacttaaata cagcacctct   46620
accccaaacc actccagcca ctcacctttc ccactttgac aatgagtctc atgagataag   46680
cctgcacctg gggtcctgaa gccatggtct gcttttaccc ttagtcaggc atcctccatc   46740
ctgagcggcc cctcccatat ctccctgtga cagtgtcaca ttcttagcat tatgctccaa   46800
gtgctcatca cacaactttc atcttctatt ccacagagaa aggagaggcc aggcagaagc   46860
ctgcctggtc catccttcat gtccaagccc acaccacacg ctttgggacc atggccactg   46920
gacctcctcc taagcacacc caggctaaca ccttccactc ctatctgccc agacaccaca   46980
ccacatgcct ggtagtcacc ctggacagcc ccattcttct cctccatgat ctgtggccac   47040
tagaatgggc catccccaca gagttctcag atctggcatg gtctgtcctt cccaggctcc   47100
cttcgtcctg gcatgctttg cttcctcact ggtcttgctg ctcagtcttc tcttcctacc   47160
ctctcagggt ccccccaggg cagtgaccta atgtttgggc atgccttcac agccatggtg   47220
ctagcaccca gaagtaggag gctgaagtaa cataagactc cattccacca atggagaatt   47280
gctctgacgt tatcagctgt atcccagaag caggggctg cagtaacaca agactccatt   47340
ccaccaatgg agaatcgctc tgacggtatc agctgtatgt gccagggagt ggcctatttg   47400
gggcaccacc gcctaacaga gtcactttcc taaaatggag atctcaaagc cttctacgtc   47460
tccactctgg ggaaaagccc agactacctg atccagcaca gacaccttgg ccttctccct   47520
cttcttggcc ttcctcaggg gactgggggg ctgctgcccc taatcccag gcctcatccc   47580 ctggtaggcc tgtatgagtc ctgtggaggg taccctctga ggcacctccc tgatccctga   47640
gataccagcc cctcttttgga tggctagcca tttctatcca ggggacctga ggggccacct   47700
gcaaccctgt ggctacctct cccccaccag cctacacact ccctgaggat gaggacccac   47760
ccattaagcc cctgcgatgc ctggggccta gcagggtgta taacccagag caggtgctga   47820
gcaaacgttc actcctggct ttcatttgtg cttgcctggt tctttctgat ttctaatttg   47880
```

```
gtttccaagt aacaatgggt gaggacacag gctctgtgag tgaatataat tctgagagta   47940
taaggggagt ctgtgccctc ccacaggaga accctgccta agatgaatgc tgtgtgatgt   48000
gctcagcaga gtgaagtgga agctgaggcc ccagaaatgt gaagcacctc cagtgtagag   48060
ctgccaggtg gggctgaccc tgcagcacgt agcatttcac tggtagttcc cacccttagc   48120
agcctgaccc tcggtcagcc ttgatacact ctgtgaaatc ctcaacagtc ctgtgcatca   48180
gagactcact gaacaagtcc tcccctctga gaagtcccca tttcaaatca cgcatttttt   48240
tctttctttt ttgattgaag gggccacaaa gtgcaaacag aataaaattc tctgtcctca   48300
aaactatgtg caaacctgaa ctttccccag ggacaggaac aagccttggc acccactaac   48360
ctgtctttat tgacagaatc gcctgcaggt ctggcactgg cagccaccac aggctctgtg   48420
caaggcttcg aggcgccgaa ggagttaggg gtactggagt ccagtggcag tagctgtgga   48480
ctgctatgag aagagagcat ggtgcccgcc agggagcccg agaggggat gctgttaaag     48540 aatgccgtgg agaagtccct gtcatcaagt aagaacaaaa gtcagccttg aaagtcaggt   48600
gccacatcca gtactttata cattcaaata acttttttct aggtccaaag gcagtatgtt   48660
ttcatgatag aaaatctgca aagttacaga aaagtaaaaa gaaaattaaa gccacttaat   48720
atactatatt taattgaatc taggatttac aggttctata tgtactacta agaaagaaaa   48780
caatgctact aattgtcaga tgccattgac tgtacaacac acccaaatct cagaggtgtt   48840
aaactgtgca aacacatgtc ttaggaggaa tgaaatgcag caatacagaa agggcctccc   48900
tttcatgaag ggccatgggg catgccacta gatgggtgtg ccataatata cctaacccag   48960
cctctactga gggaccacaa gactgtctcc agcttttcc agaacagatg ctgctgcacc     49020
aggaagcaag gtattgcagt gtcagaactg aggattctgg gacagccagg tctgactcct   49080
ctgccatttg ttagcttgtg acttgctcta actactcttg tgcctccagt catgtctgca   49140
aaatacaaag tgccaggact ctccccatgg ggttgctgtc aggactaaag cagttggtgt   49200
aggacactct tagaacacac attggctgct caaagaatta tgaaattcta ataattgtca   49260
ttacacctaa gattcacata atatatggga taaattctta gaagtggaat tgtagcagca   49320
aatgaaatgt tcactgatga tttggaataa atatttctaa agtgccctcc tcagaggttt   49380
aaattacaag ccatgtatga gagcgcctat ttctccacat aggtgcttag taacacttt     49440 atcaaatttc ttgacactta acaatctgac agaagaaaaa tggtatctta ttttgatatg   49500
agtgacgttg acattttttc ttttttcttt tttttttga cacagagtct ctcccgccgc      49560
ccaggctgga gtgcagtggc gcgatctcgc tcactgcaa gctccgcctc ccgggttcac     49620
gccattctcc tgcctcagcc tcccgagtat cccgccacca tgcccggcta atttttgta     49680 tttttagtag agacggggtt taaccgtgtt agccaggatg gtctcgatct cctgacctcg   49740
tgatccgccc gccttggctt cccaaagtgc tgggattaca ggtgtgagcc accgtgcccg   49800
gccggcagtt tttcaaagta gaaatacttg atttccggcc aggcgcagtg gctcatgcct   49860
gtaatcccag cactttggca ggccgaggcg ggtggatcac gaggtcaaga gttcgagacc   49920
agcctggcca acatggtgaa accccgtctc cactaaaaat acaaaaatta gccgggcatg   49980
gtggtaggcg cctgtaatcc cagctacttg ggaggctgag gcaggagaat ctcttgaacc   50040
agggaggcag aggctgcagt gagttgagat cacaccactg tactccagcc tgggcaacag   50100
agtgagactt cgcctcaatt aaaaaaaaaa aaaagaaat acttgatttc tttttttttt    50160
tttttgtgaa ctgcttgttc atatgctttg tctactgttt tgttattggt ctttattact   50220
gatttgtaaa aatcatttac atattaaaaa aattccttat atggtaggaa atattttacc   50280
```

```
tgggatgttg tgtttcaact atttatggcc ttttttttg agacgaagtc tcgctgtgtc    50340
gccaggctgg agtgcagtgg cgcaatctcg gctcactgca acctctgcct cctgggttca    50400
agtgactttc ctgcctcagc cttccaagta gctgggacta caggggcgtg ccaccacgcc    50460
cagctaattt ttatattttt tagtagagac ggggtttcac catgttggcc aggatggtct    50520
tgatctcttg accttgtatc catctgcctc agcctccgaa agtgctggga ttacaggtgt    50580
gagccaccac gcccagacag cctatctttt aaatgcacta aaattttaaa attttgtgt    50640 actctaaatt gtcatttaca gaaaacactt ttttgacctc tgagattata aaaatattc    50700 ttccagggaa tcttctaaaa ttttaaacaa aatatttta ataacaatt taaaagaaa    50760 caaactataa gctgtttaga atgtatgtaa tgataagtta tgaggctggg acccaacatt    50820
gtttctagga ggtgccatgt agtcctgtct tccatttacc gaattagcca atgttttatc    50880
actgatgtga aatgctacct ttaaaattcc cataaatatt cgggcctgtt tcctcatatt    50940
ctatcatatt ccactgcact atctactcat gtgtcagtat ctcactgttt tgagttatga    51000
cagcttttaa gtcttaattt ctggtggggc tagtcttccc tggctaatct tcttttttcag    51060 aaatatttcg gccattccta tttatttttc cagataactt tatttatttt atttatttat    51120
ttgatacaaa gtctcactct gtcacccagg ctggagagtg gcactatctt ggctcactgc    51180
aacctcccag gttcaagcaa ttctcctgcc tcagcctcca agtatctggg atacaggtag    51240
tagctacagt agctacaggt gggcaccacc actcccagct aatttttata tttttagtag    51300
ggacggggtt tcaccatgtt ggccaggctg gtctcaaact cgtgacctca ggtgatctgc    51360
ctgcctcggc ctcccaaagt gctgagatta cagttgtcag ccactgtgcc cagtcgattt    51420
ttccacataa ctttatagtt accttgtctg attcccaaaa ttcctacggt tatttgtact    51480
ggttaaattt ataggctaca agagagctga catctttatg atgccatcct agctaatcaa    51540
tggtatgaat ttctagttat ttctttgagt tttctttgaa gcctctcagt agggttttta    51600
attttttctt cattaagata tgcatctctg gttgcatcct agttattta tttgtgaata    51660 tgacttattt ctttatgtgc tctgagggta gttggtgcta cctgacttca tgttgattgt    51720
atcctgccat gtgactatct tctttcattg cctatggcag cttttccagt tgattctctt    51780
ataaaccata tcatccttaa ataattatcc tttccaattt gttctttcct ttgactaact    51840
acatgggcta ggacctatag aacaatgtta aattatagtt gcaagagtag gcatttgttt    51900 agttttgaa cttaatttga aataagataa tttatcaagt taaggaagca tccacctatt    51960
cccatttaac tgagttttaa aacaacgttg aattttacca aaacgcctat taagcatcga    52020
tgagagatca tataattttt tttcttttga tctactgata cgtagaatta aatagttacc    52080
taaaatttga acctccttac tttcccaaaa caaacctcac ttggtcatgg tatattagcc    52140
ttttaacaag cagtaaggtt ctgtttgtta ctattttact taggattttg cactgacatt    52200
cagaaatgag aatgatcttg aatttattat gtttatcct tgtaagattt tgatatatta    52260
tgttcatttc aaaataaaaa tttgcacatt tcttctccat gcactagaat atttaaaatg    52320
gtattaacag ttacctgagt tacctgttcc ttaaaagttc ctgaagtttc cctgtgaagc    52380
catcttagtc cggtggcttt ggtggggtta actctgtcct ctatttcttc cacaataatt    52440
tttcactttt agtaattta ttttcttcaa aaaccatcca ctttctgtgc aaatttattt    52500
gcacagagtt cagcaaagaa gtctctcatc tttttgattt gtctattatt tctcacttat    52560
acctactttg tatattttatg cttttctct tctttcttga ttagctaagc taataaggac    52620
ctatcctgtt gctacgtgtt agaacgtggg aatcaggagg gcaaaaagct tttaatacca    52680
```

-continued

```
aaaggatcag gtcctgatgc tagaaatatg catcctatgt cagaaagttg gccccagacc   52740
agttaggaag ccacctacac cttctcacca ggtaacgcct ggaaggatcc acagaacaaa   52800
gtgtcaccat caccaccacc acctccccat cccacaggcc cagtatgttc agagctcaac   52860
cacacactgg gtctcacttg gtctcaataa aaggtaggta ggggcattac cccctacagg   52920
gtcacaatag gaaaaagact tagtcaaaag aaaatgagtg ctctgtgggg agccagcaga   52980
cctggttctt gctctactcg tggggacctc agagcctgca catctaacat gaggagactg   53040
gatctgtaca ctgtacgagt gaaggtttct ttagacacca aggaagattt ggaatagctc   53100
gtggatggac aactgcaaaa cgcagaggcc taaagtgtgt ggcctccatg aagggcttac   53160
aaatgccctg agcagataga cggaatgaga ataaacccca gagtgaactg ccttgacagt   53220
gggggtctat ttctttcaca cagtgcttta tcattttcct ttcttttttt tttttttttt   53280
gaatcaacac acatcatttt gggaagatta accaattcaa aaacaatctt cactatatac   53340
actgggacaa cagcaagtgg tgaatgagtc tcttccccct tctctgtccc ccacagggaa   53400
atatgtttgg gagccctact ctctgcccag taattccact tctagaagtt atcctgagag   53460
aacaaccaca ggtgagctca aagactcatt tataatcacg agaaactgga cacaaacaca   53520
agtctacagt gagctggcta agcaaatcct aggatgggaa tctggataat cagatagcaa   53580
acacctcaga ggactagtta ttaaaatgga tgaatgggca tgaaacagta acgagtgggg   53640
aaaaaaaaga ctggaaatac agatataaaa acattaacag tgactgtatc tgattatgga   53700
taatgttttt ttcttctttg ggcttttact attttctaaa tttaaccatg tgtaaatata   53760
cctttcataa tcataaaaat aactttatga aagaaaaaaa agaaaaaaaa aatcagcctg   53820
actgactgct ttccttgtgc gtcctctggt gccctggcaa cagtgaagtg cagcagatgt   53880
gctggccgcc ttagcactcc caccccctcac atgattcagg tgtgcacaag ggctccagga   53940
ggagtatggg ctttgagact gcgggaagct gagcttcact tccttgcttc catgttctac   54000
cagtcaggtt gtgaaggacc cgtgaagatc ctcactgtga aagtgttaac cgctgaaaga   54060
agacaggaag atctcgccag ataagaccat gaaaggggaa tgaaccagta cccagtgtcc   54120
agctgtgcta tgcagagagg cgtgattctt ctccggccat ctgctgtccg agtctcaact   54180
tgtttcttca aaagattctg gcaaagcaga gttacataaa tgaatgcaaa agttttggcc   54240
aactatttcc aaatattaaa aaataaagtc tctttttttc ctggtgataa gaacactaag   54300
cataagatcc accctcttag caaagtttta agtatgcaat atcatattgt gaactgtagg   54360
cactatgctg taggggagat ttctaggact tattcatctt ctataactta aactttatac   54420
cctttggcta ataactccca ttttcctctg accccagtat tcaccattct attctctgtc   54480
tctgtgagtt tgactatttt agattcctca tataagaggt atcaggcagg ccaggcacgg   54540
tggctcacgc ctgtaatccc agcactttgg ggaggccgag gtggacagat cacaaggtca   54600
ggagatcgag accattctgg ccaacatggt gaaaccccgt ctctactaaa aatacaaaaa   54660
ttagctgggc gtggtggtgt gtaactgtaa tcccagctac tcaggaggct gaggctgagg   54720
caggagaatc gcctgaacca gggagtcgga ggttgcagtg agccaagatt cgcgcactgc   54780
actccagcct ggtgacagag cgagactcca tctcaaaaaa aaaaaaaaa aaaagagag   54840 atatcatgcg gtatttgtcc ttctgtgtct ggcttatcat taatttgtac acactaagta   54900
tgtataactt tttatatgtc aattgtactt caacacggta ggtttaaaaa taataaggct   54960
tctaaggaaa tgtattctaa attgccctcc tggtacaact aaataagaca cccaagcaaa   55020
gaacaagcag tgggtacatg ccacactggc cgcctcgcac aacagccatg ggaccaatga   55080
```

```
aagggctaaa ggactgagct ctgtacccgt gaaccacaca tctgtcacta agctagggat    55140
tttctttctt tctttttttt ttttgagaca gaatctcact ctgtctccca ggctggagtg    55200
cagtggcgca gtctcggcac actgcaatat ctgcttcccg ggtttaagca attctcctgc    55260
tcagcctccc atgtagctgg gattataggc atgcaccacc atacccggct atttttttt    55320 tttttaagta gagacaaggt ttcaccatgt tggccaggct ggtcggaact cctgacctca    55380
agtgatccgc ctgcctcagc ctcccaaagt gctgggatta cagggtgag ccactgcgcc     55440 tggcctgagg tagagatttt caaactgact ttcaaaatag aatccttcct tccacagaaa    55500
gcttgtaact aggggttttc tctcatactt tatatctgaa ttgcctggag gaggtttgtc    55560
agcctacaca ggctcctgga gatggtttat actccccagg caataacgtt ccctacccctt   55620 ttcccgcccc atttccaacc ccttcccatc aaacatggct tccagatgaa gaaggggag    55680 cccatagaag tctcctaagg gcagagcctg aaatccactg ttgttagcat ctaggatttt    55740
tagaaagacc agaaggataa aattcgtaag ttcttacaag agatgacctc ctctgggctc    55800
ctggggataa ggaggccttt gataaagagg atccaggccc cattactgca tcatgcagca    55860
gtgggcaagg ggccaacagg cccgaggctg gctaacccac agatcccgta ccactctaaa    55920
caaacccctt ccttaccacc actggtgtct gcccctcacc ctgtccctgg gcatatgtcc    55980
atgtctttag cgccaccagg cagggctctc accttcctga tatcttcaag actctccccg    56040
ttgacaacgc ctgcgactga ggtggctgag cccatctccc tggtcgcagc actcttctgg    56100
tccagctgct gctgctgctg ccttcgctgg tacttgagca tctcagggtt ctcaatgacg    56160
gctgtggaga gctgggcctc ggtcatgatg gctaggtctc tgccataggt ggactggtga    56220
atgcggctct ggggaagcaa ggagaggcat gacatgccag catgagtgcc agtgtggcca    56280
gtgctgccca ccagcaggca aactacagca gggctctcct ggctctgagt ggagaaggga    56340
cccaaggcca actccccatc gcctcccatc ctattctgcc tgtccctcat tcgacagctc    56400
tgttgatgtc tcatgcccac ccttgatttt tatggcctcc cttgtatctg tagctgggat    56460
gacagtaaat gagacagcca acaagacaac acctgcccca cagtctggtg gagaacaaat    56520
gacaatccac agtgcttcag tggaaaggaa gatactcaag gtgctaactt aaggctctta    56580
aatcactcct aggacccaaa tgatttttggg aatcagatcc tagaacaaaa gtctactttc   56640
acagctcatc tgcagccata agccctgtgg ttggaagtcc ccattggcct gcttagtgtc    56700
tctaagagta tgggaaggcc tggcacagca gggctgggga gcctccttta ctcccacccc    56760
tcctagtatg tcatcatact cccctccttc taggcccctca tagtcttgtg ccctaacaag    56820
ctagacagga gcctcatgag agcagagatg gtgtccccag cacactgtag tgactgctgt    56880
acatgaaagt gcatgaggaa cacacttcca tgggatgtgc aaatgtccaa tgtgggattc    56940
tgctcaagaa cagggactgt ggttaacagg acatctgctt tacagcagag catgggttga    57000
gaggcagcgt tccaagagag gtgccttggg acctgctcct gcagggcttg aatgtggcca    57060
ggaacctcct tttcttgcca tcttggctcc tgcccttctc tcctgagtct atcccctgga    57120
atctcgaagc agaattcagt gtttggccag ggtttcccta gtgttcctcc aacatggagt    57180
cccagcctga cttgggaaat ggtaagcaga tgggttatta ggctcccaga gtgactccaa    57240
gggagtgcat agtgatccca ggtacctgat gacagtgaca aggttggagg aggacctgag    57300
gcctctgaga tactcattcc ttcatggaaa aatgatgggg tggcaggccc cattctaagt    57360
gtagtcatta aggcagacct ctcccccaaa ggggttcaca ttttagtggg gaggtcacac    57420
tgtaggttaa gaggaagctt ccaccagcaa ataaggtcat gaggagagct gccagcctgc    57480
```

```
tctgggcttt cacagagctc ccttcagaca catacacaca acccaccaag tgggggcagg    57540
tttctaagcc tctggtaggt gaagcagggc ttttctcaaa gcctggcaga agggcagaga    57600
gaccccatca ccccagcaga gcacagaggg gaggcagcct ggcccagagg cagcaggcct    57660
tgttcactct tctgacctaa gggtcacata cagtctgggc aaagagccat gctattttct    57720
gaggcttagt ttccatatcc acgaaatgga tgagccttgc cttgaagggt tttgtgcaat    57780
ttaaatgaaa tcatatgtgc aaaacacatt cccagagcct ggcagacaat gcgttctaag    57840
aaatgaccaa tattactacc atgaaggtga aagtgacatg agcaggggcc cctgaggagt    57900
cacttcagct ctttcccagg gcaaaaacct cccagtggat ggcctattat cagctcaaaa    57960
agagatgcct aaaatagttc tactcttaac tccaggactt atttctgaaa tggggactcg    58020 tttttttaatt aatctatttt gtaaagaagg attacaagat ataaaagatg aatacccccat   58080 tacatgttaa gaaatgactt gtctgtgtat ctcacaagaa gagggtgtag tcaaaggggt    58140
ctctcagagc tattgtggca atggccacag agcacccagc agcacaagag ccgtcagcct    58200
accttctcct cctcgctcag gggatcgcca agctcatcct gggagaagtc gaggaatgcc    58260
acagagccgt ccatagagca taccaagatg cccagcccat tcagagtcct gaaagacatg    58320
gccatcagca gcctggtagc aagagcccca ggcagacaca tgtgccgcag tagctggcct    58380
gtgaggatgg tggcagtgt tctagggaga tgctggaaac tcctggttcc cttctgtggc    58440
ctggttccct tctttggcct gggcggggg gggaggggc gacaattgta tcccaaggg    58500 ccctggtgtt ctttagctct aagcaggtgt acaaaatatc tcctttacca tatgttctgt    58560
aagaattttc aattttactt atcttacttt tgaaactatt aaaataaaaa aaacttgaca    58620
aagtatacat ataaatcagg tcactgagaa gcagaaagtg tgcttctgac tttggttcat    58680
gcactgacgg agtaaagtgg aacatactag gatcacgtca ttctcctcgt cttagacaaa    58740
tcctgaaaag gcattttcca gtggcaaatt ctacacaggc aggacattct cgcagcagca    58800
ggtacaccgc tgccagttcc caaatcacgt gcaaacagca ctcttggtct gcgctactat    58860
gacacctggg gaggggccac tggccaccctg accctagtca cacccagaag gcctcatgtt    58920
ccaatgtgtg gcttctcctt tcttaaccta ttcctgtaag tagaatccac cttaccagga    58980
aatatccatg atggatttgt caaacagttc atggatgacc accagcggcc gtttcagaca    59040
tgtgagctgg aaggaaagac acagtcaagg ttaatgaaat tactgaaatc cccttctgta    59100
ttcagctcag ttaacataac caacctagaa gcctgggtca aagtggctgc tgatatttaa    59160
ggcatcttca actctattca aactgcagct gcagagatcc caaactgtgg gaaccaaagc    59220
ctgccaaaaa tgtgcatgct acctagagtg gaccctgcct ccagggcttg ctgtggtctg    59280
acaggggaaa tagctttata cacagataac tagcaacaga gaaggcagag tgggagtggg    59340
tttctgaagg gctatggtcg gaggagaggg acagcccag ggtggacctc tgagagggtc    59400
tatggagcag gagacacgat gccaaagcct agacagggga tgaggcaccc tgagagagaa    59460
cacaacacat cttccctggg cccaagggac tctggtacac atttatccaa ggctcattct    59520
acactatgtg taggtagtac agaaatacac acctgggccc ttaatctggg cctagttacc    59580
gactattaat actttgatga attattatct tctattttgt gcaaatattt atttattct    59640 tcaaagtaag aatttatttt attcttcata gttgtgtctg tttttttcatt taacacacaa    59700 taagtatgtc attaaatatc ctgtaaaagt ctcttctgga tgactgcata gcatgcactg    59760
tgcatattct ctatcgagtc actcaattgc tggcatacac tctgactcca cgttcccaca    59820
actatggtag gcctttccac ttgtgcacaa gtgcctggct accctgctgg ctggccctga    59880
```

```
actgcaggac aatgggcagg gaagaaacac acttcctcac gggatggtgg gctcccatag   59940
gtgctgctgc agcttctggg aggctgtggg gctgagcgtc ccagtgcagc ctgagactgc   60000
tatgtgggga aggagaagct gtgtctaccc tagtggtgga gaggggggctg aagtctgaac  60060 gatctggaac ccacattaag aatctcgcct ccaccttaat tccacttcta gaaaaagctg   60120
ccttgtccct cctctcataa atgtgcctac agacccctca gaaatctaca ggccgtgtga   60180
ctgcctaacc tgagcattct aagaaatatg ggcatcacag tcagtgatgt tttggttgca   60240
gcgccacaaa cagggcctct ggctgggagg aaacagggaa ggtcccctga acggcaatct   60300
gtggtactgt ggttcaggtt ccagaatggg tgttaagtga atacttggcc taaaaaaaaa   60360
aaaaaaaatc acaacgcaca cagtaatata tttctctata ccaaactaat aaatgcagcc   60420
agaggataac cttcaaaccc agaacttcca acttgctctg cttataggga cactttttta   60480
caaaatgaaa aaaaaaaaaa attaatgtgt gtgcactttg ctttatcaaa ctttaaatat   60540
attggcacct tgatgctcag caccaagact gctccctgca ctgcatgcgg aggtgtctct   60600
taccacacag tcaggtcaca gcacaccagc ccctggcagt gagaaactta acccttcagg   60660
agccctcact tagaaaccgc cacagttctt acccttgggt tctcactcgc caactaccat   60720
tgagtatatc tgctgagaac ctgctctgta gagggcactg agttaggaag gtgaggggaa   60780
caatgaaact gaagacacat cgggctgggt gtggtggctc acacctgtaa tcccagtact   60840
ttgggaggcc aaggcgggcg gatcacctga ggtcaggagt ttgtgaccag cctggacaac   60900
atggtgaaac cccatcttta ctaaaattac aaaaaaatta accgggtgtg gtggcctgta   60960
atcccagcta ttcaggaggc tgaggcagga gaatctcgct cgaacccagg aggcagaggt   61020
tgcagtgact caagaagcca agattgcacc actgcactcc agcctgctgg gcaatagagg   61080
gagactctgt ctcaaaaaaa aaaaaaaaaa aaaaaaaag aagctgaaga catcgcctca   61140
tctcagggga tccagcgagt gaggagtact aggctcacaa ccttacccat cacagcatca   61200 cccagggtg aaatggacta ataaaggcgt cagctttctg tgtgtcttt tctgtggaca   61260 taagcactta tctgtcttgg ttgtatgcct aggagtggaa gtgctctagg tcatatgctt   61320
agctgtggta gaaactgcca gacagttttc ccaagtgctc atgccagcgt aaacacctgt   61380
cagcaacacg tgtcagcaat gtatcagttc cagcttatca tgtccttgct gacacttggt   61440 actattttt tgttttttt tttaatttta gaactctact cataggtatg tactcataaa   61500
tgaaaacgta catccacata aagacttata caagaatgtt catatcagct ttagtcataa   61560
tatctcaaaa ctgaacaat cttaatgtcc atcaacagga gactgtataa acaaattgtg   61620
gtgtattcat acagtggaat gctacaccga aattataagg aataaaatac tgttaagtgc   61680
agcaacatac acgaatctca aaaacactgt gccaagcaaa agaaatgaag acacaaagaa   61740
gcaagtacca cacaattgca tttatatgaa gttcaagagc aggcaaaact catcagtgta   61800
acagaggcca ttagagtggt tgctttggtg tgagggagg tcttgactgg ggagggacaa   61860
agggacaaaa aggagtgctc taggcagtga tgacactggt gtgtaaacat gtatgacaac   61920
tcaccaaact gtacctttca ggtgaataca ctttatataa agattttct ttttcttttt   61980 tttttttttt tgagacggag tctcgctctg ttgcccaggc tggagtgcag tggcgcggtc   62040
tcagctcact gcaagctctg cctcccaggt tcacgccatt ctccgtctca gcctcccgag   62100
tagctgggac tacaggcgcc caccaccacg cccagctaat ttttttgtatt tttagtagag   62160 acggggtttc actgtgttag ccaggatggt ctcgaactcc tgaccttgtg atccgcccac   62220
ctcggcctcc taaagtgctg ggattacagg cgtgagccac cgcgcccagc catataaaga   62280
```

```
tttttctaat aggaagcaag cccaacatgc tgctcatggc attgaccact gagggtgctg    62340
cctgagtctg gacacaagag ctggtctagg tggggtcaa ggtggcctct cctggctggg    62400
cacagaccca gtcttcagca cttccttctg ggagagcagg agagcctgtg agcttccaag    62460
gaggggctga ccccaggtgc agaatagaaa tacactctta gcatcaccca aagcaggtct    62520 cttcctcca cttgctactt taccaaccta cacctcccgt cctgcaacaa agctcagga     62580 tagcaggctc acccagacag aaagcgagcg tccttgctg ccaacagcac agcagcagta    62640
cgggcagcta ggcttcgcag aactcccatt cttctgcttc tttttgaaga ttttgggtt    62700 gaatttctaa agccaaataa cagatgttaa aaataattaa tcaagcatca ggcatgtccc    62760
ctgtgcccaa gtcccagccc actgaaggga gtctcccaca gacattctct gagcccaggc    62820
actgagcatg catttcatct tcccgaccac ctatgaggca tctggctgat gatgaaagg     62880 aagcttaggg aggtcagaaa gtatgtgcgg aggcaccaaa tgagtaagct gggaaatgca    62940
gatttgaaac tagagctacc aaactctcca tttctggagc ttgccaagta aagggatgc    63000 gtagctactg aaactagcct tctcaattcc ctctggccag gcagggccag ccctaggacc    63060
tgcagaaaag ctgagcctgc aagggggctt cagaaacaaa gacctactca ctccctatct    63120
cctaagggag gccaagggga tgggcaggag gggtgtgaat ctctgaattc cttattgcct    63180
cactgcattt gttgttcagt cataaccgtc tagcagagat ctgctcagtc agagagtcat    63240
ttgtgatctc cctgggccag tgaccatggc aatatcacac aaaggtgctt ggttggctgc    63300
ttagtccagg gaactacccc gagagtaact tgtctttgtt tctgcaaagg atgaaagcac    63360
tcactgagct cccagacacc ctcctggatt taaaggggtg ggcgctctgg gaatccccaa    63420
cctaggacaa ctgagggcag aagaaggagg gttcctgaaa gcctggtgtc aggtagccta    63480
gagatgtttt aattccagag ggcaggcagg aatggccggg gtgcacagag actggagaag    63540
atggaactca gaggcgtgtc cctgggcttg ctgtctctaa caccaatgag gctgcagggc    63600
cttaggagct ctgtgagcca taggcaggcg tcgtgatctc ccagagctgc taataaagtg    63660
gttgtgagga ctgcatggga gaatcacgta gagcactaac catgaagcac tgatttccaa    63720
agactttagc aacaaagctc tggttcaaac aaaaccctac atgaactcca aaacaaaaaa    63780
atttaataag taatatttta ttcatataaa atttgtgttt taaggtacaa tatatgatac    63840
ttattatctt ttttattttt tatttttgag acggagtctc gctctgtcgc ccaggctgga    63900
gtacggtggc gcaatctcag ctcactgcaa cctccgcctc ccgggttcaa gtgattctct    63960
tgcctcggcc tcctgagtgg ctgggattac aggcgcatga caccatgccc agctaatttt    64020
tgtattttca gtagagacgg ggtttcatca tgttggtcag gctggtcttg acctcctgac    64080
ctcatgatcc gcccaccaca gcctcccaaa gtgctgggat tacaggcatg agccaccgtg    64140
tccggccgat acttattatc tatttaaaca cgggcaaaag tgagtctatt ttcatcaggg    64200
tcttggatga tccttcactt ttatcaacct tagtccacca atctgtttat tttatttggc    64260
tgcccagtgt tgagaaaatc ctggttctca cagattattc gcaactactt aacagcttgc    64320
cttgggctct gtcaggacac tatttaatta aagtcatgga gaagcataag acgagtggcc    64380
agacaactct catgcctaag gactgacagc agttcacgcc tctgagctct tcacctgccg    64440
cagcaagatc tggcagcagc tcccaactca gtgatccatg gcatggcctt gcacctgtgg    64500
ttgatgctgc caggtgtggg gacaagcaca gtgcttggtg ggtataccag aattgtacct    64560
gtattcactg gagccaggtg agggtggcac cgtgcttggg cacccaagc atacctgagt     64620 gtgtaaaagg ctgatgtgga gctacgatgt tcctaaccca agactgattt tggtgatgtt    64680
```

```
cacatgtaaa gtttgccaat aaatcaacca agtacatact ctattttgta aaattagctt    64740
ttaaatattt aagtataact attcaaaata aaccaagaat taatatttgc tgaatcttgg    64800
agcccatctc cctttagttc cctgggcact caccacgaca gtcacagctt tccggtgccc    64860
aacaaagtcc atgttggtct tccatccctc ccgttcgatg atctgggcag tggggcctga    64920
gttgttcatg gcatgggcag acaccaggta atgcccatca ggtgaccagc tgagccgcaa    64980
cacatgggtc gttcctccac actgaaagaa gcatctgcac ttgaaaggag ctcaaggcca    65040
cctttgtgac caaaactctg gcctcgagga taaagttaaa cttcaattta taaatgtgtg    65100 atggtgagc atgcacccca agcttctggc tacactgaca gcttctgtct caccagatgg     65160
cccaaccaaa aagggctctg tgaaatgaat ttggaaactg cagcatccta cactccccca    65220
gaggagctga acaaagaaat atagtacaga agtgtatgcc ctgaggagat ctgcaggaag    65280
gctacctgtt tgaaccatag cctctgcatg ggccaaatct ctctggccac tgacccaatt    65340
cttctgtgta gcacctgtta acccacagca tggcatctgc acagcatcct caagatatac    65400
tctggtggag aaaaagccct ttttaaccca ggagcctggc agaagcctgt gtctgtaatg    65460
tagctgatga ctgtgaggca ccacctactc tcttgagcct gttgcctcac ccaaggggtg    65520
gtgaggatac ccgcaaggga gaagaggttt gtaacatcct tataaactat aaaaggaaca    65580
gtagaaaggc actgctcccc cagtctggac tgggggctga ggcagagcat ccctccacat    65640
tatccctcct gcaaaaagag atgacatggg tccagagcca gctccttgaa gctcaaggtg    65700
ggcccagggc agctctaaag acttaagggt taagatcatg acctcacagc tctagagcag    65760
gacatgacaa accagagcct gagtatagtg aaatcaccca cctcagctct cagcctaggt    65820
gacagaacca cccctacct ggaaggatgg gcccacccag tagaggctga agagtactac      65880
cacctcctgc tggtactcaa gacactccta aagccgtccc taggagtcca cctcatggga    65940
ccccactgcc tggcagtcag agccctgagg aactccagaa ggagcaaaag ctccttaggg    66000
caagactaag taaggtaaaa accagtactc atatacctag cccaggagct ggtgttgtgc    66060
gggaagaact gaacatatga ctatcacttt acttttgcag ccatcctgac cagtgggcaa    66120
atgcgtgctc ttcctgcaaa ccttccctca tgtgtccctc gctctgtgaa gtctttcctg    66180
atgcactcac ctctcctggg ctgtttctgc actctggaca actccattat catgcaacta    66240
atgggaatgc ctgtctttcc tatggggctt taagcttcaa gaggagagac tccatctcaa    66300
tccactttta tttccctgtg cccagttatt gccttctata cagtagacac ttaataaatg    66360
tctaatgaac aatggtgatc ttgagctctc attccatttg aaatcagaac tcaaataacg    66420
gaagagagat taaaatacca gagaagctac tgcagtctga tctccaaaca tgtgcaaact    66480
gtactgctaa ctccagccag gaaaaaaggc ccctgaactg cagggtgcat atcaacaagc    66540
acagcacagt cgaggatggc acaagagtct cctccatcct ccccaacaag ctgctctgcg    66600
ggaggctcag agtaaactcc gcactataag aagcagtttt atccacgtct gtgggagtga    66660
gctgggtgac agaatgatgt ggagacatct ctaaggttca cttcaacttt aaacctataa    66720
atccgggcca ggcgcagtga ctcatgcttg taatcccagc actttgggaa gctgaagcgg    66780
gtagatcacc tgaggtcagg agttcgagac cagcctggcc aacatggcga aaccgcatct    66840
ctgttaaaaa tacaaaaatt agctaggtgt ggtggtgggc acctgtaatc ccagctactc    66900
aggaggctga ggcaggagaa tcgcttgaac ccaggaggcg gaggttgcag tgagctgaga    66960
tcgtgccact gcactctagc ctgggcaaca agagcgaaac tctgtcgcca aaacaaagca    67020 aaaacaaca aaactataaa tcccttttat ttcaaagttg gaaattaaac agcgtctcag      67080
```

```
aaatgaagga ttctgtatta tctgactctt agggccagag tcccacccca gagagccttg   67140
gtgaatccgc tcaggccccc ggactctgtg cattccccag gtggcctggc ccatggccag   67200
ctccctctct gtacacagaa gtcaggaaga ggctggggca gctgcggggg ctcagctccc   67260
tgagctgtcc ccacttacct catcaaaagg cttggtgatg ctggtctcca actgccagtc   67320
cagcgtcctc cacaccttta ggctgcggtc atcagcttga aagctatgt atttaccaac    67380
agggtcccat gtcaaccctt tgaccaagcc agaatgacct ctcagagtag ctagaatttc   67440
tgtgaagaaa aaggaatgt ggagaggtgt tgtctgaggg aaacatgacc tgcaatccat    67500
gggccatggg atggatatgc aagagagggg actcagcagt ctgccatggc cagccccac    67560
accagacaga agcagaaggg cctcctcatt tgatctccac caaggcaaaa gccaattgaa   67620
gaaatgacag catcaaggag gcaggcacca aggggctagt tctgatccag gtcttatctg   67680
tatctagcgg ccctgcctat ggctgccctt cctgggctgt gacaccagca cttctgacgt   67740
tagcctccct ggtagctccc tgataaggag gaggcctact agctcaaagg gcctgactgt   67800
ggctgagtct tttataagtt atggctgaag acaaaggtgt gtacgacggt accccatata   67860
gatctgtaat ccaaatgcta ctccggtctc taaagcttcc ctctccatag ccagactgag   67920
tgtttccaca catgctggtg gctttcaaag agttaaaatg acctggatcc ataaggaaag   67980
catacttcaa atacagagct gaaatatgag aagaatttta ctagttataa actgcagcac   68040
tgtgccaggt tatgccatct gttgtgactt taaacacaat gaataagaaa aatcaatctt   68100
ttgcaaaact gggtttgtgt tagcccgtat ctgctcaagg gtttcacaga ggagatggtg   68160
actgagctga gcccagagcc cagtggtggg ggtgcacaca gcaggtttag gagcatcagg   68220
gtccccaaca acagctgccc atccattacc ctcctgatct gtggcatgcc atgctagcac   68280
tcagttacca tttttcttaa gcatgaatct ctttttaaag cttaaacaaa tgtaactgac   68340
aaagaaaaac tgacaagaca cataaatcct aggccactgt gacacatctg ttgccaccaa   68400
gactaaggag acagcccaac ccctgctcca gaaactgaca ggcagtactg cttgctgtta   68460
accagtcaga ggaggcccca gacctgggaa ctttacagca ttccagatga cgacagtgtt   68520
atccacgctg catgaggcta gccaggcatc gtggggagac catgctacat ccatcacatc   68580
tgaaagaaga cagagggttc tggtgagatc tcttacctgg tgatgccctt gtctattagc   68640
ttggccagtg ccctgggac ctgggaccat cataaccact ctggtatttt ttaaccaacc    68700
tgaaaaaact ccccccagaa ttttttcaatt ggtcataaat ttaaagcatc taaccgaccc   68760
cagtgcctca ctccttttac agacgaagca actgagggcg tggttcagag cttgggcacc   68820
atatggcacc acacccatgc atgagagcct gctacttcgt gggtctgtgg cctggagcat   68880
gctcctcagc cctgctgact tgctttgcca atcataacag gccttcctc cgagagcctt    68940
ctgagcatga gacacagtgg gtaaagcaca tggcagaatg cctggcacag tcagaactcc   69000
agggctgctg acaactgaac acaagtcatc ttgaggccct cgtctggttc atggactggg   69060
tctcatctcc cagaccctga caggagtacc ccttcactat ggagcctcca aacagaatta   69120
ttcacattca cttctttgtg actccatttt atcatttgtt aagtgcagat taaaaaacaa   69180
aatctaggcc aggtgcaggg actcacgtct gtaatctcag cattttggga ggctgaggtg   69240
ggcagatcgc ttgagcccag aggtacaata ccagcctagg caacatggca aaaccctatc   69300
tctacaaaaa attggctggg cttggtagca catgcctgta tccccagcta cacaggaagt   69360
tgaggtggga ggatcacttg agcccaggga ggttaaggct gcagtgacca tgattgcacc   69420
actgcactcc aggctgggca acagagtaag accctgtctc aaaaaacaaa caaaaaaacc   69480
```

```
aatgaaacaa aaaaccccaa aacctatcct cataggggtca ctgtaaggat taaatgtgat    69540
aaactgctgc aacaccatgc caggcacaca ccaaggcatc gatgagggtc cgctgtgacg    69600
atggtgccaa ccttgcctat cctgccatca ggggtgaagg gcgcagtctt agttatttct    69660
ctaacctcag cgcctggtgc agtgctaggt atacagaaga atgattggtg agttgaagaa    69720
acaaacatag cagcaaggta atagctatca agtcctttct ttgtacaaga ggtttaagca    69780
aaatattcca aatatctatt gtatttttc cagttaaaaa aaaactatag taacagctta     69840
acaggttttt ttttttttt caaattgtct cacatgctgt ggttcacatt ttgtattcta     69900
aatgcctatg tgatcttcac agcttctttc ctttttgcc ctgcattcta tgtggttgag     69960
agtattcact actattaatt gacctaattt aacactgaag attaactgga ttctggtttt    70020
ttgggcccgt gtgtatttgt cactctccat actccagatt attactctga gacgcatacc    70080
ctagagtggg aatcctgggc agaatatctg agcatcctca taggtctgga ttctcataaa    70140
actgtagact gcttttccaa gatccctgtg gttttacatt tctacatgca gactgtttgc    70200
ttcaaaactc ccttattagc attgaggatg atgactttt ccccttccga cttatttatt     70260
caatacaatt ttatatttaa aattttaat tagattatta gtgaaagcgt tgtctctta      70320
tctaatgtgt ttttggactg atttgctgac ttattgtgac catttactgg gaagtgtttc    70380
gggcagtggg tctaacaaca taatgcagt gcctacaaaa atgaagaaaa caacaacttt     70440
ctctagtaac tgagagtcct ggaggggcac acatgcaaac gccaggacag caggggagtg    70500
cccacatcct agaacagaga atatgtggtt aggtgggagc ccagaaagga gaagggattt    70560
tcttagcaat ctccacagac acatataatg cagctattaa ctgcaaattt cacctctcta    70620
cttttttata ctgtagtagt tttatggagt aaagtctgtt attctccttt gtgatttctt    70680
ctattgcctt gttaaccttg aaaaatattc tctctgctag aggtctggta aatattcaat    70740
tctattttt ccttgtgtag ttatttagaa tgtttctctc tttagtatct ggtttggtgt     70800
gtgctgtatt tggtgaggat tgaaattaat ttctcctcac taactgctta acagttacta    70860
tgctccatgt gaggaagaat ccattttgat aagcgatgcc tcctttcaca acacaccaac    70920
ttcttaggta tactgtagcc tctttcagtg ttacgagttt accctcaaac ccatgatgtt    70980
tctatcactg gaactttgaa tgtttttcatc cgtaacattc ttatccttcc agatacgatc   71040
ctttagaatc actgctgagt aaatccacat acatgacata attttctcct aaactcccag    71100
tttggagttt ctgtcttcag actatatagc acctcctttt tatggtgcat ctacacacac    71160
aggagaccct cccctcactt gtagatttac atttctggcc actgttctca ccatcattct    71220
tggtgactcc aagaggatga ttcttctaac actccaggct cttggttcct taaattcctc    71280
cttcccttct gatgaccgtg gcttccacta ctttcacccc acggtcatgt ccagaggcct    71340
tccatgacaa atcactgcaa tctgtctcaa ttccaacctt cccacaggcc aaccatcagc    71400
cccgtgctcc tagctcaccc tcagctccaa cagcactttc acgccaccag gaactccgat    71460
ctactgatgc tgccgtcccc tcaccacttg ccaaccacct ggtccttacc tctctcctcc    71520
agctgagagc ccaccaccac tcccccttt cttctcctcc atcttcctac acgcctgaca    71580
aagctcagct cctctcctag tgttttttga gtactctcca atgacacctt tggcccaatg    71640
acaccacatg aatattgcac ttgcctaggc ccccagcacc ctccatgctg tcaagcccag    71700
cagtctatcc ttggtcttca cttttgcccct cagcaataag caatacgctg cctgttcccc    71760
tctccttcaa atactctctt cactgtccgt tttgttgttg ttgctgagac agggtctcgc    71820
tatgatgccc aggctgttga gctactggcc tcaagtgatc ctcatgcctc gcttcttttc    71880
```

```
actgtcttaa ctggcctctc cttctagctt cttttcctgg tttcagctct ccaatccta    71940
ggctcatcct tggactctgc tcatacccag aacctcatat ttccaagatt catatttcca    72000
aatgtctaca cagtatgtcc atttacactg gcaaacttaa catatccaaa accaaactct    72060
gaaaacactt cccttaacaa acatttctgt cccacctgca gacttcctgc ttcaggttac    72120
agccactgca tcctttccac tgtttggacc atagtccggg aagccatcct gactcctctg    72180
cttatctcac atcccatatt caatgcacca ggaaatccgc ctctgatcac ttctcaccac    72240
ttctgtgtta tgactccaaa ccaccattgt ctctcccttg tttttcggag cggctccttt    72300
actagtcttc ccagtgcagc cctgagaccc ccatggtaga atccacactg ctgccacagg    72360
tctcaactcc tctgcctaga tccctgcgga gacttcatat tcttgctcag agaagagcct    72420
ctgccacggt ctcaaaggca cactgcctcc cgcaccctcc tccccgccc cagctcccag    72480
gggttcactg ggcacagtaa gcacatgtcc atgctccaag gccttcgcac tggctgtccc    72540
ctcactgccg tccagtcttc cctcaaatgt catctcctca ctggcccca gcactcatct    72600
tccaactcct tacaggactc tgccttctag gctcatcttc aaatctccta tactactcac    72660
tcgtctgtct cttttacaag aacaaatctc cttgagagaa gaacagtgcc tggaacatgg    72720
caggcactca ataaatgttt ggtatgtgga caagtaaata ttaatttggg aaaaaatgta    72780
tttcatctag cctttcaatt taggaagcca ttttctatct ctcaatgtca ttttgtatct    72840
taaaacgttt gtgatttaag tcttacaaaa ctaattcatt tcttggtaag attacttatt    72900
cctggatatt tataactttt gatcccactc tgtataattc tctttttatc attagatatt    72960
ctaattggct attagtagca aaagaccaat aatttaaaat tgttctgtta tgaggccaat    73020
ataaagactc atttattag ttctaagtat ttttcagtgc tttatttgtt ccaagagctt    73080
tatcccccta tggttttcc taatatgaaa taatgtcacc ttcatttcct ttttgcctta    73140
ttttccagtt tctatttaac tgtgttgcag aaattccaga gcaacaaatt aaatgacagc    73200
acccatcatt gtcttttctt gatataaacc gcaaccaggc ttaactgtga actgtaatat    73260
ttgccactgg tttgaaaaag actaaggact ctaccatgtt aaggaaatag ctttaggaca    73320
ggtgtggtgg cttatgcctg taatcccagc actttggaag atgcaggtgg gaggatcgct    73380
tgagcccaag agttcaagac cagcctgggc aacatagtga aaccccatct ctacgaaaaa    73440
aaaaatcagc caggtatggt gatgtacatc tgtagtccta gctactcagg aggctgaggc    73500
aagaggatca cctgagccca ggagttcaag gctgcagtga gccgtaattg caccactgca    73560
ttttgcctgg gtgacatagt gagacacagt ctcaaaaaaa aaaaaaaaaa gaaaagaaa    73620
aagaaatatc ttcctatggg catttaaaa aaagcatttt taataggaac tgatgttgaa    73680
ttgtctaatg ttccttttaa aacacctaag atgactgtag cttttcccat ctaacttcct    73740
agtatgtaaa gttatattaa tagattccct tgtactacac ttacaagtca catttaatca    73800
taataaatta ctattttctg gccggtcatg gtgactcatg cctgtaatcc cagcacttcg    73860
ggaggccagg acaggcagat cacgaggtca ggagatcaag accatcctgg ctaacacagt    73920
gaaaccctgt ctctactaaa aatacaaaaa aaagtggcc gggtgtggtg gcacgtgcct    73980
gtagtcccag ctactcagga gtctgaggca ggagaatagc tggaacccgg gaggtggagg    74040
ttgcagtgag ctgagatcgt aacactgcag tccagcctgg gcaacagagc aggactctgt    74100
ctcaagtaaa taaataaata aatgagtaac tgctttcaag tgttattata tttactagta    74160
ttgtttctga ttttctatc tttattcata ttattctatg cttttgttac attatttttc    74220
ttaggttttc ttgtattttc cagatacaat aaccctggct tatatcttcc tttcaattat    74280
```

```
aaatattgct attgttctgt ataatttttc ttaaaagctc aaaacaatgc acctacaact    74340
aatttagaac caagaagcat ttctgaagac agcctttcat ttcttcattg gttactattc    74400
tgttcagttt ttcctaatcc tatggtatca attatgaaag ttcctatttt ctagaaaatt    74460 atttttagt attttgttct ttagcttaat agtacaaaca ttatattgta ctgtttgatg    74520
atttttttct gtctgggtta aatgttttc tagatcttta aactctaatt ttgtctaggt    74580
tttttcttcc caacccccaa ttaaatatac caagtatata tttctcacac tttgcttttc    74640
aaagatccgg ttctttctta ttcatttact tctgcttttc attgattttt cttcttgaat    74700
ggttctgcct gcacctgcta ccaggaccag tgagtaatga gtgtcaggtc cccagctgaa    74760
ggtggtcaac tctacttgtc tggtaaagga gccccactgg gcggtgggta ggaaagagaa    74820
tgcaaggctc tggttagggc cttgtaaaag tcctcacttg aggcctaccc cacacttggg    74880
caccctcata gacatgtgca ccaagttcca gaaaagtcca actagacttc actgttagta    74940
ctgtgacaca agtaagggcc aattacacaa tttaattatc aaacaataac acaacactaa    75000
ccgtttcagc tttcacaaat gtggactcaa tctatggccg ccaccaagat gggtttgttc    75060
tccttttaac agtctacagg gaatctgcta agcatacact aacaatggat tatagctgat    75120
gccacctccc acacctctca ctcctgccct gtcctcgccc agagctccag gctcaatttg    75180
aaggtttctt gacatttctt cccctacccc tcaagccagg ggcaactcca ttctgaactg    75240
gtatccgtcc ccataagcct gttgtcctta gggtctcagc agaggtgata cctctgacta    75300
tctaggcatc cagccaagaa tctatctcat acctctctgt gccctatcct aagtattccc    75360
aaatcaatct cctcttctct acctcaatta tcacaggcct agctcaggcc ctgacagtgt    75420
ccatctaaac gactggaaga acctccactt cactgagctg tcacaatgac ctctctgttg    75480
tgcttcaaag cttttagtgg ctccctatct cttccatgac aagggactcc ctcagtaaca    75540
gggagcacaa gctttccatg atccgactct ggcatacctg accagcctca ctttgtgctg    75600
ctccctgcct tgtctataaa gatccagcca tggtgaaatg cctccaaatc cccattcaca    75660
ccaagacttt ctcacttatg ctgtaccacc ctgcctggaa aacccttttgg tccattcctg    75720 gaccaaacgg actcagactc ctaagtcaag tctaaattgc actcaacctg gtatccttga    75780
cacctgagtg tacagtgcat gggcaacctt ccccctcagt ctaaattcat aaaatgtgct    75840
tctttccatg ccaagtttat ttaaaacact gcaaacatac tcaaggtcaa gttgagaaac    75900
ttttcaatgg gcatctgtga gctgattttct ggggaataaa caaagtgtgc ttacggactt    75960
agtgatccgc tgatgaaggt actgattctg ttcagcagga caaacagcag aacgtgggaa    76020
gttctacatt aaagatataa acatataccc catgagggca agagtgggga gactgaatgc    76080
agctggagac aggtagtgga cccggtgact gcacagatct taagggacag gcagggtgtg    76140
actgattgtg atgggtggg acagcccaga catagggctg ctttaaggac caaacagtcc    76200
cacaggggac gtggcggtgc tgctgatctg agccaggtgt caggggccca cccaccccaa    76260
caggcagtcc cactcaccgc ctgaatgatt ccggaggata gagacacacc gccactgctc    76320
cacattggca agcttaccac tggagccgaa cacggtgctg gggccgatgt acctgtgtga    76380
gaaaggggcc aaaaaggcac tcatggagtg ctctgggcac tgcatagaaa tgctccctgc    76440
agccagctta tcagggcaca cagaacaaag caaaaacaaa caagaactgg aaagcactgg    76500
gttgttgaat aaaagggggct ggttaggtga attatgatcc atgcacttga tgaaatacta    76560
cacagccatt acaaatcttg catgggaaaa cgttcacaat aagtgaaaga agcaggccac    76620
aggacatcac atacaatatg atatcactta tgtaaaggaa aaaaaccac atgacatgga    76680
```

-continued

```
tagcatctat gcatggaaaa tggattagaa ggacacacat cccaaaatgt caaaatatta   76740
actgtagctt tctttaggtg gtgtgatgag ggatatttt tcttttgtat ttttagtttt    76800
ctaaattgta tactaaatgt tacttatgtt ggctatttaa agaagcaaaa tcaacagtat   76860 tttatttta agcatctcac aatgaatcaa atggctttga catctgaggc agagaaacca    76920
cgcgatctat aggtactagc ccccaccaca ggagccagag gagcatcaat cacctggggc   76980
ctggtggagg cagtgctgac acaccgatga tcagagcctc tgataacacc ttttgctctt   77040
gtagagctca tcacaaatcc acagaaagag tgtgctgaga tagccaagta ggctgaagag   77100
acagcctctg cctctgctct tgaagccaca gccacagggc cactcttggt gagcaatggt   77160
gcagggtctg gtgccccaga ctgactggcc cagagacctg ggagcaatag ttttccaggt   77220
gatggttagc tccttttgag agtagagcag aggctgcccc aggtggggac caacagagaa   77280
taaagtaatg gcaaagaggc tggactctgg atccctgcc ccagatcctg ggcaagaacc    77340
agagcaccct gacttttaac catttttgtat attgggcttc catgtgaaat ttcacttgaa  77400
aaaacaaaag caacgaagcc ccacccacat cggcactaga agagatcaga ctttccttt    77460 caggtgagag cctgcagtcc tgtgaggggg cagctgacca ggtctcctga attcctggtc   77520
aggctccacc tgctcctgac ctacatgcac tttccactac ttatgaggtc agggctatgg   77580
gaacttcagt gacagggtag ggaaaggtga cttttgataaa gaccagcaaa gcagcttcta  77640
aaaataaaat gtgaagaaag gaaaatgatg cttacgtagc ccgcttccac accataatca   77700
gtttgtcatc tccccagaa gctaaataca tcccactgtt tgaccaccgc acacagttca    77760
cacatgctgg gaagaaaaaa aataaggtg atgaaaatcc agtagtcatg cccatttgct    77820
ttatgtagag tttggcaaga tgtaaagggt ttataaaatc taatctatct aatctattta   77880
aggcatctac tgtgtgagag ccccagaaaa acaattcagt ttaagcacta acctacttgt   77940
gctataaaaa caaattacca gaacagtctg gaggggggaaa aatatacatt atctgagaat  78000
cgttagtgct gaatgacata gtcaatagaa ggcttctttc taagaaaatc aaaaaatgat   78060
aaccaaatct cattatttca aaagggtcat ctattaatga dacacatttc tgagtagaga   78120
ttattctcaa aaaagagta cgtgctaaaa agggtcagat gcttttttcta gatttttcag    78180 atgaacagtc tgttacagta taaaactctg acttcatctc atctgtcaga gccagccctg   78240
tcacattcgg attttccaaa ctcgccagca ctgcagattg actgactctg cgcttataag   78300
ctaagatcag cagaaattcc cccaggcccc tgatgggcca gagcctccaa gagcactcac   78360
aacttggcct ttggaagacc tgaaagatgg ctatcaaagt tgtagccccc acatggcccg   78420
tgagtaacat gctccaggtc tgaagacact gagaggcatg ttgagaggac aagaacacac   78480
agaggaaagg aaggagctga tgtccaaagg ccagtgactg ttcattaagc atctcagggg   78540
tgggaaacta aggcactaca gcaggaaagg aaaccatcac actgtctgat ggccaaaagg   78600
gtcctggcag agagcctcag agtgacacag taacaacctg atgatgtttg gcaaattgtc   78660
tcttgcgcac ccttccccag aaccctactg tgtccaggtc gctggcccca aagccccatg   78720
gaatcaggca gtaacgactc atgagcagga aatcaccaga ggtacctgca gactgtccaa   78780
agatggttct gtgggcgggc cgagtcttct gctgaataac tcacccaggt gtgcagccaa   78840
catctgtgcc ttcagacagc aggccgaggg gagttaccgc cgcacgggc cttatctttc    78900 taattacaaa cacatgtgct aaccttgggc actctgccaa cacgcaaagc ctgcaaaggg   78960
ccactctgta ataccttaagt gattgtccat ctggcaaagc atcttgggaa tattttcatc  79020
cttctcgtca tcctcctgga ggactggaga catattccag atcacaacct tcccagaatc   79080
```

```
ctgccctgga acaaaggagc agaaatggct gaatgtgcaa ggagtagaaa tttgatatta    79140
atatttaatg tcaaattaaa ttaggagaag tcctcactta gcttccataa acaataatta    79200
actagatcta aggagactga atttaaatta ctaatttaag ttacagaaaa gatgataagt    79260
actcatgggg acgaaacgga gcggacttag cagtcagcag aagtcaacct gactttacaa    79320
aaagaacttt agactagcaa tcaggaggga actgagctct gatctggcct ctaacacgga    79380
tccaccaggg gtccctaaaa ggtcttcatc cctgcccagc acctagactc cgactccttg    79440
actcctcatc tgtgaaatga ggagaaggga aagtcaatgt cataagacct tttctgttct    79500
gtgtacaccc taaaaagcaa acagaaaagc acccctagt ggggtttccc tccccttcca    79560
ggtgctgcct ggaatttagg ctgttccaga gccgactgtt ttgagaccca aatgtaccct    79620
gaacacagga aaaatggctc attatcttgt tatccaccct ttgcagttac ctacagacga    79680
gagaccacca aaagagggga tttagggctc ccgtggtcat gagttgatgt attgctcggc    79740
taaaaaatat acccatgcct tttagtaatg atttcttttc tttttttttt tttgagatgg    79800
agtctcactc tgtctcccag gctggagtgc agtggcacga tctcggctca ctgcaacctc    79860
cgcctcgcag gttccagcga ttctcctatc tcagcctccc gactagctgg gattacaggc    79920
gaacaccatg acacctagct aattttttgta tttttagtag agacggggtt tcgccatgtt    79980
ggccaggctg attcgaactc ctgacctcag atgattcgcc tgccttggcc tcccaaagtg    80040
ctgaaatcac aggcgtgagc caccgtgccc agccttagta atgatttcta agctttccat    80100
cactgatatc taacgaagtt tagcccctca cttaattttc ctattataat agggccaaat    80160
ccaatgaaca tgccaaaatt accataaagc atgtttgaaa ctgcctcttg gccaatatgt    80220
aaaagtattt ccaaaacatc tctgctggac caaggtggca aaatgtgtgt cttctgggta    80280
caggtgcgaa ccctctgatt ccttcagcta agtccatgtg ttctctctca tgtgctgcac    80340
ctcctcctct cgggtgcagt ccacagcatg aagggagaga aaggcttccc tgcccacagc    80400
ttccctacac tcccttccag ctccttgatt ctgggtggaa gcatctgctg gaaacccacc    80460
ctgcagcacc tggcctgagg acctagagct cacaaaggca ctctctaagt gctgcctggg    80520
gaggcctggt tggagggagg ccccgctctg gggtaaagat gacagagggc tgggctctgt    80580
ggaatgctac attgtgtcac tatatataca tcttggtatt gtggcatgaa gaacagctct    80640
gtctttccaa atagaaccat gcaacattgc aaaagatgct ggctgaagca taagggcaat    80700
actaccaata acagtttcaa atggtgtggg ctttcttact tgcccacagt gtgctttctc    80760
tttaacctaa ctgaattcct ttgacgagaa aatgggccta ataactacac gattgcttta    80820
gaagcttaaa ttaccctcat tccctttttt cagatgagaa aaatgctgac agagcccttg    80880
tctctggggc tgggctttgc ccactggacc acctaccgct ctcgatgctc tacaagtttg    80940
gggatacaaa ctgattttaa tattaactca ataaacagaa attagaatga tacatccgct    81000
gccaaaatac ttacagagag cacactaaag ccataaaagg attttgattt tattcattca    81060
gataacacat tataactgta catttaaaac agcgttgcat ccatcctgaa aaatagcaag    81120
tattccctct acagctaaat ggacagcagg agaagagcaa ggtggcaggg ctgttaagct    81180 ttcccttttct ttattccata acataccttt gtcctccagt tgcgaacttg gtcccgtcag    81240
ggtgaatatc aactgaaaaa atcggcttgc ctggaaacaa agaaaaaaaa atacagtatc    81300
taaattggct tttattcatt gaagtgtatc aaactcaaca gattcagtta aagtctaaac    81360
tgctagaaga ttctccaaac atcagacaac tgaaagtcca acagtgggag aaagcattcc    81420
atcactgaga atggctgagc ccataggatg cctgggcatt tgtctgccat cttgtaggga    81480
```

-continued

```
tgtgtgtttg taatggctat gagctgttca tgattgaagt tctgagtctc aggtacttag    81540
tgaaagggc acacagctgt aactccagac atctccctat tgcatggatc tgcacttgac     81600
tggcagccta gacagaagga ctgctatttg tcttttctgg ctgacagctg agcaggacca    81660
gcgctggctg caaccaagga gcattgcttc gcttgtcata cttctgcttc caaacagccc    81720
tcttttgttt gtgctgtgaa gttcccatac cgtctgccat ctcagcatct cctctggctg    81780
aacctccttc acagtttgta ctctatgtta aattagctgt tcaattcctc caggagaaag    81840
gactgtggct attagttctt agaagcccca aagagcccag tatgggccta ggcttgcact    81900
aggatcccat gaagctagct ggctggctgg gtgggtggat cagaccggca aaagcactgt    81960
aggagcttga aacccagcag accatagaag gcactcacgc ctggtgggca tttgtccagc    82020
tccctgcttc taggacaaag gtttaagagc tacaagtggc atgtcagttg ctgttgagtt    82080
catcacatct tcagcctcta gcacagtacc cagtgtacag tagcgcagta atatttgttc    82140
attgacaaag gagatacatg acaatgatct gagcatcaac aattgctgat atagatgggc    82200
tgttgccaag agtctcttaa ttgaacatgt tctgtctctg tcacccaaga ggaggcaatg    82260
tggacacagt accagagtca ccagccctag aatcactcag caagtactgg gatcaggagt    82320
gtgtgggcag gcagtggctg tctgagaact gtgaagtcct gccagggctc ccatgcaagt    82380
gtgaaaatta aatgctggtg cccaaaaggc actgcccagc atgggaccca ggcagcaccc    82440
agctgtggag agccgcagcc atgtagtcaa atcaagcatg aacttgagat aaaatacact    82500
ttccttctta ctggtcacta tgtagtatag gttgagtatc ccttatctga acacctggg     82560
acccgtttta accaaaggga aatgacagaa gtaatgttgc tccagttcca ggtgtaggcc    82620
ttaagagtct agcagttcaa cttggctct ctggagaaac ctagttgtca tgtgagaagt      82680
ccaagtaccc tgagaccacc atgttttgaa gaggcccaag ctggccacat gtagagcatc     82740
aaagagcccg gacaagtgag aatcaaggtc acagacacag gcctggtgag gtgttctatc    82800
cccaagctat tcgagccatc ccagcagatt ccatagagcc aagatgagct gaacctgcta    82860
agtcctgaca agctgcagaa ttatgagcaa ataataaaac tgttattggt ttaagccagc    82920
aaatttaggg gtttgtcata taagagataa accaaaatgc caattcattt gcttttctgc    82980
ttaagccagc ttgagctggg catttgtcat tttaacaaaa aatgttctag ctgacagctt    83040
tggtcttgac gggcaatcag ggcggaacat tcccctcccc ttggagtgct tttcagttcc    83100
ataagtctgt gagacattgt attacatcag tcccctcaag aagcacacca gaaaccctta    83160
cctgcaagtc acagttcccc tgactaccca agagcacgta caggctgagc caggctgtgc    83220
tgagggctca gctgcacaag taaccaatta cagcccatgc gctttagatc atgcccactc    83280
acagcatcaa ctgcatgttt tctcactcag tctctgtttg cagatttcta ctatgtgcca    83340
ggcattaggc taagcaatga gaaagtaaag atacataatc atacaaactc ccctagtaag    83400
atgtccactg atggacactt cacaagcaga aagccacctg actcagcctc gggcttcctg    83460
cagaaataat aactgaattg ggtcccaagg gttgagtaag agttagccag aagatcgggt    83520
gaaggagagg gttttcaggc tgaggggacg cacggcatgg aatcaagaaa taggctgatg    83580
taatgttgca gagcagactg caggtagaga gtgtgagaaa gaagaggaga cagagatggc    83640
tcagcaagca tcagtaagga gctgagacat ttctctaaag gtactttcaa ggcagggtaa    83700
tgccaaggtc agattcacat tctggctcca caatagcagt gtggaaaatg ggggtggggg    83760
cctcaaggct ccaggggaag gcagggatgg aggctggcaa caagtttggg ttttggcatt    83820
aaacatcatg ggctgaatct ttagccctgc cacttaccca gctacaaagc cttgagattt    83880
```

```
tatttttattt tatttttatt attttgagaa ggcgtgcctg gttcattggc accaggtttc    83940
ctttcctagt gctatgcaga ttagatgaaa tatggtaggg gacctacaca gataccagcg    84000
cagtgctggc tccccgcctc cttacagcac taggcctttc catcccaagg aaagcagtca    84060
ctcacattcc attagtggga atgaaactat ttatttattt atttatttat ttatttattt    84120
atagacagag tttcgctctg tcgcccaggc tagagtgcag tggcgtgatc tccactcact    84180
gcaagctccg tctcccaggt tcacgccatt ctcctgcctc agcctcctga atagctggga    84240
ctacaggtgc ctgctaccac gcccagctaa ttttggtatt tttagtagaa cagggtttc     84300 accatgttag ccaggatggt ctcgatctcc tgacctcatg atccgaccac ctcagcctcc    84360
caaagtgctg ggattacagg ggtaatcccg gccaccgtgc ccggccagga atgaacctct    84420
tctaaagggc tctctgaggt ggagctaagg aaagggacct tctggctgag ctagttagac    84480
aactcttcct gtggcacagc atgatgatga caaagatgag ttcccaacta cctccagtgt    84540
ctggcctttc tttgtaatag agacagaaag aaaagacaaa ttaacacacc ctagactcta    84600
gagacaccaa gcaatcacct atccttagat caaccccaga tcagaatgtt gtccctgcac    84660
acccaataca cagccaatat agtcagccac tgtctactgt ctggggattt gctgatttga    84720
caagagcagc acaaatgctt tccacctggc agggaataaa gaatacatta aggaagctgg    84780
gattatgaca gggcatgctc aggtagaatc gtaccctcct tcacactagg ggaaagattc    84840
ctagaagagg actaaacatg ggaacttaaa ctctgagcac agagaggtgg ccagaggcaa    84900
agcagagagg gcacaatgga gagctgctgg cccttccctc tcagcagtcc cacagacctt    84960
tggtttggct ccaaaaagtc tctgggcttt tatgttctga tagttcattg ggtagagctg    85020
actggaacac atgtgcatat gtccttttgg aatgaagctt gggaaagttg aggcttttgc    85080
ccagtgaatg ttgctcctgg gaacacttcc tgcactgccc aatagaactt ggttttaacc    85140
aatgttgaca aatttagaat taaaaataag aaaatgtttg aaacatttat taaatgaaac    85200
agttacagaa caatactaaa atataaggtg gggccggtca tggtggctca cgccggtaat    85260
cccagcactt tgggaagcca aggcaggtag atcacttgag gtcaggagtt tgagaccagc    85320
ctgaccaaca ggcgcaccat tgcactccag cctgggtgac agagtgagac tgtctcaaga    85380
aacaaaacaa aacaaaaaat atataaggtg ggtgcaaaca acacaaactt atttatttat    85440
ttatttattt attttgagac gaaatctcac tctgtcaccc aggctggagt gcagtaacgc    85500
aatctcagct cactgcaacc tctacctcct aagttcaagc gattctcctg cctcagcctc    85560
ccgagtagct gggactatag gtgtgtgcca ccatgcctgg ctaaaaagtg ctggaattac    85620
aggcttgagc caccccgccc agctacaaac aacataatct taaatgtaga aaaccctaaa    85680
aattccacag aaaaactatt agtgctaata atgaattcag caaagttgca ggatacaaaa    85740
tcaacaaaca aaagtcatct gcatttctat acaccaacaa tgaacaatct gaaagggaaa    85800
ttaagaaaac aattcaattt acaacagaat caaaatgaat aaaatttgta ggaataaact    85860
tagcccagga ggcgaaagac ttgtacactg aaactataaa atataaaaca ctgctgaagg    85920
aaatcaaaga cacaaataaa tgaaaaaaca ttatatatgt actcatggac tagaagattt    85980
aataacttta agatgttagg ctgggcacag tggctcatgc ctgtaatccc agcactttgg    86040
gaggctgagg tgggtggatc acatgaggtt gggagtccaa gaccagcctg atcaacatgg    86100
agaaaccctg tctctactaa aaatacaaaa attggccgga catggtagca catgcctata    86160
atcccagcta cttgggaggc tgaggcagga gaattgcttg aacccgggag gtggaggttg    86220
cagtgagcca attttgtgcc attgcactcc agcctgggca acaagagtga aactccgtct    86280
```

```
caaaaaaaaa agatgtcaaa actcttaaaa gtgatttgta ggcttaatgc aatccctatg    86340
aaaatcccaa tggtactttc tgcagaaata aaaaaaaaaa tcgatcccaa aattcacatg    86400
gaatcttaag ggactctgaa cagtcaaaag aatcttcaaa aagtacaaag ttgaggatct    86460
cgcatttcct tatttcaaaa cttactacaa agctacagta atcagaacag tgaagtacag    86520
gcatagacag acacctagaa caacagaata cagagcccag aaataaactg ttgtgtatat    86580
gatcaaatga ttttgacaag gggccaagac cattcaatgg ggaaagaaca gtctctttta    86640
caaatggtgc tgcgaaaact gcacatgcaa aagaatgaag ttggatccct atctcatacc    86700
atatacaatt aactcaaaat ggatcaaaga cctgcatata tatcttagaa ggaaacatag    86760
gggaaaagct tcacaagatt ggatttggca gtaatttctt tttctttttt ctttctttct    86820
tttcttttt tttgagacag cacctcattc tgtcgcccag gctggagtgc agtggtatga    86880
tcttggccca ctgcagcctc aaccttccag gctcaagcaa ccctcccacc tcagtctcct    86940
gagtagttgg ggactgaggg cacaaccacg cctggtgcgc accaccacgc ctggctaatt    87000
tttgtatttc ttgtagagat ggggtttcac catgttgccc agactggtct caaactcctg    87060
agttcaagcg atctgctacc tttacgtccc aaagtgctag gattataggc gtgcaccact    87120
gcatctgacc atgaatttgg caataatttc ttagatatga gactaaaggc acagacaata    87180
aaagaaaaat aaactgaact ttatcaaaat taaaaacttt tgtgcatcaa aggaaaatat    87240
caacagaata aaaaggcaac ccatagaatg ggagaaatat ctgcaaatta catatctgat    87300
aagggattaa tgtccagaat atatagagaa atcctgaaac tcaacaacgt gactcaaaat    87360
tgggcaaata acttgaacag gcatttctcc aaagaagata tacaaatgag gcacggtgca    87420
atggctcaca tctgtaatcc cagcactttg ggaggctgag gtgggtggat cacctgaggt    87480
aaagaattca agaccagcct ggccaacatg gtgaaacccc atctcttcta aaactacaaa    87540
aattagccaa gcgtggtggt gggtgcctgt agtcctatct actctggagg ctgaagcagg    87600
agaatcactt gaacccaggg ggcagaggtt gcagtgagct gagatcgtgc cattgcactc    87660
cagcctgggc gacagtgtga gactctgtct caaaaaagaa aagaaaagaa aagaaaagat    87720
acacaaataa ccaacaagca catgaaagaa tgtcaacatc agtaaccagt agagaaatgc    87780
aagtcaaaac cacaattacg tattacctca catccattaa gatggctact aacggctggg    87840
tgcggtggct catgcctgta atcccagcac tttgagaggc taaggtgggt ggatcaagag    87900
gtcaagagat caagaccatc ctggccaaca tggtgaaacc ccatctctac taaaaataca    87960
aaaattagct gggcatggta gcgtgtgcct gtagtcccag ctactcggga ggctgaggca    88020
ggagaatcac ttgaacctgg gaggcggagg ttgcagtggg ccaagatccc gccactgcac    88080
tccagcctgg agacacagtg agactccgtc tcaaaaaaaa taaataaata aaagatggc    88140
tacttacaaa aaacctcagg aaataagtgt tgatgagggt gtacagaaat tgtaactctt    88200
gttaaaaata taattaccat atgacctggc aattatactt ctgggtatat aaccaaaaga    88260
aagggtcttg aagagctatt tgtacaccca tgttcatagc agtactattc actacagcca    88320
agaggtggaa gcaaccccaag tgtcccttga ccgatgaatg gatgaacaaa atgtggtata    88380
tatccataca atggaatatt atttagcctt aaaaaggaaa gtagttctga tgcacactac    88440
aatgtggatg aacctcaaag acattatggt aagtgaaaaa agacaaatgt cataggattc    88500
cacttatatg agctatctat gaatagtcaa attcatagaa acacaaagta gaatggtggt    88560
tgcctacgtc tgagttgagg ggaaaatagg gagttgttgc ttaattggta taaggtttg    88620
caagatgaaa atgttccgga gactggctgc acaataatgt gaattgtgac agtactgaat    88680
```

-continued

```
tacatactta aaaatgatta agatagtaaa ttttatattg tgaatatctg accacaattt   88740
ttaaaatgct aataaaaacc aaacaaaacc aaaaataaaa ataaataaaa tggaggagtg   88800
taggagggag gtgggtgtaa ttataaaaat tgttggcggg gtgcggtggc tcacacctgt   88860
aatcccaaca ctttgggagg ctgaggcggg tggatcatga ggtcaggaga ttgagaccat   88920
cctgactaac acggtgaaac cccgtctcta ttaaaaatac aaaaaaaaaa aattgccagg   88980
catggtggtg gcaggcgcct gtagtcccag ctacttggga ggctgaggca ggagaatggc   89040
atgaacctgg gaggcggagc ttgcagtgag ccgagatcgc gcctgttcca gcctgggcaa   89100
cagagcgaga ctctgtctca aaaaataaaa aataaaaaat atataaaaat tgttggaact   89160
gttcagcatc tcgactgcag tggtagatac atgaacctgc acaggtgaca aaattgtata   89220
gaactaaaca tacacacgca caaataagta caaacaaaac tggggaaata aattttaaaa   89280
aataggtagc atatgtcaat gtcaactata gttttgcaaa atgttaacat tgggagaaac   89340
tggactaagt ccagaagtac cttctcagta tttcatacaa ttcggtgtga atctataatc   89400
atctcgataa gaaataaaca cacacacaca cacacacaca cacaaggcct gttttttaaaa   89460 aacgatatat atgtgtgtgt actaatatat aaggcagtag aggtaaatat ccaaacacca   89520
gaggttaggt cataataaaa atgattcttt tcatgtgcag gtgacaatat gcacactcta   89580
taacaagcaa tccctctgga gaaactcatc agccaaacac actaatgtga cctatatgca   89640
agtaactcct atggctgact gccttctaga cacctcaccc tgatcttctc tataacggtc   89700 tgatcttttcc aagaaacctg ctctacccac tgtctgcccc aacacagtta aggccagacc   89760
ttgagaggag aggccaacaa tccttgcaca atggccaccc cgcccccacg acttttctga   89820
cctcatctcc tactaacccc caccatcgct ggtcttcctc ttttcttgga ctgtaccagg   89880
tgcgctccta tcttgggcct tgtactgact cttccttgcc tccttcaggt cttttgctcaa   89940 tgtcaccctc acattgaggc ctactctaac aactttaatt taaaggatta tttccccaat   90000
gtggcacaac aaatcccctt agtcctgatc tatttatttc ctcgggaatt tcttacatat   90060
taatttcctt tattgtatgt ctgtctactc tgcccactag aatgtaaact ccagtaagta   90120
gatcagctct tttgtctgtt ttattcacta attcatcctc aggacccaga gctgtggctt   90180
ggcacataac aggcacaaca ataaaaactt gttgctgttg aatggctgga gaaagctcat   90240
gacagaagca ctacattcaa acaccttcag tatcactggt gtaacaatct ttggaaggca   90300
ggctcctgat ctactgctgt ggggactcag atttcgccaa ctgcctgcag gtgggaagca   90360 caccccttggc tggttcacag ccatctgctg ctgttatctc taccactttc gaccacaaaa   90420
acttatcccc atcttcttta gtaagcatga cacaatgaca tctcataggt gtcagatgcc   90480
taagagattg aaaacatagc acaggaagga agctgttgca ccatacaacc attgtgtgtg   90540
tgtgtgtgtg tgtgtgtgtg tgcacgcgcc acaaactaaa gtggaaaagt gtcacaggta   90600
tatcatttag gagaccttaa tcacttctcc tgaagcatct gccaacatat aatcaacaaa   90660
gttttgagat tgggcgcagt ggctcactcc tgtaatccca gcactttggg aggccaaggc   90720
aggcagatca cttgctctga ggaattcgag accactttag gcaacatggt gaaccccatc   90780
tctacaaatt aaaaacaaaa aacaaaaatt acccagtagt ggtggtgcaa gcctgtagtc   90840
tcagctactc aggaggctga ggtgggagga tctattgagc tcgggaggtc gaggctgcag   90900
tgagccgtga tcacgccact gcactgcagc ctgggcaaca aaaaaaactg tctcaaaaaa   90960
aaaaaaaaaa aaaccaaacc aaacaaaaa acaaacaaac aaacaaacc ccaaaaaaca   91020 aaaaagttttt gacgaaaggc atttctgttt cttaatactt ctttcccccc tcattttgca   91080
```

```
aaacagaggt attccctaaa aagtatctgc acaggaggat tgcttgagcc caggagctca   91140
aggctgcagt gaactatggt catgccactg tactccattc tgagcgacaa agtaagacct   91200
tgtctttaaa aaaaaagtt atctgcaagg gtacaatgta tattattcag gtgatggttg   91260
cactaaaagc ccagacttca tcactaagca atatatccat gtaacaaaac tgcacttaca   91320
tcccttaaat ttaacaacaa aaagttatct gcaaatgta ctcctataaa tctagtccct    91380
tccacctact tccattagaa aattaaaagc tacatttcca tagtgggaaa aatctgctag   91440
ctcaacaata accacaatta agaagacaac aaacctacaa tactatttaa gtgaaaaatg   91500
cacagcaggc tgggcgcagt ggctcacgcc tgtaatccca gcactttggg aggtcgaggc   91560
gggtggatca cctgaggtca ggagttcaaa accagcctgg ccaacatggt gaaacccat    91620
ctctactaaa aatacaaaaa atttattggg tgtggtggca agtgcctgta atcccagcta   91680
atcggaaggc tgaggcagga gaatcgcttg aaccctggag gcagagattg cagtgagccg   91740
aggttgcacc attgcactcc agcctgggca acaaaagcga aactccgtct caaaaaaaaa   91800
aaaaaaatg cacagcaaca ttttagctat gccagttatc tgtacaatgc aaggtctgta    91860
agggaggcta cacaccaaag acattggatt tgctatggtg actgatgggg atttggttaa   91920
agtcttaaaa aaattcagac acttgtataa tgtgcataca ctaaatgcgt cttctaaaat   91980
cacaaaatca cccagttgtt ttttccaaa tggtttgaaa gaccacatta aaagttttaa    92040
caatgtgttt tcctttgtgc attttctaat ttttcctaac ttctttcaca gtcttactga   92100
gctcagtaga tagcaactct gcccttagac tggaactcat ccttctgttc tctcttaact   92160
cttttgtgtg tgtgtgtgta tgagatggag tcttgctctg tcacccaggc tggaccgcag   92220
tgatgcgacc tcagctcact gcaacctccc actctgggtt tcaagcaatt ctcctgcctc   92280
agcctcccga gttgctggga ctacaggtac atgccaccac acctggctaa ttttttgtatt  92340
tttagtagag acgcattttt gccatgttgg ccagactggt cttgaactcc taacctcaag   92400
tgatctgcct gccttggcct cccaaagtgc tgggattaca ggtgtgagcc accatgcccg   92460
gcctgttcta tcttatctca taccccatat ttgaccctac cttcccaaca tacccataac   92520
ccaaactttc aggagagatg caaatgttcc ttaactttat cagggaacag gttacaaagt   92580
acattaactt gtcaaaagtc aacacattat acatttaagg tctggacatt ttatttatac   92640
ctgaaaagaa tgtgtttata tatacacaca cacacacaca cacacataca catatatata   92700
tatacatata tatattacat atacatataa acacatatat acatgtaatg tattacataa   92760
acacacacac acacagagtc tcccccacca gctccaacca tttcttgcca tcacagccat   92820
caccatcctg atccagacca tctcttgctt ggattactac cagtagttgg cattataact   92880
ggtcctctgg ctcctccctc cctctggtcc cccacaacca atctagtctc cacgtagcag   92940
tcagaaagat ctctaaaact cacgtcagat cacagtagtc ctctgctccc cttgcagtga   93000
gaatcaaggc cttctagtag cctactaggc tctcccaatc agtctgctat tcactctctg   93060
gcctcctctc tcacagccct tgccttgctc caaccacaat gacatctgtg ctactgctca   93120
aaccctccag gcaagttcca gctcttcttt ctgcctggaa tgctcttccc tcagatggca   93180
ccttcctcat ctccatgagg cctgcagcga atgctgtggt atcatgccca ggtccctacc   93240
ctccaggggac taaagcacac tcccatagct atctgtggag tgttggcagc cccaacagct   93300
ccctgtagtc ttcctccagg tcagacctgc cctcagtgga agcactcttt tggcagggtc   93360
aggtctcctt tccaaaagag cctatatcca ggctgtggac acgggagtaa agggccctgg   93420
tctcccaccc caatccacga caattctgaa gggcctcccc agctacagaa ctcccagcag   93480
```

```
ggctggctgc ggctttctct gtgcttacat catagcttgc cttctccctc tgtctggtgc   93540
tgcttccttc actccttcaa tggtgtggat cccgagagcc ctccccaata atcctgcatg   93600
caaaaatctg cagctcagaa tctgactcct gcaacaaggc cttttgctcaa atgttacctt  93660
ttcactcagg ctttgccaaa gcgtcccact taaacccgtc tatcccccgc ctctgcctca   93720
gcattcctca tctctaagtc tgctgtttct ccaattcaca ggatcttgtt tgtgattccg   93780
ctatgtgtct caccaggaag ctcccctccc acatctcctc ttttccactt acacaggaaa   93840
cccccagcag atcccatccc agtctcactg gccaggatgc ataacaggct gctcctcaag   93900
agcctggcat gctgcttggt tcactgctgt tttaagagct gaaaacatac acacactgac   93960
tcacacacat gcatacacac acacacacac acacacacac acacacacac acacacatat   94020
tttcagctct taaaacagca gtgaatttat caactgtttt ttccatgtga gaccttctgt   94080
tagaggatgc agcagacctg gagtctgctc caacgtaggt ctatccctgg acctcaaata   94140
aggcctgctg tcccttctgt ctggtcttca ccacagtggc ttttgccagg gtagcctccc   94200
agggaattgg cctaccctag gtttgttaat gcatcgaggc agacaatgct tttaggagca   94260
acaaatgtta atctaaatgg gttttctttt tgccaggagt gttttaaaac catttgctat   94320
ctgtttcatc cacttccttt cctaaaatgg aaggctctag aagacagaat catgtaaatg   94380
aactccttgg gtaaggcttg ggcagaatgt ttcccctcat cattggaatt gccagcagat   94440
tccactagaa agagccagcc aggatgaaca agaagtttat ttgcagtaca tcaactctac   94500
cagccaagga caacagacac tgttagctgc ccatccatca gccactttcc atcaccaact   94560
tccagcactc agcactcctt caacatttac tgagtgacta ctatggtgtg taccaagtac   94620
cattcctggc cctgggaaaa gggcatgagc aaagacaaag tctgttttcc aggagcatat   94680
gctcccccag ggaggtgtct aatagaactc cagtttatt cagatatcca ctctgcccgt    94740
tatgtaagcc agtaggcaac gatgattgat gcaagagagg gcacatgacc tagttggacc   94800
aatcagccaa tggggaagac ccaaagtcca aggctggggc acagacctct cccttctgct   94860
tctcactgaa aacattctcg ataccccaca accagagaac tcttgaaaat caaatgccag   94920
aaaaggctca ccaagcacat ttcaagagaa acctaccagg ttagaagccc caaggcactc   94980
agaatggcta cagaagcagt cagaggacaa gctccaggga ccagactcct ggtcccatgc   95040
tgtaccacgt ggtttctgaa agctgtcctt ctgaggagga aatgggcctg aagctctcca   95100
ggacggagtg gccagcctca gcacaaagac cagtgcttag caaattagaa agagtaagtc   95160
tgggcttggg ctggagtcta agtgtgactc tcaacacatc tccatcacat ctagtggaat   95220
cttggtgcca gggggtcacc tcatctcact cagcctaagt ttccatctgt gaactgtaat   95280
gctgcaagtc atagagaatt tcgagggtaa tcttctatcg tatataacaa gtcctgagat   95340
aggtcagctt cagggtgcat taatttagca acttaaagag acgtgtccct ctgtcttcct   95400
ctcctgtcat cagtgtcggc cctgttccaa gctggctttt acacgcagac ctagtaaagt   95460
ccagcagaag agactagcct gtcaagcatc tcctcttatt taattcccta ggaggtccca   95520
gcagacgtcc cctcctagtc tcaagggcca aatggcatc acatggctgt tcctcaacaa    95580
atccttggca tttacccaca catcagctta gggctatcag caggttggcc tgcagaaggc   95640
agaccaaaaa aattgggggtt ctgctaacaa ggaacaaggc aggcaaccct acaatatttg   95700
caacactccc tttgtgctat ttgacaatat gcacaatgtt cacaatccca ctcacttcta   95760
ggtgttgttg ctgactctgg caggatgata aaatgtgctt tgcataaatt tttggtcccc   95820
agggctcatt ccatacctct ggttcatgtg ctagacactt ctgcagtcca taggcaaaca   95880
```

```
ccccggatga acagaacatg ctagcaacct ctggggaaag ggaggggtca agccagacac    95940
agagcatcct cttcctggtc accgacagga cccaagatca gcacagtgga agcaggtctc    96000
ctacttggct tcagtggtca aggccagacg ctcctcagaa gtccctccca gctgtgtaac    96060
tatgattctg ctcataaagt gaaaatagtt ttcaaccact tcttagagta aaacaaatgt    96120
ttaagaaaat cccatttcct ggccttcatc catattcttt ctgcagcata ttaaagaaat    96180
aaattcagag agaggctggg agcggtggct cacacctgta ataccagcac tttgggaggc    96240
cgaggcgggt ggatcacctg aggtcaggag ttcgagagca gccaggccaa cgtggcgaaa    96300
atgtgtatta aaaatacaaa aacactaaat accgaatact aaaaatacaa aaattagcca    96360
ggcgtggtgg catgtgcctg taatcccagc tactcgggag gctgaggtag gagaatcact    96420
tgaacccggg aggtggaggt tgcagtgagc tgagaccatg ccactgcact ccagcctggc    96480
ctgggtaaca gagcgagact ctgtctcaaa ataaataaag aaaatatata agtaaataaa    96540
tacattcaga gtggcccaaa tctacagtca cctgcctaca tggccaagtc ccattaattc    96600
tacctctacc ctgtctttag tgcctctcta tttctcacct ccatcacctg tgatctccct    96660
gtctccctga gcatctcacc aagactagaa attcctaact cctctagggc ctgcctaaga    96720
cacaggttgg gtgtttcatc cagcttcctc agaagcctca atgttctcct ctctccccta    96780
accccaagaa ggaagttcaa gctgctggca aggctctgcc tccagcccc attctccctc    96840 ttgccctgtt tagcctccct cctaacatgt tctatgtctt tccctaaatg ctttcaccct    96900
ctgggccttt tctcctgatg gtctcatgtg ctgtagcgcc ttctctgcca tcacaattct    96960
agtcacgtca aggttcagtc caaggacaca tccacaaacc cgactctgct ggtgaagtgc    97020
ccttcctcct tgggctatca cgcttattcc tctagctcct gtttcccctg ccctgcattc    97080
tagaatacgg tttgtatgtc aatctctctc atctatcttc cacacagctt tctgttcaga    97140
gagagagcct tatttacctc tggtcccac agaactctta ccagaaaggt tcaatgtttg    97200
ttgcataaat cagtgaaaaa tccacagcaa aatctcaccc agttttcttc tgactcttca    97260
gatgtactct ggttatttc ctaaatcaac ctactgtctt caggcataag tcaggagaga    97320
aattgctgag agaatttgca ttttctgagc taccacatgg agcaggtgag gcaagaatta    97380
ctgacttcat gaacagatta ggaagagatg gaaaaacttt ttatgtcaca tatttagtaa    97440
gcagcagggc acagagactc cagagcagga tatctgattc caaaaacaga agacaaaatt    97500
cttgtcctca agaaacttac agtctagtcg gaactgtaag acaaatacac caaaaggcaa    97560
ataacttatt cagagcgggg tttctcaccc ttagcactat tgatatttgg ggctagataa    97620
ttctccatga gtgggctgtc ctgcatgcta tacgatgttt aacagatttg tccctaccc     97680 acttgatacc agtagcacgt accctgccca accctgttgt gacaaccaca aatgtctcta    97740
gacattgccc tgtagaacca ctgatctaaa gcaactgcca tgtttatctc tcaaccactg    97800
caatcatata acctcaccat taggatcctt tccctgccaa ttctcagaca taggtctgca    97860
gtgccctccg gcagcaggct ggaccttacc cacccactcc taactttatc attatatgat    97920
tctgcctaca ttttcccttc aagctgaatt atttaattt catgctgatg tctcagtagg    97980
acagcttcaa atccttttca gaatgacaca aggtaggggt aaaaataatc caatcgcagg    98040
acaggagaaa atacacacca taaggccatg tgattaccag caaattaccc tgttcttgaa    98100
aatttcccaa atcccttttc ataacactgc catcaaagtg tgaaccaaag gccaaaggtg    98160
gacaagagct ctttcagtcc tggccctctt ggttagaact ggcttcacca aagagctgag    98220
cataagcgct gtctgcccag gcatgagaat tccagaaaaa actcaggagc aaaggcccag    98280
```

```
agttgggaag agccatgaat ctcaacgaga ttttctaaac atacaaactc catatttcta    98340
caaactttaa aaccagaaac ctagttgttt ttactttctg accttaacct aacttagaaa    98400
taaagcttat tttggtcaat tctaaaataa aatatataga gaatactgta tccaagaaca    98460
cgaagtaaaa tgtgtatgta tgaacaataa ctgacacatc ttctatataa atgatagcta    98520
ttatatttca atttaacaat cttttatatt tggtcccagg ataaaatgga agaggtaagt    98580
cttattttac caaggcccag aagtagagtt ataagtccaa gaatttacag ctagtaaatg    98640
atgcagtttt gaacccagtc tgattccaca ttcaaggctc atttcactac aacgtgacaa    98700
cttcaagatt aacttattga taaccttaga caagtgcttc tcaattgggg gtgattttgg    98760
ctaccaatgg acattggcaa tgactggaga tattttggt tgatacaact agaagttgta    98820
tcaacttact ctaagaaggt gtttgtgaag tgctactggc atctggtggg tagaggccaa    98880
ggatactaga aacattctat aacatagatg acaatcacac aattttatgg cccaaaatgt    98940
caacctgctg aagttgggaa accctacctt agaggtgtct ctattatcag ccaagaaaat    99000
gaagaccaaa gtacacccac atttcaataa atacttcttc tcctgttcta gctaccctct    99060
ccactttgaa tggattccct gccacaccag agaaaaatgc tgagctgtct gctacttccc    99120
cctttagact ctcgaaaaac agaaaaagta tgttcatgct gggtgcagtg gctcacgcct    99180
gtagtcccag ctactcagga tgctgaggca ggaagatccc ttgagcccag gtatttgagt    99240
ctagcctggg caacactgca agatcccatt tctattaaaa aaaaaagtta tgtttgtgct    99300
tcacaaaatt gggagacatga atatagaaca aggaagccag aaagtgcaat gatggcttta    99360
caaaagcaag cacaatttta ctggccacta cccaccccct caggcttccgg ctgagcagcc    99420
cctgctccca gcagccacca atactcctac agtatttaaa ggcctgctcg gtagtgattc    99480
agaccagcat catctcctcc agggcagtgg taatttacct cttgacagtc cttctgaaca    99540
ttccatgaga ttttaaaaga aaggaaattt aacaaagaac aagtttaaaa gaagttaaat    99600
cccatcctgc cagagttgcc atatcttttt tttttttttt tttttttttt gagatggagt    99660
ctcactgtca tcaggctgga gtgcagtggc gcgatctcgg ctcactgcaa cctctacctc    99720
ccgggctcaa gcgattctcc tgtctcagcc tcccgagtag ttgggactac aggtgcgtac    99780
caccacgccc agctaatttt tgtattttta gtagagacgg ggtttcacca tgttggccag    99840
gatggtctcg atctcttgac ctcgtgatcc acctgcctca gcctcccaaa gtgctgggat    99900
tacaggcatg tgccaccgtg cccagcctct ttttattatt acttattatc tcagatttct    99960
aaagcactta acagtttggg gagcattttt atatctacgc tcccaactga gtatcacaag    100020
catactatga agtggttaga gtagatatta tcatgctcca ttctagggct gtagagaggc    100080
cctcagcaat aagggccact gttgtgcttg ctctgccagg ctgatgcact tggctgctga    100140
tctgagtgta gtctcttatt catttgtacc tagttcgtca cttaagcatc ttgacttact    100200
tatgtttaca tagcataaaa cttttggcct acaaaggagc ttatcaaaaa ggaacaagtt    100260
atatgacagt agaagagagg ctggagaagg gtaggctatt cacaaaaact gatttaggta    100320
aagcatttta aaataaaaat tctatcagac cttcacacag taaactagtt cataataaca    100380
tttttccttt cctaatcaca agcatcataa ttcataatta caatatttgt ccagttctcc    100440
agggaaagat ctgcacagta cacatcagga aatgctcttg gagatcaaca ggagaaatga    100500
aactaaaact caaggcttcg gctttcatgc acagtaaacc taacttcatc ttgataaatt    100560
atgaaaacct cagctttctt acctgtttta gccaatattt atcacatacc catcatgtgg    100620
aagaggttgt tcaatgcagt agggcataca gaagggactg aggcagtccc tacccctgggg   100680
```

| | | | | |
|---|---|---|---|---|
| gcatatggaa | agtaccctca | caccttccat | gccaggcaaa | acacacagac agtgatacag 100740 |
| cacatctacc | ggggtaactc | aggatgaaca | gtttcaaaag | aaacacgtga acctagtccc 100800 |
| tgaaaaatgg | gaaagatgtc | acacaagatg | gaaggagaga | gaggtggcag gaggagaaca 100860 |
| cacacatgat | cagttcagtt | tagttgtggt | agtagagagc | atcctgggac caaattcaaa 100920 |
| acgaaaaagc | cacatgttaa | aatatctatt | ctcgctccta | aagaaaacgg tagcaccctg 100980 |
| tagtcgcact | gcaaagtaga | aatgaggaac | aagacagcat | cagggtgacc ctttgcctgt 101040 |
| caacagtcag | acaggccaga | atcaggccct | gggctggagg | agtctccctg ggttgatttc 101100 |
| tgtgctacag | tgctgtcagc | agagtggggt | ggggagggg | gaggcgcgct tttttcatct 101160 |
| acccggggag | caaacaccaa | ctcctgcagc | agttctgcca | acaaggcaga actatgacga 101220 |
| aactgattac | cactagcctc | tctgtatcag | agtcaagata | tggggtggat gagtccgttc 101280 |
| cccaagggtg | tgctttggag | ccactgccac | agagctaaga | agcccctctg ctagaacaca 101340 |
| cctgtgccct | atctgcccaa | ccctagttca | ccctgatgtc | ccagctcagc attaatcgtg 101400 |
| gatccttcgc | gggggcccgg | ggcccccaaa | ccctcctatt | tagggaccac aattccccaa 101460 |
| ctgggggcac | tgtccccaga | tccagagggg | cagtaacagt | ccctcttgca gatttcggat 101520 |
| cttcatcctg | ccactgaaag | gccacaaggg | ggatttcatc | ccggtttcac cttcaggacc 101580 |
| gtctgagcac | ttctcgggcg | atgcagacca | gtggaaggca | ctggctggca ccaaggcccg 101640 |
| ctcctgggag | ccaggccgcg | gcccctccaa | ggaccacagg | tgggcagcgg aagactcaga 101700 |
| gcaagagcca | ggggcgaaga | tggccctcgc | tgcggtcaac | ccggagcacg tgctggggct 101760 |
| caccagcctc | tccgcgctga | ggacaaagtc | cgctcccgcc | ggcttcttgg cttgggcacc 101820 |
| gggtaccggg | cgtcagggc | gagacaggca | ggacttgcgc | gcgccccgac tcgactccag 101880 |
| accccgaccc | gactccgggc | tcggcctccc | gcgacccctg | cgcgcactca ccattgtggt 101940 |
| tgacccaggt | cggcttcagg | agcttcattg | ttcggccgcc | gccgccgccg ggctgaggcg 102000 |
| agcgccgggt | ccctcagcgc | gcccgggcca | tggagccacc | gccgccgctt cctcccgcgc 102060 |
| cacccgccct | ccggccgccg | cccgccccgc | gccctcaggg | ccgccgcgcc atcgccggcc 102120 |
| cgcgcccccc | tccgccgcca | cagccgccac | ccgcgctcgg | ccgccgccgc cgccaccaca 102180 |
| gccgcatccc | ctgcgccgct | cctcctcagg | cggctcccgg | gcaacgccgg aagtcacggc 102240 |
| gcgcacctgc | caaatcgccc | cggcgggaaa | ccgctcccca | cgcggactgg gccgccccgg 102300 |
| ctcctccgct | ggcaggggct | tcgggtcggg | cccgggcgcg | ggcgccccag aaagggcggt 102360 |
| tcgcctggac | ggcggacagc | gagcgggcc | tgcagttgca | acccgggccg cccgcagagg 102420 |
| caggcggggc | ccaggtggcg | tggaccgccc | gtcaccagct | ctgcctcgcc agtctgagtc 102480 |
| cgacttatta | actagcttcc | gtcattcatc | aacacgcgct | attgggcatc ttgcgagcgc 102540 |
| cgggctccgc | gccggcgccg | gaatgcgatc | cgggcttcgg | actcgaacga atgcggggga 102600 |
| cgagccaacc | ctggtggggg | aggctgggc | ggacgcgttt | attagaagat cggggccgtt 102660 |
| tgcctagaca | tgaacatttg | gactcggagg | agcagaggga | cgcccctcg gccgctccgg 102720 |
| ctgcactgcg | gagccgaggc | ccgcgcgagg | gcgcagaccg | accaaccggc tagggcctga 102780 |

<210> SEQ ID NO 2
<211> LENGTH: 103863
<212> TYPE: DNA
<213> ORGANISM: Homo sapiens

<400> SEQUENCE: 2

| | | | | | |
|---|---|---|---|---|---|
| atggtggata | agcttttga | tgtgctgctg | gattcggttt | gccagtattt | tattgaggat 60 |

-continued

```
ttttgcatca gtgttcgtca aggatattgg tctaaaattc tcttttttgg ttgtgtctct      120
gcccagcttt ggtatcagga tgatgctggc ctcataaaat gagttaggga ggattccctc      180
tttttctatt gattggaata gtttcagaag gaatggtacc agttcctcct tgtacctctg      240
gtagaattcg gctgtgaatc tatctggtcc tggactcttt ttggttggta agctattgat      300
tattgccaca atttcagatc ctgttattgg tctattcaga gattcaactt cttcctggtt      360
tagtcttggg agagtgtatg tgtcgaggaa tttatccatt tcttctagat tttctagttt      420
atttgcgtag aggtgtttgt agtattctct gatggtagtt tgtatttctg tgggatcggt      480
ggtgatatct cctttatcat tttttattgc atctatttga ttcttctctc ttttttcttt      540
tattagtctt gctagtggtt tatcaatttt gttgatcctt tcaaaaaacc agctcctgga      600
ttcattaatt ttttgaaggg tttttttgtgt ctttatttcc ttcagttctg ctctgatttt     660
agttatttct tgccttctga tagcttttga atgtgtttgc tcttgctttt ctagttcttt      720
taattgtgat gttagggtgt caattttgga tctttcctgc tttctcttgt gggcatttag      780
tcctataaat ttccctgtac acactgcttt gaatgcatcc cagagattct ggcatgttgt      840
gtctttgttc tcattggttt caaagaacat ctttatttct gccttcattt cattatgtac      900
ccagtagtca ttcagcagca ggttgttcag tttccttgta gttgagcggt tttgagtgag      960
attcttaatc ctgagttcta gtttgattgt actgtggtct gagagatagt ttgttataat     1020
ttctgttctt ttacatttgc tgaggagagc tttacttcca actatgtggt caattttgga     1080
ataggtgtgg tgtggtgctg aaaaaaatgt atattctgtt gatttggggt ggagagttct     1140
gtagatgtct attaggtccg cttggtgcag agctgagttc aattcctggg tatccttgtt     1200
gactttctgt cttgttgatc tgtctaatgt tgacagtggg gtgttaaagt ctcccattat     1260
taatgtgtgg gagtctaagt ctctttgtag gtcactcagg acttgcttta tgaatctggg     1320
tgctcctata ttgggtgcat atatatttag gatagttagc tcttcttgtt gaattgatcc     1380
cttcaccatt atgtagtggc cttctttgtc tcttttgatc tttgttggtt taaagcctgt     1440
tttatcagag actaggattg caaccccctgc ctttttttgt tttccatttg cttggtagat     1500
cttcctccat ccttttattt tgagcctatg tgtgtctctg cacgtgagat gggtttcctg     1560
aatacagcac actgatgggt cttgactctt tatccaattt gccagtctgt gtcttttaat     1620
tggagcattt agtccattta catttaaagt taatattgtt atgtgtgaat ttgatcctgt     1680
cattatgatg ttagctggtt attttgctca ttagttgatg tagtttcttc ctagtcttga     1740
tggtctttac attttggcat gattttgcag tggctggtac tggttgttcc tttccatgtt     1800
tagcgcttcc ttcaggagct ctttttagggc aggcctggtg gtgacaaaat ctctcagcat     1860
ttacttgtct gtaaagtatt ttatttctcc ttcacttatg aagcttagtt tggctggata    1920
tgaaattctg ggttgaaaat tcttttcttt aagaatgttg aatattggcc cccaccctct    1980
tctggcttgt agagtttctg ccagagagatc cgctgttagt ctgatgggct tcccttgtg    2040
ggtaacccga cctttctctc ctctggctgc ccttaatatt ttttcctcat ttcaaccttg    2100
gtgaatctga caattatgtg tcttggagtt gctcttctcg aggagtatct ttgtggcgtt    2160
ctctgtatt cctgaatctg aatgttggcc tgccttgcta gattggggac gttctcctag   2220
ataatatcct gcagagtgtt ttccaacttg gttccattct ccccgtcact ttcaggtaca    2280
ccaatcagac gtagattcgg tcttttcaca tagtcccata tttcttggag gatttgctca    2340
tttcttttta ttcttttttc tctaaacttc ccttctcgct tcatttcatt catttcatct    2400
tccatcgctg ataccctttc ttccagttga tcacatcggc tcctgaggct tctgcattct    2460
```

```
tcacgtagtt cttgagcctt ggttttcagc tccatcagct cctttaagca tttctctgta    2520
ttggttattc tagttataca ttcttctaaa ttttttttcaa agattttaac ttctttgcct    2580
ttggtttgaa tgtcctcctg tagctcggag taatttgatc gtctgaagcc ttcttctctc    2640
agctcgtcaa agtcattctc cgtccagctt tgttctgttg ctggtgagga actgcattcc    2700
tctgaaggag gagaggtgcc ctgcttttta gagtttccag ttttctgct ctgtttttc     2760 cccatctttg tggttttatc tacttttggt ctttgatgat ggtgatgtac agatgggttt    2820
ttgatgtgga tgtcctttct gtttgttagt tttccttcta acagacagga ccctcagctg    2880
caggtctgtt ggagtaccct gccatgtgag gtgtcagtgt gcccctgctg ggggtgcct    2940 cccagttagg ctgctcgggg gtcaggggtc agggaccccac ttgaggaggc agtctgcccg   3000
ttctcagatc tccagctgcg tgctgggaga accactgctc tcttcaaagc tgtcagacag    3060
ggacatttaa gtctgcagag gttactgctg tcttttttgtt tgtctgtgcc ctgccccag    3120 aggtggagcc tacagaggca ggcaggcctc cttgagctgt ggtgggctcc acccagttcc    3180
agcttccctg ctgctttgtt tacctaagca agcctgggca atggagggcg cccctccccc    3240
agcctcgctg ccgcttttgct gtttgatctc agaaggctgt gctagcaatc agcgagactc    3300
catgggtgta ggaccctccg attcaggtgc gggatatgat ctcctggtgc gccgttttt     3360 aagcccgtcg gaaaagctca gtattcgggt gggagtgacc cgattttcca ggtgccgtct    3420 gtcaccccctt tctttgacta ggaaagggaa ctccctgacc ccttgcgctt ccctagtgag    3480
gcaatgcctc gccctgcttc cgctcgccca cggtgcgcgc acccaccgac ctgcgcccac    3540
tgtctggcac tccctaatga gatgaacccc gtacctcaga tggaaatgca gaaatcaccc    3600
gtcttctgcg tcgctcacac tgggagctgt agaccgagc tgtttctatt cggccatctt     3660
ggctcctcct caatggagtt cttaacactg aaggaacatg atcaatgtca acatttgaa    3720 tgtaggcaaa taggtaagag ttttggaaac agaataaata caggtaaatg aaaccttttt    3780
ttcttatttt tatattctga cacataacct gcatttaaa gcaaaaatag taaccatgtt    3840
ttatctgttc atagcatata tatataaata attataaata taaacatatt catagcatat    3900
atatagcata tatataattt atagcatata tataattcat agcatatata taatttggat    3960
ttaataaaag attatatata aactatatat ataatttgaa ggcaattata tatatacaat    4020
ttataatgat tcatagcata tatataattt ggattcagaa tatatataat tatatatata    4080
aacaatatat atgtaattca tagcatatat atagttcata gcatatatac atactcctat    4140
atataaaatt atacatatat tatcaaaaat tatatatatt tgtaaacata tgacaataat    4200
agcacaaagt caatccaaag tgatactggg agggagagat tggaaattta ctgtcatgaa    4260
gtctttatat gacatgtgaa gaggtataat attatttaaa agtacactca gattacattt    4320
aaatgtatac tgtaaacccc aggacaacta gttttgtttc ttttaatgga agtcaacttc    4380
tggtttacaa gtgacactga agtcatcatt cctattctta caaaaagagg aaaacttaca    4440
atcaataact tttcttagac ccatcagaga tgtgaggtcg caggagaaag tgccacctga    4500
aatctgaaga gactggtgaa cacagagaca cagctgagct ctcacacctg gagcagaagc    4560
cactggagcc gtaatctggt aggaattctt aaacggtaat tttagtgaat ttctggacag    4620
tgaatttgga ctagcataga gtaaaaagct cctggaggtc agagtcttga ggggccctcc    4680
ccgacctttg tgggtttacc tctacctcta tgaacctcat tgttacctgg tgtaatggct    4740
acatgacata actgaatttc taccccaccc aaatgctgct taaaaagaat acctgttgga    4800
tactatgctt attacctggg taactaaata atatgtacac caaacccca caacatgcag    4860
```

```
tttacctaca tagtaatctg gcatatgtgc ccctaaacct aaaattagag ttataaaaag   4920
aagaagacac atgcagtaca aagttctctc tgtaactaca ccagccaaaa ctggctggaa   4980
cctagatagc tgactgaatg gcttcaaaaa gttctcaggt ttcattataa tttcatttct   5040
gtgttaaatg acacttccac cagcaccatg acagttgacc atcgccataa aaacaactgc   5100
aagaagccac agaaggccaa aaaagaaggc ttcactctgg ttccaagttc actgcccatt   5160
tctggaaaag acataactat ttatcctatc acttttaatg tccagtccct ttgtttatat   5220
tgacgcccta tattttaacc tcctcacccc cgactagtag agaagctgat tgtgacaaa   5280 catccctgct tcttcatttc ctggccatga atagctctgc ttgatgctca ctttcggttg   5340
cttattggct ctgtgacacc aaatggggac agagcccatc ttttcaggct accaacttta   5400
ttggttaaaa aatggcaact ggctgggcac ggtggctcac gcctgtaatc ccagcacttt   5460
gggaggctga ggtgggcaga tcacgaagtc aggagatgga gaccatcctg gctaacatgg   5520
tgaaaccccg tctctactaa aaatacaaaa aattagctgg gcacagtggc gggcgcctgt   5580
agtcccagct actcgggagg ctgaggcagg agaatggcat gaacatggga ggtggagctt   5640
gcagtgaccc gagatcgcgc cactgcactc cagcctgggc aatgagcgag actccgtctc   5700
aaaaaaaaaa aaaagaaaa gaaaaaagaa aaaggcaact gtgacaggac tgtggaatag   5760
atagttcact tccctgtttg ggaagcctcc ttacctcctc agagactggg aaactggtgc   5820
ccaacaacac tggccagcaa aggatatgca tgcccatttt ctttccagct tgagtttctc   5880 ccctttggg aaatgcccct tccaccactc ctccttgcct ttggtcagtg cagccactg    5940 ccctccattt aaaagagaca gagaagttaa cctttgggca atccctaacc atctggactc   6000
cccattaccc agaccctcat aaaggaaagg ggggcagaat gactgtcccc aggcagggct   6060
ctccagtaac acataatgct tattgataac cctcacataa cttttttctt ttttgagagg   6120
gagtctcaca gtgtcaccca ggctggagtg tagtggcgcc atcttggctc actgcagcct   6180
ccacctttca ggttcgagcg atgctcctgc ctcagccacc tgagtagcca ggactacagg   6240
cacacacccc aacacctgtc taatttttttg tatttttagt agatacagtg tttcgccatg   6300
ttggccaggc tggtctcgaa ctcctgactt caagtgatct gcctgccttg gcctcccaaa   6360
gtgctgggat tacaggtgtg agccaccgca cctggccgac ccacataacg ttgaaggtgt   6420
gtaacatctt gaagccagac atcctctttc catatgaaga cagtcactta tctcttgact   6480
gcttaggggt gatggaggaa gtgtacccta gtggaccaga ccataaaagt gaacctgtta   6540
aaaattctaa agccaagatc ttcactgatg gcacagcta tatgctggag ggacagtgga    6600
gggcaggata agctatggtc cttctcagtg gggttgcaga agctggtgct catccaccaa   6660
gatgctattt gtatctgtaa taaacaagcc caggtggcag taatccattg ctacagccac   6720
cagaagggtg ttgttgaagt agttaaagaa aataataaag ctgatctcct gtcaaatcat   6780
gtggctttag ggaagatcac ttttcaaatg ccacttttc ctccccccc atgccaatcc    6840 tactttttta ccccactttta ctctcgaaag gaatgggaaa ccgcctccaa atgggatat   6900 accaaaagtc ttaccatcca ggagggttaa tcaaccctca tggacaactt ttcccagaag   6960
cagttgcatt gcaggctgtt aaaaagccca tacaaatgct cacttttgtc aggaggccct   7020
gtgtaactgg cttttccaga gcatgactgt cccaaacttc agggagctaa tcaaagaggc   7080
ggttgagact tgctccacct gctatgttaa taaccctaac atccacccca caggggagtg   7140 cagaggggc cattcagctg gtccagtacc aaagtagata accagggaaa gattgacaaa    7200
ttgattccgc agttatgtcc agagccttgg tacctcctgg tcctcactga tagcttttct   7260
```

```
ggatgggtag aatttttgcc accctcactg agatggcacg tgaggtagca aaggtgctgt    7320
taaaggaaat tgttcccaga ttcaggttgc ctcagccaat ccaaagtgat accagaccag    7380
cattcatatt ttccattact gagggtactt cttgggacct agaaataaaa cggtgctcac    7440
atgtccctg gagaccacag tcttccagta cagtgggcta gccagaccct tgaaaggacc     7500
ttagttaaat tacgccagaa aactcatctc ccatggattt cattactctc catggcactg    7560
ttaagaataa gaatagctcc aaaaggaaag atcaaactga gcccttacaa gctgatatat    7620
cgccaatggg tcccagtctg gctaggtgac caggaggtcc tcagagctgt ggggaaaaaa    7680
tatggtatgc cacccaaatt ggaggagtaa tgaaggccct tcaggcctat ggaaatcaat    7740
cattactttc gccatctgac ataaccctcc atcctttcca actcagggat tgggtttact    7800
taaaaaccta gagagaaggg gaaccgcagt catttagaac ctaaatggaa gggcccatat    7860
cttgtggttc tcacaaaaaa attctgcctt aaaattacag ggagtttgcc gggcacagtg    7920
gctcatgcct gtaatcctag cactttggga agccgaggca ggcagatcgc ttgagctcaa    7980
gagttcaaga ccagcctggg taatatggtg aaacccccat ctctactaaa aatacaaaaa    8040
aattagccag gcatggtggc gcacgcctgt agtcctagct acttggaggg ctgaggtggg    8100
aggatccatt gagcatagga ggcggaggtt gaagtgagcc gatatcacac cactgcactc    8160
cagcctgggc aacaaaacga gactctagtt caaaaagaa aaaaaaaata cagggagtga    8220
cgccttggat acaccacatc tgggtcaagg cagccatgga acctaaggaa aaaagccgca    8280
tgtacccagc taaccactc tcagatctaa aattcctgtt gaaaaagaca gacttatccc     8340
cagccagatg agcaacctta ggcctacatg catttcctgc caggacttag tctattagcc    8400
ttgcttatag gtattctcat cttactccat caagaaccta cccctttattt agggatttgc   8460
ctcctcctat cagtcactac catattcacc ttaaacctca tctgtgcaca cctgggaact    8520
acagcgcagt ggtgcattta tcaacatgcc ctgttcttcc tattgctatg ggttgagata    8580
tggggagagt tatcagaata atggagtgaa ataaccttg ttaaaattat agctattata     8640
gctaaaggtt cattaactgc tggatttccc atctacaccc ctaagcccaa tctccttggc    8700
ccatagcttg atcaacagcc tgaccaataa ctgtgatcaa tcatctaact ttaatccatc    8760
ttgcctggac ccacctgaag tcccattagt gatcttcctg gaacaagact ttttattatc    8820
ttggcccttgt gtaaacctca ctggcaatgg aatctgggtc agtctccctt taacctgtca   8880
aaaggatggc tatattaaag taatctatga tcaggccaag tgtttatacc aatttaaccc    8940
ttccagggcc ctgtagcttc tacccttgat ttccttggcc tgtctcctaa atttctggtc    9000
ttgtttgtgt ctaagcaaac tgaggtcgta caactacaaa tgacagttac tcagggatat    9060
aaacatctgg gcttgcaccc aggagataac cagtcctagc taagaccagc tagggaaaaa    9120
attcacccctt ctaatgggcc ctatatcaac acccaaattc agcttgaaga agctatagaa   9180
gacagacctt ggcctgtcag caccccttcaa gaatgaggag tgaatataaa gatagggag    9240
atttgttacc cagtgtaatg cctacatgac agctggattt ctaccccact ctgactgctt    9300
atctttaaga aataggatgt ctaccttaaa aagttcccttt tgtaaccaga ccagctgaga   9360
ctgtctaaaa ccaagatagc tgaccgaatg acttcaaaaa gacctcaggc ttcattataa    9420
tctcattccc atgctaaata acaattctca acagtgccat aaccattgac aaccaccatg    9480
aaacaactg gaagaagcca taaaaggaga gaaaggaaag cagcactcca gttctgagaa     9540
gatcactgcc catttctgga aaaggcactt ttaaggctga ccccttcat tatagaaacc     9600
ctatatttta accccctctt ccctactagc agataagttg atttatgagc cacactccca    9660
```

```
cttctccatt gtttggccat caaataaagc ttactctgct tgacactcac tttcagtgag   9720
tgtactggct cagtgtcacc caacaagaaa atattctatc ttttagggtt actgagttta   9780
ctggtaacat aagagtctca tggcaaaaag ccaagaaaat gtccctcata gctccagcag   9840
atggaaagga aaagtaactc tttcctgagt tactgagaaa taactgagaa ttgtatatta   9900
aagattcaaa tggaaaaagt agtcaacttg caagagcaaa tgcataatgt gagcagaaat   9960
atggaaacta taatatacat gtaaaaaatg ctagcaatca aagcactgta atggaactga  10020
agtgtgcctg tgatggaatc atctgtagat ggaacatggt tgaagaaaga attactgatc  10080
ttgaaggcat gtcaacagaa gctactcaaa ctaaaatgca aaaagaacaa tgggaaaaac  10140
acaatagaac atttgagaat tggtggacaa agttaaaagc tgtcatatac acatagttgg  10200
aatacaagaa aacaaagaga caatggagca gaagaaatat ttgaaataat agttatcaag  10260
agtttacaaa attaatgaca aacaccaaac catggatatt agaataaata ctaaaaaatt  10320
cacatttagg cataccatat taaaattgag agaaccaaag acagagaata ttctgaaaga  10380
agaaagagag gaaaaagcat gctagctata gaggaacacg gatcagaatt acactggact  10440
tttcatcaga aatcacgcaa gcaagtacaa gaagagagta gaatgaaaca tgtaagatag  10500
tgaatgaagc tgggtggggt ggctcacacc tgtaatccta gtactttggg aggcagacca  10560
aacctcgagc tcttcatctc tagagtctca gaagcaaaga atgggtatac aactgaaaaa  10620
gtatctgaaa agttcatgtc attccccttt ctaaatttgg aaaaatacac aagtatatga  10680
gttcacgatg ctaagaaaac ctccagaagg aaaaattcaa agaaatccat acccagttac  10740
atcacaatcc atttatttga aaactaaagg gctgggcatg gtggctcacg cctgtgatcc  10800
cagcactttg gaaggccaag ttgggtggat cacttgaggt caggagtttg agaccaacct  10860
ggctaatgtg gtgaaacccc atctctacta aaaatgcaaa aattagttgg gtgtggtggc  10920
aggcacctgt aatcccagct acttgggagg ctgaggaagg agaatcactt gaacccggga  10980
agcggaggtt gcagtgagcc aagattactc cattgcactc cagcctgggc gacaagaggg  11040
aaattcagtc tcacaaaaaa aaaaaaaaa aaaaagaag gcagggcgcg atagctcacg  11100
cttgtaatcc cagcactttg ggaggccaaa gagggtggat cacgaggtca ggagatcgag  11160
aacatcctgg ctaatatggt gaaatcccat ctctactaaa aatacaaaaa attagccagg  11220
catggtggca ggcgtctgtg gtcccagctg ctcaggaggc tgaggcagga gaatggtatg  11280
aacccgggag gcggagcttg cagtgagcca agatcgcacc actgcattcc aacccaggcg  11340
acagagcaag actccgtccc cactcgccaa aaaaaaaaaa ggaaaaggaa agaaaagaaa  11400
aagaaaacta cagatgtaga aaaaggtctt gaaaataccg tggatttcta tgtgaaacca  11460
tggagatcag aaggaagggg aacgccagtg aaaatatctt tcagaaataa aggtgaaaga  11520
catacattcc cacctaaaag aagtgataaa ggaagttcca cagacagaat ggaaggaaga  11580
taaaaacaga aggaaatgtg cagcatcacc aattagacaa gagtagtata aagatttaag  11640
gaataaacca cacacacaca ctcacacaca aacacacaca cacgaaccaa tctaaaagag  11700
ctgccaaggg ccaaagctga agtaacttaa acaacaaaat aaatttcaca tgtgttaatt  11760
tataacccaa aagataaaat aagtatccat gagtccatac tgatataaat gtatgcttga  11820
ataaattaac aaatgaggag aaaaagacaa atccttatgca taaaagaatt ttatttaata  11880
aatgtagaaa aatatatgac aacagaaaac caccactaaa ataccacagt aaaaaatgct  11940
gcaggcaaga ctcatgatac atgataaaat tcctggtgta gactttaaaa agaaatagaa  12000
taacaggtta ttcacatggc ctcgaataat tttcactaaa aaatgtatca gttaatgtgg  12060
```

```
ttattttaat atatgtccat acatactttc atatcattcc ctccaataag tgaaacttag    12120
ttcctagtca ttgagtgtgg tctggagtta gtggtttccc tctaccaaat ggaaagagaa    12180
aatagtaact ttacagtcaa gaatccagca gacatcatcc tatgtgattc agcttaatat    12240
tagcaataga taaagttgat aacacataca ttctaatatg atatggtgag aaggacacct    12300
gacttccatg ttattcttcc ccaaaatcca tggccaaagc ataatcatga gaaaacatca    12360
gatgaatata agtgggtaga tattcttcaa aatgcctcac ttggacccct caaatgtgtc    12420
acagtcacat aggagaagtg cagactgaga aactgtcaca gatgggggct aagaagaaag    12480
ggtgactgac gcagtgtgta tccttgatta gactccgaaa tgaaaaaaga cattagcaaa    12540
agaatacaaa gtggatgaaa tatgtataca gttttttagtt ttgttattag tatttcacca    12600
atattaagtt cttagtttgg gtaaatgtgg catgattatg taagatgcta gccttagggg    12660
aaacgcggtg aagggtgtac tcaaattcac tgtactatcg ttttcactct tctgtaagtc    12720
taaaattatt tcaaaataaa aaaattaaaa ttgcaaacat tgtcagattg gatataaaaa    12780
gcaagattca accatatgtt acttatgaac ataatacttt ttttttttt gagaccgagt    12840 tttactctgt ctcccaggct ggagtgcagt ggtgcaattt cagctcactg caatctctgc    12900
ctcctaggtt ccagcaattc ttgtgcctca gcctcccaag taactgaaat tacaggcatg    12960
atccaccacg tccggctaat ttttgtattt ttagtaaaga cagggtttca atatgttggc    13020
caggctggtc tcaaactcct gacctcaagc gatcagccta cctcggcctc ccaaagtgct    13080
gggattacag gcctgagcca ccacaactgg cccaaacata atactttaaa tataatgaca    13140
taaataagtt aaaaggaaag gatggaaaaa tatagattcc atgctagtac taagtaaaac    13200
aaaactgtgg tgcctatttc aatattggac aaagtcgatt tcagaggaga gaaaacttcc    13260
agaagataat tttacaaata caaacataaa tacaaatata aatatactat ttatccagaa    13320
aacaaattaa cccaagatga gaatctgcaa gaggacatgc ataaaactat atttataatt    13380
gacaatttca atattttctct ctgaataatt gatggaaaaa gcagacagac aaatatccaa    13440
agtacaaaaa gcattgaata acattataaa ccaaattgac ctacctgaca tttatataac    13500
atgtcatcaa ataacaccaa catttctatt atttcccaaa acacatttaa catgtgcaag    13560
ggtccttgtt ctgggccatt aaaaaaaaaa aaaaacagga ttcaagaagt acaaagtatg    13620
gttattctct gacctcaagg gaattaaatt aagaattcac aatattccct actctttta    13680 aaagtaaatc ccacacttct aaataaccat gggccacacc aaacaaatat caatggggaa    13740
aaatcaaaat gtatgggata tcattcaaga agtctttggg aggaatatta tagaactaag    13800
tgcctatatt atgaataaga agggtctcaa atcaatgacc ttagcttagg aatacaaaaa    13860
aggaatagca aattatacac ttagaaagta gaaaaaatga aataataaat gtcatgaaga    13920
acactcaaaa acaatagaga gtgtcaatga aacaacaaaa aaacaaaaac ctggtttctt    13980
gaaaaattaa gaaaattggt aattatctag tcaaactgct cagcatcaaa tcagagaacg    14040
atcaaataat attaccaatg tcaataatga ggaaggcagc agcactaaag gttcaaaatt    14100
attaaccgga tcgtaatgac ataaaatgaa taaacttcac aattaagaga tggacaaagt    14160
cctagggtga caaacactcg taaaccctac tcagcatacg cccatatata tatgtatata    14220
tccattaaat aagaagaatt tttagttaaa ataattccga ctaaggaaac tgttagagat    14280
caataagaga gagatatctg taaggttttt gtaacatttg aaaattgatt aatgtaaccc    14340
acattagtaa caaagtaaca aagaaacaaa atcatcccag tagggcagaa aaacacgata    14400
cttaacggtg aaagcttgca tcatctctca taatataata gtggtgaaat aataattttt    14460
```

```
ttaacagggt gaacttgatt cataactaat attttataca aaattttatc aaaaatagat    14520
aattatgaat gtactatgtg cattgtaatt gtacccaaat attcaagcta aaactacaaa    14580
atctctcaag gaaaacatag gagatattct ttgagacttt gggctagcaa aatatttttt    14640
agctatggca tcaaaaggca aaatacatta atgtacacat tgttgaattt tatcaaaata    14700
gaaacattct gctctcaaaa tatactgcta agggaatgac aaggccacaa attggaataa    14760
aatatttgca aagcacattt caccaaagat tatatgttca tgatgagaag cacacgaagg    14820
gttgttcaat atcattagcc ataaggtgaa tacaatcaaa ctttgaatga aatgccacta    14880
ctatcctatt aagatggcta agattaagaa aattgactgt atccactgtt tgtaagaatg    14940
tggaggaagt agaactctca ttcatttctg ttggatttaa aattttacaa taactttgag    15000
aaaaaaaatt ttttttagtt tctttaagag ttaaaaattc acccaccata tgatccagcc    15060
atttgatttc tagtaagaga aataaagaca ttttttccata cagagtattt tacatgaatg    15120
ttcttagcaa ttttatttgt aatagctcca aagtggaaac aatcaaaacc tcatcaatag    15180
aaaaatggca aacaaactgt ggtatatttc tacaatgaaa tactgctcag caataaaatg    15240
aataactctt agtatatgct atgacatgaa agagtcttaa aataactatg ctgagttaaa    15300
gaagccagat aaaaaagatt aagcactgta ggatttcatt atataaaatt ctagaaaatg    15360
cacactactc aattgtggca gagagcagat cgctggttac tgaaaaagta ggatagagtg    15420
ggtgggggag aaattacaga ggggcatgag gaagcatgtg ggggtggcga acatgttcat    15480
tatcttgatg ggggtaatgg ttgcatggat ttatatgtca aaagttgtca aattatacac    15540
attaaatatg tgcagtttat catatatcaa ttacacctca ataaagctgt taaaaataag    15600
ctctggagct tcacctgtgg gaagtgtcag tggtgaagaa agtaagacac aggaaagtca    15660
aggttttcaa tggtatatat taaacagcat ctatgcctgt ttatctctgc cctgtaatga    15720
atgaacaggg ttccaatgcc cctaagggag atgtgtggtt ctagacccct atgttctatg    15780
aatagtaaag tctcttctct gttgggaaca ggccctcaaa tctggccata aactggcccc    15840
aaaactggtc ataaacaaaa tctctgcagc actctgacat gttcgtgatg gccatgatgc    15900
ccacgctgaa ggttgtgggt ttactggaat gagggcaagg aacacctggc ccaccccggg    15960
tggaaaaccg cttaaaggcg ttcctaagcc acgaacaata gcatgagtga tctgtgcctt    16020
aaggacatgt tcctgcttca gataactatc cagagcccat cccctttgttt cccttaagga    16080 atactttttag ttaatctata atctatagaa acaatgctta ccactggctt gctgtcaata    16140
aatatgtggg tcaaactctg ctcggggctc tcagctctga aggctgtcag cccctgatt    16200 ttccactctg cactctgtat ttctctgtgt gtgtgtcttt aattcctcta gcaccactgg    16260
gttagggtct ccatgaccaa gctggtcttg tcaaggggtg cccatacta gggctggaac    16320 ccgggtcgaa gggttgctgg agcgatggtt ggagaaggtg gaactaagct ggaggacacc    16380
cgagtactct taagcaatcc ccatggtgag taagaagggg agcttggaag catcaggta    16440 acaatgggac aagtgtggga tctggttcgt tccacctggg aaccttttca cactgatgag    16500
gaggaggaag gaaagtataa ctaagtaaaa gaagaggtaa cagagaaggt ttgtttccca    16560
gctaaagcta aagcggcaaa ggaggaagag attcatccct acccttctgc acccctcat    16620 tattttgaag aaaagagtg gcctgaccct ccagatcttt cttttccgga ggacacgggg    16680
tgaaaggtgc cccagtgact gtttgagcag tgcctcgagt accgctctca gttctattca    16740
ggcaggaatc cagcaagcta gatgtgaggg tgatatagag gcttggcagt tccctttgg    16800 gatacaccc ccagatcaac agggaaatat tatagctaca tttgagcctt ttccttttaa    16860
```

```
aatacttaaa gaatttaagc aagcccttaa tcaatatgga ctatgttctc cttttgtaat   16920
gggactgtta aagaatgtta ctgtctccgg tcagatgttg ccagtgggggg caataggatt   16980
acgtctaggt atatatagtt taaatttatt tatttattta tttttgagag ggagtctcac   17040
tctgtcaccc aggctggagt gcagtggtgc aatctcggct cactgcaagc tccacctcct   17100
gggttcacac cattctcctg cctcagcctc cacagcagct gagactacag gcacccgcca   17160
ccacacccgg ctaattttt gtattttaa tagagacagg gtttcaccgt gttagccagg    17220
acggtctcga tctcctgacc ttgtgatccg cccatctcgg cctcccaaag tggtgggatt   17280
acaggcgtga gccacagtgc ctggccatca aggttaaatt taaaggagc acaaatacat    17340
acaggagtaa ttgattcaga ttacaatggg gaaattgaaa ttgttatatc tactgttccc   17400
tggaaagcag agccaggaga gcatatagca cagctcctga ttgtgccgta tgtgaaatg    17460
gggaaaagtg aattaaatga acaggaggat ttggaagcac aaatcaacaa ggcaaagcag   17520
cttattgggt gaatcaaatt actgataaat gtcctacctg tgaaataact attcagggaa   17580
agaaatttaa aggtttgata catacaggag cagacatttc aatcatttct ctacagcaat   17640
ggccgtccac gtggccaatt caatccactc aatttaacag agttggagtt ggtaaagccc   17700
ctgaagtata tcagagtagt tatattttgc actgtgaagg gcccaatgga caaactggga   17760
ctattcaacc aattgtaact tctgtaccta taaatttatg ggggagagat ttattacaac   17820
aatgggaagc acaagttcta attccagaac aattatatag ccctgaaagt caacatatga   17880
tgcatgaaat ggggtgtgtc cctggtatgg gactagaaaa tatttgcaag atttgaagga   17940
accacttcaa gtggaaagac aaagttcccg ccaaggttta ggatatcatt tttgatggca   18000
gacattgtta agcctccaga acgtatacct ttaaaattgt taacagataa gccaatttgg   18060
atagaacaat ggctgctaag taaagagaaa ctggaggctt tagaggactt agttactgaa   18120
caattagaaa atggacacat agctccaaca ttttcccctt ggaattctcc agttttgta    18180
attaagaaaa aatcaggtaa atggagaatg ttacctgact taagagccat taattcactt   18240
atacaaccta tggggacatt acagccagga ttgccttctc ctgctatgat tccgaaaaaa   18300
tggccttca tagtcataga tttaaaagac tgtttcttta ctatcccctt ggctgagcaa    18360
gactgtgaac agtttgcatt tacaaaacct gcagcctgct aagcgtattc attggaaagt   18420
gttgccacaa ggcatgttaa acagtccaac aatttgcgag atgtttgtag ggcaagcaat   18480
tgaacctact catacaaaat tttcacagtg ttacattatt cagtatatgg atgatatact   18540
ttgtgctgcc cccacttgaa aaatattact ctaatgttat gatcacttgc aaaatttgat   18600
ttctcatgct ggtttaatta tagctcctga caaaattcag actactactc cttactccta   18660
cttgggggacc ttagtaaatg acactaccat tgtgctacag aaagtaacca tacgtaagga   18720
tcaattgaaa acattaaatg actttcaaaa attactaggg aacattagtt ggatacgacc   18780
tgctctaggc attcctacct atgccatgag taatctattt tctatcctta gaggagatcc   18840
tagtctcact agtccttgac aattaacaaa agagcctgag gcagagttac agctgcttga   18900
aaagcaagtc cataaggctc aaataaatag aacagatcca gagaagactc tagatttgct   18960
aatttttttca actcatcatt cacccactgg tgttattgtc caagagcagg acttagtaga   19020
atggcttttt cttccacatg ctaattcatg gactctaact ccttatttgg atcaaatcac   19080
tactatgata ggaaatggga gaactcagat tgttaaatta catggatatg atcctggata   19140
aattatagtc cctctcataa agacacaaat acagcaagct tttataaaca gtcttacttg   19200
acaaacccat ttagctgact gtgtgggtat tctagataat cattttccta aaatgaaact   19260
```

```
gtttcaattt tgaaattaa ctaattggat tctccctaaa attactaaat ttaaaccaat    19320
tgaaggtgct gagaatgttt ttacagatgg gtctagtaat gataaaactt cttattctgg    19380
ctcaaaaggt aaagttttc agacaccta tacttcagct cagaaagcag agcttgtagc    19440
tgtaattgag gtatttactg cttttaatat acctattaat gtgtttctga ttcttcatac    19500
atggttcatt ccacacaatt agttgaaaat gctcagttat gatttcatac agatgaacaa    19560
ctgatgactt tatttaccca attgcaaaca gcagtctgga gtagaatgca ccctttttac    19620
atcactcaca ttagggctca tacacctctt ccaggacctt taactgaagg gaatcaaatg    19680
gctgatcgcc tagttgctac tgcaatatat aatgccagac acttttacaa tttaacccat    19740
gttaatgcct ctggtctcaa acgcagatac agcattacct ggaaagaagc taaagctatt    19800
atccagcaat gcccaatttg ctaaatggta cattcctcat cttcacagg aggagttaat    19860 cctcgaggat tggaacctaa ttctctttgg caaatggatg tcacacatgt tccctcattt    19920
ggagactagc ttatgtacat atatttgtgg acaccttttc tcactttgtc tgggctacgt    19980
gccaatcagg agagtcttct gcctgtgtta acatcatct tttgcagtgt tttgcagtga    20040
tgggcattcc agcttgtatt aaaacagata atgccccagg ctatactagc aaagctcttg    20100
ctacatgttt ctctatatgg aatattaaac acattactgg tatcccatat aattctcaag    20160
gacaagcaat agtggaatga atgaatctct ccctgaaaca gcagttgcaa aagcaaagtg    20220
gggggaaaca gggactgtgg gacaccccat atatgcaatt gaatctagta ttattgactt    20280
taaatttttt gagcctgcct aaaggccaga tgctatcagc agctgaacaa catctacaga    20340
aaccagctgc aaagacagaa gcagaacaac tggttagtg gagagacccg ataacaaaaa    20400
gttgggaaat aggtaaaata ataacttggg gtagaggtta tgcttgtgtt ctccaggcc    20460 aaaaccagca gccgatttgg ataccatcaa aacacctgaa accttatcat gagccagatg    20520
ctgaggaaga gattccagga ggattctgag gaccccctgg ttgcagccat gtcgagactg    20580
atgctgagaa ggaccccaac tgtcatgagc aacatctgtc aaacacagcc acctatctgg    20640
ggacagatca agaagctgtc acagatggtg gaagaaaacc tgaggaaagt gggacaacca    20700
gtcacaacga gtaattaat tgtagctatg atagcggtga tcaccactgc catgagtatt    20760
ccttcaatga gggctgacac agagaacaat tatacttatt gggcatattt atcaatcttg    20820
aatggcaata atgcctggat gtaatcactc tataacacag ttacacatgc tttctgatct    20880
cagtatttac cataataaat ctgctcctat aattgaggga taccaccctc aaaaacctat    20940
ttgtaaacag aattggacct gaccagaaat aatgaacgtg cttgtttggg aagatttcat    21000
tgcagaacag gcagaggtgc tgcaacgaa tcctatggaa tcattattga ttggtcccct    21060
aaggggatgt ttagcttgaa ttgcacctct cagtctgcgt cccacgacca cactatgttc    21120
agctggtcta aacaaaatgg tcagatggta gaaatggtaa gaaacacggc aagagttcct    21180
attatctgga aacatggcag tatagtggca cctcaacttc aaatgatatg gcccgctgta    21240
ggagctaaac ataagaattt gtggaaacta ttaatggcac ttaataagat caaaatttgg    21300
gaaagaataa aaaatcatat agaaggacac tctacaaact tgtctttaga tactgcaaaa    21360
ttaaaagaac aaatatttaa agcatcccag gcacacctga ccattatgcc aggaactgga    21420
gtgcttgaag gagctgcaga tggattagca gctagtaacc caataaaatg gataaaaaca    21480
cttggaggct ctgtgatttc aatgatgatt gtgcttttaa tctgtgttgt ttgtctttgt    21540
atagtctgca gatgtggatc ccaattcctg caagaagtag ctcactgtga taaggctgcc    21600
tttgtccttt tatcatgttg caaaagcaaa aaggggaat gtgttgggaa caggccccca    21660
```

```
aatctggcca taaactggcc ccaaaactgg ccataaacaa aatctctgca gcactgtggc   21720
atgctcctga tggctatgat gcccatgctg aaggttgtgg gtttaccaga atgaaggcaa   21780
ggaacacctg gcccacccag ggtggaaaac aacttaagga gttcctaaac cacaaacaat   21840
agcatgagcg atctgtgcct taaggaaatg ttcctgggac agataactag ccagagccca   21900 tcccttttgtt tcagcccatc cctttgtttc ccataaggaa tacttttagt taatctataa   21960
tctatagaaa taatgcttat cactggcttg ctgtcaataa atatgtgcgc caaactctgt   22020
tcaaggttct cagctctgaa ggctgtcagc cccccgattt cccactctgc actctatatt   22080
tctgtgtgtg tgtctttaat tcctctagtg tcgctgggtt agggtctcca tgaccaagct   22140
ggtcttggcg cttctcagct ttcctttgag ggtacaaact tctgtccaaa ggagcctaca   22200
gtaagcatca aatagaggaa gctagaatac caggaagcag ggtggataaa ttcaagtcat   22260
cttatcagag cctgtgttac aataaaaaat ttacctgatc tttgtcctaa gttccttgct   22320 tataacctttt ggaatttctt gagtgatagg agtgtctttg ctatgctaat aaggtaactc   22380
atgatggatc aatacaaaac tttaaaatgg ggctggtcac aagactaaat atatgattac   22440
agagttggga cttcagttgc ctgaccttct gagtagtaag gggacctggt ggctgagttc   22500
aatcacatgg cccatgattt aagcaatcat gcctacatat gaagcccag taaaaactct   22560 gaacaatgta gctcagtgga gattcctggt ttttgtgaac aaatggatgg tcctagagag   22620
tggcatgccc tgatcccaca tggagaggtc ataaatctct gctgttcctc caagaccccc   22680
tcccaaacat gtttctttttc taagaaagtg ataatcataa gtacagcact ttcagtgagt   22740
tctgttagtc agtatagcaa attattaaat ctactagggt catgggaatc tccaaatatg   22800
taggtagtta gttggaagtg tgggtgtcct gagggcccct gaagtacagc tggcattgga   22860
agaacattct tgttgggggt cacacacttc agcttgtagg atctgcacta aatttgtgtg   22920
attactgtaa gatttgaatt atggtacacc cagttggacc ataattcaac aaagtagaaa   22980
tgacgcaata aacttaaagc agaatggagc tcatttattt ccctaattga cacattagta   23040
ataactgggg gggggcatat aaggccatga ttataaaaat tatttcacat aattttatgt   23100
aattataaaa aattaatccc tgacaacatc agcaggtgga agcaactaac aagtctgatc   23160
caactgggga tgatggggtc ccatcttaat gaacctaaga gccttccata ttccaaaagc   23220
tggtacctga atgcatgctc ctgacttttc aatggataag tgggatttga ggctatttttt   23280 catgagactc cagaatatag ccacctgaac ctaacaatat tgaaacagca acatcctttt   23340
ctcttgagac cagcctattg tggatcaata tgactgtgct gtaccagtaa ccaggaagtt   23400
aggagaaacg ctagaattgg actttatttta gcagtctttt ccagcctcat tgactatgaa   23460
tgtgaaaaac cctgtggtta cttagaaatc ccacagtact ctatgccatt tgtgaagatc   23520
cttgtgaaga tgggtagaga ttggagttat tttgctacca gtcaaggaat gccagaagcc   23580
tctagatggg aggaagggca ggaacagatt ctcccttaaa gcctttggta ggagcatggc   23640
caaaccaaca ccttgattta aaacttctgg ctgccaaatc tacaagagaa tacactcctg   23700
ttattttatg ccacccaatt tgtggtgatt ttttatggca gccttaggaa acaaatatgg   23760
gagaaatgtt ttaatttcag aaaatgtact ggtttcagtg tgcaaagtaa actgcagtga   23820
ataaactagt gagaaggcac agagggtgtc cacggtggtg atccaattgt gaaagagcgg   23880
tggaatatag tcgtggatgg cagtaagtgg cttacagaag gtgagaatta tgtgattatc   23940
tagatatgaa ggatacagga gaatcagtgg tgtcctcttt tcttcctcag gaccctgggt   24000
ggacagctat gccatgtact gtgaggtagg gaacacactg gcagcagaag gtttcaggca   24060
```

```
gacactgatg aagtagagta aaatgttgaa tttaaaactc agactgggtg tggtggctca    24120
tgtctgtaat cccagcactt taggagtctg aggcaggtgg attagttggg tccagcagtt    24180
caagacaagt ctgggaaaca tggtaaaact ccatctctaa aaatatgaaa atttagccaa    24240
gcgtggtggc acacacctgc agtcctgcta ctcaggaggc ggaggtggga aaataacctg    24300
agcctggggg attgaggctg cagtgagctg agattacacc attgcactca agcctgggca    24360
atcagaagga gactctgtct caaaaataaa ataaaataaa ataaaataaa ataaaataaa    24420
actcaaaggc acaatgttaa gatgacattt aggcagttgg atatccagtt atataacata    24480
aaagagacat ctgagtctgg agaaatgaat tttggactca tttgtgtata gatgtaaaat    24540
tcaagctctg ggagatggtg ttgctcagaa tacaaggtga caggaacaga agaggtgaga    24600
taggaccacc agaaacttca acttttagag gatggctgga gaaagatatt tcaaaagatc    24660
tgaaaaggtg aagagagttc tcagcaatcc ctgaagtcta tggtatacc tgaggactca     24720 gggctatctg gaggaatagc catgacatgg gtggtgcatg tgtgtgtgtt gcgtatttgc    24780
acgtgtgtgt tcccaatata gataaggaac ccaagactgc ttggtagata attctatcat    24840
taaaaggata acaagaaata cgcaaacacc aggacacaca taaatttgac aaattagatt    24900
aaatggccag atatggtttg gatttgtgtt cctgcccaaa tctcacctct cgtgttggag    24960
gaggggcctg gtgggaggtg attggatcat gggttggtga ctggacttcc tccttgctgt    25020
tctcctgata gtgagtgagt tcttacgaga tctggctgtt caaatgtgcg tggcaccttc    25080
ttcttggctt tcctcctcct gctctggtta tgtaagatgt gcttgcttcc ccttttcctt    25140
ccaccatgac tgtaagttcc ctgaggctcc ccagtcatgt ttcctgtaca gcttgcagaa    25200
ccatgatcca atgaaaccac ttttctttat aaattcccca gtctcaggta gctctttata    25260
gtaattccag aatgaactaa tacatgagcc aacaccctaa gaccacaaag taccaaaacc    25320
catccattat gaaagataaa tctgaatagg cttacaatta aaacaaatag ttacaaacta    25380
tctgaaaaag aaaacttcag gcactgatgg tttcactgaa aattcctacc aagcatttga    25440
agaagaaata aaaacaattc tacacaattt attccataaa gctgaagaga aggagggacc    25500
agtagtttta tgaggttata atgtcaaaac cagatacaga cattcagaaa agtgaaaact    25560
atagaccaat atcactgttg agcatataaa taaaaactct cagctaaata ttaccaaatt    25620
aaattcggtg acatgtaaaa ggaataatac aggacaaact ggaacccaac atcttcttga    25680
atagagttta tcttagagaa gagtgtttaa gatgaggcaa gctatttta tatgtcccag     25740 aaatagctcc aattggatgg tcataggata gtctgcaaag aggcttaaat cacctgggcc    25800
tattgctatg cctgtctctc ctcactcctc tctgcttgtt attttctgtg gttctcagtt    25860
ggggaccgcg ctgcccataa aagggctttt ggtggtgtgt gggcatggtt ccttttctct    25920
tttctccact ttcctgttag ttttcccatg tctggagggc atttatgtgt gcatgtgaag    25980
ggagacagcc tctgtggcat gtgctatgtt ctcacacaat gaaacattac gccattctca    26040
gatcattaaa gagccctgct ccagacactc tcagggtgat gtgatttatc ttctttacct    26100
tccaaactta actttccagt gcaggcgttt ttgctgagtt gtgtcaatcc agatatccgc    26160
tgggtaagac cgttcggtct tcccagaatc ttctggtcct tctctctgca tggtttcagg    26220
aaatggcacc tgaatctcat agctgcactg tcctgctcaa ttggctgcct gagacagaat    26280
cctggatgtg cctgttattc acagtctccc ctccccttcc attgctgttt atatcttttg    26340
aacctggcat ttctattgaa cctcggctcc ctctgtccca ctcttggtga taatattgct    26400
tcacaatatg catcataaca tatgatttga tcaggcattt gttttctctt ttaacgctct    26460
```

```
ttttctccac cactttccct cagtacagat tacagagacc atgtctcttc tcattgtatc    26520
cccaggcaca aggcctgaaa tgtaatgtta gtaaacagtt ggcgaatgaa gatgaaatgc    26580
aagccatcac ccattttcac atggagtcct gggaagggac ccctaatgag actccctgcc    26640
tctgcttgtc cacctgcccc aaactctaat cttactctgt atgcaggtga cttttcagaa    26700
gacaccctag actccttaac tatctgagag agctgctcct tggggctgtg cagaacagaa    26760
aattctccca tttcagtgca tgcgatggac cttgaatgga tgagcatgag cagtggcccc    26820
ctagggaggc tggggatgag gggccagggt ccagtccctc cctacaccct cccaactttg    26880
gaaagcagca ctgcctgtcc taacttctta atgttttcta acaaaaaaag ggcccagct    26940 gccatgggtt tttccctcag actgagactt ttctgaaatg caaatatttc aggcacatga    27000
cggatattgc tcaatatttg ctgaacacat taaagtgaat tccgtttaag atccttggcc    27060
tgaaaggcat ttggggccca tttaggggct acaaggtgga ggttgctgcc tatgtggaca    27120
gggaagagcc agaggattca catttcatcc agggcctctg ggcccctgca ctgcgagcat    27180
gcgcacttcc cactagaggc tctggggtga cccccttcc tccgttcact atggaaacca    27240
aggctgggac tggcctctcc tcctgttcct gggtctgcca agaacagcct attcacagc    27300 tgtgtaatct gttccgtatt acagagttcg aagtaaccca ccagcaaaac tgtctgctcc    27360
agaatatttt aagttacagc ttctccgtat attttctgtg tctattcaca gaacttctat    27420
ttacagaatt ttgatttaat gagtagttga gatatatttt tgtagtcttc acactttct    27480 actaagctgc tggccctgag aggacttatt gcccaactca ataggggcc ccctggaga    27540 cacccagcaa gatttattat ccccatgact ctcaggacag cattagagct ccatcccaga    27600
tcttgagcct tgggtcaagg tagttgtgga tgccttccaa gtactagctt cgtctcattt    27660
ctcacagtgt ctttggtcct ttttgttatt actctgaagg tcggaatctc tggttcgtgg    27720
gcacacacct tattaggcag ccatcaagct actgacccgt ctatcccatt gcacctgcgc    27780
atgtgtgctt tccccactaa caggctatcc caggctttat tttgtcccac taccccacct    27840
acccaaactt ctactcccag taatttgatt ttgggggga attgaacctc ttcattcttc    27900
aggaagaaga tgatatcatt ttagcaggtg tacagttggg ctccaggtct agcctgtgct    27960
tcatttcaga cttgtgcatc agacctaagg ctttaagcct tccaagtgta atctctcagg    28020
gtggtcttaa tcgacaggcc ctggtacagc attggacaac ccttctgtca gaagtgtagt    28080
gtgttgtgtg ctgcaggaga ggccttctgc acagtctgct tgatgctggc aacttcacta    28140
gaatgaagtc caggtagaag ttatccagtc ctgcccaggc agcaactgaa gtccaagcag    28200
ctctctggcc agagcgctga tactcacttc agcagagcca cctttattg ttgtcatgcc    28260 ccaagcctgc actttaattt caagaatcca ttacatctcg gagggtgaca tgtgagaatg    28320
cagttttaat gagatcacaa tgttaaaaac catagcctat ggccaaagcc aagttgagat    28380
ttaaatagta ggttcaaaca cttttcttat taaaaatat atcaaatgaa ctaaatattt    28440
tatttcttta tttatttaat gtttgagaca gtctcgctct gttgcccagg ctggagtgca    28500
gtggcatgct ctcagctgac tgcaaactcc acctccagg ttcaagcgag tctcctgcct    28560
cagcctgcca agcagttggg attaaggtg cccaccacca cacccggcta attttgtat    28620 ttttagtaga cacggggttt tgccacgttg gccaggctgg tctcgacctc ctgacctcag    28680
gtgatctgcc cgcctcacct tcccaaagtg ctgggattac aggcgtgagc caccgcacct    28740
ggcctaaata ttttatttaa atagttagaa aataatacat acccaaacaa aataaagaat    28800
aatattgatg gagatttaaa tgcaataaat gaggattata tttatgaagc atgggggtaa    28860
```

```
taagtctgtt caagagacat tcttaaaaac aatgaatata attagcatat ttctgtaaga   28920
tgttcccaag aaaatggtag atatctataa atagaagaag gagaaaaagg agaagtagat   28980
ggagaggaga aggaggaggt ggaggagggt gaggaggagg agaaaagtgt tgaaataatt   29040
ccaactaaga ctgatatcta ggaattaccc tggtgaagtg ggaagcttaa gagtcctgtt   29100
ggagggactg gtgtggtaat ggctctgcca aaagtgttat gtgcgtgcaa acccaaagag   29160
agaaagcaca gaaaaccttt caacatcaac ctgcttgagg aaaaataaag tgggaaaaga   29220
tacatactca cagtgaggac tctagacatg tcaagacaat ttttaaatat gcttttggct   29280
tcgagtggca ataactagat tcaagacagc atatttaaga agctgctgat gagaagaaac   29340
ccgggaagag ctgaaggacc acatcagccc agaccaagga tgctgaagca gcattaaggt   29400
ccctggtttc agatgctcag gcaatgaccc tttttttcat ggagagcctg taggagtgac   29460
agttttgtct ttgcccactg ggaatctgtt ttccatacct ggaaaacagg gttacctatg   29520
tttcccctgc tacccttttgg tcatctcaga gacactacca gatattaccc atgggaccta   29580
tttttttttt aaatctcagg aaagacttgg gtgtggcttc caacgtggag gactcagtag   29640
cttcagagag ggtcctgaga gaaggtgaat tgaagaatga gggtgctggg cagagggaaa   29700
agacattatc atacaagttt gtgctaaaag atatagcaat ccttctgcta tggactaagt   29760
atggaaaaaa ataaaatgga atcaaagtta cccaaaggaa gtgtaaaacc caaatttatg   29820
cccgttaaag cattaatgat gctctaagtc cactgcctac ttaaaaagtt catagttcac   29880
atgggttgat aggaaattac gttaacgaca cactgcattt cccctttttct tatagcctat   29940
ctgatttggt agggagtcga tcattttttta ttggaatttc tcaggattcc aacctcagac   30000
atccacttta cagtttacac attttcttgg acaagcccga ctgttcctct cactggttcg   30060
cataaagctc atgtttacaa agccgcccag acctttctct gggactctca tatttaactt   30120
aattctggat atacccaggt aagcgttttcc caagaaactt gaccccaaca tcccaaaaac   30180
ttaaggtatc tttcccttaa actggcccct tctccagtac gcatccatct cacttctctc   30240
ctgccctaga tcttctcagc ccaaacagga aaccccggga tcgctctccc agcaggtgaa   30300
gcctcgccat ggaccctccc cgtcggggcc ccgcgctgcc ccgcccgccc ccagccgctg   30360
gccaaggccg cggtcgcgca ggcgcagtgc cgcgtcccgc cgccgccccg ccctgcccgt   30420
cgctgcggaa ggcgccgcgc gcagcaacgc gcacttcctc tccaggaatc cgcggaggga   30480
gcgcaggctc gaagagctcc tggacgcaga ggccctgccc ttgccagacg cgcagacat   30540
gtcagaacaa agtaaggatc tgagcgaccc taactttgca gccgaggccc ccaactccga   30600
ggtgcacagc agccctgggg tttcggaggg ggttcctccg tccgcgaccc tggcagagcc   30660
gcagagccct cctctaggcc cgacggccgc tccgcaggcc gcgccgcctc ccaggcccca   30720
gaacgacgag ggcgacccga aggccctgca gcaggctgcg gaggagggcc gcgcccacca   30780
ggccccgagc gcgcccagcc cgggcccggc accgccagcc ccggcgcagc tggtgcagaa   30840
ggcgcacgag ctcatgtggt acgtgctggt caaggaccag aagaagatga tcatctggtt   30900
tccagacatg gtgaaagatg tcatcggcag ctacaagaag tggtgcagga gcatcctccg   30960
gcgcaccagc ctcatcctcg cccgggtgtt cgggctgcac ctgaggctaa ccagcctgca   31020
caccatggag tttgcgctgg tcaaagcgct ggagcccgag gagctggaca gggtggcgct   31080
gagcaaccgc atgcccatga caggcctcct gctcatgatc ctgagcctca tctacgtgaa   31140
gggccgcggc gccagagaga gcgccgtctg gaacgtgctg cgcatcctgg ggctgcggcc   31200
ctggaagaag cactccacct tcggggacgt gcggaagctc atcactgagg agttcgtcca   31260
```

```
aatgaattac ctgaagtacc agcgcgtccc atacgtggag ccgcccgaat acgagttctt   31320
ttggggctcc cgggccagcc gcgaaatcac caagatgcaa atcatggagt tcctggccag   31380
ggtctttaag aaagaccccc aggcctggcc ctcccgatac agagaagctc tggaggaggc   31440
cagagctctg cgggaggcta atcccactgc ccactaccct cgcagcagtg tctctgagga   31500
ctagcaaagt ctggaggcag atgaatggtt tctgaccctc accagggctg tggaagggtg   31560
ggggtgggtc attatagtat tcaggattta cagtgcagta ttcacgtgta acttttaagt   31620
tttcagtaca gtgcttttat acctttaatg caatgttgta ttcatttggg tactattgtg   31680 tagtattag  gatgtatgca tgtttgttta tatgtaagct tggttggtgc tttcgctttt   31740
gtgctacctt tcttggattt ttgtaccaga gatgtgctaa actgatgaaa tacattgaga   31800
aagtttccat cttattcttt tatatgggac tgatgatgtg tgttggggta gactgctcct   31860
gcagagtttg aagaagtca  ccagcaaagc cggcctaacc aagaaaagtc aaggcccttc   31920
atgaccttgc tgggcacaga aaacaccctc gtggagtaca ctaatttgaa ctggactggt   31980
ctcagtgtga gcacttggca cactttacta aacacatata caaccccacc gtgagtcaac   32040
tttaaagtaa acattaaaga ttcttgtgat acaatcattt ttggaaaagt gtactttatc   32100
attttaacaa agcagtatgg ttgggaatga gacaattctc tattttacag tgtatacaga   32160
tacaactatt tcccctaata gggtgggaaa atcgctact  catgattact cctaaatttg   32220
tgaagtttat agttctattg tctttaaatg taactcatgt ttatttcaaa aacattcaca   32280
aatatagaaa agtatacaaa acaaaacagt aagattgtct gtaatcacat catatgggaa   32340
taaaaaacaa aaataatttc cttcccttaa gtttctacat tttatcaaaa ttaatagatg   32400
tcttgtgaca tctattaata tacatataac atatttataa tataaagag  tgagacattg   32460 tgctaagccc taacatgtat ttttctcctt taatccttgc aacaggcctg tcaggcaggc   32520
acctactgcc tctgcaccat ggaggaaaca caggaataat gtaggtaatg aactttccat   32580
agctcataaa ggttaataag agaaggagct aggacttgaa ctcagaatga atccagagcc   32640
cacatttgtc tccacctgcc tacgactgcc ctataccccg tggcttttag gttatttatt   32700
tttaaattta ttttttacatt ttatgtggga gcctacaatc acatgggttc atgggccaca   32760
catacaaaaa ggctaggaat tttattttc  taattctcat gatattttgg agaaagcaat   32820
atcattctga ttgtgcaaat taagaaactt acttttggag aggttaatta acctaacaaa   32880
gtgatattcc tatttagcag tgaagctagg atttgaaaca atctctcctg agggttggag   32940
gtgaaggcac cttctctgac aaacacacaa gacacctgag agagggaggt gggttgtcca   33000
tcaggatgtc tgtggccttg cagcccttca gttgcggtga gccactaggt aatcctcaga   33060
ggatggggtg ggctgcgggt gggcattagg ggcaatgcct gaagaaaaat ctcactgtga   33120
atttttagtc ctgcaagggg tagcgggag  aaaggggggct ttaataagac tagaagtcct   33180
ttaaactaca aaagagtggg aaagaccatt tggccaaagc cagaaacttt tctgtggaag   33240
atggataatg aagaggacac atgtcacata acaccccaaa gaagtaaact gggagtccta   33300
ttagggtgag ggaattataa tttgaaattg ccaacactta ctggcattac ttaacaggtg   33360
ggggcaggtg ctggaaatgc ttaggaagcc cctgttcatg ctgagatgaa atccatcccg   33420
gtttaaaagc ttcctgtgaa gattttcaag ggggttctgc agagaaaggg ggacatttct   33480
gcaatcaccc aggcaggggt gacctggctt tgatggcacc tcttacacaa aaccaatgtg   33540
agtgtctcac ctgttcagaa gtgttaggat tgtttggaaa tcttacctcc ccacaaccca   33600
tcgaaaagtt tctccagaat caaaataaac ctgcccgtta tcatttaaaa ttgtggggat   33660
```

```
atccaggatg tttcatttct ggagtaggac tgtgggctgt tgttcctgcc acacatggtg   33720
ctggtcatct tctctaatgc cttaatactt ccctcactgc tggattgatg ccttgcagga   33780
gctgtaaccc ctgtgtgctt cttgcagtaa agcccagaaa tcaccaggca aacagtctcc   33840
ttacatcccc gttaactcc ttatgttgtg tccactttcc tctctgctgt cagaggcagg    33900
gagaaccacc ctttccaaag ctgtcccaag ctcactcaca caggcaccct agccaggcca   33960
tagaggacct agcccttgca ggagaaacag aatgtgagaa tgtgagaatg tgagaaagga   34020
gtaaggcatg gggcagagcg actcgtccct aatgctgcct aggaggcagc cagacctaga   34080
gaaagaggct tccagatgtg aaatgagttt acttcatgac acctgatcct gcagagatag   34140
cagcttgggg catggggaga gagaacccag cagctctctt gggttttcat gctgggctct   34200
aaatagaaag actggagggt ttgtcaaata tttaccaaaa gattcaccta caaggtcctg   34260
ggataggtca atcaggaagg ggtcagctgg tcctcagtgt tgcagtccaa catgacagtg   34320
tgctgaagcc cagactgctg tgggtgggag agactttcct aaatccccat aacatgtcaa   34380
cttttacctg ccaactggaa cctcatttct tcacaaacac ctgcaaacat attttgattt   34440
gttaatttca ttttatgaaa ggaagggaaa agggatcttt ataaatttaa tataaaatat   34500
aaagacacct ggtgtaagtt gtcctgagag gaaataaata actttaagca gtatcattat   34560
taaatagaaa tgttttaagt gaacttctta tgcagttaaa tatttcctct gcttgaaaac   34620
ccttttatgt ccttctccaa cctgagtctt acctgaccaa ctcatgaaca ctatttcctg   34680
ggagaacaca ctccctaacc tctaagcaca gccatgttct aaatgcaccc aaaatacacc   34740
tgctgtttat aattatgtgc cttttatttc tctcctcctg gattgttaca tacttaaggg   34800
ttagaattgt ctttatcctg ttcattattt gcttgacact tgaggtaagg atggggcata   34860
agggctgcac ttgatacata tttgttatat aagttaagta actcaacata ttagaaaaga   34920
cctacccatc cacacaagaa aacaaaacca tatgtggctg acaaaaatta gccaatttaa   34980
agggcgcggt ggctcatgcc tgtaatccca gcactttggg aggccgaggc aggcagatca   35040
cgaggtcagg agatgagacc atcctggcta acatggtgaa accccgtctc tactgaaaat   35100
acaaaaaaat tagccggacg tggttgcggg tgcctgtagt cccagctact cgggaggctg   35160
aggcaggaaa atagtgtgaa cccgggaggc ggagcttgca gtgagctgag atccgccac   35220 tgcactccag cctggggcga cagagccaga ctccatctca aaaaataaat aataataata   35280
ataataaaat agaggtaacg taggacgggc gcgatggctc atgtctgtaa tctcaccact   35340
ttgggaggcc gagatgggcg gatcacttga ggtcagaagt tcaaggcgag gctggacaac   35400
atggtgaaac cctgtctcta ctaaaaacac aaaaattagc tgggcgtggt ggcacgtgcc   35460
tgtagtaaca gctactcagg aggctaaggc aggagaatcc ctcgaacccg ggaggcggag   35520
gttgcagtga gacgagatca tgccactaaa ctctagcctg ggtgacagag caagacaccg   35580
tctccaaaaa aaaaaaaaag caaagtggag gtaatgtaga taagttgaaa ttagtgaaag   35640
aaaaaaaaac agaaggcaga aaaacaatgg aagcaaaaac ttgtttcaag aatcactgct   35700
acaaacactc taacaaaata acccaatatc tagtagtttt tttagaaagg aaaaatagta   35760
caaagaaaca acttatttcc tgactttta atgatcgcca ttctaactgg cgtgagatgg   35820
tatctctttt cttctttttt tttttatttt tcattttga cagagtct ctctctgtca     35880 cccaggctgg agtgcggtgg tgcgatctcg gctcactgca agctccgcct cccgggttca   35940
cgccattctc ctgcctcagc ctccccagta gctgggacca caggcgctgc caccgcgcct   36000
ggctaatttt ttgtattttt agtagagacg gggtttcacc gtgttagcca ggatggtctc   36060
```

```
gatctcctga cctagtgatc cacccgcctt ggcctcccaa agtgctggga ttacaggcgt    36120
gagccaccgc gcccggctgg tgtgagatag tatctcattg tggttttgat ttgcatttct    36180
ctgatgacca gtgatgatga gcatgggtga agctggaagc catcattctt tatatatata    36240
tatatacata tatatatatt ttttttcatt atactttaag ttctagggta catgtgcaca    36300
acgtgcaggt ttgttacata tgtatacatg tgccatgttg gtgtgctgca cccattaact    36360
catcatttac attaggtata tctcctaatg ctatccctcc ccctcccc caccccacaa     36420 caggccccag tgtgtgatgt tccccttcct gtgtccaagt gttctcattg ttcaattccc    36480
acctatgagt gagaacatgc gatgtttggt tttttgtcct tgaaatagtt tgctgagaat    36540
gatggtttcc agcttcatcc atgtccctac aaaggacagg acctcatcct tttttatggc    36600
tgcatagtat tccatggtgt atatgtgcca cattttctta atccagtcta tcattgatgg    36660
acatttgagt tggttccaag tctttgctat tgtgaatagt gctgcaataa acatacatgt    36720
gcatgtgtct ttacagcagc atgacttata attctttgag tatatacccca gtagtgggat    36780 ggctgggtca atggtatttt ctagttctag atccctgagg aattaccaca ctgacttcca    36840
caatggttga actagtttac agtcccacca acagtgtaaa agtgttctta tttctccaca    36900
tcctctccag cacctgccgt ttcctgactt tttaatgatt gccattctaa ctggtgtgag    36960
atggtatctc attgttgttt tgatttgcat ttctctgatg gccagtgatg acgagcattt    37020
tttcatgtgt ctcttggctg cataaatgtc ttcttttgag aagtgtctga tcatatcctt    37080
tgcccacttg ttgatggggt tgtttgtttt ttcttgtaa atttgtttga gttctttgta    37140
gattctggat attagcccct tgtcaggtga gtagattgca aaaattttct cccattctgt    37200
aggttgcctg ttcactctga tggtagtttt tttgctgtgc agaagctctt tagtttaact    37260
acatcccatt tgctaatttt ggcttttgtt gccattgctt ttggtgtttt agacctgaag    37320
tctttgccca tgcctatatc ctgaatggta ttgcctaggt tttcttctag agttttatg     37380 gtgttaggtc taacatttaa gtctttaatc catcttgaat taattttgt ataaggtgta     37440 aggaagggat ccagtttcag ctttctacat atggctagcc tgttttccca gcaccactta    37500
ttaaataggg aatcctttcc ccatttcttg tttttgtcag gttgtcaaa gatcagatgg     37560 ttgtagattg tggtattatt tctgagggct ctgttctgtt ccagtagtct atatctctgt    37620
tttggtacaa gtaccatgct gttttggtta ctgtagcctt gtagtatagt ttgaagtcag    37680
gtagcgtgat gcctccagct ttgttctctt ggcttaagat tgacttggca atgtgggctc    37740
ttttttggtc ccatatgaac tttaaagtag tttttttccag ttctgtgaag aaagtcattg    37800
gtagcttgat ggggatggca ttgaatctgt aaattacctt gggcagtatg gccatttca    37860 cgatattgat tcttcctacc catgagcatg gaatgttctt ccatttgttt gtatcctctt    37920
ttatttcatt gagcagtggt ttgtagttct ccttgaagag gtccttcaca tcctataag    37980 ttggattcct agatattta ttctctttga agcaattgtg aatgggagtt cactcatgat     38040
ttggctctct gtttgtctgt tattggtgta taagaatgct tgtgatttct gcacattgat    38100
tttgtatcct gagaatttgc tgaagttgct tatcagctta aggagatttt gggctgacaa    38160
aaaccacctg attatctcaa tagatgcaga aaaggcccctt gacaaaattc aacagccctt    38220
catgctaaaa actctcaaaa gttaggtatt gatgggatga tctcaaaat aataagagct     38280 atttatgaca aacccagagc caatatcata ctgaatgggc aaaaactgga agcattccct    38340
ttgaaaactg gcacaagaca gggatgccct ctctcaccac tcttattcaa tacagtgttg    38400
gaagttctgg ccagggcaat caggcaggag acagaaataa agggtattca attaggaaaa    38460
```

```
gaggaagtca aattgtccct gtttgcagat gacatgattg tatatctaga aaacccattg    38520
tctttttttt tttctttgag acggagtctc actctgtcgc ccagcctgga gtgcagtggc    38580
gcgatctagg ctcactgcaa gatctgtctc ccgggttcac gccattctcc tgcctcagcc    38640
tcctgagtag ctgggactac aggcgcccgc caccacgccc agctaatttt ttgtattttt    38700
agtagagacg gggtttcaca gtgttagcca ggatggtctc catctcctga cttcatgatc    38760
cgcccgcctt ggcctccaaa gtgctgggat tacaggtatg agccaccgcg cccggcctgg    38820
aaaccatcat tccaagcaaa ctatcacaaa gatagaaaac caaacaccgc atgttctcac    38880
tcataggtgg gagctgaaga atgagaacac atggacacag gcagggaac atcacacacc     38940 gaggcctgtc gagaggtggg aggctggtgg agggatagca ttaggagaaa tacctaatgt    39000
aaatgatgag ttgatgggtg tagcaaacca acatggcaca tgtataccta tgtaacaaac    39060
ctgcacgttg tgcacatgtg cccctagaac ttaaagtata caaagaaaa aaagaagcaa     39120 cttattacta gataaatggg ccaaggacac agagaggtca gtgccttaat aggaaacaca    39180
aacatcaaat gagaaaatga aaacaaata caatctcact gattaagtaa agatactttg     39240
tgtatatgaa ttgatcaaag atacaataaa atgaatatc ctgtactagc aagagtgaat     39300
tgaaattggc atccttggac cctgctatag ttgtataaat tactacatgc tattttatgc    39360
attcattcag agtgcttact gagtacctaa tatgcggcag atgcagggct aggagttagg    39420
gatgcaagag tgaacagaat agacattgtc ctgtgcttgc cgagcattca ctgaattgaa    39480
agaagcaggt gaataaaaat aattacattt cagcgcagtg agtgccatcc taagagaagt    39540
gtggggccta agaggcaca aacaggtgca cacgactcag actgtcctag agaggtgagg      39600
cataaattgg ttctatagga tgagaagcaa ttagcaacgt gaaaacggtg tgtggaaggg    39660
tgaagttggg aggaggctct ctttgtgtcc cgggatctgc tgtgtgacca cacacacaag    39720
catacggggc tatataatga gtttctcaaa ataaatagag taaaaaggag aagggaaata    39780
aacaaatttc agaattggct agaggctagg aaaaaaaaac atgctggctg aagatacagt    39840
caatttcctc aaggatgtga caaagaagag ggctcatatg aatcacatga aaggctaaca    39900
gatttagaag aagccatgct gaaggatagc cttcttttga acagacacct tgttttttt     39960 attgctgctg ttgttgtctg ctttctgatg aggggtctaa aacatccctc cttatctctt    40020
tatttgccca attattcttg ggttcagcta ctcagggttt ggagcccta actatattac      40080 atattttccc atatctaaac ggtttcatgt ctcttctatt agcccaccaa ctttatacta    40140
aaaaatcttt aagattcctg tttgctgtat aaattagttt gtttatgtat ttattcaata    40200
gagatttctt gaacttcaac tatatggctg acttgtgcta ggaactggta caatttggtg    40260
aattaaacaa gatggctctt ggcctcaagt agtttgttta taaactttt ttttttttt      40320 tttgagatgg agtctggctc tgttgcccag gctggagtgc agtggcgcca tcttggctca    40380
ctgcaagctc cacctcctgg gttcatgcca ttctcctgcc tcagcctccc cagtagctgg    40440
gactacaggt gcctgccacc acgcccggct aatttttgt attttagta gagacaaggt       40500 tttgccgtgt cagccaggat ggtctcaatc tcctgacctt gtgatccacc cgcctcggcc    40560
tcccaaagtg ctgggattaa aggagtgagc caccacacct ggcttattga taaattttgc    40620
attgatagag cacaacaaag aggtacaaat gaaacttcaa atacaaatta tatgattgga    40680
taagatatat gaaaaaaatg ggccaggcag agtggctcac atctataata ccaacacttt    40740
gggaggccaa tatgtaagaa ttgcttgagg ccaggagttc aagcccaacc tgggcaacat    40800
agcaagaccc catctctaca aaaaaagttt aatttaaata aatgacgtgg ttaaattgat    40860
```

```
agagaatggt tgagaagaca aactaaggca ggaagcccaa gaaataattt tctgaaaagg    40920
tgaaatttaa gctgataatt aattgaagga taacaagaga gttagcaaag atcaaaggga    40980
agatcaagat aaatccaggc atgtatgtat gtatatataa attacgcatg tatacatata    41040
tgtgtgtaat atatatacat atatatgcac atcatcccat ctgggccttc atatatatgt    41100
atatgtgtat aatatataca tatatatgcg cataggtgtg tatagtatat acatatatgt    41160
gcgcatagat gtgtatagta tatacatata tgtgcacata tatatgcaca tatatgtgta    41220
taataagtac acatatatat gcacatatgt gtgtataata tatacatata tatgcacata    41280
tgtgtgcata tatatacata tgtgcacata tgtgtgtaat atatacatat atgcacatat    41340
atgtgtgtaa tatatacata tatgcacaaa tgtgtatttt atatgcacgt atgtgtatta    41400
tatatacata tatgcacata tgtgtgtata atatatacat atatgcacat atgtgtgtat    41460
aatatataca tatatgcaca tatgtgtgta taatatatac acatatatgc acatatgtgt    41520
gtataatata tacacatata tgcacatatg tgtgtataat atatatacat atatatgcac    41580
atatatgtgt ataatatata tacatatata tgcacatata tgtgtatgat atatatacat    41640
atatatgaag ggccagagtg aatcacctag atttttctgg tggcctttac catgagaaat    41700
agcattataa atgggctgag cagcatgtga cacccagttg tcttttcttg tctgtctcca    41760
cagttgaggc tgcacaagtt aaatatttaa cttcttggtt tttcagctgt gttccagtca    41820
agagatgtac agagaggttt atctgtgctt ttccttccta catccttttt ctctttcagg    41880
gaatgtataa ggaaagtcag gagctattgt tgctcgtatg atggcagtat aaaaacagct    41940
aaagaaatca tagagaggtt gagcctgaca tctacaaact gctggacaaa taccaatagc    42000
cacctacttg tatctatagt ttttggcatg tagaataaaa tctcattctt taagctattg    42060
tcttgtgggt tttttgcttg ctttgtgcag ctcaaagcat ccctaactgg taaagtctcc    42120
aaaaaattct tttctcgtct cccattctgt gtctggtact cacatgaggg tattactgac    42180
cataggtgga ccccgattag gttatgacaa gcagagtaat tctatctcct tgctgcagtt    42240
cttagatcag atatgagaac ttaatcagtt ctgggcaatc aggtcatgta gattagaact    42300
tccattcatt tcatggcaat gttcatgaga atagaattag ggcttctggc tctgaagttt    42360
gtaccacttt ggcatttaga gttatctcag aaaaatgtat aatttttta aaaattcagc    42420 ttgttattta taagccagtt ttgttatttg ctcaagaaat catactaata atggtggtgc    42480
tttctggggt tgcgaagggg aaagaaaggc tcagaaccag gagagagagg aaggtatcag    42540
ggcagccctg taggcaatgg taagcaggca gattgtattt aaagagtaaa tggaaaccac    42600
taacgacttg cagactcatc taattgacat taggctttta aaatattgcc ctccttagta    42660
tactcagaat gaattgagaa gggaaagcat caaagttgag agtctgctaa gagatgaaga    42720
tgatgtagac atgatgaagg agggtatatt tgtggctcaa ttgaggaatg gaggatggat    42780
aggtaaggga catggaagat tagatctgga ttctcaggtt tcaggcttga gcactcggtg    42840
aatagtgtga tttttttttt ttttgagaca gagtctcggt ctgttgtcca ggctggagtg    42900
tagtggcaca atcatagctc attgcagcct tgacctccta ggctcaagtg atcatcccat    42960
ctcagcctcc caagtagttg agactataga agcacaccat cacacctggc taattttgt    43020 atttttgta aaggcggagt ctcaccatgt tgcccaggct ggtctcgaac tcctgggctc    43080
aagcgatcct cagcctccca aagtgctggg attatagatg gtgagccacc gcacctggcc    43140
ataagtgtga tttgatgaaa tggagaaggg aggtgaaaaa caggttttgg atgaaaacag    43200
taaagagttc atacaaacac tcagtgacat gtcctaaaag aaatatgagg ttcacaatta    43260
```

```
ttaaagatgc ctagctcaag atagagaatc atagccctgc actggagcaa cccatttatc    43320
cagagtgaaa gcacagagta actagaagcg gatattctgg gaaactaaga cattaccacg    43380
tgtagtattg aaggaaaagc tgctacggag actaaaaaca gtacctggtt aagagataga    43440
aagtaagcca ggagagtgat agagatgaga atcaaaatag cagcatttca agccaaagga    43500
agtggccaat agtgtcaaac actgttgagt tattagaagt atttgagggg tttatttgca    43560
tttagtagga tctttgctga taagagaagg gaataaagga gattaagttc aaaggcatga    43620
cgcgtgttca cccttcactc aggtgagaga taatggtaac tttaactagg gaatgaataa    43680
tgaagatgga gattaattga aaaattgaga ataattgggg ggttacattg ccaaaaatgg    43740
atgattgatg aaatgctaga aataaaaaca gggaggaatc aggtttatgg ccaggtttct    43800
gacatgcaca ttttgtgtg tcgtatcagt tactgagttt gtgagaaaag agaaagcaga    43860
tttacgtggg aggaggatga gttcagtttt atatattttg agtttaacgt aaatgccagg    43920
catctaaaca gagatgtcca tttgattagg gataaatgca taagaaaaga tgcagattaa    43980
aatgtcatga acctatggat gggaagggat ggatttgcaa aggtattctc tgcttcacct    44040
gagcagttta ggcaggacag acactcttct gcttaatctc agacacttac accagctatc    44100
cacacttgat cttagccaaa aggccgagaa gcaatacacc agctatcctc aggtacttac    44160
attacttttt gttcctaaag gcatatgagt ttgggaatct cggagagtga gagggaagag    44220
gtgcaggatg gagcattgag gagaacaaat attacatgga aaagcagaaa gataactctc    44280
aaataatatc aagaaacagt gggaagagat taggaataag tgagatttag agaatgtagt    44340
tttagaaatg ccaaggagg gattggtcag ttgttaaatt tagttgaggc atgaagcaat    44400
aaaataacta agaagtgttt actgaaatta ctcataaaga gattattttc attttatgaa    44460
gaacaatttc aatgggatag ttgtcaacag aaaccaaact tcagcgaatt aagtatggag    44520
caggatgtga atataaatga tgtatatatt caatggttga tggagagata ccagtattga    44580
agacatggcg agatctatat tataaaatgg agttactata caggattggg aatgcatcgt    44640
ccataggaat gagacagaag tatgaaatga ctgattgatg tatacctgtt gtatctgtgg    44700
cagaaagttg atggtgcttc tattttccca gaggagtgtc agggaaagtc aaaatttaag    44760
acagagaagg aaagtgatga gagagaaaga cagtcccaga tgtgtcccat agaatggaga    44820
aggcagggga tcttcccagg agaatctctc atgggagact ccagcagata ttagaaaatt    44880
taatttaccg atatgtacaa ggtaccacca ctgcatttct tatttgttcc acaaatgcaa    44940
gactgtctca gtatattcat catatctgta atcttaagaa aaaccacatg atcatgtcaa    45000
tgcatgcagg aaaggcatct gacaaaattc aactcccatt cataacaaaa gctctcagca    45060
atctaggcac agaaaagagc attaccaacc tggtaaagca cattataaaa gaaacaacaa    45120
ctactactat agttaacatt gcttagtgtg tttaatgacc aaaaactgga tgcttccctc    45180
taagattgga gggaagggta gagtatgctg tccactctta tcactccttt tccacttggt    45240
gatgaaagtc ctagccagtt caataagaca ggaaaaggaa gtaaaatgct tacaggctga    45300
aaatgaagaa ataagctac ttctatttgc agatggcata attgtctatg tagagaatct    45360
caaataatgt ccaaaaaacc atacctgaat taagaagaga ctttagcaat gtcacaagat    45420
acggggtcaa cacacaaaac caattacatt tctatatacc agcaataact cttgaaaaca    45480
gaaatttaaa catttaaaac tcagtaccat ttataataac tcaaaaatac ttatgaatac    45540
atacatcaaa acatatagga tctctatttt gaaaagctta taaagcactg attagaaaat    45600
caaaaaatac ctaaataaat ggagagaaat atcatgttca tagatcagaa gactcaacat    45660
```

```
ggtaaacaga tcaaacagac atgtaggatt catgcaattt ttatcaaaat cccagcagtt   45720
tatctggaat tgtcttgatt ttggcaccag aagtcccact ttctaggaat cccctctgtg   45780
ggatgtgaaa accccaaat ttttggccat gagtaaagaa gattggagaa aaaactagaa    45840
aacccatatg gcatcaccca acaagggct gtatgcattt tactgccaaa tggagacagc    45900
acatattatc tgtttcttgt aattgctgtc actgttttt tcctgaccac taatgcgtat    45960
aaccacgatt tgcagttcac agtgatcagt gaattactgt gagctgcaaa tcgtgaatca   46020
ttctaactct tgtgacttaa atatgtaaat gaagcatgtc gtaatcatga gtgtttgtct   46080
gtatttgact ttagctgtgg attaactgtt ctactttgaa tcaattttgt gctagttcag   46140 ttttttaactt tacaaacctt gagaccatat tttctaataa ttcagatagt aaaaacacaa  46200
acaattacaa taccaatgca gcaaggccca gaaggctaaa tgattgtgtt attttaatgg   46260
tacatgaagg acacagacaa ctgtattaca aaggtaagta aacaaaacag agcatattgc   46320
acaataggca gaaaaataat gtggggctgg gtatggtaga ggaggttaca tgatctgtgt   46380
gactttgcta gggctgccgt aacaaagtac catagattgg gtggcttaag caacaaaaat   46440
ctatctcctc acagttatgg aggttggaag tcccagatca aggtgtcagt gggttggttc   46500
cttctggggg cagtgagaac atgatctgtt cctggtctct ttgcttggct tgtagatggt   46560
gcagatgact gtcttctttt tgtgtctttt cattatcatc cctctgtgtg aagactaaat   46620
tttaccattt aaggatgata taagcacgta attctaaaag gaacaaaagt ttcttttctc   46680
tttttctttt cttttctttt atttctgtta ttttttggat ttttggtctc ctaaacaaac   46740
actgatgttc agttgaaaat ggcagccact gaattacctt tggtatacca aacaaaccag   46800
cacacatcat tatatcattt tattgattttc tatttgaaaa tgagtaaagt tacattacct  46860
ttaaaattat tcgaacattc agtgacatat cctacaagag atatgaggtt cacagttaat   46920
aaagatgcct agctcaagac agagaatcat agccctgcac tggagcaacc catttatcca   46980
gaaagtgcag agtaactaga agtggatatt ctggaaaact aaaacattgt attagttttg   47040
gtatacaata caaccagca cacatcatta tatcatttta ttgatttatg ttaacctaca    47100
agttgcattg aaaatgtctt tcaacaaaca aaatgggaaa ttttgataat agatacattg   47160
gttctttaca gtgtagagct gactctgaca agtcttactg tcaatcatgc tccctacaat   47220
acagcaagtg atgcgtcaaa taatgataac caaaaaaaaa atgcactcca catttttagac 47280 atgtttatt gaaaatgga gctttaaatt atcttttggt ttctatgaaa cttttcatta    47340
aaccacagaa aacatgaaac aaaagattat taacatcttt tccaaatctg aactagaatt   47400
tgctcatcta tatgcatatc tggcagacag cacaaatgta aatttgccag actccattca   47460
gtctatgaac ttcttatcaa agaaaagata ttacctacta aatgcctcac acacatttaa   47520
tatagaactg ctaaaaggg gcctggtgtg cttacttgtg atttttaaggc tttcataatt   47580 aaaatttttc accacttttc agttttctta aaacatacag aaacaagaat cataacttcg   47640
gctttatgga aatggaagga gatagcatcc ttacacctat gcccacaaga cagcttgcat   47700
tgcggccagc cgtagaaaag ataccaaaat gttagcctgc cataaaatca tgttttcaga   47760
gtatgaaaga agaagaatgt tctctaatct gaaagcaaat taaggatgag aataaagaga   47820
agggagaaaa aatgcaacag aagtgaatat gcttttttcc caaaactgtt ggtgatcttt   47880
gaagaggtca tatggagcct agaaaatgat aagctggctg catttgagtt acgtgatgtt   47940
gtgttctggt tgcaacaaaa actaatacag caaaaacagg atgaacaaaa accctcatgt   48000
tttagggaaa tgatactatt tcagaacacg agaaaaggtc atcagaaaag atcagctaag   48060
```

```
ttaaatagaa ctttctctga gatggagtct ggctctgtca cccaggctgg agtgcagtgg    48120
tgcgatctca gctcactgca acctctgcct cccgggttca agccatcctc ctgcctcagc    48180
ctcctgagta gctaggactg caggcgtgca ccatcatgcc tggctaattt ttgtattttt    48240
agtagagatg gggtttcacc atgtgggtca ggctggtctt gaacacctga cctcaagcaa    48300
tctgcctacg tcagcctccc aaagtgctag gattacaggc gtgaaccacc acaccaggcc    48360
tgttttaaac agaattttct caatttcttt ttagaaattg taaattattt agaatacaaa    48420
tttgatttca caacttcaaa ttacctctgt gctttgaagc cattttcatg acaaagaggg    48480
ttaacttatg atagcatcca atacacttat gaatgttcat aaatcatgga cttttttaca    48540
tgtcagcagc ctatatgatg gatctctaga tgcaaatgat ctcattaaca aacagatagt    48600
ctacgaaaat aacccttaaa atacaaagtg agtggtgttt ttttgaaagc tggacatgaa    48660
tttggtcaaa ttcaaaactc tgctgctgct ggtaagtaaa atcctaaata tcttatgtcc    48720
aaacactctt tttgtaaaca tatttagcta tgttttaca tcagacttac cactggaatc    48780
aatgtaatgt ggacttgatg agaacagagc agcaagtcaa agtgaattat atgtttgact    48840
gtactcaatt ttatcaccac ataaaataaa agaaagatat catgaaggct gtaggcagta    48900
tagagaaata ttactaaaaa ggaaacagaa gaagaaaaaa tatatatatc ccactgtatc    48960
actggacaga aataaaaatg tcattcttac ttttaaattg aatattagaa tatcctatag    49020 tcattttaa tttacattct cctcctaaaa gtcatatgat tacatatttt aagaataact    49080
gaatatagcc tacaatatat aagtatgcaa ttgggaatta aaataaattg ctgtaacaag    49140
aaatataaaa cattgttata ttttcatat atattacttg tttattaatc ctatcattaa    49200
ttactactaa ttagcactgt taattagtct ttgttttgtg taaaaaatgt caggaggctg    49260
aggcaagagg atcactggag gccagggggtt caagcccagc ctaggcaaca tagtgagacc    49320
ccatctctac aaaaaatttt aaaattaact aagtgtggtg gcacatcttt gtagtcccag    49380
ctactccaga ggctgaggtg ggcagatcat gtgagcctgg gaggttgagg atgcagtgac    49440
ccatgatcga gctgctgtac tccagcctgg tgacagagtg agaacctgtc tctaaaataa    49500
atatataaat aaataaataa atgcagttcg tgtaacataa aaataagtga tatagaataa    49560
tagatatttt caaagaaacc tctattttat atgttatatt aaagtaataa tgtgtataat    49620
tattatatgt tacattatta tgatttattc tgtctgggtt aactctaaaa agttggccac    49680
cttagatata gacaagctga ttctaaaatt aatattgaaa agcaaaggaa ctagaacagc    49740
taaagaaaaa ataacttgta aaagtgaat taagttaaaa aagtgtgctc taccaattt    49800 aaggcttaag gcacaattca gcaatcaaga cagtggtatt tagcagaggg atagacacat    49860
agatcactgg agcagaatag ataactcaga attagaacca cacaagtaca gccaactgat    49920
ttttgacaaa ggtgcaaaag taattcaatg gaaggatagc cttttcaaca aatgatgttg    49980
gagcaattag acatcagcat gcaccaacaa acccccaaac cttcaacata accccacac    50040 ttcatacaaa aataaattca aaatggatta cagctctaaa tggaaaatgt gaatctataa    50100
aacttttaaa agaaaacaca gggggaaat tgtcataaaa tggtgttaga tgcagagatc    50160
ttaggacacc aaaagcataa tccaccaaag aaagaacgga tcaatttgac ctcaacaaga    50220
ttaaaagcta ttattctctc aaagacactg gggtttttt tgttgttttt ttttttttgg    50280
tttgtttctt tttctttttg agacggcgtc tcgctctgtt gcccaggctg gagtgctgtg    50340
gcacaatctc ggctcactgc aagctccgcc tcccaggttc acaccattct cctgcctcag    50400
cctcccaagt agctgggact acaggcgccc gccaccacgc ccctctaatt ttttgcatct    50460
```

```
ttagtagaga cgggttttca ccgtgttagc caggatagtc tccatctcct gacctcgtga   50520
tctgcccgcc tcagcctccc aaagtgctgg gattacaggc atgagccacc acgcccgcc    50580
gaagtcactg ttaagagaat aaaaagacac agacttgggg aatgtatttg caaaccacaa   50640
gtccacagaa ggatttatat ccagaatata taaacaactc tctaaactca acattaagaa   50700
aacaaacaat cctattagaa aatagtcaaa gattgaacca gtagatggaa ggcaaacaca   50760
taaacaacaa aaaaaagatg gtcaacacca ttagccatta ggaaaatgca aactaatgtc   50820
acaataatgt atcactatac acagaaatgt aaaatataat aaaatatgct gtaaattatg   50880
acaaaagaaa atatactgtc ggctgggcac ggtggctcac ccctgtaatc ccaggacttt   50940
gggaggccga ggcgggcgga tcgcgaggtc aggagattga gatcatcctg gctaacacgg   51000
tgaaaccccg tctctactaa aaatacaaaa atttagctgg gcgtggtggc gggcgcctgt   51060
agtcccagct actcgggagg ctgaggcagg agaatggcgt gaacccggga ggcggacttg   51120
cagtgagccg agatggtgcc actgcactcc agcctgggtg acagaagcga gactccgtct   51180
caaaaaaaaa aaaaaatgaa taaataaaaa taaaaagaa aggaaatata ctgtccatat    51240
ccaagagagg atatgaagta agtggaactc tcacatagtg ccaggggaat gtacaagcat   51300
acatacacca ttctgcaaaa tggtttagca gtttcttaca aagttatcac atccttaagc   51360
gtaacccaat tattctattc ttggttattt actgtacaga aataaaggca tatgttcata   51420
ccaaaactac gttgcaatga cctacaatta gaaacaagcc atatattttc caacatgcaa   51480
atggataaac tgtggtacat atattcaata caatattact cagcaacaga aggaactaa    51540
atattgttac acatagcaac ttgaataaat ctgaaagacc ttatatgtat tcagagcaaa   51600
agaaatatca aagggttgca tactctacaa taccaatta ataacattct agaaaagaca    51660
aaattatagc attgaatgta acagataagt ggtttccaag attagtgggc agctgtgact   51720
gaaaaggggt aacagagaat ttctttgtga ggatggaaca gctctgtatc ctatgttgat   51780
ggttacacaa atctatccat gtaatatttc atagaactat aagctccctc agaaatgagt   51840
gcatttcaaa actggcaaaa tcggaacaag gtcagtagtt tacttagtag tattatacca   51900
atgttaattt catagttttg attattttta ctatgcttat gtaagttagc atcactggaa   51960
gaagctagac aaaacggaca taggaactct ccatactatt tttcaactt ccatgtaagt    52020
ctaaaattat tgcaaaatga aaatttaaaa taaacgagtg ctaatagtag tgccagagat   52080
agaactatat atttttttt cttttttttt tttttgaga cggagtctcg ctctgtcgcc     52140
caggctggag taaagtggcg cgatctcagc tcactacaag ctccacctcc caggttcacg   52200
ccattctcct gcctcagcct actgattagc tgggactaca ggagcccgcc accacgcccg   52260
gctaatttt gcattttag tggagacggg gtttcaccgt gttagccagg atggtctgca    52320
tctcctgacc tcgtgatccg cccgcctcag cctcccaaag tgctgggatt acaggtgtga   52380
gccaccacgc ccggctgaga tggagtcttg ctctgtcacc caggctggag tgcagtggcg   52440
cgatcccagc tcactgcaac ctccgcctcc cgggttcaag ggattctcct gcttcagcct   52500
cccgagtagc tgggactaca ggcgcacgcc accatgtcca gtttattttt gtattttag    52560
tagagagggg gtttcaccat gttagccagc atggtcacaa cctcctgacc tgattcgccc   52620
gcctcggcct cccaaagtgc tgggattaca ggcatgagcc atcgtgcccg gccagaacta   52680
cattttttaa ataattattt ttaagggaaa agtatggcat tcatcctctt gaatacatga   52740
tgtgccagat aatgtgagaa aactaaaatc caacatttta caataagcag attataaatg   52800
ctatgtcata aaaagagaaa ggatgcactt ttataagtct gtaaaatcat aactgtcttc   52860
```

| | |
|---|---|
| atgatatgat agcatagtaa ttatcatatg aaccacaatg gctcatgctt acaaaacact | 52920 |
| taatatgtga tcctttcaac aagcaagagt acgtgttatt attaccagca ttttatagag | 52980 |
| gaggaaactg aaaaacatag atgttaactc atatcctctt gatcactagc ttgttaatga | 53040 |
| cctcactggg atttttcatc caaggtggtc tggccctaga aactgtacag aatttagaaa | 53100 |
| attatgtaaa ataaaattct gaaaggtgta aagagaaccc acttgcagga ggagaaaata | 53160 |
| gccactctca gcatgttggt gtgttttctt tttgtgtgtg tgctttcatg catttattga | 53220 |
| ttaataaata aaatagtgac tgaaaatgta tgtgtgccaa tatttgttct agaaacatgc | 53280 |
| gctacagcac tgaatgaagg attcgaagtc cctgccagca tggaccatag agtctagtgg | 53340 |
| gagaagatag gtaatgcaaa ttttaaaagt acaagaaaac ttcaagccac aagtcttaga | 53400 |
| gtagaataag ggactaacat taacagggtt gtcaggaag gcctctctga ggagatgacc | 53460 |
| cttgggcaga gccctgaaag acacgaggga gtgagccaca cgaatttctt cgtgaaggag | 53520 |
| taaagcattt ggaacagagg acattgcctc tgcaattgtc caggtgctgg gactggatcc | 53580 |
| aaggtctgca aggagaccca tgtggatgga attgggtgag ggagatggaa tgtagcagag | 53640 |
| agctgcccag ggtcacgtcc ttctccccag ccgatatggc tcattcagaa actctcttta | 53700 |
| cacacccatc agcttccatt ccatgtttat tttattactt gtttgtttac tgaggaattc | 53760 |
| aatattccct tatccaggca gaaccgaatg tgcaggtgat actgctctgt ccactcccct | 53820 |
| tcacctttca ccaggcaaat ttccttgggt gtacttggaa gatgcattct catgggcacc | 53880 |
| cccgctggaa cctcatccca gcccagcctt gagggagctc agtagagctg ttgtcaatgc | 53940 |
| tcattctcca ttcttagtag acccagcaga acaagaggaa cctcaacccc aaaaccctcc | 54000 |
| acattggttc aagaagaaat tgaggtctct ccaggctgtt agtgaagggt gtggctgaac | 54060 |
| tctgccacct tgtgactgat tccatttctc ccttcccatc agatgcgtgg ttctccagaa | 54120 |
| actcttggga tgggaattta gttttcagga gatgctcatg acagaaccaa gaatgtggg | 54180 |
| gatgagaagc cacaaagaac ttttcaacat atagctaagc ccaaggatgt ccttaacaat | 54240 |
| gcaatggagg gcagatagtg agaagcaggc ctgagaatac tgtatatttc aagactgtct | 54300 |
| gagaagtagg gtggcaaaaa ataaataaat aaataaacaa gattgggtgt ggaaggaag | 54360 |
| agctaagggg ttaaatcaca cttaagaact aaggggttaa gtggtatgct ctatgcaccc | 54420 |
| ttcctccatg tagctcctct caattgcctg tgacttgcat ataacaaatc ccaagctcca | 54480 |
| atgagtccaa tatctccttc cttcatctgt ccactgggga tcaaaacttc tgcacatttg | 54540 |
| tgtactccta actcattggg aaatgcatct gccagaccct agtcaaatct gcatcctctt | 54600 |
| cccaacagca cactacaatc taccctcact gtcctcaagc tcaccctgtc ctatttcatg | 54660 |
| aggaaatcta gacaacgtga gaagtcgctt caatgttttg tccttttact gttcataggt | 54720 |
| ggttcctaga cgcagtctct ctgcatttgt gcattttatt aagtaaaaat acaactcttc | 54780 |
| caccaccaca tcacatctcc ttgtagacag caacttctc tcagctcatc caaatatcct | 54840 |
| tccaattgct ccctctctcc tttgtagact catgccctga atatacttag tgattttctg | 54900 |
| tactggcagt aacaacagtg ctctttgtca cacatttcct attctgtgct gccctaagcg | 54960 |
| tttcacaact tggggcacag atatgtagtt cccagactga tagtagagtg tagcagagtt | 55020 |
| aatcaaagtg ttttttacac tgaaatgaag tgtaaatgaa gttttttaca ctgaaatgaa | 55080 |
| gttttttaca ctggcacctt tattctttga ccctgtcata ttttgaagta gaatgtccac | 55140 |
| tttgggtaaa cttttaatat aaatcatcag atgtcaagga aatttcaggg gtaagcaggg | 55200 |
| tcattacagt ggtatctcca gttctatttc acagtgatga atcctctatg ccttttgggg | 55260 |

```
attctttgga taaaaggttt ggaaaggact tctgggttgg aagctaaaag ttccacacta   55320
atcataagat aaatatggat aaagcataaa attatcagac agcaaagagc cttgttgcta   55380
ctttaatccc ttctggatgt gatgcagaaa taggaatcta ctcaccatgg atggctccat   55440
tgaggaaatg gccgaactat taactaattt atattgactg cgtgttattt agcatgacag   55500
attagaatta caaggagtct gaaggaagtt gaaatccacc tgccaaatca ctccttcagg   55560
gctttcacta actgcataag aggagcacac caatggctga aagcagggct ggggaggtga   55620
agagtcatgg actcttttact caacgcaagg tagtggctag gggaaggctg ccatgataca   55680
ggacgctgag aaagaccttg tagggtgcac agatgctacc taagtgcaag gtggcagccc   55740
gtagggattt tgtgcagaaa aagagaactg aagcaatcct cccagggtgc acaaaagctt   55800
ccttgagtgc acatcaatgg gccgacaaag actagaggca gagaattagg aagaagaata   55860
atctcctaag gctacaggac aagccaggaa aagagctgga gagtaaagaa aactctccat   55920
tgaacaataa caacaacaac aacaaaacta gcaagtgggt ttaaagaaaa aaaatacaag   55980
caggagaaag gagaggacag caaaacacag agacagagag attccctata ttcataaaac   56040
ataaaacaag ccgctggggc taatgcatac agagatatct gaagtctctc tggtcttaaa   56100
tttgaagctc cgcttaaagg aatgtcttcc tctcaccctc aaactatgtg aaattctcag   56160
tgtggagctg aatctaagta tacttgcaaa aaaatatctt atctaactca accgcgtatt   56220
agattgtttc agtcccacgt attattggtc tgatagaaga aagcttgcac tttttctggg   56280
agtaaatatc actttcttca gtctctattt gttcatacac attatctcct gataaaaaat   56340
attaagaaat ataggaagag gcagaaaaat gtgaagcatg aacaagcaag aaaacaacca   56400
gtagaagaag tcttagaggt aatctcaatg tgtgaattgg caaggaaaaa ctttaaaaga   56460
actatgataa atatgtttaa gtatctggtg caaaaggtag acaagataca tgagcaaatg   56520
aggattacgg caaaaagata actacaaaaa ggacaaacag aaatgttatt aaagaaaaat   56580
acaacatcaa aatgactaat tcattcaata ggcttcatag cagactggat acagcagcaa   56640
gagagacaat cagggaacat gaaggcagaa tgaaaagcat ccaaattgaa acacaaagga   56700
agagagagag aaagagtgaa agcactgaag agccatgagg caatttaaaa atatagtcat   56760
aacacatttg taatcggagg tacaggacaa taggagagaa aataagcgag aagaattctt   56820
tgcagtgata atggccatgg attttgtaaa aatggtgaaa tgtattatcc tacctaccca   56880
atacgctcag tgaatcccag tcaggataaa tacatagaaa ctcgcgcttt tgcttatttt   56940
tgtccaactg ctgaaaatca aagataaaat cttaaaagta gctgaatggg agagaacatt   57000
acaatacagt gaaacaaaga ataatgatgt cttattgcaa ggagacaatg acaaaacatc   57060
tttgttcatt ttcaaattta ttttacttttt gaaattgaca gataaaattg tatatgttta   57120
tcctacacag catactgttt tgttttgcag tatatgtcta catacgtaga taacactgtg   57180
gaatagttaa atctagctaa taagaaatg cattatctca catagttatc attttttgtga   57240
tgagaacagt taatatccac tccgttaacc atttttcaag aaaacaatat atcaccatta   57300
actgtagtca ccattttgta caatagatct cttgaactta ttcctcatat ctaactgtaa   57360
atatgtatcc tttgaccaac atatccctaa ccctcccttt cttctagcca ctctagcctc   57420
tgataatcac cattctactc tctacttcta tgtgatcttt ttaaaattcc acatgagtga   57480
aatcatacag tatttgtctt tctgtgtctg cctaatccca tttaacgcaa tctcctccag   57540
attcatccat gttgctgcaa atcacaggac ttccttcctt ttatggctga atagtattca   57600
gctgtgtata taaacacatt ttatttatcc atttatccat tgatggacac ttaggttgat   57660
```

```
tccatatctt ggctattgtg aataacactg cagtaaacat gggagtgcag ctgtctcctt   57720
gacatcttga ttatattttt aaacatacgc ttagtagtgg atttactaga tgatatgaca   57780
gttcaatttt ttaattttg gagaaacctt catactattt tcattatggc tataataatt    57840
tacattctca ccaaaaaaat gtaatggttt tcttttctac acatccctgc caacatttgt   57900
tggttttttg tttgtttgtt tctgccgggg tgcatagtct ttttgataat agccattcta   57960
actggagtga gatattattt cattgtaatt ttgatttgca tttccctgat ggttaatgat   58020
gtcaagcact ttttcatatg cttgttgacc atttgtatat cttcttttga gaaatatcta   58080
tgtatgtatg ttgcccgttt ttaaacctga ttattgggat ttttgctatt caattgtttg   58140
aggttttttt tttttttttt tttttttttt ttagatggag tcttgctctg tcacccaggc   58200
tggagtgcag tggtgcaatc tcaacttact gcaacctccg cctcccgggt tcaagcaatt   58260
ctgctgcctc agcctcacaa gtagctggga ttataggtgt gtgccaccat acccggatga   58320
tttttgtatt ttttagtaga gatggggttt caccatgttg gccaggctgt tctcgaactc   58380
ctggcctcaa gtgatctgcc caccttggcc tcccaaagtg ctgggattac aagcatgagc   58440
caccacacca gcctctttga ggttcttata agttctggat attaacctct tgtcagatat   58500
ataatttgca gatattttct cctgttctgt aggttgtctc ttcagtttgt ggattctttc   58560
ctttgctgtg cagaagcttg ttagtttgat ataatcccat ttatctattt ttgcttttgt   58620
tgcttgtgct tttgaggctt atccaaaaaa tcagtgccca aaccaatgtc atagagcttt   58680 tccctatga tttcttctag tagttttata tttccaggtc ttacgtttaa gtatttcatc    58740
catattaagt caattttgt atttggtgaa tgataagggt ctaatttcat ttatttgcac    58800
aaggatatcc agttcttccg acaaccttta ttgaagagac tgcccattcc tcattgtata   58860
ttttggtacc tttgttgaat atcagttggc tctaaatgag tgggttaatt tgtgtgttat   58920
tcattctgtt ccattggtct atgtgtctgg tttaaggaaa aataggattg tctgtttata   58980
attctatatc caacaaaatt tctttacaaa atgaaagtga aataaagtca tcatcagaca   59040
aagactgagg ggatttgttt catgcagatc tacactatga gaaatgctaa ggaaagtttt   59100
tcaggctgaa agaaactgag aggtgatgga aacctggata tgcagaaggt atgaagggag   59160
ccagaaagta catgatgtgt gcatgtgtgt gtgtgtgtgt ttctgtgtgt gtaataaaac    59220
gtgccactag taggcattta caattattta atatgcatta tacgagtatg aagacatgtt   59280
atgtgcttag tctaattatc ttcttaaaag cacagtatga aaaacagctg aatcttccct   59340
tcattacacc caactgaatt taagaatga acaagaaact gccagaaaga acactgagta    59400
cccagatatg agtacagaaa ccccacatgc ctttctttct gattgtctat tatacaaagc   59460
ctccatagga ttactgggac acttcctcca gactagtgag taggatctag agataatcca   59520
ccactgccct gcatccactg tacaagatca tccaggtgaa tagagtgctg ggacccagtt   59580
tatcatttct taatccatta cctcaatgaa catggccact ttgcttactt cacttctgct   59640
ttggatgttg ccacttgagt ttccttttca tcaagtagcc aggtgctagt cattgcccag   59700
tgaatctcca ggtctctagg cttctcctag agatagctga aatgggttcc tagtcactaa   59760
tgcctttaat cagattttct catatggcaa cccactttt gccatatgct aaaatatatc    59820
cctccatgaa tcttaatgtt gcatctagcc tgcctctcct tcaagacttt gcaaaatgtc   59880
atattctctg caatgacttc ctgtttcttt atctccatag ctttcattac cttatagcat   59940
gtactacaat gtgcttgtta tactattgt ctctctccct atactagaat atgagctctc    60000
gaagggctga gattttttgcc tgtatgcttc aatgatgtat ttccagaacc tacaggactg   60060
```

```
cttgttatat agtaagtgct cagtaaattt tgcttaatga gaaggtatat acaatgtaca   60120
cacaattatg tttatattag tttaatatat ttgatataat atgctttaca tatattacat   60180
gcaaatattt atataattaa tattaaacac acacatatat ataatgcagg tagtcctcat   60240
tttgcgcaat agtgtgttga ctgcaactca tgcgtgtttt gctttgcaga agatctcagc   60300
taccacagaa ttgtgcaaag taagttacac ttttcctgtg tgtgtaaatg tcagttaaat   60360
attgttttgt ttaaagcaag gacttcatag acatagatag atagatgata gatagataca   60420
tagatggata cacagataga tacatagata tcttcatatg tatatataca tataattata   60480
taaaagctca ctggctatt t aaagtaaaag gaatagctac ctattgtggg gttttaaagc   60540
aaatatagat gtaaaataaa tgacaatgag aacacaacag ttgtaagaag tttaactgga   60600
attatacatt gtaaagctct tattaatgaa gtagatagta ttttt gaggt agacagcact   60660
aaattaaata tgtatattat ataatgtgta accattgaaa aaacaaataa gatataaacc   60720
aaaagccaat gcagaagata aaatggaata ctaaaatact taattagcca taaatgtgaa   60780
acaaatgata acacacagat aaaagaagta ccaatacagt caacttatac tctaccctat   60840
cagtaattac gttaaatgtt ccatgaaaaa tggaagacat ttctaaaata gatttaaaaa   60900
ttataacctc agtgcgatga ttaaatttat gtgtgaattt ggcccatgca gtgcccagat   60960
atttggttaa acattatttt gtgtgtttct gaaaggatat tcagatgcc t aatgtcctt   61020
ttaactgaga catcaggtgt tttcctgtct ttggattgga actgacatat tgactttttt   61080
atggttatga gcctgccagc ctttggactt aaactacacc ctcagccttc caagttctta   61140
gctcttgggc acatactgga actaaaccag tggctgtcct aagattccag cttgctgagt   61200
ctcacggtgt agattttggg acttgccagc ctccataatc acatgagcca attccttata   61260
atgtctttct ctcccttt ct ttcatatata tatatataga gagagagaga gagtttggca   61320
ggttgatagt taaaaggatg caaataaaca gaggacataa ttacaaagct taagaaagct   61380
ggggtggctc tgctagtatt agacaaagta gacttcaaaa gaaggagtat gagcagaact   61440
aaggagata t ttttgtgaga atgaagaacc aattcactaa aaagacatag tcacacatgt   61500
aatgtgtatg acctaataaa agagataaca ctaagttaaa ttgccaaact aaggagggaa   61560
aatagataag tctacaactg tgtttggaaa tgttaacata cttctttgag tgattgatag   61620
aaggaccaga ttttaaaaat cagtaaacat actgaagatg tgaacagtat gttcaaccaa   61680
ctagacctag gcgacattta tagatatatc tcactacagc agaatgcatt ttcttttcaa   61740
gtgctcacag aatattttaa acagactcaa tgctgggcat taaaccaggt tctaatataa   61800
aaattattca agccgaatcg ggcatactct tatcataatg gtattatatt cataattaat   61860
attattaaaa tttgtataaa atatcctaat gtttggaaat taaaccaaaa aataaaaaca   61920
gcccatgagt caaagaagaa atcacagtaa aaattatatt ttgaaataac tggccgggcg   61980
cggtggctca catctgtaat ccagcacttt gggaggccga cgcagatgga tcacgaggtc   62040
aagagatcga gaccatcctg gccaacatgg tgaaaccctg tctctactaa aaatacaaaa   62100
attagctggg catggtggcg ggtgcctgta gtcccagcta ctcaggaggc tgaggcaaga   62160
gaatcacttg aaccctggag gtggaggtta cagtgagcca agattgcgcc actgcactcc   62220
agcctggcaa cagagtgaga ctctgtctca aaaataaata aataaataaa taaataaatt   62280
attaaaaaat aacaaaccat aatgtgtaag atgctgctat aatagggcta agagataact   62340
ttatagcttt aaatatctgt actacaaaag agaatatatt taaaatcaat gacataagct   62400
tatacattaa gaatgcaaaa aacaggatta aaataaaaag aaactagaaa aatgtacaga   62460
```

```
atagcgccag gcgcaaggta gctcatgcct gtaatccagc actttgggag gctgaggcag   62520
gcggatcacg aggtcaggag atcgagacca tcctggctaa cacggtgaaa ccccatctct   62580
aatataaata caaaaaaatt agccgggtat ggtggtggtt gtctgtagtc ctagctactc   62640
tggaggccga gggaagagaa tggtgtgaac ccgggaggca gagcttgcag tgagccaaga   62700
tcgtgccact gcactccggc ctgggtgaca gagcgagacc ccatctcaaa aaaaaaaaa   62760 aaagtaacct gcacatggat gtttataaca ggtttgttcg taatggacaa atcttggcag   62820
caaccagggt gtccttcatc aggtgaatgg gtaaataaac ttcggtacat ccagacaatg   62880
gaatattatt gagcattgaa agaaatgag ctattaagct ataaaaatat atggaagtta    62940
actaaaatgc atgttattaa gtgaaagaag ccagtctgaa aaggatacat actatatgtg   63000
tccaactagt ttacattcca gaaaagataa aactatggag acagcacaaa gatcagtggt   63060
tgccaggtat ctgcagggga ggggagggga tgaataggta gaacatggag gatttgggag   63120
ctaggaaact atcccgtgtt atactataat ggtggatgta ttacattaga catttgtcaa   63180
aacacagaat gtacaatacc aagaggaaac ttaatgtgaa ctccagactt tgggtgataa   63240
tgacatgtca attgatgttc atcagctgtg agaagcatac aattttgctg gaggacgttg   63300
acattggggc agatcgtgtg tgtgctgggg gaaccaaggg gtgtatggaa acttgctgta   63360
gttttggctt aattctgctg tgaaccaaaa actgctctac aaaataaggt ctatttgata   63420
agaagaaaaa catgagttac caggccacaa aattaggaat attaaatgtg tattgctaag   63480
tgaaagaagc caatctggaa ggctacacat tttatgattc ccactacata tgatattctg   63540
gaaaaggcac aactatggag aaggtaaaaa aaatcaaaat ttgccagggg tttggtagga   63600
gaaagcacag gttttttagg gcagtaaaat tcttctatat aataatgcaa tggtggacac   63660
agaaatctgt tatcacacaa ttgtgataac ccatttatca cacaattgtg tgaaaaccca   63720
taaaatgtat acataaagag tgaatactaa tgtaaactag ggagttcaat taatgatatt   63780
ggctcgttga ctgtaacaaa tataccgctc taacgcaaga cattaaaaat aaggggcatt   63840 gccagggggta gggggacagg gatggtggga gaggagaggg gatacatgag aagtctctgt   63900
acttgcctct cattttttct gcaaacctac aactgcttta aaaataatc cattaattaa    63960 aaagaaaaga cacaaacaaa actcacaata aatgacatac catttctcat ttactgaact   64020
gcctaaaata ctgaaatgcc taaaataaaa atggctgact gactgtatca atttgcaat   64080 gatgtggatc cattggaacc ctcatatttg ctaattgcag tgtaaaactg caatcaccat   64140
ttcacatcca gttgaataac aaaaatcaaa aaagactgac actacaaaat tttgcaaggt   64200
tgtcaagtac ctggaattcg tatgcattct taattcttaa cattattctt atgttagagt   64260
gtaaaatggt ctaacccaac tatggagaac tcttacagtt tcttataaac agccgtctat   64320
cctatgaccc agacattcaa ctcccaggca tttacccaag ataaatggaa gcatatattt   64380
acaaaaggct tgtaaaataa tttgtaatgc agccttttc tcataatagc atcagatttt    64440
aaatgtctca catgccaaca ggtaacagat aaattatgga gttataaata caatggaata   64500
cttttcagca tagaaaatag caaacttcca atacttgcaa catatttaca ttaaaaaatg   64560
ttgaacaaag gaatattgac ctctatctgt gtgtctttct ctctccctcc ctccctccct   64620
cctatgctga ttccatttta tgaattttta gaacaggcaa aataatctag ggtgagagaa   64680
ataaggaagt gtatgttttt ggagatagaa taattgactg gaaaagggtg cacagtaatt   64740
ttctttgata ataaaactat tatttatatt gttttgagtg ttaattactc agtggcaaag   64800
ctcattaaat tgaatacttt agatctgtgc atgttgttgc atgttaatta tatctaacat   64860
```

```
attttaaaag gttttggcag ccctggtgta atggtaagag tgatgggctg ggcacagtgg    64920
ctgatgccta cggtcccagc actttgggag gccaaggttg ggggctcact taaccccagg    64980
agtttgaggc cagcctgagc aaaatagtga gacccccatcg ctacgaaaaa caaacgaaca    65040
aaaatcacct gcgtgtggta tggcctgtct gcagtctcgg ctactcagga ggctgatgca    65100
ggagaatggc ttgagcccag gagtttcaga ctgccgtgag ctatgatcat accactgcac    65160
tccagtctgg gtgagagagc aagaccctgc ctggtggtca gcggcaaaaa gaaaaaaaaa    65220
gaatgcaagc tctcacaacg aatagattgg gatttaaatc tgaattctga tatgtattgc    65280
tagatcttct gagcctcaaa ttcttgccat gtaaaatcaa gccaaatact tatgattttt    65340
gtgagaaatc aatgaataga gtctattata ctctgaggat ggtattttat caaataataa    65400
attgttgata actagtagtt acactatttt aatccttcca attctttgtt ttcaaacctc    65460
atacttatga tatctcctat gcttttttaaa taattttttct acttagactg tctatctgga    65520
tcacatgaat ctttcacagc ctcaggtttg ttttctttct tttcactgct acaatcagca    65580
tcacagctcc cctcaccccca tgttccaagc agaagtgagt atttgattat tttcatcctc    65640
tatgaccaat atgaggttta acaatgcaa caacaacacc ttattgtact aaaaaaccat    65700
atgaatatcc ctatatgact aacaatagat tcgtgaaatg tccctatgtg actaacgata    65760
gattagatta atgtccctat gtgactaaca atagatgtaa ataggacttg catcagattt    65820
ttctctgtag tcttatctat agcacagtgc tgggcatata gtgaatgctt aataaaaggt    65880
atttcataaa taagtaattt tagagtttat gaaaatcata actgattttg ttactcactt    65940
atgaatattt acacaaagtc taacagctac agaagattgg aagacaggca gttctggtgc    66000
taatcttacc atttcatttt gtagctcctt agtgaccact caatgcgagc tggggatacc    66060
aaggtgagca aaacaggctc ccgtctgctc ctagttccgc aattttccta ctcccatcac    66120
aatacttcag ttctcccttc cctgttttta aaaatcattt tgtatactgc tgttatatac    66180
tgacgtaagc cattaaaagt cctttctaat tagggaacag aggccaacat ttcatggatg    66240
ttttgtatgt ttttcccttt tgttttctac tcaccttgaa ttttcaagct gtttcatata    66300
aaagtgagga aagggaattt tgacaacact tggttcaaag gtgttgagga ggaagaacat    66360
atgcacagaa agggaaagag ggcttcagga agcaggaagg tttcacagga gtgatttggg    66420
aagacccaac acttgtggtc taatgcctca ctagactcag ggcaatatta tgttttgctg    66480
tgattaaggc agtcagtttt caaaaacgac ccgtatgtcc ctgtttcctc aggtgaattt    66540
tgctcacaag taatttgtaa atagctaggg agagccccag gaacagcctg ggtctgagag    66600
cactgactat ctgaaataag cagatgtttc ttccagggag aataaactgg gtttaccctc    66660
tttacttgtt cctatagaat caatggatac ataatctctg attttcccct gccggttaaa    66720 gaatgttttcc aagcagtggc aatagtgctg gtgtagaagt tattcatctt ccatttctaa    66780
ctactcctac gcacctgttt ttcctttgt ataatacctaa atcttttctt tctggctttg    66840
gtgttgcctc ttaacataaa ccggacctct tttcatagaa cagattcggt gggagttgac    66900
actgtatgtc agtgctattc actgacctcc aacatcagtg agaatagcca gaccctagtg    66960
ggagccattc attgtgtggg atgaccaaca gcatggtgga cggcaggata aacctgtcat    67020
aattcccgaa aataaacggt tagtgggaga acttaatctc tgtgtagttt atacatttgc    67080
attagagtgg aaaaaaagta tgctttagaa atgcccctagg ctaaaaaata aactgatttt    67140
tccaaagcca tccatagcca gtaacagcca tgtagcagag ttgataatag caggtcctga    67200
gggttaggca tttagagttt gtccttctac agtgtttcca aaccccatg aaactgagaa    67260
```

```
atcctgtgtg gatctgggcc attaacccaa gggagaaacg aaaaccatga aacacggtag    67320
tatccattct gcagaagctt tttgtgtgct gtggtagatg gccttctctg gggatacaca    67380
ggagtgatgt ccagtagtcc acccttatcc ttggggata tattctgaga ccccctgtg      67440 gaggcctgaa actggaaata gtactgaatc ctatatgtac tacgatgttt tcaactgata    67500
gccgagacag ctactaagtg aataacaggc gggtagcata tacagcatgg atacactaga   67560
caaagggata attcatgccc caggcaggac gaaacagaac aatttcataa tactactcag   67620
aatggcatgc aatctaaagc ttataaatta tttctggaaa tttccattta attttcgga    67680 ctgcatttga ttgcaggtaa ctgaaaccac acaatgtgaa actgcaggca caggagtgct   67740
actgtattcg ctacctgctc attaaccact tagtagctgc ttcagatatc agatctacca   67800
tcggtttccc agtgtttgtg ttcaaggaac ccttgtttta cttagtaata gccccaaaat   67860
gtaagaatag tgatcctggc aatttaggta tgccaaacag aagctatgaa gtgcttcctt   67920
gaaggaaaaa ggtgaaagtt cttgacttaa taaggaaaga aaaatcgca tgctgagatt    67980 gctaagatat atggcaaaaa caaaactatc tgtgaaattg tgaagaagga gaatgaaagg   68040
gatacatggt atatataagg tttggtgctg tctccaggtt cggcatcga gagttttgga    68100 atgtatcccc tgcaggtaag gtgggggagg ctactgtatc atcaagcacc cttaaaaatc   68160
tgactgtttt gaaaagagtt tcctgggaat aacaacatcc cttaagtgtc cagaaaatca   68220
ctgaaacttt accccccaaat tcttctatta ttgtttaagg caataataac attgggagtg   68280
tgtacatacc ttctcttggg tccataaatt accaaatttg aggaccctg gctaaggta     68340 cctgggaagg agtggggtgt acccttcatc gtcctcatct gccccctggt ggcacgtttt   68400
gtcactctgg actcctgccg taggctgcca acagcctatt taaacgaaac atccttgata   68460
tttagtgctt tgtatatttc cagaaagctt ttcaattact gagattatca cttcctctca   68520
ccataaagtt gtatagcatt gcccaataat actattgtca tctgctttat ctgttaatac   68580
ttgatttgtc tcatatttaa actgattttt gtcacgagaa gtttccccag aaatttttt    68640 attctttgcc tgttttttcct atatatccaa atatatcaat ttttgatcta tttatatacc  68700
cattttgtta tcttcaggtg cgttatttgg ttttcatttt ttaaatttct ttcccattct   68760
gcagatgaaa aatactgaga aacctactct gttcctgcat ccgagccatt ccacaggcag   68820
ttttcccata ctaaaaatgc tgtcttccac tgatgtgtgg catgtctcag ttccgtgact   68880
tcttttcctc tctctctact cgctgctgtc cttttctcc atgtgtctct aacatgcctg    68940
tgttcttcaa gacctagtgc aaccacattc cctcccacaa ctctatttc atgaggaata    69000 gccaagcagg actcccaaga catcatacag gagtgcctac agggtatctc tccttggcag   69060
tcccacagca ccgcaaatgc cctgtgtctg ccaatactca tcagcctctc ttcccgtgtg   69120
cctctcctgg gaccctaaga gagtaacagt ccctgcaact tcccactttc tccaggcagg   69180
gacttgtgtg cctttccat gtctttgact cctttattca attataatac aggtatctgt     69240
ctgctataac tcctggaact ctcttatgta aatgcgcttt tttcattctc cgcctcacat   69300
cttagcccag accacaccat ctcccccgc cgccttggat accttccatg tttccagtgg    69360
tctgctccca ctccacactg cagtacagtg atttttctaa aacatggatg ggttcctgtc   69420
actcccctgt gaaaagtcat ccatgtggag tctgactggt ctgcatttgg ggactggaca   69480
gagtgagaag ggatcctgtg tcagccagga ctccggtaga cgcccctatg caatatccac   69540
ttgtggtggt cggggcggg gaaggggcgg gattgagccc ccttcccccc tcctccttac    69600
tgcggaaagc tgcggagcga gcagcactca cttcctattc agcattcagc agggagggag   69660
```

```
cctctgaaca gccacgtagg cattctcttc tctctggagg aaaaggccca gcagctgtcc    69720
gaggaaaaga cccaccagct gtcagcaaag ggacatgtcg cagctaagta agaatctggg    69780
tgactcgagt cctccggcgg aggccccgaa gccgcctgtc tatagccgcc ctacggttct    69840
gatgcgggcc ccgcccgctt cctcccgggc tccgccagtc ccttgggatc cacctccaat    69900
tgacttgcag gcttcattgg ccgcttggca ggcacctcag cctgctggga aggccccaca    69960
gggccagctg cccgccccgg tggttccgat gacccagcct cgctgcccct aggggggccc    70020
atagtcccgg gctcccccgc tgggggggccc gatgggtaag cctccgactc ccggggtcct    70080
gatggtgcat cctccacctc cgggagcccc gatggcccag cctccgaccc cgggagtcct    70140
gatggtgcat ccttcagctc ccggagctcc catggcccat cctcctcctc cggggacccc    70200
aatgtcccac cctcccccctc cggggacccc aatggcccat cctcctcctc cggggacccc    70260
gatggcccat cctcctcctc cggggacccc gatggtgcat cctcctcctc cggggacccc    70320
gatggctcat cctcccccctc cggggacacc gatggctcat cctcccccctc cggggacacc    70380 gatggctcat cctccacctc cggggacacc gatggctcat cctcccccctc cgggtacacc    70440 gatggcccag cctccagctc cgggagtcct gatggcccag cctctgactc cgggagtcct    70500
gatggtccag cctgctgctc cgggagcacc gatggtccag ccgcctccag cagccatgat    70560
gacccagcct cagccttcag gagcaccgat ggccaagcct ccaggtccag gagtcctgat    70620
gattcatcct ccaggtgcga gagctccgat gacccagcct ccagcttcag gagcaccgat    70680
ggcacagccg gcggcccccac ctgcacagcc gatggcccca cctgcacagc cgatggcttc    70740
ttgggccccg caggctcagc ctctgatcct gcaaatccag tctcaagtta aagggctcc    70800 tccgcaggtt ccccagggcc cgcaggcacc cccagcgcag ctagccacac ccccgggctg    70860
gcaggcgacc tcgccaggat ggcaggccac gcagcaaggc tggcaggcca ctcccctgac    70920
ttggcagacc acgcaggtca cctggcaggc accagccgtt acctggcagg tgccgccgcc    70980
catgcgccag gggcccccgc ccatccgccc tggcccacca cccatccgcc ctggcccacc    71040
accggtgcga caggccccac cgctgatccg ccaggccccca ccggtgatcc gccaggcccc    71100
acccgtgatc cgccaggccc cacccgtgat ccgccaggcc cccgctgtga tccgccaggc    71160
cccacctgtg atccgccagg ccccacctgt gatccgccag gctccacctg tgatccgcca    71220
ggccccgccg ctgatccgcc aggcgccgcc gcccatccga cctgccccac aggtcctggc    71280
cacccagcca ccgctctggc aggccctgcc accccacct ccactgcggc aggccccgca    71340
ggctaggctg ccggccccgc aggtgcaggc ggcgccgcag gtgccatacg gccccacctg    71400
ctacgcaggt acccgcggcg ccgcccgctg gccgcaggt gccccagcct gtgctgccgg    71460
ccccgctgtc tgcccactg tctgcccccgc aggctgtgca ctgcccttcc atcatctggc    71520
aggcccccaa aggtcagccc ccggtgccac acgagattcc aacgtcaatg gaattccagg    71580
aggtgcagca gacacaggcg ctggcctggc aggcccagaa ggcccccact cacatctggc    71640 agccccctgcc tgcccaggag gcccagaggc aggctccccc cttggtccag ctggagcagc    71700
cctttcaggg agccccgccc tcccaaaaag ccgtgcaaat ccagctaccc ccccagcagg    71760
cccaggcatc gggtccgcaa gcggaggtgc ccacactgcc gctccagcct tcctggcagg    71820
caccgcctgc agtcttgcag gcccagcccg gaccccggt agcagcggca aattttcccc    71880
tgggctccgc taaatcattg atgactccat caggagaatg cagggcctct tctatagacc    71940
gcagggctcc tctaaagagc gcaggacctc ctcgaaggag cgcagggccc cttcaaaaga    72000
ccgcatgatc tttgctgcca ccttctgtgc tcccaaggca gtgtcagctg cgcgagcaca    72060
```

```
cctgccagct gcctggaaaa acctgcctgc cacaccggag acctttgctc cctcctcaag    72120
tgtcttccca gctacctccc agtttcagcc tgcctctctg aatgccttta aaggcccctc    72180
tgctgcctca gagacccccaa agtcactgcc atatgctctg caggatccct ttgcctgtgt   72240
agaggccctg cctgcagttc catgggtccc acagcccaat atgaatgcct caaaggcatc    72300
gcaggcagtg cccaccttcc tgatggctac agcagctgcc ccccaggcaa ctgccaccac    72360
tcaagaggcc tccaagacct ccgtcgagcc gccacgccgc tccggcaagg ccacccggaa    72420
gaagaagcat ctggaagccc aagaggacag ccgtggccac acgctagcct ttcatgactg    72480
gcagggccca aggccctggg agaatctaaa tctgagtgac tgggaggtcc aaagccctat    72540
ccaggtctcg ggtgactggg agcacccaaa caccccccgt ggcctgagtg gttgggaggg    72600
ccctagcacc tccaggatcc tgagtggctg ggaagggccc agcgcatcct gggccctgag    72660
tgcctgggag ggcccgagca cctccagggc cctgggtctc tctgaaagcc cagggagctc    72720
tctgcccgta gttgtgtctg aggtcgcaag tgtctctccg ggatccagtg ccacccagga    72780
taattccaag gtggaggcac agcccttgtc tcccttggat gagagggcaa atgcgttggt    72840
gcagttcctc ttagtcaagg accaagccaa ggtgcctgtc cagcgctcgg agatggtgaa    72900
agtcatcctc cgagagtata agatgagtg cttagatatc atcaaccgtg ccaacaataa     72960
gctggagtgt gcctttggtt atcaattgaa agaaattgat accaaaaacc acgcctatat    73020
tatcatcaac aagctgggct accatacagg gaatttggtg gcatcctatt tagacaggcc    73080
caagtttggc cttctgatgg tggtcttgag cctcatcttt atgaaaggca actgtgtcag    73140
ggaggatctg atctttaatt ttctgttcaa gttagggttg gatgtccggg agacaaacgg    73200 tctcttttgga aatactaaga agctcatcac cgaagtgttt gtcaggcaga agtacctaga    73260
gtacaggcga atcccttaca ctgagcccgc agagtatgag ttcctctggg gccctcgagc    73320
attcctggaa accagcaaga tgcttgtcct gaggttttttg gccaagctcc ataagaaaga    73380
tccacagagc tggccattcc attaccttga agcgctcgca gagtgtgagt gggaagacac    73440
agatgaggat gaacctgaca ccggtgacag tgcccacggc cccaccagca ggccccctcc    73500
ccgctaatag gtgtagcaga gatctcgctc ctgtgtttcc ctggccagag gccactgaca    73560
gggtgggggg acatttttgt tcctggtgtt tgtgttccag ttccacgagt gtaagtttgg    73620
attttcaact tggtttcgta tctgccaaag cttttgtacat tttttatgtg gtgttgattt   73680
caatcggcta ctgttctgtt ctgtattttg gcatctgtgt tttttaagtga gatctgtggt   73740 tctctgttttt gtgttataat tgttatgttt tggtatcagc tttgtgctgg ctttgtgaaa   73800
tgaattgaga agctatccat ctcatttctg gtatagttca tgtagcattg taatcggttg    73860
ttctttgaac gttcaaatga ctcatcagta aaaactgtct acagagaagt aaatatctat    73920
atctatatat ataaatatac tttcagcata acagaagtgt ttgtctttat tctaatttt    73980 acactagatg gtgaagcca agttttgccg tattctctga atagacatga atagcaagac    74040
tactctcagt tatagtaaaa accacggtga tggaattgtt ttccaaggag agtactccat    74100
tcatctttat aaggatgcag tgatttcagt gggtggttat acataagatt tctccaggag    74160
attaattaaa gcacacacgt tagtgcccag ctggtaacgt tgttattaga agcagaaatg    74220
tccttaaggg tatgtggaga agaagggcca tctgcctgca ggactacaaa taaccaggtg    74280
gtcccgcttc atggagaatt tggccaaaag ggtatttgtc aatcatgtgg cccgtggggg    74340
ggtgtccagc agttcaaatt tgggtttcat caacacactg ctaccgggat ggaaacgtgc    74400
tccctgcagg atatccaggc ttataacagg gaaaaggaaa aaacagtctt catttaatta    74460
```

```
gaaaccctgc agattgccag cagtagtggc tgggttaggg gagggcgtgg cagggtgcat    74520
tcctatcaac atagagttct aggggaaggt cctgggggga agggtcattc taacttgtag    74580
gggaaggcag ccggcaacgc ctgaagttgc tgaacaaccg cggtcagccc ttggctatga    74640
acctggtcta ggcaggaaag ggacaaggga atgaactggc ctgagtgttt tgaggaagga    74700
tattcaagca cacaccaggc tggtgtacac aaaaggacgt tcttgtggtc atactctctt    74760
cctgtggaca ggggaccatc agccctactt gccaccgcat actgtcttat cagaaggaag    74820
aaatccaatc ccatatcccg cttctagggt gaagccaaag tcccagatgc ggttagtggc    74880
gatggtggaa ttctcctgcc acctagcggc agattagagg tgccaccgca gctgccgcag    74940
caacagcccc tcccacagtg cttaacttca caaccatgta tatacttgga ttgcagctac    75000
tccttgcttc accactttg ctcataattt tatctatatc tgtgcccaga gattccttct    75060
tttctcttat aggccaaggt agcatctgtt ttcaagtcca atccgctctt cactcaacaa    75120
tttctatcct tggtcctgca gcgctgccac ttaggaagct gactaggaga ggagcccaca    75180
agatgcagac tctactccta gcacccgcag aactgagctt ccaggacga tgatccccgc     75240 cccaggacct gccaggccgc aggagctctt tctcaagttg tctaagtggt caggtagtcc    75300
aaaaactggg aggcagtttc ctataaactc cttgggtcag agagtcctgc gcatttgtcc    75360
gcaagcaatg tttacttatt tttacaacaa cagcaaatgt ccattgaagg agacagcaat    75420
gccccagctg agaactgtcc ccaaaggagg tttagctggg ccagtaaagt ggcatattgg    75480
tctagtattt cttgttttgtg tttagtttat ttatgattgc ttataaagtt ttctccagac    75540
cattaactca tggcgtgcct gagcaagatg ctctttgtgg aacaaaattt gggactttgt    75600
tccaaatttg ggacttttgtc ccatcatggg actttggtgc catacttaag gtggggggctg    75660 gctctgctcc atggtagaga ggcttacttc ccagctgcaa acctccctct cacacgtgac    75720
atatatctaa tggccttctt taagtaatgc caaggactta aagcctaaat ttgttttatat    75780 tgtaatgaga tataaattgc aacaatgaaa aatgtgttca ttaccaatga gtaaactagt    75840
tagatattca actgaaaagt ttaagaaagt gcagctaaca tgacagtgaa aagcagaaaa    75900
caaagaccag caatatagaa aaatacaggt taaaaaacag cgggaactgg ccgggggtgc    75960
ggtggctcac gcctgtaatc ccagcacttt gggaggccga ggagggtgga tcacaaggtc    76020
aagagatcaa gacaaccctg gctgacaagg tgaaacccca tctctactaa aaatacaaaa    76080
attagccggg tgtggtggcg agcgggcacc tgtagtccca gctactcggg aggctgaagc    76140
aggagaacgg catgaatcat ggaggtggag cttgcagtga gccgagatcg caccactgca    76200
ctctagcctg ggcaatagag tgagactctg tctcaaaaaa aacaaaaaca aaacaaaaa    76260 caaacaaaca aacaaacag tgggaacgaa ttcaaatccc acttatttga aagtgctaaa    76320
atgtagaaaa tgtagaaaat gtaacacaaa tcttttttac tataaaattg agcaaaaagc    76380
ccaaacctag taataggcaa aatgtatcac aggaaaaaaa tggcaaataa ctgttgaaac    76440
tgttacacct cactaataaa gatagaaata ttaaatctgt attccagttt tcatttatta    76500
aattgtcata gaataaacta aaaccccatg taatgtccaa tgtcaatgat attgttatga    76560
aactggaacc attatacaca accagtgaaa gtataagtta ttacaatttg cctggaaatc    76620
aatgcagcca actctgtctt caaaaggctt taacatggta atactatttt acctagaaat    76680
tcttcatttg ggaatatgtt gaatgagaac aatccacaga gaaggcaaag acttcttcat    76740
agagaaagct gttcatgaac atatgggaaa tttatcaggg tgtgagcagg ccccctccc    76800 caatataaac ctacagtgtc aagggagtac agtgagtttc tgctgaaaaa accacaggct    76860
```

```
tcctcagaaa acaacttgta gtttgtttca acacacagaa aatgaaagac tcagcatcca    76920
ccattatggg ctgtagagaa gtcattgcac tctgtgcctg aaaattttaa aactaggtgc    76980
tagcacactc tccaaagcca taaatgacct cagtaaaata tatgatttct agtgaagaaa    77040
aactatagtt ctcaaagtga tgaaattcaa tgtgctccta tgtcgagtgt tcaactataa    77100
gcaagttaat attttaggat atttgtctta agaagatgat ctgaattttg gaataatttt    77160
actcaaagac attactcctg agagcaacag agaaaaggac cggttgtttc tcaaagccac    77220
cagtgaatca accttgtcag caaacgagag ttaaggattg tggctgcaat tgacagagga    77280
cttttcaagat taaggggccg gggccctgtg gccgcagtaa tatccatttt actgggcatg    77340
tagcctatat tattgatttg ccctcagagt tataggcacc cccagaactc agcaattcac    77400
cccgatggtc atgatacttg aaaggataca tcattcttgc actcctgccc ctagctgccg    77460
gggctggaag cctgggtccc ttttttctctc tgatttgatc ggttgtcagg tcttgcccgt    77520
tttgccaatt tgtatgtcag tgttttttct cctctccatc cctgtggaca cggcaccctg    77580
ccagaacttg gcagtttcct ttttcatggt ctctgccttc agtactgccc cttaatcaaa    77640
cctccacatt ggctgcacag gggctctgt gccgccgcca cacagctgtg cacacctcat    77700
aatgcctctc cctgcctaaa gcatttcaag gccttcagtg ttccttagag taaggtgcag    77760
caaccctcag ctcaccttcc acacgtgagg gtccaggagc ggctggttag agtaggttta    77820
cctacagaga aatctacaga ccatgccagg ggtccctctg tgggacagct caaagaattc    77880
ctcggattct gaattgaaag cctaagcaga ccaccaggag ggtcctaaag ggaaaaaggc    77940
cttgatatac agggcccaag ctacattttc ctgtgtgcaa gcaaatttgt tctttcggat    78000
ctcccagagg gttccattgt gaattccacc aagggatata taacaacacta ctagcacagt    78060
aagtagtaca atcctctaat ctgtcgagat tctgaaagtt gtacctgcct cttttttaaga    78120
gatgacactt acgaggagcc ttcttcatta tcagcttcct cctactctta ttagtgacgc    78180
taaatagatc atcctggctg tgtcagcggc atgcgcttct ctgtgcaaat ggtctggttc    78240
tgcaagctgc ccattcacct cccaatgaga cttgctttct gtgctatccc ttgttctgag    78300
tgaattcagc ttgtgagctg ctgttaacag aagcaatcac cacagaacat tttctagacc    78360
caggagactt cctggagctt ctctccaatg gctcagaatc ttcccctgaa acagccagct    78420
ggatggggcc acaaagctgt ggaatcaaaa tattggcctt gtaacaagct tctgcgagaa    78480
agcctcaaaa acattctgtt ttgaaataat catagattca caggaaatag caaaaactgt    78540
gcagggtagt ctcatatacc cttaacctag tttccccccag tgtttatatc ctgtatagct    78600
gtagtacaac atcaaggacg tggacactgt accatctgca cgttcagctc aactcaatgc    78660
catcttatca cgtgtgtaga tagtgtaact agcactgcaa tcaagatgca gcactcttcc    78720
accaccacca agatttctcc cacgctactc ctttacagct gtgtccatct cttcccccca    78780
catccttaac ctctggcaat cactactctg atcttcatct ccataacttt gtaatttcaa    78840
gaatgtgctc taaaagcatt aatacctttg agactggcgt ctttcactga gtatcatgcc    78900
ctcgacatcc atccacactt tgtatcagt cattcatttt ttgatgctaa taaaatattt    78960
actgttttgt gggattggct atttccattt tttagctact gcaaagttgc taggaacatt    79020
taagcgcagg tttttctaag gacacacatt ttcattgtc tgtggcaaat gcccatggcc    79080
ataattgctg tatcatttga taggtctatg gttacttatt caaagagcct ttcaaactat    79140
tttccagagg gactgtaaca ttttacattt ccaccagcaa tgtatgagaa caaatttctt    79200
tctttttttt tcttttcttt tttttttttt tcttttttg agatggagtc tcactctgtc    79260
```

```
gcccaggctg gagtgcagtg gcgccatctc agctcactgc aagctccacc tcccgggctc   79320
acgccattct cctgcctcag cctcccgagt agctgggacc acaggcgccc gccaccacgc   79380
ccagctaatt ttttgtattt ttagtagaga cggggtttca ccgtgttagc caggatggtc   79440
tcgatttcct gacctcgtga tccgcccgcc tcggcctccc aaagtgctgg gattacaggc   79500
gtgagccacc gcgtctggcc ccagaaatcc aatttctctg caacctcacc agcaattgat   79560
ataatctttt tgttgttgtt gttaattcgg ctgtcctaat aggtgtgtgg tgatatggca   79620
ttgtggtctt aatttacatt cctcttatgg ctggagttgt cgaacatctt tctgtcggct   79680
tctcatttct atatcctcat tgataaaatg gcttagtttt tctaagtgac ttttttttt   79740
ttttttttga tggagtcttg ctctgtcgcc caggatggag tgcggtggtg ccatcttggt   79800
tcactgcaag ctccacctcg tgggttcaag cgattctcat gcctcagcca ccagagtagc   79860
tgggaccacg ggcgcacacc actatgcctg gctaattttt tgtgttttta gtagagatgg   79920
ggtttcacca tgttggccag actggtctcg aattcctggc ctcaagtgat ctgcccgcct   79980
cagcctccca aagtgctgag attacaggca tgagccacgg tgcccaggct ctaagtgagt   80040
ttttttaaaa atgtattggg cttgagaat gatttctata ttccggatat gagtccttta   80100
ttatatatgc attttgcaag tcttttcccc agtgttgagt gtggctttcg ttatcataac   80160
cgggcctttc acacagcaaa agttttaaat ttcgatgaag tctgattgat tttgtttttc   80220
tttatgggt catgatcatg gtgtcatata tatgtaagta ctcttcatca gaccccaggt   80280
gccgaagatt ttctgttatg ttttcttcta aaaatgtaat cgttttatgt tctgtattta   80340
aatctatgat cgattttgag ctaattttga ataaggcgta agtttaggc tgagattctt   80400
tctttgctgt gtgtgtgtgt ttgtgtttgt gttttgtttt gttttgtttt tgcctttgga   80460
tgtccagtgg tttcattaac attttaacat ttgttaaaaa tactatatac tatcctttca   80520
acattgaata ttttctttg cacatttgta aaaattcagt tagccctatt tacgtgtgct   80580
atttctgagt tctgaattct atattctgtc ccatttgctt gataagatag gtatttaaaa   80640
gatagatata gatatgtgta ttatacagag atatatccct ccaccaatgc catactgtcg   80700
tgattattgc agtcatataa taagtcttaa aattgagtat agggattctt cccatattct   80760
tttttcaaaa ttatgtttag ctattctaga tcttttgatt tttcacataa attttaaaat   80820
aagcttgcat atatttacaa aatgtcttgg tggaattttg ataggaattg agttaaactt   80880
gtatattaag tgggggagaa ctgacattta ctgcattgaa tcttccaatc cataaccaca   80940
gtatatcgct ccattatt ggatcttttt tggtttcttt catcagcact tgtattttc    81000
agcatacatg tcctatacat gcttattaag tttataagta tttaaaaata aataaggttt   81060
attttgagt gattgtatat tatattatat taggtgagct tatcttatta tattatatta   81120
tgttttttga aatggagttc cagttttgtc acccaggctg gagtgcagtg gcacgatctc   81180
tgctcactgc aacctctgcc tcccaggttc aagcaattct tctacctcag cctcctgagt   81240
agctgggatt acagacgcct gccaccacgc ccggctaatt ttttgtatt tttagtagag   81300
atggggtttc accacattgg gcaggctggt ttcgaactcc tgacttcagg tgatccgcct   81360
gcctgggcct cccaaagtgc tgggattaca ggtgtgagcc accatgcctg gccctatatt   81420
atattataag ttttagtttc cacctgttca actcaaaact caaaatggtt gagttttgta   81480
tgttgatctt gtagcttgca ccttgctgaa ctcacatatt agttctagga gttttcatat   81540
atcctttggg attttctttg cagaccattg tgtcatctgc aaatagagac agttttattt   81600
cttcctttca tatttgtatc cttctttttt ttttgagacg aagtcttggt ctgtcaccca   81660
```

```
ggctggagtg cagtgatgcg atcttggctc actgcaagct ccgcctccca ggttcacccc   81720
attctcctgc ctcagcctcc caagtagctg ggactacggg cacctgccac cacgcccggt   81780
tcattttttt ttgtattttt agtggagatg gggtttcacc atgttagtcg ggatgatctc   81840
gatctcctga cctcgtgatc cacctgcctc agcctcccaa agcgctggga ttacaggcgt   81900
gagccaccgc gcccggcctc ccttgggatt ttctttgcag accattgtgt cgtctacaaa   81960
tagagacagt tttatttctt cctttcctat ttgtataatt ttaaagtaaa aagtccctta   82020
ttatgctgga tttccagtga tatgttgaat aggagtggtg agagcagata tgaattcctt   82080
gctcctgatg ttaggaagaa aacattcagt tttttgctat gaagtataat gttagctgta   82140
ggttttgtgt aggtacccta tatcaagttg aggaagttcc cttctatttc tattttcttt   82200
agagtttttt ttcttttttgt catgaatggg tatgaagttt tgtcaaatgt attttctgca   82260
ttgattgcta tgatgatgtg atattttttct ttttagctag tcaatatggt ggattatttt   82320
catttatctt ttagcattga atcagccttc tatttctaga ataaacacaa tttgatcatt   82380
ttatatgtat gtaattgctg aattctcttt actaatattt tgttaggatt tttacatcca   82440
tattcatgaa gaatgtttgt tcatagtttg gctttttttgg attgttttttg tctgattttg   82500
gtatctgggc actatttatt ttataaaata aattgttccc ttcttttctg ttttctgaaa   82560
gagattgtgt aaagtggtg ctaattcctt tttaaacatt tggtagaatt cgccagtgaa   82620
accatctggg catggagatt tctgttcttc ggaaagcatg tgtataattt ctcaatgaag   82680
cacatttgca tcatttcagc atttgttttct gatgactttc gtttctcatt ccagttgaga   82740
tttttgtggt tcttggtgtg aagagtgact ttttattgta tcctaaatat tttgggtgtt   82800
gtgttatgag actttggatc taattaaatt cttctctttc aatagacttt ccttttttaag   82860
agactgtatg agtgggaaat aaggaccccca cctcagtacc gcctggtagg aacataagtc   82920
cgggaccccc agtggtctc catggacacc cagtgagcgg gaggccgtgc tctccagcac   82980
agagctgggg taaaagttca gcttctgcac tctgcctttg ctgacaccac cctgttcaga   83040
ggggaagagg ccccttttca ttgctcgcct gtgaactcca aggacagaaa atggggaggg   83100
aggcctcatt agcatgggaa ggcttctcac ttgccacccc ttaacagcac cccagcaggg   83160
aaggtgcagg aagtaaaag ttcaagctcc ccaggttgtc tccgtcggca ccacactgtg   83220
gcagcttgtt actgcctggt gaacgtcgaa gtcccagatt ctcaccctga caccacacca   83280
gcaggggagg gctacctcag tatcaccagg ccaggctgga agtctaggct ctcccctctg   83340
tcctgctgag tgggtcgagg gtggggccac aagttttcct acgggcgttt gtctccagta   83400
gggaaactag cctccgaaag ttttctgtct tgctagcttt ctcctttcat ggtcttttgg   83460
ctagtgattg caggttattc aggggccttt tgtgtgtggt ctcataggag gggatattca   83520
tggattggga agaagacaat tttaagtgtg cccggaacag agtgagtatc agagttgaat   83580
aggctaggat aaggcagcag gtgtaaaaat ccagaaagcc ggctgggtgc ggtgctcacg   83640
cctgtaatcc cagcactttg ggaggccgag gcgcgtggat cacaaagtca ggagatcaga   83700
ccatcctggc caacacagtg aaaccccgtc tctactaaaa atgcaaaaaa agtagccggg   83760
cgtggtggca ggcgcctgta gtcccagcta cccgggaggc tgaggcagga gaatggcgtg   83820
aacccgggag gcggagcttg cagtgagccg agatacgcc actgcactcc agcctgggca   83880
acagagcgag actccgtctc aaaaaaaaaa aaaaaaaatc cagaaagcca aaatctgcct   83940
acaaaatgcc cattatcagt ccaatctacc tgacgccttt tctactgagc ttaatctgcc   84000
tccccatgca tttccgtaaa gtaggcaatg acagctatta tcattactta ggcttttctc   84060
```

```
ttttggatag ctgctttatc caacctccta ttctccaatt cacaattgaa ttggaaacag   84120
cgtgatcatc ggtagagagt gtattgggga aaaatattcc atgcagatat tggataaaca   84180
atttttaaat ttattttgct ggtactcaga cacccatgct tgtcaatttt atgttaggag   84240
accaaacttt tttatcattt aggcagaatc caactccatc cttccccata ccccattaat   84300
gagtaatgca ttggccaggc ttggtggctc acgcctgtaa tcccagcact tgggaggcc    84360 gaggcaggtg gaccacttga ggtcaggagt tcgagaccag cctggtcaac atggcgaaac   84420
cttgtctcta ctaaaagtac aaaaattagc ccagtgtggt gacaagcgcc tgtacaccca   84480
gctacttgag aggctgaggc aggagaatca ctggaaccca gtaaacggag gttgcagtga   84540
gctgagatgg cgccacacgc cgctgtactc ccgtctgggc aatagagcaa gactctgtct   84600
caaaaaaaaa aaaaaaaaaa gcattaagtg tgtgtagcat tctctattgc ttcccatttc   84660
cactctttcc acttgatcca gtctccttct ttgctgatag agacttgatt tgtaaggatg   84720
tttactctcc aatttattca ttaatcataa atcccttcct tcatccaggg tcagcttaat   84780
cataataaat tcaagtatca ccctccattc atgcacatgt ggcaaaatct agtcggaagg   84840
gtttgtggat attttcctcc ataataaaag cattgtttta aaagagacg gccaggcatg    84900 gtggctcacg cctgtaatcc cagcactttg ggaggccgag atgggcagat cacctgaagt   84960
caagtcagga gttcgagacc agtctggcca acatggtgaa atctcgtctc tactaaaaat   85020
acaaaaaatt tgccaagcgt ggtagcagat gcctataacc tcagctactg gggaggctga   85080
ggcaggaaaa tcgcttgaac ctgaaaggca gaggttgcag cgagccgaga ttgtgccagc   85140
cactacactc cagcctgggt gacagagcga gactccacta aaaaaaaaaa gagagagaga   85200
tttgaaaata gtttgtcttc agcactgatg ctctaatatc tgcatgggat tccgggaact   85260
gccctagtaa gcacacagtc gtgaaagaaa catcaccaaa aatctcagga acaaaggcag   85320
aaaccaccca tggcttcagt gatccggttg agccactgta tcaagaaatc ctggaatggc   85380
ctacctgtag ggcatttaaa aagtaatttt agttgggttg tattttactt atagctacaa   85440
gcatctgaat tgatcccaag cattccgcag tctgatttgg gcaacaagtt acgtgtttct   85500
cctccaagta gccatagatt cctggtttca tgcaccagca ccgcttcttt gacttttggt   85560
agagtcccca ggtcaggtgg gtgctgggga ggctccaagt aacctcaaga caaacatgag   85620
atggaatacc tcatctccct agtcaatttt actcaaatag aaatttttg aatgcaaaat    85680 accgtgcaga aacatattac aataaccaac gaccataaat tacaatgaaa cttgattcac   85740
ttctgaatca ctatttactt tcagcccttg ttttcttaca tggtatttgg gactcagagg   85800
cttcatggtt gcagcaggtg taagcatgca cacaggattt tttttaaacc catcagggaa   85860
ctaaggttac agggcaacct gccaccctga aatccagaga gaaggttact ccagggagat   85920
acagcatgta agacacagag aaaaagccac tgggcaccct aggctggagg aagccctaag   85980
agctcgcttt agacaggaat accgaaatct catcccatct tggggagggg aagtgcaccc   86040
agtccagcgt cactccagcc ttcttgtgtc ataaacttga tgacctagat gaaatgaggc   86100
aattctttga aagacaccaa ctgccaaaac tcactcaagg agaaatagct acctaaaaca   86160
ccagcccccg atgctttcac tggtgaattc taccaaatat atatatatat tttttgaga   86220 tggagtctct ctgtgtcgcc caggctggag tgcagtggcg cgatctcggc tcactgcaag   86280
ctccgcctcc cgggttcatg ccattcttct gcctcagcct cccgagtagc tgggattaca   86340
ggcgcctgcc accgcccg gctaatttt tgtatttatt tttattagag acggggtttc      86400
accgtgttag ccaggatggt ctcgatctcc tgacctcgtg atccacccac ctcggcctcc   86460
```

```
caaagtgctg ggattacagg cgtgagccac cacaacccag cctctaccaa attttaaaa    86520 agaaatagta caaattaaca cttttttttc tggaaagttt gaggttggaa tactgcttaa    86580
ctcattttat gaagctagca tattcatatg aacactacct gattcattta tgaagctagc    86640
attaaccaaa accagataaa gacattacca aaaaggaga ctatggagaa atacctctga    86700
ttaattgaga cacaaatctc cctaacatat tttaacaaat catatccagc aatatataag    86760
aggaacaata taatgtgacc aaatggggtt cattccagga aggcaaggct gattcaacat    86820
ttataaatac tgatgtatat aatttatcct attaacagta taaataagaa aaaatatgat    86880
catgtcaata gatgtagaag atatattcaa caaaattcaa cacccattca tgatatacag    86940
tcttgaaaac tagaaatagc agggatcttc cttaacctaa taagggtttt atatgaaaag    87000
tttgcagcta attttattct aaatgactag agaaagaatg ctttccctct aaaatcaaga    87060
ccgcatgaca ttggtgaaag agtagccaca tagatcaatg gagtagaata gaaaactcat    87120
taatgaatga acacaaatat tgtcaatgga tttgtggcaa aggtgcaaag gcaattcagt    87180
ggtgaaagaa tacttttta acaaatgatg gtggaaaaat tggatgtccg tattcaaaaa    87240
gtgaactttg acacagatct cacatcttac acaaaaagtg actcaaagtg gattatagaa    87300
ctaaatataa aatgcaaaag tacaaaactc ttagaggaaa atatgggata aattttcatg    87360
gctttgagtt tgttgacaaa tttttagata tgataaaaaa tacaacccac aaaaaaattg    87420
ataaattgga ctttattaaa attatgtttc cctctgtgaa attaactctt gagggaatga    87480
agaaacaagc ttcaaccttg gaggatatat ttgcacgtca catatctgat aaaggacctg    87540
tatccaaaat acacaaagaa ctcttacaat tcagcaaata aaaacaaata accaaactca    87600
taaataagca aaagaatacc ttatataaca tgttcaagac acctgtagat agtgtacagc    87660
aagtccttgt tttagacttt tttcttcatt atattattca ctatttatac aattcccaaa    87720
taggagtgtc taggagcttt tctcatgaaa aagagggaag tgatctaaaa ttacgaaact    87780
gaagcctgag actaagatta cacattttac acacatgcat atcactattt ttcattctaa    87840
aatgagtgtt tttctatatc agagaaatta tattcaattc cattttgtag gactctatag    87900
cagagcctct ccgatatgaa cctgtttaat ttgtataatg ttgataatta ttttccattc    87960
acaataacaa caacaaaggc tttttacact atatagtttt cagcaacaaa ctgcagtcac    88020
ttcagtgtct agctccgagg tctatgaagt agagtttatc gggccatcta gtggccacta    88080
gatcaaccaa cagttttttg tatttctgt tactgtgaac aactacaggc ttcactaaat    88140
ttacactaag tctaaaaaag ctaaaactag acctccctgc agactgtcta caactgtcct    88200
gaacataaca taattcatga cccatatgtt ttgctaatgt aacaattgta ttgtatcttt    88260
gtggtattgc accttacacg gggcaccagt tgaggtatgg cgtcttacca gagggcatta    88320
gctgcggggg tttgcccgca gaccctgacc caaagacgg atgaataaaa cgtacattga    88380
catacagata ctttgtttcg ccagtccagc tgagcgtccg actgcctgca caccaggaga    88440
ggtttgtcac tgcggctggt cctgagcagc ttgcacttca ggcatttatt tagtatacaa    88500
tgaacaacag aagctttgag taaacacact tgaggataat taacatggtt aagaaagtag    88560
ttttacaaat gattaaaact taggtactac ggtttaaagt aaataccatt aggggggcaat    88620 ttccctagtt gacctccccg cccctacccc cacccacaac cacccagagg gccatttggc    88680
ttaaagatta gttaatggag gtagggtaaa cagaagtaac tggggaatcc tctattgttc    88740
ctagtattta ccctatgacc tagtgctcta aggtaagaac cggctgcctt tagcctgttc    88800
aattattaca agctatttaa gcttttggcc tttcaaaaga tttgtgatta tttcctataa    88860
```

```
ctttccctaa tattcccttt aatatttttg ccattatcct aagtgactca caacagatct    88920
taatataatt attacataaa tgtataatcc atatttttta gacctgatta attgaatgat    88980
tcagtgggat atatcaattt ttcctctttc cattgtaata aatcttgttt aagtcactaa    89040
catgtcttgc ctggaagatt attatctcct aactggtccc ttgtcatcct ctctggattc    89100
ttaaaattca ttcaacaaag agtaactcaa tcttttaaag acctgtgtat catagtaaga    89160
tcatggattt tctctgctta aaattttcca atgaggtttc atcacaatta taatgaaatg    89220
tgaactcctt ttcactgttt acacagtcct gtgggatctg gtctccacac tcctcttaaa    89280
cttcatttcc taccactctc ctctccattc actagaaacc agctatatta tttttttgtcg    89340 tcgttgtgtg ttgtttctta aacacattct cccagacttt gggctttggg tgtgttgttt    89400
gtctaactgg aataattggt gcccacatac ctacatgggt tgcttcttct ctaaaaccat    89460
gggtggttgc agaccaaata ccatgtcctc aaaaatgtat tccttcttag ttactcagaa    89520
attaaacacc agctgcaatc aaagaaactc gcaaatctca gtggcttagt tatatattac    89580
attatattaa tcatgtaaac ttcagtatgg gtaaggggga gtgaagactg agaagttctg    89640
ttccatgaac cattcaagga ctcactcggg caccgatcct tttatgactt ggctctcttc    89700
ctggttctca gaatccatgc cgttcacctg tcagagaaag taaagagtg tggaggatta     89760 tgtcagagat ttttataaac tgtatttggg agtggagtac tttatttcta cctatattag    89820
ttggaattca gtcacatgac ctcaactaac tgcagctagg gatggtatat gtggggcagc    89880
tgtgtgccca agagaaaaca ggatttgatg cgatcacagc gttctcctct gccatggtag    89940
cccttgtgtt tatcaaatat ccactttaca cttccttta aatgttgaac acactctccc     90000
tagaggagac aatccaaaat tcacctacgt attgaatcca gctcaaagtt caggatttca    90060
gaattatact cagccttctc caccaagttc tgccgtggtt tgtcaaggtc agggacccag    90120
gaactaaaaa gataagttat gtttcaaaca gccaataggg ggaagcaaaa ataaccata     90180 atgagaattc tcgtttggaa acgaaaagga ggcacattac cgttatggac tcacaggaat    90240
tacggaatct tgctggtact tgatgatgtg tctgtgaagc aagtgggaat tagtattcca    90300
gaagagcaaa tacatgggat agaattttag ttgccaccctt tcaggtaag atgggataga    90360 aatggagtcc ctgaaataag aagtatgttt ctgtacattt caatactgaa ccaagaaagg    90420
acatgtggct tgatgatacg ttgaaatatt tatctgggtg tttcacattt ttcctctccc    90480
tcttcccatg tgtactctga gggtcagacc acttgcagac atgagtcacc tactttgaag    90540
gagcaaccag aactctgact ccaaagagta aaacttgata acggaaaaga cagtgaaaag    90600
aaatattctg tttcacactt acagagttag ttttaaaatg gtcctaagag gtgaagagaa    90660
catgctgatg gaagaaagaa cggaatggat aaaatttgat ctcgagaggt gaggttaaag    90720
ctgaggttga tggtaggata caaatggatg ttcttttaca gcacaaatca ttttttatagc    90780 aggatcctga ctcagtgctc aggtctgttt tcctggaac tttctcttgg gagaagtcaa     90840
cccatcagcc attgagcatc ttatgcttat ctgtccttcc ttgtttgtat ccaatgattc    90900
tggacacttg tagataattc taggaccaag ggtgagttat ttgaatacag tgggagtga    90960 tagcagaata agcacctagt cacagtcagt ttagaatgac tcttatagaa agtagactct    91020
gattcagcat gaagaaaaat ctataaagca aatggaaaac aaaaaagggg cagggttgct    91080
attcttcttt cagataaaac agtctttaaa acagcaatga tcatgaaaca caagaaggg    91140 cattacataa taataaagag ttcaattcaa tgagaagatt taattgtcct aaatatatat    91200
gcaaccaaca ctggaacatc cagattaaaa aaacattttg ttagagacct gagaagacaa    91260
```

```
ttagatatcc atacaataat aatgggagat gtcaacgccc cactgacagt attagataga    91320
ttatagaagc agaaaactca caaagttatt caggacctaa aactcgacac ttggccaaat    91380
agacctaaca taacaacaac agaatataca tttttctcag ctgcccatgg catatacact    91440
ctataatcac tcacacactc agccacaaag caattcgcaa caaattcaaa ataaatgaaa    91500
tcatcccaac cacatggtca gacacagtac ggtaaaaata gaaatcaata ccaagaagat    91560
ctctcaaaat cacacgatta catggaaatt aaaaaatcta ctactgaatt tgggtaaaca    91620
ataaaattat ggcaaaaatc aagacatttt ttgaaactaa tgaaaacaca gatacaacat    91680
accagaatat ctgggacaca gctaaacagt gtgaagagga agtttacag cattaaatga     91740
ctacatgtaa aagttagaaa tacctcaaat taacaaacta aaatcacacc taaaggaact    91800
agaaaagcaa gagcgaactg atgacaaggg taacagaaga aaataaataa cccaaatcag    91860
agctgacctg aatgaaatgt agatgagaaa aaccatgtaa aacatatcaa agaaaccaaa    91920
agcatgttcg ttaaaataat aaataagatt ggtagactgc tagctagaca agaaagtaa    91980
aaagatccga ataaacacaa taagaaatga caaagaggac attactacta atcccaaaga    92040
aatacaaaaa gtcctcagag gctattatga acacctttat gtacacaaac tagaaaacct    92100
agaggaaatg gttaaattcc tggaattgaa tctggaagaa attgaaaacc tgaacatacc    92160
aataataagt ttcaaaattg aatcagtaat ttaaaaaata ccaaccccaa aaagtcctgg    92220
accagagaga ttcacagctg aattgtatca gacatataaa gagattcagt agtatcaata    92280
ctactgaaac tattccaaaa aatagaggag gagggactcc tccctaactc attctgtgat    92340
gccagcatta ttctgatatc aaaacctggt agagacacaa tgaaaaaaga aaacttcagg    92400
ccaatatccc tgataaacat agatgtaaaa atcctcaaca aaatataagc aaaatgaatc    92460
cagcagcaca tcaaaaggat aatccaccac aatcaagtag gctttattct tggggtgcca    92520
agttggttca acagatgcaa attttaaaaa atgtgattaa tcacataacc aactagaaac    92580
aaaaaacaca tgattatttc aacagatgta gaaaagactc tcactaaaat tcaacatccc    92640
tttatgttaa aagccctcaa tcaactaagc atcgaaggaa catacctcaa aataataaga    92700
accatctgtg acaaacccac agccaacatc atactgaatg ggcaaaagct ggaagcattc    92760
cccttgagaa ctggaacaaa acaaggatgc ccactctcac catttctatt caacatagta    92820
ctggaagtcc cagctagagc aatgaggaaa gagaaagcaa taaaggctc caaataagaa     92880
gaaaagaagt caaactatct ctcttcacag attgtatgat tctataccta aggaaacgcc    92940
atgttatctg tccaaagctt cctaggtctc ataaacaact aaacaaagt tttaggatac     93000
aaaatcaatg tacaaaaatc agtagtattt ttatatacca ataacatcca atctgagagc    93060
caaatcaaca acacaatccc cttcacatta gacatacaaa aaatataata tatatagaaa    93120
tccagctaac cagggaggtg aaagaccttt acaacacgaa ttaaaaaaca ctgctgaaag    93180
aaatcagaga caacacaaat ggaaaaacat ttcatgctca tggataggaa gaatcaatat    93240
tgttaaaatg gccatactac ccaaaacaat ttatagattc aatgctttc ctatccaact     93300
accgaggaca tttttcacag aattagaaaa aaactattcc aaaattcata tggaacagaa    93360
aagagcccaa atagccaagg caatcccaag caaaaagtac aaagctagag gcatcactct    93420
acccaacttc aaactatact gcaaggctac agtaaccaaa acatcatggt actgacacaa    93480
aaacagatac aaagatcaac agaacaggtt agggaatcca gaaataaagc catatactta    93540
tttttcaaaa tgtgagaaaa tatttacaaa atatgcatcc aacaaaggcc caatatccag    93600
agtctataag gaacttaagc aaatcaacat gttaaaaaca atctcattta aaaatgctga    93660
```

```
aagaacatga acagacattt ctcaaaataa gacatacacg tggccagcaa ggatatgaaa   93720
aaatgctcaa catcactaat catcaaagaa atacaaatta aaacatcaat gacatactat   93780
ctcataccag tcagaatggc tattattaaa aagtaaaaaa aacaaacaaa caaaaaaaag   93840
cacatgttga tgatgttgca gagaaaaagg atggctattg aggatataaa ttagttcagc   93900
cattgtggaa agcagtttga agatttctca aaaagcttaa aacagaacta ccattggatc   93960
cagcaatccc attactgagt atatacccaa aagaatataa attttttttac cataaaggca   94020 tatgcatgtg tatgttcatc ataacactat tcacaataca aagacatgga atcaacctag   94080
atgtccatca actgtggact ggataaagaa aatgtggtac atatacacca tggaatacta   94140
tgcagccata aaaagaaaca agataatgcc ctttgcagca acatggatgg agctggaagt   94200
cattatccta agcaaactaa cacagcagca gaaaacctca tgttctcaat tataagtggt   94260
agctaaacat ttagtacata tggacacaaa aaaaggaaca atagacatca ggacccactt   94320
aaaagtggag ggtgagagga gggtgagaat tgaaaaacta cctatcagtt actatgctca   94380
ttaattggat gtcaaagtaa tctgtacacc aaaccctgt tacacataat ttacccattc   94440
aacaaacctg cacatgtacc ccttgaacct aaaataaaag ttggaaagaa aaaaaaaagg   94500
accctctgat tcaggaaagg ggtgcataca tggtccatgc tatataggac atgccataac   94560
tgttggagtt ctctgatatg tagttgtctt tcctactagg ctataagctc tatgatggca   94620
aaagtagtgt ctcctttcct cattatttat tcctcagctc ttagtgcagt gcctgactta   94680
tagtaagttc tcaataaaat gtgttgaata aatgaataac tttccagtag ccatttattg   94740
ctcaactcaa tgagagtcag gcatcaaagc ctgtacattt tctgtgtttg taccaggtcg   94800
gagacaaatg tttatgaaac atagatgaag tccctagaac cttcttcaga aataatgaat   94860
tgtgttaagg ttttttgtgcc ccagatcttc aagttgacca taaagattcc accgtgtcta   94920
acaattaacc caacttcacc atctaggata gaccatttgg tggttagagg gtggtgggta   94980
tcgattcttg gcaaccaaag cctaaagttt atgcctcaac tgagctttga gggagcaaat   95040
tacatgatat agacttatgt actatgcctt catcctttgt attggcagca atccttagat   95100
aagcgagatg gcttttaagt gaaaagtcac ctaaggacat gaatagcata aggtacatgg   95160
tgagcaaaac gacttgatct acgtattttg gagttcccgg actagtaggg gtgggaagga   95220
agacagagta ataggtaggt agacaatata atgcaatcat aatatgatat aagtttaatg   95280
atactgaaag tacaatggat tatagaatca caaatcagca atagttaatc agtttaagaa   95340
ggttaggaaa tgctatccag cagaaatgtc actaaaattg aaacttggcc aaatgagtgt   95400
taaaatactg gggatcagat gttccaaaca ggagagcatg gatgaaggcc cagagaagag   95460
agagatcata gggcatgggt gggaagaaat ggggcgagg agaaggcagg gaaagatcaa   95520
gaatgatagg aatgatgtac ttcggtgaaa gtatggtgca tttaaagaac tgcgataaga   95580
tcattgttgc taaagcttca tgtgtgcttg cattcgtgtg tgtgcataca cgtgcgtatt   95640
catgagaagg ggttggatat agacaacagt acatctggaa acacgaagaa ataatacaat   95700
gaaagagaac atgcattata gtaataggtt tggccttgt tcattctaat agcaacagga   95760
agcctctgaa ggttttaatc aaatttgctt tttgggagag ataaaataac aaccttctct   95820
tcattctcct taagtcgttc catcttttag tgctcctttt gtctggttaa aaactctagg   95880
gcttaagtgt aattgatttg gaaaaatcac caatgagtgt cagtgtcatt tgggggcttt   95940
gaaagtaacc aagagcttgc atgcatagct tcgttaagac cattcgcact aggctgggtt   96000
gcctttgatg cctttgtatg ggttcagatt cttagaaaga gaactatcta tggttcataa   96060
```

-continued

```
aggagaccct tccttcact atgcttaggg tgaaagtgca tccctcccct tcccttccag    96120
agtcagcaga caattaggaa aacaaattaa ccattctctc caccaaccgc taaatcagct    96180
taaactgagc tgaagcaaaa gtgactaaga agcagtggtc ataagaggtg gtataaaagc    96240
cacttggtga ccagaatccc attatgcaac aaggcgaagt gggggcagac aaggagaggg    96300
caggcaccct ggatatacat tttgagggag gtgactgtgg caagggacag agaaaatgcg    96360
agttacaaga tgatgaaacc atcccatgag actgcctctc agatatggga cgtgggagtg    96420
tgctaatgag actgaaacgc acaacccata gtttctgtcc cagattccaa attttacatc    96480
tctttgtggt aactggcaga actctacaga aaatcgaagt agaaatattc tttgtggttt    96540
attagctatt tggtttgtag agggaaggtg agacattatc agtacctgta atgggaatgg    96600
tgagctccac tccatggctg ttgcatggca ggaggctaca tccaaaacat gtccttctgg    96660
gcagagagaa ggcaggcacc ctggatacag catttcaagg gagatgactg tggcaaggga    96720
cactggttac ttttccacct ggataactgt aagcctactc caaaacattc tattcctaca    96780
ttcccaggac agagggtcct tctccttagg ttacaaagat catcctgact tgggtaaagt    96840
gaatgaattg tggtggggat aattaagacg gcagggagc cagacgcaag ctgttgcaac    96900
aatccagtag tgagcagaag ccggctaaac gaagacagtg gcagtggggt ggagaaaaaa    96960
ggcagaattg gagaattcaa gaagtcgaaa cttgctaatt accttgcact ccaggtcaag    97020
gctgacatag ggaaatgatg atagagccaa ggtttctggc ttgaggaact ggatgaggaa    97080
tggatgtttt taagtggaaa agtgaagaaa gacaggaga tcttgagatg gcagagaagg    97140
gataaattcc atttgtgata ttgacatttg cattgcatat ccaggaaata atgtcacaca    97200
ggtagatgtg gttgtctttt gttgttgtta tttgtttgtt tattgcttca ttccggacag    97260
tattttaggt gttccagaaa gcattcatac atatggttgt ggatttagct ccaaatgtga    97320
gtggatagaa aaatatggga gtcagcacag acagtggatg aaaccctgca tgggactgag    97380
acgctgaagg ctgagtagat ggacaagaaa caagccaagg atgaggactc tagaaagcat    97440
cccagtccag gcaggcagtg gaagaaagac ctacaacaga gaaaattcga aaacaagatt    97500
caaaagaacc acagaggcac tgggaaaacg tgatggtaag gaatccaggc agagagacaa    97560
tcaagcactg cacacagatt tagatggtga tagaaagtca tgaatcgggt ttagcagaaa    97620
taaggtacta gaagggaat ttgataagag tgatataaga aaaagaaaac atgaagaaat    97680
ggaagcgagg gtctagaaat taattctaaa taggggactg gtagagggta atcgagggaa    97740
atagatggaa gacaagcaga agtgagtgcg tgtgtgtgaa aaagaatgtg tgtgtttgta    97800
tgtgtttgtg tttgtgtgtg taaaattgtg ttcgcttgtg tgcaagtgtg ttcacacatg    97860
tttgtgtgta taggtttaaa tttgtgcgtt tgtgtgtatg catgtgtcaa tatgtgtgtt    97920
tgtgtttgtt ggtgtgtatt taagtgtgtg tgacttgtga ctgtgtatct gtgtacacgt    97980
gtgagtgtgt ataactgtgt atgtacacat gttaatgtgt ttgtatgtga aactgtgtgc    98040
acttgtatgt gttcttgtgt gtttcagtgt ttggtgtttg tgagttatgg cttatgtgtt    98100
tgtgtgactg tgtgacttct ggtgtgtctc tgaaagggtg ttttgtatat gtacagtgaa    98160
tgtgtatttt gtgtgtgttt gtgtgtacat gagtatgtat atgtgtgtga gtgtgtgaaa    98220
gtatgtaact atgtgtgtga ttatgctttt gtgtgtgtat gtattcatgt taatatgtgt    98280
tgtgtgtgaa agtgtgagca ctttgtggtc ctgtgtgtgt ctatgtttct gtgtgtgtgt    98340
tcgtgttttg tatgaatgtg tgtggctgtg aattttgtc tgtgtgtgaa atagtgtttt     98400
gtgtgagtgt acacgtgtgc caaagtgtat ttatgtttat gtgattgtgt gtaactgtgt    98460
```

```
gtgactatgt gtgtgtaagt gcacatgtac taatgtgtgt gtttctgggt aaaagtgtgc   98520
acttgtttgt gtgttagttt gtgtttgtgt gtgaatgtgt gttagtgtgt tggtgtatgt   98580
gactgggtga cggtgtgaaa gggtgttatc tgcatgtaca ctgcatggat tggtgtgttt   98640
gcgtgtgaat gttttttgtgt gtggtgtgct tttgtgtttg tgtgtatgta tgtgagtgta   98700
tgtttgagtg ttcgtgtgtc tgtgtgtctg tgtgaaaggg tatctgtgtg tttgtatgtg   98760
aatgtgtttc tatgtggtgt gttttttgtat ttgtgtttgt gtatgcaagt gtttctgtgt   98820
cagtgtgtac acgtaagtga gtgtgtgttt ctgtgtacat gtgttttttgt gtgagggtgt   98880
gtctctgttc acataggcac ttggagtaaa tatagaggtc acctgcttga atcttgctct   98940
accactcatc agtgacattg tagcattgga gactttttttt tcacttaatt ttttgtttta   99000
attttaggtc cagggttatt aatatatgtg caggtttgtt atatagataa gctcatgtca   99060
caagcgtttg ttgtacagat tatttcatag tccaggtact aagcctagtg tccaaaagtt   99120
atttatttat ttatttatttt ttgtttattt atttttttgag atggagtctc cctctgtcac   99180
ccaggctgga gtgcagcggc gcgatctcac ctcactgcaa actctgcctc ccgggttcag   99240
gccattctcc tgcctcagcc tcccgagtag ctgggactac aggcgtctac caccacacct   99300
ggttaatttt ttgtattttt agtagagacg gggtttcacc atgttagcca ggatggtctc   99360
gatttcctga cctcgtgatc cgcccaccta ggcctcccaa agtgctggga ttacaagcgt   99420
gagccaccgt gccctgccca aaagttatttt ttttctgatcc cctccctcct gtcaccttcc   99480
cccctcaagt aggccccagt ctctgctgtt ccctcttttc tgtccatgtg tcctcataat   99540
ttagctctta cttataagtg agaacatgtg gtacttggct ttctgttttct gcattagttc   99600
gcaaaggatg gtggcctcca actccatcca tattcctgca atagtcatga tcttgttctt   99660
ttttatagct gtgtagtatt ccatggtgta tatgtaccac attttctttta ttggagactt   99720
aaacttattc acaattatgt cataaataaa attaatctga caatagctac ctcactatga   99780
tgattttaaa agttatagcc agccgggcgc agtggttcac acccgtaatc ccagcacttt   99840
gggaggtgat gcggagggat cacgaggtca ggagattgag accatcctgg ttaacatggt   99900
gaaaccccgt ctccactaaa aatacaaaaa tttaaccagg tgtggtggca ggcgcctgta   99960
gtcccagcta ctcgggaggt ggatgcagga gaggggcgtg aacccgggag gcggaggttg  100020
cagtgagcgg agatcgcgcc tctgcactcc agcctgagca acagagagag actccatctt  100080
aaaaaacaaa caaacaaaaa aaacagttat tgcctagagt ttctaaaatt ctactgcatt  100140
tttgtgttct ttcaagtctg ctaaaattaa gaacttccta caatttccag gcaagatctt  100200
tgttaagatt cttttgaaata actgagaact atttcaggaa agcaagggtt aggggccata  100260
gaagagggct ttattctcct tgattctctt caaaatgcag tgccacacaa ctcattcatt  100320
caagtactca tttattaagt aaatatttat atatttttatg ctgtgttctg ggaacgactc  100380
cgggagattt gatatataaa atgatcaaaa cataaaaagt agtacctgca tggagcttac  100440
attctattag aaaagccaaa aaattagcaa tatagataaa cctataaatt atataatact  100500
ttagaaagta ataatgcact atagaaaaag aaaaagctag atcaaggcaa agtagatcaa  100560
agtttccagg aagagctgca attttatgtg gaacggccag ggaaggcttg aatgagatca  100620
aatcatttca acaacgaccc caggatggtg aggtcattaa caatatgcac cgtgcagagg  100680
gaaagccagt gtacacgccc gaaggctgaa gaatgtccgg tgttcaaaga acaacagaag  100740
gccatcgtga ctgaagtgct tttaaagagg aagaggtggt aggagatgag gtcagtatgt  100800
ggtaataaag cattgcaagg attttagctt tgagattgag agctgttgga aggtttgacc  100860
```

-continued

```
agaggagtcg taagacttgg gttttgaaat aatcgctatg cttgccccac tgatgataga    100920
ctgtaacagc acgatagtgg aagcagggaa atttctttct ttctttcttt ctttttttt    100980 tttttttttt gagacagagt ctggctctgt cgcccaggct ggagtaaagt ggcgcgattt    101040
tggttcactg caagctccgc ctcccgggtt cacgccattc tcctgcttca gcctccggag    101100
tagctgggac tacaggatcc cgccaccaag cccggctaat ttttttttgta ttttttagtag   101160 agacgggggtt tcaccgtgtt agccaggatg gtctcgatct catgacctcg tgatccgccc    101220
gtctcagcct tccaaagtgc tgggattaca ggtgtaagcc accgcgccca gccgggaaat    101280
ttctttaaaa ctactgcaat gatgtaggct agaaatgatg gtggcttttt accagagtga    101340
caggaatgaa ggttttgaga aagtggctat atatatatta tatatgtgtg tttagatata    101400
tatgtatatg tatatataat gtagagcctg caaaatttcc taccagcctc catagattat    101460
gcacacaaaa ataaatcacc ttatgacaaa tgcaagggtc tgagcaattg gaaagatgga    101520
gttgccacca attgagatgc ggaaagttat tgctgatgga acagttttttg agggactcat    101580 ggggcacaaa gtgttcttct tcggactttt aaaggtatca gacatccatt agacatgtta    101640
atagagatgc tgaatggaca gttgggcata taagtgaaac ttaggaactt aggaggaagg    101700
tttgtactag agatataaat gttggtatca tcaacatata gatgttatttt aaagccatat    101760 aacttgatga ggtcatcgag ggagtgactg tcggtagagc agagcaacag ggatgaaacc    101820
ctggatgcac ttttcattag gaagttaact tacagaggag atatctacaa aaaggagga    101880 aggaggaacc agaggtaaga gaagcaccga ggggatgagg ggtttctaga agccaaagga    101940
agaggtatgt cattgaagaa gacaccatca gatgtgtcac atactgtggg tagcaaagca    102000
agatgaagac tgagaatgga ccattggatt cagcaacatg gagatcatcc atgaacttag    102060
taagggaagc tccaatagag gtgagtggtg aaagccagag tggagtggct ttaagagagg    102120
acagagtctg ggtgcggtgg ctcacgcctg taatcccagc actttgggaa gctgaggtgg    102180
gtggatcaag tggtcaggag atcgagacca tcctggctaa cacagtgaaa ccccgtctct    102240
actaaaaata aaaaaaaaaa aaaattagct ggacgtgttg gtgggcgctt gtagtcccag    102300
ctactcggga ggctgaggca ggagaatggc atgaaccccg gaggcggagc ttgcagtgag    102360
ctgagatggt gccactgcac tccagcctga gtgacagagt gagactccat ctcaaaaaaa    102420
aaaaaaaaaa gagagagaga acagaaagct gaattggaga tagtgagtat acacaatgtt    102480
ttggagagtt tcactttaaa gagaatcaaa gatatggggc aatggctgat aatagaacta    102540
tggttaaaag gttttactg ttgagataag aaataccagc acaagcacta tttacaatag    102600
caaagaattg gaaccaacct aaatgcccat gaatgataga ctggataaag aaaatgtggc    102660
acatatacca catatacact atggaatact atgcagccat aaaaaagaat ttcaccgagc    102720
acagtggctc acgcctgtaa tcccagcact ttgggaggct gaggtgggtg gatcacgagg    102780
tcaggagttc cagaccagcc tggtcaatat ggtgaaaccc cgtctttact aaaaatacaa    102840
aaattagctg ggtgtggtgg tctgtgcctg tagtcccagc tactcagtag gctgaggcaa    102900
aagaatcgcc tgaacccagg aggcggacgt cgcagtgagc cgagatcatg ccactatact    102960
ccagcctggg caacagagca agactctgtc tcaaaaaaaa aaaaaaaaa aagaataagt    103020 ttatatccctt tgcagggacg cggaaaccat cattctcagc aaactaacac aggaacagaa    103080
aaccaaacac cgcatgttct cactcataag tgggagttga acagtaagaa cacatggaca    103140
cagggaaggg aacatcacac accagggcct gtcgggggggt gggggacaag gggagggaga    103200
gcattaggac aaatacctaa tgcatgcagg gcttaaaacc tagataacgg gttgataggt    103260
```

```
gcaacaaacc accatggcac aggtatacct aggtaacaaa cctgcacgct atgtacatgt    103320 acccccagaac ttaaagtaaa aattaaaaaa agaaattcca gcacagtttt atgttcatga   103380
gaatatttta attaagtgtg atacattaat aatatataga gagaggggag aattactgaa    103440
ggctaccact ggtatgcaa gaaggggttgg gaactaatag accagtgcaa ggaatggcat    103500
taaatacaaa tttttacagt gtgtctgtgt cctcaacctg tggtgtgggt atcactgaag    103560
tctgtgaacc cttccctcta atcaatctgc tgatatttag gtataagtaa tgctttataa    103620
agttcctgaa agttatttat tttgctctat gggatctcct ttagctcttg tcttaatcca    103680
ttcaggctgc tataacagaa taccatagac tgggtggctt ataagcaaca gacatttagt    103740
tctcatagat ttgtaggctg ggaaatccag ggtcaaggtg ctggcagatt tggtgtctgc    103800
tgagggcctg cttcctggtt caccaatggc tgttttacg ctgtgtcctc acatggagga     103860
aag                                                                 103863

<210> SEQ ID NO 3
<211> LENGTH: 110608
<212> TYPE: DNA
<213> ORGANISM: Homo sapiens

<400> SEQUENCE: 3
gatcatcaga gtgacagaat gagaagccac catctggcca ccatcacgat catcatcaca      60
atcacgacga gtcaccaaga gactaaaact actgagtaaa agcttagaaa cggctgggcg     120
cgctggctca cacctgccat cccagcactt tgggaggctg aggtgggcgg atcacaaggt     180
caggacatcg agatcgtcct ggccaacaca gtcaaacccc atttctacca caaaaaatta    240
gccaggcatg atggcgcgtg cctgtaatcc cagctactca ggaggctgag ccaggagaat    300
cgcttgaacc caggaggcgg aggctgcagt gagcggagat cgcgccattg cactcctgcc    360
tgggcggcag agtgaaactc tgtcccagaa aaaataaag cttagaaaga ggctatgtag     420
tctcgagata aatccagccc tatgaggcac atgtcaatca cagagggaaa gctatgcacg    480
cacaaagcat gtgtgaatca gagagaaagc tatgcacgca cgatgagtag aagacaaaca    540
cgtcctgcaa ggagacggag cgcagggaa ggggcggcag ccgtcctccc aagacatgag     600
gacttctagt tcagtctgag accttggtgc agggctgggc gagtaaacaa atgcaaaaga    660
ataaggacct cgaggtcggg cgcggtggct caagcctgta atcccagcac tttgggaggc    720
cgaggtgggc gcatcacgag gtcaggagat tgagaccatc ctggctaaca cagtgaaacc    780
ccgtctctac caaaaataca aaaacttag ctggacgtgg tggtgggtgc cagtagtccc     840
aactacacag gaggctgagg cacgaggatc acttgaacct gggagacgga ggctttagtg    900
agctgagatt gcaccactac actccaacct ggctgacaga gcgagactgt ctcaaaaaaa    960
aacaaacaaa caggtctggt gtacccagaa tggaggcacc acgagttgct gaagaaggaa   1020
actttattca gtctatgata ccaggacagt tgtccatgct gccaggcaaa aagaaaaact   1080
ggattctgat ctcattatca gtacacaaac agcgacaatt agtaacactg acacagccct   1140
gactgtgctg ctggagggtc cgaagcactc tctgcacagc ggtgaatccc acaatagcc    1200 ctctagggaa ggtgctgtta tcacccacgc gagacacacg aaggaaaggc acggctttgc   1260
agcagcaggt tcacgattcg aacccaggtg gcctgctctt atgataaact taatgtgta    1320 aaactttatg ctcaggaaaa tataagagaa tgtcttcctg acccttttg gggtaggaca    1380 ataatttctc taaccaaacc ccaaaagcat gacccattaa aaaagggtc aggtggacta    1440 acttggctaa atgaagaatt ctgtttcacc aaagtacacc acaaagtggg ccgggcgcag   1500
```

```
tggctcatgc ctgtaatcct agcactttgg gaggccaagg tgggcggatc acttgaggtc    1560
gggagctcga gaccagcctg accaacatgg tgaaaccctg tttctactaa aaatacaaaa    1620
attaaccagg tgtggtggta tgcacctgta atcccagcta ctcgggaggg tgaggcagga    1680
gaattgcttg aacccaggac ggggaggttg cagtgagccc agactgcgcc gctgcactcc    1740
agcctgggca cagggtgag acccgtctc aaaaaaaaaa aaaaaaggcc agacttggct      1800
cacgcctgta atcccagcac tttgggaggc tgaggtgggt ggatcacctg aggttgggag    1860
ttccagatca gtctgaccaa catggagaaa ccccatctct actaaaaata caaagttggc    1920
cggcatggtg gcacatgcct taacccag ctgctcagga ggctgaggca ggagaatcac      1980
ttgaacacgg gaggcagagg ttgtgatgag ccaagatcgc gccattgcac aacagcctgg    2040
gcaataagaa caaaactctg tctcaaaaaa aaaaaaaga aacaaaaaaa aatatatata    2100
tatatataca taccataaag tgaaatcaac agccacaacc tgggaaaaaa tacttgcaac    2160
atggcaaagg attaatatcc agaaagtata aagaattcct acaaaccaag tagaaaaaca    2220
ggcaaaaaaa aaaaaatgtt ggcggggcat ggtggctcat gcttgtaatc ccagcacttt    2280
gggaggccaa ggcgggcaga tcacctgagg tcaggagttc gagaccagcc tggccaacat    2340
gatgaaactc cgtctctacc aaaaatacaa aaattagcca ggcgtggtgg caggcgcctg    2400
taatcccagc cacgcaggag gctgaggcag cagaatcact tgaacctggg aggcggaggt    2460
tgcagtgagc tgagactgcg cctgctccag cctgggtgac acagcaagac tccgtctcaa    2520
aaagtaaaga aaaaaaaaaa acaaaacaac atatttcaca gagaagaatt tatgttttttg  2580 gagaaggagt ttcgctcctg tcgcccaggc tggagtgcag tggtgagata tcagctcact    2640
gcaacctcaa cctcccaggt tcaagcgatt cacagaggac aatttctaaa aggcaaataa    2700
gaagcaggaa gggtgcatgc tccttctcta ctgccctgta acagtcattc cacacttacc    2760
acctcaaaac aacaaatgct tttgatgttg ctcctgtgg ggcagcaatc tgcgggaagc    2820
ttagccaggc acctctggct taaggtccct cctgaagctg cagtcacacc atggaccagg    2880
gctgtgacct catccgaagg ctcaactggg gctgaggccc acctctgagc tcactcaggt    2940
ggacgctggc tgggttcagt tccttgctgg ctataggtgg aaagggcccc caccagtttc    3000
ttgccagctt ctccacagga cgccccacag cctgacagga gctttcatcc agcaagctca    3060
tcagggagtg ggagagagca gccaggacag gagcccagac ctttctgaac ctcatctcag    3120
aagtgacatc cttcccttct gctgtctggg cacagctccc cgggtggagc ccgaggacta    3180
gaaggaaaag aaaacttgga tttaaaatgg gataaagcca taggagctgc tcgtcccacc    3240
acaggaatct caacgccggg ttactgacaa agcgtcactt tgcacctcgt ccaactgtgc    3300
agacctctcc tagccaggcc cctgcaccag aggttaagaa tccgtgcccc tggtcaggaa    3360
gtccaggtgg gttcaaacgg ccagcaggga atttcaggca aaatgtgtcc caaatcttca    3420
aaccatgccc cagaactcag acctccccct gggagttcgt cccaaggaaa ccacctgcaa    3480
gaggctcagg ctgcagggga cactccgctt ccaaaacccg gaagctggag accacacaag    3540
tgcccaacgc caaaggcacc ccgtggaggg acgccctgtg ccctcccccg accaggtgac    3600
ccgctgcgcc ctacacatct tcaccaggaa acatctgtta tcgatgtgga cgaagcgcag    3660
cctgcactcc cagatccgct catttttcgtt ctgccctccg ttttacgatt cgcctacact    3720
gaaaatgcgt gagtggagtg gaaagccttc ctactcctgc ctcagcgacc ccttctaaaa    3780
tactgcctcg tttggcctga aaatgtgatt tgcaggcttc ctgagcaaag tagatttcac    3840
tccattaaag aaaaaaaaaa agaaaaggca ccgaacgggg ctcggctgtc gggagttttg    3900
```

```
ctttagtttt ttgcgtgttt tgttttgtgt tttttttgttg ttgttgttct ttttgcggcc   3960
acgcacaccg cgttcccagg cttcagggcg tgggggtcgc cgtggactcc cggacgtgaa   4020
aacgcttaaa gccagctggg aaaaccccac cagcgttttc cgcgcacagc gccagccata   4080
ggaaaggacc cccaggagcg aatccgggca gggaaacccc ggacgcccgc acactcagca   4140
tcagtaccgg cacccagcac ccagcaccga gcaccgagca cgcagcaccc agcaccgatc   4200
accgagcaga gcaccccgca cgcagaaccc accgagagcc tgatgcagtc tccgccgcag   4260
gcatagcgct aggccccggc gccttcacaa caaagggacg ctggcgggcg gggcctgaga   4320
ggcgcgcggt ggaggggccg ggcgcgaggc cgcggagaca gctcggagct cggcactggg   4380
gagtggcaca gcgctggcgg atccaggtgg gcttcacggg gcgcccgcgg gaccggaaat   4440
gacgcgcaga accctgcatc gggctcctcg ctgccccgcg ggcgccgctc ctcagtgccc   4500
cagagccacg gagccgggga acgcgccgc ggcccacaac gccccgcgg ctgcccgttg   4560
gttccgcccg ggccgttcta ctccaggcag acgggaggag aaacacggcg cgctcagcgt   4620
cccctccccc gttggttctg ctcgggccct tccactgcag gccgacgggg gtggaaacac   4680
gcagttttt tttttttttt aaggtctagg gtaacacggg gcttttaagt gcctctccgc   4740
tgccgcctgg tggtccagcc cgggccgttg cagtgcagcc acacggggag ggacacggcg   4800
cgccgagtgc tccgggcggc cgcacgttgg ttccgcccgg gccgttccac tgcaggcaga   4860
gggagaggac gacggtgcgc gtagtgcatc cccgtggccc gttggttccg ccggggccgt   4920
tccactgaag gcagaagggg ggggaccgtg gccccacccc ccgcggcagc ccgttggttc   4980
cgcccgggcg gttccgcccg ggctgttcca ccagcggcac ttcagggcgg gatcggccag   5040
tctgtggagg cagcggcctc taagcccggg agggtttact gcccaggttt gggttccagg   5100
aataagaaat ccactgaata ggcttaactt agaagacaca aaggcgcctc ctggcggaag   5160
tggccacgct ccgcccagcc tgagggaaag ctgctctgac agctgggccc ggagctgcgg   5220
ggggcggggc cgccgcgcgg ggtgaggact cgcctcaggg cgctgattgg ctggtggcgc   5280
gctccggggc ggggccttcg tatccaggct ggcgtcgggg ctgccgcggg acatccggag   5340
cagacacccg cgggcgcgcc tgcggccccg aggaccccg gctccggagc ttcgtcgagc   5400
gttttcctag cgttactttc ccaaataatt ttcaggaatg aagttacggc taaagggctc   5460
tttagagatt acttttgggc cgggcccggt ggctcacgcc tgtaatctca cactttgggg   5520
aggccgaggc cggcgcatca cgaggtcagg agcttgagac cagcctggta tggccaacgt   5580
ggtaaaacgt cgtctctact aaaaatacaa aaattggccg ggcgtggtgg cgggcgcctg   5640
taatcccagc tactccggag gctgaggaag gaggatcacc tgaacccggg aggcggaggt   5700
tgcagtgagc cgagatggcg ccactgcact ccagcctggc gacagagcga gactccctgt   5760
caaaagaaaa aagaaaagat tacttttggc cgggcgaggt ggctcacgtc tgtaatccca   5820
gcattttgag aggctgaggc gggcggatcg cctgaggtca ggagttcgag accagcctgg   5880
ccaacatagt gaacccccc ccatctctac taaaaataca aaaaaaatt acccgggtct   5940
cgtggcgcgt gcctgtggtc cccgctactc gggaggttga ggcaggagaa tcgcttgaac   6000
cttggagttg aaggttgcag tgaggcgaga tagcgccgct gctctccgac ctgggcgaca   6060
gtgggagact tcatctcata aataaataaa taaataaata ttacttttac gttttgttaa   6120
acttccactt gttttttgttt ccgttgcatg aaccttcgta aagcttcagg aggctgatgg   6180
cagcctcctt ccccaggctt cccccgtgcg cccgcagccg ggttgggcca gaggctggga   6240
ctgtttcctc ccgtggggtc tttggtgggg atgtccccag aggagtgggg caggaggagg   6300
```

```
ggcacggagc gccccgggga gccggtcaga gcgcagcgat ggtgtctgtg gttccaacca   6360
ctcgggaggc tgaggtggga ggatggcttg agcctgggag cttgaggctg cagtgagcta   6420
gaatcacagc accacactcc agcctgggcg acagagtgag acccttgtct cacaaaaaaa   6480 aaaaaaaaa aaaaaaaaa aaaaaaagg ctgggtgcgt tggctcgcgc ctgtaatccc      6540
agcactttgg gtggccgagg cgggcggatc acgaggtcag gagatcgaga ccatcctggc   6600
taacacgatg aaacccgtc tctacaaaaa atacgaaaaa aaattagccg ggcatggtgg    6660
cacgtgcctg taatcccagc tacttgggag gctgaggcag gagaatcact tgaactcagg   6720
aggcagagct tgcagtgagc caagattggg ccactgcact ccagcctggc gacagagtga   6780
gactccgtca aaaaaaaaa aaaaaaaaa aggaagaaag aaaattataa aatgaagtga     6840
aattaacgca gtggagtgcc acctgcctgc tgcctgagtt cactatccac acggagttca   6900
taaatttgag agcagtttac aaagtagatt ctcctacttt ccaggaaacc cagaaatgtc   6960
tggtgatttg cccaacagtc tcagctgttg tggtcagcag ggccgctgtg gtatccaaat   7020
gatttcaaaa gcagatttat aaaaagtact ccttttttt ttgagatgga atttcgctct   7080
catcgcccag gttggagtgc agtggcacga tctcagctca ctgcaacctc cgcctcccgg   7140
gttcaagtga ttctcctgcc tcagcctcct gagtagctgg gattacagat gtgtgccctc   7200
acgcccagct aatttttata ttttagtag acagggtt tcaccatgtt ggccaagatg       7260
ttctccatct cctgaccttg tgatctgccc gcttcagcct cccaaagtgc tgggattaca    7320
ggcgtgagct accccacgcc cggcctttat tttttttga cggagtct cactctgtcg       7380 cccaggctgg agtgcagtgg cgcgatctcg gctcactgca agctccacct cccaggttca    7440
agagattctt ctgcctcagc ctcccgagga gttgggatca caggcacccg ccaccatgcc    7500
cagctaattg ttttgtattt ttagtagaga cggggtttca ccgttgttag ccaggatgct    7560
cttgaactcc tgacctcatg atccacccac cttggcctcc caaagtgctg ggattacagg    7620
tgtgagccac cacgcctggc ctctcaaagt ttttatagca aagccttaca tttcatgagg    7680
aaccatgcat tttatttat ttttgagatg ggggatctcg ctactttgcc caggctgggc     7740
tcaaactcag ggctctctgg cctcagcctc ccgagtagct gggtctgcag gtggctgtca    7800
ccgtgctggg cctggggtgt gcgtattaat gattttggaa tagtgtctgg aagcctgtgt    7860
gctttcctct cttcctctcc ccagaaggac ctcccacctc gtcctcccaa agtgttggga    7920
ttacaggtgt gagccaccat gtcccctctc tttgctattt tgcctgggag gagtgtatta    7980
ataattttaa ttttaaagtt ctttgattat gttctagttt gattattgat catttacttc    8040
ttagctattt atattcttcc ttgagtcatc ggtttctgcc ctttgacaat ttttctgtga    8100 atgtttgtg tcgattatat gagctttgtc tgtattgaga acatccacga attgtattat     8160
tgcatctgtt ttgctagttg agaacatcga cctgctgtat tattgcaaat gttttcctgc    8220
ttgcatgtag tcatttgttg tgcatattaa tgaatttcta tccacatgac gccggaaggg    8280
gatagagtgg gtggggagga agagggaagg gtccccacct ggagacccag cctgcaggcc    8340
actcggccac ctgcgcagag gtaggggagc agcagccgct catgcccctg caatttgtcc    8400
tcatcagcag gtggggaaac tgaggccggg gagttctcca ggccaaggtc actcacgggc    8460
aagttcccgc agcctttgga ccctccatac atgtcagggc cgctcatgct ttcctgggcc    8520
cttcactggt ttgaggaac catcctgttt cccagagcgc actgcctgtc tctgagtgta    8580
tgtgtctcag tggcgtccat gtgtattttt ctgtgtgtgt atctgtgtga gtctgtgtgt    8640
gtggtgtgtt tgtgtctgag tgtgtggtgt tagcgtgtgt ctcagtggcg tccatgcata    8700
```

```
tttttctgtg tgatgtgtct gtgtgtgtgt ctctgagtgt gtggtgcctg cgtgtgtctc    8760
agtggtgtcc atgcatattt ttctgtgtgg tgtgtctgtt tgtgtgtgtg tgaatctacg    8820
tgggtgtttg tccatctttt tgtctggcct cctgtccct ctgcacagag cagctgggtg     8880
gggatgctgg tcctgggggc ttgtcagcag gatgtgggcg tggggcagcc ctgggtgagg    8940
cctgagtaca ggccccaggt gcctcctgca caggggtggc tgagccggct cctctgtggc    9000
tcccgggtcc ccaccgccgg tcactgggca ccacctgtcc tggccaccca ctcctgccca    9060
ccctgctctc cgcaggggcc tccttcctct ttcagctgtg cgccctggtt gtggaggctc    9120
ctaaggaggt tgtggcctcg gtttaccacc tgccttggct ccttggtgtt gccagaccct    9180
gaaggcagcc catgccctgg ctgagatcct tctggggcag gatgtgctgg aagcagctga    9240
aacatgtggt gatgtaccag ctcctgctgt cccctacatc cccagcaccg ccagccttcc    9300
ctgggctcct ccagctggct tctctaccct gtacctgccc caccctgctt tcccccgacc    9360
ctactacccc ccaaccagac ttccagctcc aggcagggtc gcagcctcct gggctcccag    9420
caggacaggc ctcacccaga ccccgcagga gccgtgggac ttgggctggg tctttgggcc    9480
tggctgcagc cccttggac ctgacctgag gagacaccct ggctgtggga ggcagggtgg      9540
gggtgccggg cccagcacag aggtgcccag ggtgcaggct ggcactggcc cggcagggac    9600
cgtggatgcc gccgtttcag gctcgaaaag gtttccatgc cccagagcct gagcccggca    9660
gcccccgagg atgtcttggg gcctctgtgc tccccaaagc caagaaggtt aggcttgacc    9720
cacagcctct tccaggccgg ggaggcagag gcgctccagg tcggtagggc ggggcccaca    9780
gcccagggtt tcacgtcccc aaaacggggc agggtgctgg aggggcaggt gtccacaggg    9840
tggtcgtttt ggtctctcct ggacttgcac gcgtgtagtg cagactggct gccggcaaag    9900
ccctgagcca cattcatctg ggccttgtta ggacaacagg gacggtgcgg ggtggggggg    9960
ttgcggggcg caggaccacg tcagtggagg gagggaggcc gatatcggtg cccaggctgg    10020
gcccaggggc cagcgggtcc tcacctggct tgtggctgcc cctgttaggc agcccggatg    10080
gaggggctct tccagccctg ctggccccgg gaatgcaggg actcaactcc ccctggtctc    10140
agtggctctt ccgggagcaa cacagcctgc ccgagtcgac accaccccctc gggtttgagt    10200 cccttctgtc taccctacc cccgccaggg cactgccccc ttgcccggaa gaggcagcgg      10260
cacccccagc cccttgggga ggatgccctg ccggccccac actcggtgga tgggcatttt    10320
ggggctagga tttaatgggg gtgaccctgc ccgaccctc tatgttggtt ccacggcgtc      10380
agaagaaagc tgttattaac ccagcttatt ttctacaagt cttgtttatt gaaaggatct    10440
gaaaagcgta ataaggcttt caatgacatt taatacattt tcaagaaatt aatatgaaac    10500
attaaaattt acttcaaaaa tccaaagttt tctagatcat tcccatctca cgctgcttta    10560
gaggtcagtt cacaccttct gtgttcagat gagcggctgg aattctgaac actgccgtct    10620
tccagcccta acgctgggcg ctggtccctc tctcctaagc ccacggctgg gcttcccctg    10680
tgcccagggt catggcggac ttcaagccag gccggctgcc cagaatcaca ctcagggttt    10740
ttggacgctc aagtccacag atgctgaggt gcccagacga gggtgagcag ggagacacat    10800
gcctcggaga acgtgcccag gctgggccag gcggctgcgg gaagctcctc acgggcagag    10860
gagaacgtct tgtgccttcc ttatcgatct ccagcagatg agggcaactt tgtgtgcaaa    10920
actcagagag cagttactca aaaaaaagac acccgggcag cagtaaccag gacaccaggg    10980
tccgaccacg gcctccacac acctgtgccc gtggaagacg cgggcgccgg ggtaggcagc    11040
atccacgtgc tccacagctg ctggtgctgg gcaggctgga gactcacggg agaggcagga    11100
```

```
ggagaatcag cgtgttgagt ccctcgctgt gttagtgtga aaaattctca ttacagttgc    11160
aaataaaagg gatcacgatc actagccccg gaaaccctca tctcccggac catcaggatc    11220
gcactgaaca gaatggtccc ctaatggtcc ctgaggacag cgtcttgcag aacataaatg    11280
taaacattga atggcagacg actcccttcc ccttgaaatc ttcacaaaag tgtgtacgag    11340
aaagtatgta catcagcact tcagaaaagg ggcccacagg acgtgtgcgg ggtgtgcagg    11400
gtgtgcgggg tgtgcgggt gttttgagggt ccggatgtgc gtcccgaggt cggagggttg    11460
gacgcccctg tgtccagttg ttgggagggg tgggaggcct cgccctgctg ttcagcccct    11520
tcccctccac tgggccgcgt tcccaggac gtgcaacagg gcgctcaggt taggagaccc    11580
gaaaccacag gcagacagga cccgccacgc ccgctcccag ccctgggcac ccccacccc    11640 gtttccttcc agtccatttt ccgcggcagt ttttggtcct ggggaccgtc accgatgcct    11700
cccacgcacg ctttcttccc tgaagggaga cgtcgctgcg ctgggcctct cggcggtccc    11760
ccccacccgg gtcccgggcc cactggcccc ccgcagacgc cgctacacgc tgactccagc    11820
caggctgcgc tgggaccact tcaacctcac ctacaggtgc gccctggctg ggccccgggg    11880
gagggggcgc ggccggcgcc cgctgagctc actctccctg caggatcctc tccttcccgc    11940
ggaacctgct gagcccgcgg gagacgcggc gggccctagc tgccgccttc cgcatgtgga    12000
gcgacgtgtc ccccttcagc ttccgcgagg tggcccccga gcagcccagc gacctccgga    12060
taggtgggcg cccgccccg ccccggcccg gccctgcgcg cccggcctct cagcccgtg     12120 ctcccccag gcttctaccc gatcaaccac acggactgcc tggtctccgc gctgcaccac    12180
tgcttcgacg gccccacggg ggagctggcc cacgccttct tcccccgca cggcggcatc    12240 cacttcgacg acagcgagta ctgggtcctg ggccccacgc gctacagctg gaagaaaggt    12300
gaccgtccag gctggcctcc tggaggcctc tcctctgcag cacagtgggc tgccgcggtc    12360
gggctttggg gcagacggca ggagggacct tccggggtgg tggctgccac tggagtctag    12420
caggcaagga ggggagcccg tgggagcccc catcccggca gccctgaact cccttttccca   12480 tcccctgcg cctctggagc gggagctgga gctgcattcc tggggccga gctcaccgcc    12540 tgggcccaga acattcttat cttccgtgg ctgcggccga gggcggctcc gcggctgcgc    12600
tccagcagat acaccgggcc tcggggagct ggcccacggg cggcggggct gggcccgggg    12660
ctcccaggcg ctgacccccg gggcccgcag gcgtgtggct cacggacctg gtgcacgtgg    12720
cggcccacga gatcggccac gcgctgggcc tgatgcactc acaacacggc cgggcgctca    12780
tgcacctgaa cgccacgctg gcggctgga aggcgttgtc ccaggacgag ctgtgggggc    12840
tgcaccggct ctacggtgag tccctttgtc gggcgggagg gcgggaccgg gcggtcctg    12900 agccaggccg tgctccccac gctcccgaca ggatgcctcg acaggctgtt cgtgtgcgcg    12960
tcctgggcgc ggagggggctt ctgcgacgct cgccggcggc tcatgaagag gctctgcccc    13020
agcagctgcg acttctgcta cggtgatgcc cacgggccg gacagggct gcgtgggagc     13080 tgggccttgg ccatggtcgg ggctgagggg gcactgacgg ggctcttcc cccacccgga    13140 gcagaattcc ccttcccac ggtggccacc accccaccgc ccccaggac caaaaccagg     13200 ctggtgcccg agggcaggaa cgtgaccttc cgctgcggcc agaagatcct ccacaagaaa    13260
gggaaagtgt agtgagtgag cgcccggc ggtcctcggg gtgggcagcc cgcgggcggc    13320
cttggggcag gggtgcgggg caggcagcgg ggggggctg tgcctgcagg agacgcccg    13380 ccccctgca gctggtacaa ggaccaggag ccctggagt tctcctaccc cggctacctg    13440
gccctgggcg aggcgcacct gagcatcatc gccaacgccg tcaatgaggg cacctacacc    13500
```

```
tgcgtggtgc gccgccagca gcgcgtgctg accacctact cctggcgagt ccgtgtgcgg    13560
ggctgagccc ggctgataaa gcactttctc tctgatggct cctcgctcat tcttgggagg    13620
gcagcgggca gccagtctgg gcaggtggac accccagccc ctggtccacc gagagctggg    13680
cgtcctcggg gctgggcacc cctgcttccc cgcacagcgg accacaggta cagcacagga    13740
cgggacgggc tttgctaagg tggcccctgg gaaagtggga taagaggagg ccccagtgac    13800
aggggcagca cgtggagcag cacctggggt agcccagaa gcctgggttc tgtctaggac     13860
ttgctcagag ctggggagg gaggcaaagg gggcttcctg aaagatgtgg ctgggatggg     13920
cctccaggat cttctgcaag gagatgtggg tggggctgg gaggactggc acagggtggg     13980
ggaccacctt gccagagtgg aggcccccca ggaggtagga gctcccctcc tgcctgggga    14040
agacactggc ccacatgggg tcagaggcca cagccgccca ccccaccctc ttcccctaga    14100
gcccggtggt ctgcgactcc cctcccacac atggtcccgg gtcactcaaa ggacgacacg    14160
gggagctttc ctcgaagaat attttaatac attttaaaac tcaacaacct tgtataaaaa    14220
cctgtcgagt ctgctggcac agctggggct ggggttggg ggccggggc ctgtgtggac      14280 agggctggtc tggacgagtg ggttgggca agagggcatc gctcatccca acacagaaac     14340
aggtctccag ctccgaagat taaacaatcc acccggctcc caccagttcc tttccaaatc    14400
acggcccagc cagccccgtg cgtgtcgaga gtggagagg gtgtgtggag gtttgtgctg     14460
ccccacgtgg gcacccgaag atgccctggc aagtcacgga gaaaacacag ctctttcctc    14520
cacaacaagg aaaatgattt aattctacaa atttacaaac caaatacaa aaacaaaaca     14580 tggagcacaa agtaagacga ggagttccga gtctcatcgc agctccagcc gcagtagcca    14640
cgcctgtggt cccggctgag ttctccccat gacggggtcc actctgacct tcagaacttg    14700
aggctgaagc cggggcccgc ggcagaggcc ccctggttcg tggtggtaag gtggaagccc    14760
gtctccttca ggtcgtcgtc accctggac gagtcggcta ccgtgagaac cctgcccaag     14820
ccagccccac ctgtgggcac gccccacccg ccaggcccct caccagctgg ctgtagccca    14880
ggcctccctc aggggcctc gggctggtgc cccgcttcac acgctgctgc tcgctcttgg     14940
cgggccacgt ggggaacatg gaggggtcga tggggagggg ggtctcgcgg aaatactcat    15000
gcttgaggcc gtcctcagcg ctgatcctcc tcccggggaa gtaggtcagg aacctggggg    15060
gagagggcca gaggcccagg aggtgctcgt gtgctccact gggtccccca agatgggct    15120 gtgttgggac ggggctcagg gcatgggacg ccaggcacca gagcagttct ggaacgtggt    15180
gagccagcag gtaggcctgg gactgggaag tcaccgctat ggctcgggac ctcccgccac    15240
ccggctgcac tgggctcact tgttcatgag gtcgaagccc tggtctgaga gcagagcccc    15300
gaagcgcttg cggaggttgt tgtaggggtg ctcgctgaag gtcatctttt tgactactgg    15360
gagctcactg tagccgggcc agattttctc actggggtc cccagctcct gaaagacaga     15420
ggtgcttcaa cagccacacc aagtggccca cagtgttggc acctgtgtcc cgtcagaaa     15480 gacaagccac caggagggct ctcagtggcc ctggtcccca tctcaaccca gcacctgtgc    15540
gccccgcagc cccattcctg caactcctct gaaatccata cgcacctgc ggcagggcca     15600 gacccacctt gaacactttg ttgatctgat cgatttccga attcccgggg aacagaggct    15660
tctgagtcag cagctccccg aagatgcagc ccactgacca catgtccacg gccgtggagt    15720
attcctaaga cgccaggaga ggtgttcagg aaggccagtg cccgcgaagc tgtgggaggc    15780
tgcatggggg acaggggagg cactcagacg cccaggactc accttggcac caagcagcag    15840
ctctggggcg cggtaccact gggtcaccac gaccggggtg taggccttca gaggggatcc    15900
```

```
gtactcccgc gccagcccaa aatcacccac ctgcaacgac agatgggcgg ctgtgggtgg   15960
gcctgggcgg gtcaccctgg gatgggccac tcggagggg gctcaccttg aggatgccgg   16020
cgtggctcag cagcaggttg gacgtcttga ggtcacggtg caggatccag ttgtcgtgca   16080
ggtgtttcac cccccgcagc agctggatca tcagggtctt cacctcccct gggagggagg   16140
gaggctccca tgtggacccg gccgccccaa gcccagggca ctcagggtgg cccgctcgcc   16200
tcggcagcaa cagaggcttc tcagggcttt ccctgtggat gcagctggcc ctccctgcag   16260
cactgtcacc gcggggtga ccaggacact gccccactt gtacgcagac aggaccccgg    16320
ggcgcggctg tacctggcag gaagggctgt ttcatggtct ccatcaggct cttgaggtcg   16380
tgctccacgt agttcatcac gatgtagatc ttgtccatgt tgctgcccac cacaatctcc   16440
tgcagggcac ggctctgtgg gtgctgggca cctccaggcc cccacccacc cctgcacccg   16500
ggcgcagatg ctgagggaca gtaaggacct ccggtgccac ccgggaggca aatacttgct   16560
tctgtgtggt ctgtgaaggg ctccactaag tgcaggagag tgtaggaagc acccggcccc   16620
aggacagcac ggggccctgt cggaaaagcc ttccacccgg ggccaggcgt ggtggggcca   16680
tgctcactct aacggtgaca atgttgggat gctgggcctt gaggatggtg ttgatctccc   16740
tcagggacgt gatcgggaag ccctccttct ccttctccat cttcagccgc tttagagcca   16800
caatttcatc tgtgaagaaa atacagacgg cactgagagg cattctcaaa gtcacggtac   16860
caacagtgga ctcgttcagt gaggaccgca ggcagtgccc aaagcgccag catttcacgg   16920
aggggggtct cgttctaggt gggggcacgt gggcaccagg agaacgcccc agctgaggtc   16980
tcggcaacac ccacggcttc ccactcaaca caccacagac actcacagcc acctacagcc   17040
acctgggatc ccagcggcca cgccgactcc acatcgactt ccccaacaga gccggcctca   17100
cctgggatcc cagtggccga ctcccaacag agttcccggc tcacacacct gcttgggtgg   17160
gacgctggga acgcaaacct gcacaccagc cccggcacag accactccac gcgctgggcc   17220
tcggccctgt ggggcaggcc gcctgctact gcaagggagt ggcaaagccc cagggccagg   17280
ctgacctctg gcttctagag gtgctgaggg gtccaacctc cagtagctgc tcaggtgaag   17340
cgggcccagg tgcagtcgca gctctcgggc agccagcccc tgccccactt cccctgcctt   17400
tgtggggtga ggggaccccca cccacctgtt ttcttgtctt ttgctctgta gaccactcca   17460
taggtgccct cctcgatcct gttcaggcac tggaactcct cgacgctccg gcagccctgg   17520
gaaggaagcg cctgtgtgag gtctcagtgg ccatgccagc tggagggagg gcggctgcgt   17580
ccacaggcac ggcacaccca gcacgggca ggtgcagggc agagccttgg gactgggccg    17640
ggggtggagc tgggagcagc tcagttcttt caaagtctct ttccttgcaa aaccatctga   17700
cactttatta tgaaacaaaa ccagtgtgaa caaaaggcca tcccagccag gtgcaagggc   17760
tcaggcctgt aattccagca ctttgggagg gcaaggcagg aggattgctt gagcccagga   17820
gttcaagacc agcctggcca acatagcaac actctgtttt cttttttttct ttttgagatg   17880 gagtctcgct ctgtcaccca ggctggagtg caatggtgag atctcggctc actgcaacct   17940
ccacctcctg ggttcaggcg attctcctgc ctcagcctcc ctagtagctg ggagtatagg   18000
tacgcaccac cacgccaggc taattttttgt attttttagta gagacaggat ttcaccatat   18060
tggccaggct ggtctcgaac tcctgacctc tgatccgccc accgcctcgg cctcccaaag   18120
tgctgggatt acaggcgtga gccactgtgc ctggccaaaa ctcttctcta caaaataaaa   18180
aaattagcca ggcatggtgg cttgcgcctg tagttccagc tactcaggag gctgagatgg   18240
gaggattgtt tgagcctggg aggtggaggc tccagtgagc tatgattaag ccactccact   18300
```

```
ccagcctgga tgacagagac agacccagtc tccaaaaaaa aggccatccg gagagtctct    18360
ctgtcaaagt ggatgtgtcc cctgcttgta ccaggatgac actgaggacg ggccctacct    18420
gccaggcgca gcatgatgcc ccatgccagg cacctaccc ctcggtgtac cttggggccg     18480
gtgcccaggc cggatgtcac gtactctggg tggcctgtgg cccgacgcct acgctcagca    18540
gcactaaggg gcagaggcgc tcacaaggca tagggcagtc gacagaggcc tgctgcatgc    18600
gccagagaga acctctccgc ccacaggcac caaggagggg gccgagtccc tgccggtctc    18660
ccaggccccc gaggccactg gtaccttctc aggcttgtcc cttccaaatc actcccaaca    18720
atatcctgcc ttattgatag ctgcctgagc aaaaggcttc tggtcacaca tctacactga    18780
ctcccgtagc cgctccccca tccaagccct gcacagatgc cggtaacaag gccttggtgc    18840
ctacataacc cgcccacgca ggggtcaagt ggaaggcact gctctccagt gcggaggagg    18900
acgcaactcg ggcagcagtg acagcagcgc ggccgcacgc ccaggctgcc tttcaagccg    18960
cagagcagtc ctgcgggcag ctccctgtcc acccagttcc gtccagcatg agaaagaggc    19020
gggacctaga agcatgaggg gccagtggct gtgcccgccc gtcactgccc cagtgggccc    19080
agcagccctg tgaggcgaca gacgccaaca cgggggccag gcttcgctca gcccctgtgg    19140
taactccgac tgccaatgcg gacagcggcc cggggcgagg ggagggcctg acctgcaggg    19200
ccggcaggta cttgggcagc tcctgcttga gctcgatggg caacagggca ggggagtcgg    19260
gcacatagtc gccctctgtc agggcgctgc tctgcggcgt tccctcaccc acttcttcct    19320
ctgcttcttc actctccccg gaatctcggt cgaaccgtga ctctggaact ggaaaagttg    19380
aacctaatta cgaagctagg agtaagtaag gatcatgaac ctcctcctgc cccgggggca    19440
tcaagcgcgt ggcagggctg ccccgtgtcc cgctgggagg tgctggcgct gggctctcgt    19500
cccctggaca caggcaccg aggcctaaga gtgctggcag gctcggctga cacagagccc     19560
ggatgctgag ctgggaggag gcgtcggggt tcatgtgggg gacaagccca catccacgtc    19620
caccaggctg aggacataac ctcactgcct gtcggaggct gggccaggcc tctgttctgc    19680
agggacaggc ccggagccac catctgacgg gcctcccctg tggggaactg gtcctgggct    19740
tcccagctcc tcggccctgc tgggcactca ggacgccctt ggtcagcact gtgcctcgct    19800
gaggaatgcg ggccccaccg gcacagcctg gagcggccaa cgaatcaggc ggcctcccag    19860
accctggcgt gccccacgcc gcgcaggacc ggctgtctta ggagagggct gctgcactcg    19920
gagacagaca aggagggggc tctgtctcca gggaggttct taccaaccaa gaggtggttt    19980
tcatttctc gttcttcatc tttcactcatt tcttcctcac ttacttcttc tgcaagagaa     20040
aggaggcgtc tgctcagacc agcaccgggg cgagtgctgc cacaggcagg atgcgggctc    20100
cgcttcagct aagcaacaag tgttcccaag aatggatatg gaggctgggc gcggtggctc    20160
acgcctgtaa tcccagtgct ttgggaggcc gaggcgggtg gatcacctga ggtcaggagt    20220
tcgagaccat cctggccaac gtggtgaaac cccgtctcga ctaaaaatac aaaaattatc    20280
cgggcgtggt ggcgcacacc tgtactccca gctacttggg aggctgaggc gggaggatca    20340
cttgaacccg ggaggcagag gttgcagtga gccgagatca tgccactgca ctccagcctg    20400
ggcaacagat caagattcca tctcaaaaaa acaaacaaaa agaatcgatg tggaggtgtc    20460
ccgagagagt cctagataga agggagtttc aactcccccg cccgccagct acttctctgc    20520
ggtttctaac actatagtga agtcacaaca cctcacacag tcgtcgcggt gcctcaccgg    20580
cagactgctc tgatgcctcc tcagagttgc tgccggtctc ctcctcctcc tcttcctctt    20640
cctcctcctc ctcctctgat tcttcactgg tgctcccttc ctcctcctcc tcttcctcct    20700
```

```
cctcctcttc ttcctcagaa cctgagcctg attccgctgt agaaagacag cagagcagag    20760
ggtgaacctg ggccttcctg ggcagcagtg gtcaaggcct tggccaggcg gttccaggta    20820
cctgacgagg actcggccga gctggtcttc ctctcgctgt cgctgatgtc ctgtaagtcg    20880
gacagcaggt ccctttcttc cattttctct tcttttactt atgagataaa ccataaaggt    20940
gaatttgggg aaatgttttt aaacaaacaa gctaccacca ccccaaaact agtgcctttc    21000
acgtaacgat taactttgct tggtcggaaa ccagctcatc cacagacgct ggaagccact    21060
tctctaacgg ggccagtggc gaatgtccca gcggataaac acacgtcctg tgtcctggcc    21120
gcacacagac actcacggtc cctctcacga cacgagagga cttcagccag cacatctctc    21180
actttcttct gaagcggtta cttagctggg ctttaaatga atcctacaca cttatgccaa    21240
acatccccca gaaagactca cactgtgct ggcttctgcg caggcgccgg cctggcctca    21300
cctggcttcc ggccgtctcc caactcgaac cgctcccgcg gcggccgagg cgggctgcga    21360
ctccagtggc tggcttttcac tttgtcgctg tagtcctctc tcatcgttcg gtgatgtgca    21420
gacactggcg cgcagggcag agagggagat ggcactagca gcactgcctt cctcaaaagg    21480 ccccaccccgg cacagctgcc tcgtctccca cacccgcacc tggcagacac acccacagcg    21540
tgcacagggt gctgacagca tcgggtcag aggccagagg tctcccagga agcccaggga    21600 gaaaagctc caacctggag gccgtgagcc cgaggaccca ggtggacctt ctagactgat    21660
cttcactggt caaaaggaa ggggcgggag aagattctgg aaagatggag taggaagcac    21720
tgggaatcag tctccccacc gagacaacac ttgcatcaca ggatcaggcc tgtgcaacta    21780
ctgaggtgct ctggagtcta ctgaaggttt gcaacttcag ggggaatctt ggagagtaaa    21840
ctgtgattca ttaatcaacg tcaccgcttc gcacattagt ggctccacc tcactccccg    21900 ctggcaggca gcagcctgca tgcagctcgc cggacccagt gggcagacg gacacacaca    21960 cccgaggtca gtgtgatgac tgcgtgtccc accccagagg catgaagagg cagcagccac    22020
ggccaccccc aagctgaagg tacttccagg gcatgagcac cacgtccccc gttgcccct    22080 tcatttctct ctattccccc tttaggaggc agacacttca ggacaagaac attaaaaaca    22140
tctgtattga cgggaacgtt aaaaagtggc tgcacgtgac caggaaaagg ctcaggctca    22200
gaaaagaccc gtgaagaccc tgagtttcca caacaggccg accccacaga cacagcccag    22260
cacaaccaaa acaacaagtg cacacccttg agtggggacc aggaagaatc acatcatgag    22320
aatcaaatgt ccatttttt gactaagaaa aacacaagag aaacaaagaa acaggacagt    22380
atgtcccatt cagaggggaa aaaagaagc caacagacac ggttcctgaa aatcacctga    22440
cggtagatgt cccagacaaa gattttaggg aactgtctta aaccttcagt tcctcagaga    22500
acgaaaggaa gatgtggaga aagtcaagaa aatgacgcgt gaacacgacg gaaatatcaa    22560
cagagacaga agatccaaca agaaaccaga gagaaattcc agagctaata agtacatgct    22620
cacaatagac actaaaaagt aaatattcac aacagaaact cacaggcaga tgtgagcagg    22680
cagaagaaat aatcggtgag cctgaagaca ataaaatcac atcgtctgag gaaaagaaag    22740
cagaagagac tgaagaaaag ggagcagtgc tgagcggcct cggggacccc aacagatctg    22800
tgggagccca ggagggagga gaggagcaga gagggtatct gaagaattcc tcaaaacccc    22860
cacattggat gaaaaccgta aatataaaca ttagagaggc tcagtgaact ccaggtagaa    22920
tgaagtcaag aggcccacag gaaaacccat tattaaacag ttgaaagcct aaggcaaaga    22980
gaatcttcaa agcatccaag ggatcctcaa ttaggtcatc agattaaagc atccaaggga    23040
tcctctataa gatcatcaga tttctcatca gaaactttgg aggccagaag acaatgggct    23100
```

```
gaaatagtcc aagtgaaaag gaaaaactgt cagctaggca tgagggttcc ttgagcccag    23160
gaattcaaga ccagcctggg caatacaggg acaccttgtt tctactgaaa aatgagccag    23220
gtgtggtggc acacgctacg cctgtaggtc ccagctacgc gggaggctga ggtgggaaga    23280
tcacttgtgc ccaggagttc gaggttgcag tgagctatga tcgctccact gcactccagc    23340
ctgggcaaca gaagaagact ctgtctcaaa acaacaacaa caaaattgtc aaccaagaac    23400
cacgtatcca gcaaactttc cttcaaagat gagggagaaa tgaggatatt ctcagataaa    23460
caaaagcaga gggagttcat tactactaga cctagacctg ccttgaagaa taagctccag    23520
ggagttgtgt ggggtgtaag gaaaggacgc gagacagaaa ccggaagctg ggtgaagaaa    23580
taaagatctc cattaaggtg aggacgtggg tgactataaa agctcgtact ggccggccgc    23640
ggtggctcac gcctgtaatc gcagcactgt gggaggccga ggtgggtgga tcacgaggcc    23700
aagagatcaa gagactattc tggctaacac ggtgaaaccc tgtctctact aaaaatataa    23760
aaaaatagct gaacatggtg gcgggtgcct gtaatcsctg ctactccgga ggctgaggca    23820
ggaggatcac ttgaacccgg ggggcagagg gtgcagtgag ccgagatcgc gccaccgcac    23880
tccagcctgg gggacaagag caaaactctg cctccaaaaa aaaaaaaaaa ggcaggggcg    23940
aaaagcaagc accggaacca agcgcccgcc tgtgacagca agtgcccagc accaggggc    24000 agcagacacg cgtcccgccg agcacagctg cccaccgcgc cgcctacctt ccctgcgggc    24060
ctcccgctcc ttgcgccgct cctccgcccg ccgctcgcgc tccttctgct cccgctgctc    24120
cttctgctgc tcccgcatct tgcgctcccg ctcccgcttc cttctaact gctccaagcg    24180 gtccctgaag aggcacacgc catcattccc cctaaacaga agcttgctta tcgcgttttt    24240
gtccacattt gtaagctggc tttctacgta attcaatccg tgaagttttt ttttcatttt    24300
tttattttat tttctttgag acggagtctt catctgtccc ccaggctgga gtgcggtggc    24360
gcgatctcgg ctcactgcaa cctccgcctc ccgggttcga gcgattctcc tgcctcagcc    24420
tcccgagtag ctgggattac aggcgtgcgc cctgtactcc cagctaattt ttgtattttt    24480
agtagagacg agggtttcac catgttagcc aggatggtct caatctcctg acctcgtgat    24540
ccgcctgcct ccgcttttca aagtgctggg tttacaggcc cgagccaccg tgcccagctg    24600
ccatttccaa ttctaattaa taaatgatcc atttctttcc attcgatcgg tgtttgcttc    24660
atggattttg ggctctgtgg ttagatgcat tcacatgtat cattgctgta tcttcctgct    24720
gtattggcct gtttctggct gtgaagtcct tgctccttct tgtttctagc tttttttttt    24780
tttttgagac agggtcttgg tttgtcaccc aggctggagt gcagtggcgc aatctcggct    24840
cactgcaacc tccatctcac gagttcaagt gattctcata cctgagcctc ccgagtagct    24900
gggattacag gtgtgcacca ccacacccag gtgattttg tatttttact agagacaggg    24960
tttcaccatg ttggccaggc tggtttctaa tatttcttaa catctgtttt gtctggtatg    25020
agtacagcca ttcaagctct cctatgacag ctgatgtttg tacgctgcgt cttttcctgt    25080
tctctagcag acagcataca gttagatctt gttttctat ctgataatct gccctgtctg    25140
tttggggcac agagaccttt cacatgtcat ataattacac gtacagttgg atttactttc    25200
cttgctttgt tgtgtctttt ttattcttcc ctttttgatt ttaaattaca tacgtttagc    25260
ataccatttt aatttatttg tactttttag aacactaaga aaacaacttt cttagtggtt    25320
gctctaggga tcaccatatg cctcatgata ctagctcaag tccagtacaa tataaaactg    25380
ttgtaacaca gcttcattcc ctgtcttctt tgtgcagtcc atttatgcca cataccacga    25440
caacagtgta attattttac acaatcgtag ttccagtaaa acctaagatg tgaggagaga    25500
```

-continued

```
tatttacagg atattgacgt caacctacac ttgctatctg cagtgcctgt ccttccttcc   25560
tgaggattca agttaccgtc tggtgtcatt tctattcaac ttgaaggtct tcctttagta   25620
tttcctttaa ggcaggtttc gccaacaatg aatcccacca gtctctgctt ctcagggaat   25680
gtcgttcgtt cccttcact tgtgtagaac agttttgatt cctggctgat ggttcttctc    25740
tctaagcagc ttgagtatgc cactccactg ccttctggcc tccattgttt ctaagaagtc   25800
agtggctggc ggtattgaag ctccccttc atgggatggg tcattcttct ctgagccctt    25860
tcaacatttt ctctttggcc tttgccagtt tgactatgat gtgactttgc atttattcta   25920
gttcaaactt cctgtgctct tgaatgtgca tattttttaa ttaaaatttg gaaagttttt   25980
aaccattatt gtaacaaata tctttcctct ctcctggaac ccccattcga cgtgctttgg   26040
tacagcagat gttgtaccac gggtttctga ggctctgtgc attttcttg tttttttctc    26100 tctgttcttc agaatggata atttctactg ctccatccac aagttgtttc caagccttta   26160
ctaaattcaa catctggaca ctcaagacag tttctactga tgatgttctt cctcagtacg   26220
ggtcacactg tcatacttct ttgtatttta gataatacat ttgtagcaat tctggattct   26280
aagttttccc tttcgttgtt accaccaagg cctgtctggt tgtccgtgaa atccatctcc   26340
ctcatagctc atggccaccc cgttccttcc cacatgccta ttttaatttt caaccttggc   26400
ttcctagggg tcaccaccat ggctgcacag cttagcaatt agccagcact ggaaaaaggc   26460
tgggctcaaa tacctcgagc acagtaaggc ttccttggcc cacggctgtg tgtggacagg   26520
gagcacactg aacgttcagg cgtcattcgc atctgtggcg gcttctattt tctgctaggt   26580
cctttcacgc agctgcatcc tcagggctgg tcacaagtgg gtggcggctc gagctctctc   26640
cagtctctgc tgcacgtctt tggcgggatc acagctgctc ccaaccacac tgtacttcat   26700
tctagcagac ctcttggcct tttcctccct ccactgagga tgctggtggg caaggccact   26760
gcccactgct ctaaacggag taacccccttc caaggcagca aggaaactgc aggtcctgca   26820
gctgccctgt cccagtggaa cctccgtgct tccaagtgca gagtggaagc agtaaaggga   26880
gcagctctca ggccagaagg tcagattctt actgctttta cccacagctc agcagttttc   26940
caagcatcag tgcttctcag attatcctta tcagtttcct ttttgtcaga acaaggtct    27000 ctctacgttg cccaggctgg cgtcatgcgg tcctctggcc ttagcctccc acgtagcata   27060
tgctaccaca cccagttctg gattggctga tctgaatcgg ccctacccag aagtctgccc   27120
ccaacaattt tgttcattc actctcctgt ctttaccttc tgggaaatca atatgacagc    27180
ccaaatttca tctaccaacc tccacttcta tcccaagctc tactctcgtg ggacaagaca   27240
cactcaatgt ctggcacagg gcgtggcata catgaatgtt tcacacacta acaggaacta   27300
ggccaactga aaccttgctc acccagcagc ggtctcggac cttgacccct gggcctcagt   27360
gtctcccaca cccttcggca tcaacaagaa ccagcgccct ctcatcatct ttacatgctg   27420
tgtacccagc cctggctgct ggcaaacatc gctgcacacg cccttccgct tcagactcct   27480
ctcttcctgg agcagcttgc aagctttctg tggactcact ctgaaggcgg agatgggcct   27540
gctcgcacct ggcctacagc cttttcctg gttcacagaa cagatctggg gctacaccga    27600
tgttctttct tgggaatctg gctcataaag gggaacgaat atacagacta atggccagga   27660
gtcctaggag tccagtgtcc cgatttccag actgtttcaa ggttttggg atctcccttc    27720 tccttttttt gagacagtct cactctgtca accaggctgg agtgcagtag catggtcata   27780
gcttactgca gccttgacct cccaggctca agggatccaa ccacctcagc ctcgtaagtg   27840
ctggaattct agcgtgagcc actgcgcccg gcgggacgtg cagatttctg atcccttcat   27900
```

```
tgtcttccct caatcaaatc acacccgttc ttacttccag atgcagtgaa aactcactcc    27960
ctcaggacag ttctcttggt cagcctcgtc cagcgttcac tgtgctgttt ccatgtctac    28020
cacttctgca acaaatgtga cttctattgc caaattcttc ttcattgctg tgacaggaca    28080
cactaccacg gcccttttcat aaagtcctca actgacccag cccactcacc tttctctcct    28140
ggaatgctcc cttgccattt cccttctctt ctgtctttcc cattcccggc gagctttatc    28200
ctgttcttct cgatgtcgtt tccgacgttc gtgctctctt tctttcactc tagcatgctt    28260
ccctaatgag aaataaagtg tcatgcaaag aaacctcact tcaaaaattt cacgaggccg    28320
ggcacggtgg cttacgcctg taatcccagc actttgggag gccgaggcgg gtggatcacc    28380
tgaggtcagg agttcaaaac cagcctggcc aacatggtga aaccccgtct ctactaaaaa    28440
tacaaaaatt agctgggcgt ggtggcaggc acctgtaatc ccaggtacta agggaggctg    28500
aggctgtaga atcacttgaa cctgggaggt ggaggttgcg gtgagccgag atcgtgccac    28560
tgcactccag cctgggcgaa aaagtgagac tccatctcaa aaaaaaaaa aaaaaaaaa     28620 aaaaaaaaa aaaaatcac atgaaaatga aattaaatca agaacattaa atatttaaat    28680
aatgatgtta agtaatccta atctttttttt tttttttttt gaagagacag ggtctcacta   28740
tattggccaa gctggtcttg aactcctggg ctcaagtgat cctccatcct tgtcctccca    28800
aagtgctggg attacaggcc tgggccactg cacccagtcg aataatcatg attttatgtt    28860
aaataaaaaa cttggaaaat agaaaactat ctgcagtaag cgtctaatta tgaagaaaga    28920
agaaaaaaga aaaacaattc tgctatcaca gaagagaatt gtaatattca tcttttaaaa    28980
attttctata ctgaataaac tataattatc agttttataa tacaaaaacc actcttcaca    29040
aagactacag aacaaagctt tgctatcagt gggcttctcc actgtgcaat gaagccacat    29100
taattaatca agcgtattta taataatgag atttcaatcg ggctccaggt ccaattttcc    29160
taacacccgt aagaatctcc tgatgttggt acgagatcaa actgctcaag cctaacccat    29220
tctttggact tgagcaaata cccatttttgg ggtgtgtttt tctcctatac ttgttgaatt    29280
caggtcattt taaatgtaaa caaactgctc ccaaacaata taatggggga gagaaaaccc    29340
cagaggaaaa atggactagc cattctgaat ggtctgtgac acacgcacgc tttcagctag    29400
agtttgctct ctctggtttt cggtctgtga cacacgcatg ctttcagcta gagtttgctc    29460
tctctgtttt tcggtctgtg acacacgcac actttcagct ggagtatcct ctctatagcc    29520
cctctgaacg gtctgtgaca cacgcatgct ttcagctaga gtttgctctc tctggttttc    29580
ggtctgtgac acacgcacgc tttcagctag agtatcctct ctatagcccc tctgaacggt    29640
ctgtgacaca cgcatgcttt cagctagagt ttgctctctc tggttttcag tctgtgacac    29700
atgcatgctt tcagctagag tattctctct atagcccttc tgaatggtct gtgacacacg    29760
catgctttca gctggagttt gctctgtctg gttttcggtc tgtgacacac gcatgctttt    29820
agctagtttg ctctctatag ccccttctgaa tggtctgtga cacacgcacg ctttcagcta    29880
gagtttgctc tttctggttt tcggtctgtg acacacgcat gctttcagct agagtttgct    29940
ctctctggtt tcggtctgt gacacacgca tgctttcagc tagggtattc tctctatagc    30000
ccttctgaat ggtctgtgac acacgcatgc tttcaggtgg agtttgctct ctctggtttt    30060
cggtctgtga cacacgcatg ctttcagcta gagtattctc tctatagccc ctctgaacgg    30120
tctgtgacac acgcatgctt tcagctggag tttgctctct ctggttttcg gtctgtgaca    30180
cacgcaggct tttagctaga gtttgctctc catagccctt ctgaatggtc tgtgacacac    30240
gcacgctttc agctagagtt tgctctctct ggttttcggt ctgtgataca cgcacgcttt    30300
```

```
cagctagagt tgctctctc tggttttcgg tctgtgacac acgcacgctt tcagctagag    30360
tattctctct atagccattc tgaacggtct gtgacgcacg tatgctttca gctagagtat    30420 tcttttttt tttttgaga cggagtcttg ctctgtcgcc caggctagag tgtgcagtgg    30480
tgcgatagcg gctcactgca agctccgcct cccaggttca tgccattctc ctgcctcagc    30540
ctccagagca gctgggacta caggtgcccg ccaccacgcc cggctaattt tttgtatttt    30600
tagtagagac tgggtttcac cgtgttagcc aggatggtct tgatctcctg accttgtgat    30660
ccacccgcct cagcctccca aagtgctggg attacaggct tgagccacca cgcccggcct    30720
tcagctagag tattctctct atagcccttc tgaatggtct gtgacacacg catgctttca    30780
gctagagttt gctctctcta tagcccttct gaatggcctg tgacacacgc atgctttcag    30840
ctagtttgct ctctctggtt ttcggtctgt gacgcacaca tgctttcagc tagagtttgc    30900
tctctatagc ccctctgaat ggtctgtgac acatgcatgc tttcagctat tctctctata    30960
gcccttctga acggtctgtg acaccattat gctttcagct acagtttgct ttctctggtt    31020
tttcagtggt gctctgggga aggcagaaga gtaggaacag gaaagaaacc acacttgaac    31080
atgatgtcaa agaaagtaaa tgcttctgta cccccttctg ctgaatggct atgatgccta    31140 cattttttctt ttctcttttc atcttttctg tgatgaactt tttctttccg agacatttgc    31200
tggggtggtt tgatggccaa agaatcatct tcttctcctc tgaaataaaa cacaacagca    31260
ctgcgtcatg cttgagaaag tgcggaaaag catcaggcta ttatgaggtt ttttcaaccc    31320
agaaaaatgc atgattcaga taggaacgaa gctgaaacat catttaaaaa attacattaa    31380
ttctccaact tcaggcatct tttttttttt ttttttttag acggagtctc gctctgtcac    31440
ccaggctgga gtgtagacac gcgatctcgg atcactgcaa cctccacctt ccgggttca    31500 caccattctc ctgcctcagc ctccggagta gctgggacta caggcacccg ccaccacacc    31560
cagctaattt ttgtattttt agtagagacg gggtttcact gtgttagcca agatggtctc    31620
aatctcctaa cctggtgatc tgcctgcctc ggcttcccaa agtgctggga ttacaggcgt    31680
gagccaccgc gcccggccta ggagtcttaa gattcagatg aaaaatgtaa gaaatcaatg    31740
ttttgtgcag atgaacgaa atgcctctca gaggacctgc aggggggtgag gggcaggttc    31800 attagcttga ctgtggtgac agtttcaggg gcatgtaaaa atacatcaca tcttatttat    31860
ttaatttaat tttatttatt tatttatttt atttgagatt ggagtcttgc tctgtcgccc    31920
aggctggagg gcagtggcga gactctcggc tcactacaag ctctacctcc tgggttcatg    31980
ccattctcct gcctcagcct tccaagtaac tgggactaca ggcgcccacc accacgcccg    32040
gctaattttt tttgtatttt ttagtagaga cggagtttca ctgtgttagc cagggtggtc    32100
tcgatctcct gaccttgtga tctgcccgcc tcagcctccc aaagtgctgg gattacaggt    32160
gtgagccgcc acgcccggcc tgtatttatt ttttgagat ggagtctcgc tctgttgccc    32220
aggctggagt ccagcggcgc aatcttggct cactgcaacc tctgcctcct gtcccaggtt    32280
cgagcaattc tcctgcctca gcctccggag tagctgggag tacaggcgtg cgctaccaca    32340
cccagctaat tttatatttt ttagtagaga cggggtttca ccatattggt caggctgatc    32400
tgaaactcat gacctcatga tccacccgcc tcagcctccc aaagtgctgg gattacaggc    32460
atgagccatc gcaccggac ttattatttt tttcagacag aatcttgcta tgtccccag    32520 ggtagaatac agaggcacaa tcttggctca ctgcaacctt tgcctccac attcaagcaa    32580 ttctcctgcc tcagcctcct gagtagctgg gactacaggt gtacaccacc atgccaggct    32640
aatttttgta tttgtagtag agacaggctt tcaccagtaa ccctaggaaa gagtaaacct    32700
```

```
caatagttgt aacagcatgc cctgtcacag taatcctagg tcgtggctcg cacctgtaat   32760
cccagcattt tgggaggccg aggtggacgg atcaccaggt cagaagatcg agaccatcct   32820
ggctaatttt ttgtattttt agtagagacg gggtttcacc gtgttagcca ggaggctgag   32880
gcaggagaat ggtgtgaacc agggaggcgg agcttgcagt gagccgagat ggcgccactg   32940
cactccagcc tgggtgagca agactcttga gacaccgtct caaaaaaaaa aagagtacac   33000
ttcagtattt acaacagcac actgagcaca ctgtcacagt aaccctagga aagagtaaac   33060
cttaatagtt acaatagcac accccgtcac gtaaccctag ggaagagtaa acctcaatag   33120
ttaaaacagc acacccgtc acagtagccc taggaaagag taaacctcaa tagttacaac   33180
agcacaccct gtcacggtaa ccttaggaaa gagtaatctc agtagtacaa cagctacaac   33240
acgccctgtc acggtaactc taggaaagag taaaccttaa tagttacaat agcacacagt   33300
tgtcacagtg accctaggaa ggactggcca ggccagggct gtgtacagtt gggtcttgca   33360
catctgtaca tccgctcacc tgtcttccat tgagtcttct cttctatacg gggagttcct   33420
tattgtgatc tccatgcagt gatctctcag ctcccctcc tcagggaat cccgcttgga    33480 atcccggtca tcagactaag aagcaaagag aaagttaatc attttcttta taagtttttt   33540
tttcttcata gataaaagta ttttaatga taatcaaacc tgggcaacat cccaaaacaa    33600
actttcacat gtactctgaa tgagccagtg ttataaaata taagaatttt ttggccaggt   33660
gcagtggctc acgcttgtta atcccagcac tttgggaggc cgaggcgggt ggatcacgag   33720
gtcaggacat taagaccatc ctggctaaca cggagagacc ccatctctac taaaaataca   33780
aaaaattagc ttggcatgtt ggtgagcccc tgtagtccca gctactcagg aagctgaggt   33840
aggagaatgg tgtgaacctg gccctgggcg acagtgcgag attccgtctc aaaaacaaaa   33900
aaaaagctaa caaagtgagc acatgctatt ggaaaaatac tcaaagcaga gttgctacaa   33960
acctttaatt tggaaaaatt tcaatatctg tgaagcataa taaagtgaag tgcaaggtat   34020
gcctgtactc actaacatcc caaatgatgc tacaaatctt agcaaagag gtactttgcc    34080 aatgcctctt accaaattac taaaaaggtt tcctgagtac attaccatgc aaaccaagaa   34140
agacgtaaaa tatttatatt aatttcaagg caagttccca ctatattaaa aatacttaga   34200
gatagtatta tgaatatact aataatgaac cgagaaaaat tagtccagtt ttgctaatga   34260
cttaacattc aacgtatttt attctccatg tatgctcaat ctagacacag ctttagtgtg   34320
ttaaatctgc ctttaatgtc aactgaatat tagaatacat tttgggctca cctgcgacat   34380
ttggaagtac aaaagaactt caccgaagaa gcgttgttct aatggaaaaa tgagggcaaa   34440
gaaattaaat ctcctttaag aaaaccactt acttaaaaaa atatggctta catttttaa    34500 gcgttttatc tctgctttct cctcttgttc cttccttcgt ttcttttcct gaagaatttc   34560
atctaaagtt ttcactttcc aagagtcctt ttcatcaccc atttgagtta aaacactgca   34620 aaagaaaaa taattcagcc tacatcagga cacagcaagc tatggtgctg aacacttgaa    34680
cctagtcact tttgagggat tcagaataaa tcctcattaa gaataagaag ttgtgcccgg   34740
cgcagtggct caagacggta accctagcac tttgggaggc cgaggcgagc agatcgctgg   34800
agttccggag ttcaacacca gccgggcaa catggcaaaa cctcgtctct acaaaaaata    34860
caaaagttag cccagtgtgg tggcgcgtgc ctgtattcct agctacagga aggaggctgc   34920
tagaggcagg aggatcactt gaatcagaga ggtcaaggct gcaatgagcc aagactgcgc   34980
cactgcactc cagcctagat aacaaagtaa gacttggtta aaaaaaaaa aaaaaaaagg    35040 taagctctag gctgaggcgg gtggatcaca aggtcgggag gtcaagacca gcctggccaa   35100
```

```
cacggcgaaa accctgtctc cactaaaaat acaaaactta gctgggcgtg gtggcgggtg    35160
cctgtaatcc cagctactcg ggaggccgag gcagcagaat cgcttgaatc cgaaaggcgg    35220
aggttccggt gagccgaggt cgcgtcactg cactccagca agaccccgtc tcaaaaaaaa    35280
aaaaaaaaaa aaaaaaaaaa aaaaaaacaa gaatgataag ttgtaagcca ggcaaggtgg    35340
cgagcgcctg tagtcccata tactctgcaa gctgagatgg gagaccgatt gagcccagga    35400
gttccaggct gaagtgcgct tgtgaacagc cactgcgctg cagcatgggc gacaaaaaag    35460
agtgatgggt tctgaaaaat gaccgcttga aatcaagtct cgtttctgtc attcttgtat    35520
ggtcttgggt aacgtaattc acctcagttc agtcttccgt acaaccagaa taacaacacc    35580
tacgtgatag tatcgatcgc ggattaaaga tcatccgttt aaaggctctt aactcaggac    35640
ctgccactca tcaaacactg cttttactgt cagaatctgc tagaaagacc gcttggacta    35700
cgtgaagcca ctagcacact ggacagctgc accttgagac cggggagatg ctccgagatg    35760
tgctcgcgaa caaggccacc tgacccgggc actgggctat ttcctcgggt tcagtcccgc    35820
acacttgagg ttcagcctgg cagacgttgg ctccagacag cgtttggacc cgccgcctcc    35880
accacccaaa gttccgtgcg ggatgagact gtccgcggaa gcgagggtgt cgctcgcccc    35940
cgggcccggg tccgccccgc tccgaggcct gctcggaaga aagacctcgg tgcgcagttc    36000
tcgtcgcgct cccacacctg gtccgcccag tcggaactca cccctacggg gccgcggccg    36060
gtccctgagc ctgagaagaa acagcaaccg gcgctcgcca gaagtatcct cacttcctgt    36120
gttgacgcct aatgatgata taatagccga cctctggccc agaactcaag acgacagggg    36180
ctcgctctgt gcggcacttc ctgtgtctgc gcgggatgat gacgcataaa acagcgcttg    36240
ctcaggtcca ggactccaaa agaaactgcg ccgtgagctg cacttccgac ttcggcgcgg    36300 gccgggcgc cgagcagagc gacgccgact tttggagcag tttgcgcctg cgcggaacgc    36360
gtggccggct tccggaatcc taccgggact ttccggtag cgaagcccgc gcctgtgcca    36420
aggcttgcga gcagaatgcc ttcgcgatgg acgcccgcat tccacccct tgaccgctgg    36480 gaccctagt ggcgggtggg tggagcgcgc tccatttacc tgctggttac ctcgtgaggc    36540
gcctcaggtc tgtgtgtctt gtaaaggccg atctcggaat ttaactctga accttactca    36600
gaaacaaagc agggagagct cttacgatgt gatttatttt tatttattca tgtatttact    36660
tttgagtcgg agccttgctc tgccgcccag gttggagtgc agtggcgtgg tcttggctca    36720
ctgcagcctc ctcccgggtt caaggaattt tcctgcctca gcctcccgag tagctggaac    36780
cacaggcccg cgccaccacg cccggctaat ttttatattt ttggtagaga cgaggtttcg    36840
ccatattggc caggctggtc tcgaactcct gacctcaagt gatccgcctg cttcgtcctc    36900
ctaaagtgct gggattacag gcgtgagcca ccgcgcgggg ccttttacaa tgtgattttg    36960
aagctgacac tggcagtggg tcctcaaagt gcagactcac tgggtatggt gcttccccca    37020
actcccaggg ccccactcca aacccatgga ttcagagcat tgcaggagaa gaggataaaa    37080
cgagcaatta attcccttc catatgtcag gttttcctct tgccttgaaa agtcacagaa    37140
aaatgcttta gacatctgaa tctcaggaaa caaacaatgg aagataaaca tccgcattta    37200
ctgggcctga aatgggaaaa tgaaagatgt ggcaagaaac tgacaagggc ccaagaaggg    37260
cgatgggtat cggaattctt ttcatcccgg aatgaaatgc tgcttgcttt gtgtacccaa    37320 gctcttttt tatttttatt tttttgagac ggagtctcgc tctgttgccc aggctggagt    37380
gcagtggcgc gatctcgggt cactggaagc tccgccaccc ggattcacgc cattctcccg    37440
cctccactcc attcgcccgc attaggctcc tgagtacctg tgactacagg cgcctgccac    37500
```

-continued

```
catgcccggc taatttttt tttattttcg gtagagacgg ggttttaccg tgttagccag     37560
gatggtctca atctcctgac ctcgtgatca gcctgcctct gcctcccaaa gtgctgggat     37620
tacaggcgtg agccaccgcg cctggcctcc cccaagctct taatgttgct tcctgagttc     37680
ttggtaactg gggaaatctc cctattttt tatttttatt tttttttgag acggagtctt     37740
gctctgtcgc ccaggctgga gtgcagtggc gcaatctcgg ctcactgcaa gccccacctc     37800
ccgggttcaa cgccattatc ctgcgagcct cagcctgccg agtagctggg actacaggca     37860
cccgccaccg cgcctggcta atttttgta ttttttttag tagagacggg gtttcactgt     37920
gttcgccagg atggtctcga tctccttacc ttgtgattcg cccgccttgg cctcccagag     37980
tgctgggatt acaggcgtga gccactgcgc ctagctattt ttatttttc tgatagggag     38040
actcgctctg gccaggctg gagggcagtg gcgggatctc cgctcattgc aagctccgcc     38100
tcctgggttc acgccattct cccgcctcca ctccattctc catcttagg ctccagagta     38160
gctgggccac catgcccggc taatttttg tattttagt tgagaccggg tttcactgtg     38220
ttagccagga tggtcttgat ctcgtgacct cgtgatctgc ctgccttggc ctcccaaagt     38280
gctgggatta caggcgtgag ccacagcacc ctgcccttt ttttgagaaa taagtctcac     38340
tgtgtcaccc aggctggagt agagtgacac aattttgggt aactgcagct tccacctccc     38400
aggttcaagt gattcctg cctcagcctc ccgagtagct gggactacag gcgcccacca     38460
ctacgcccgg ctaatttttt tgtgttttta gttgagacgg ggtttcactg tgttagccag     38520
gatggtcttg atctcatgac cttgtgatct gcctgccttg gcctcccaaa gggttgggat     38580
tacaggcgtg agccacagca ccttttttt tctgttttga gagaaagtct cgctgtgtca     38640
cccagactgg agtgcagtgg cacaattttg ggtaactgca gcctccgtct cctgggtaca     38700
agtgattctc ctgcctcagc ctcccgagta gctgggatta taggcgtgcg ccaccacacc     38760
tggctaactt ttgtattttt agtagcgaca gggttttgcc atgttggcca ggctggtctt     38820
gaactcctga cctaaagtat ctgcccacca gcctcccaaa gtgctggaat tatagtcatg     38880
agccaccgtg cccggccaaa atctccagt ttacccttcc tttgtgaaat ctgttgagta     38940
cccaaatgca gccactcatg tcaaacccta acaaaatcga ccccagagcc cacgaggagg     39000
gggtggcctc gcacttgcgc ttgataggag ctgccacaaa ggccttccc aaccagaact     39060
ttgggtccag ccacttctgt gaagagcctc tttgctagca atagccagcc ccaccggtga     39120
acaaagtagc atgaacacca gaggtccaca aggaagaaaa caaagcagtc catatttaac     39180
atttattta ctttgctgag caagaatcat agacagctac taccacggct gcttcgtttg     39240
gacaaaaata accaggaggc atccacggga ttagttacac ggtatcaact taccaccaca     39300
gcagaatcaa cagtgactcg ctaattaaca gaaccgtttg ctagaaagca ctaatctagt     39360
tatataaata ctgaaatagg tcacatgcaa aacactataa acgttttgtg tgatgtactt     39420
ttagttctcc atagttttgt ttggtataaa ggaaatataa tttggctgtg acgtagactg     39480
ttgatgtaat tttcaagttt tcctgtatgg ggaaagttgc cctgactgtg gccctttca     39540
aggtggagcc tccaacacca cgttggcaga ttcagactcc gtgaacagtc taaatgagca     39600
agtcagctga atgccacttt cagatggaag ggaaatgaga tggaaaacaa caaaaaagga     39660
ctgccaggcg gaacagtttc caaccgagtt ttcgttgagt gaggatccag cagccatcaa     39720
actcaaacat aggggcccgc agggaaactg gaggaaatac ttcagagaca gcaaagctga     39780
aggtttctgt gctctgaggg atccgagagt ggatgtccca ctcctgtatc ctcagccaga     39840
cacagaacta gccagattca ttagggaagc tcagatgctc tcattctata aagtaaggcc     39900
```

```
cccagcaggg cacgtacata cattgggaaa gaagaaaccc cttagtacca tgttggtcaa   39960
aggcaagaga gagaattcta tttccatctg gaatgtcatt cttgtttact tcttccaaca   40020
gtgaaatact tccaggcctt cgaaaggcca tcctttggac acatgtaaaa agctgtcttg   40080
ttggcccgtt attcccactg acccgtctga gtgatcaccc aggagcgcgg cggcagcaag   40140
cagagctcac cggatttggg acaaggattt taaaggcagc tacaaagctg agctctattt   40200
gctgatgata gtctctgttc agctgtttaa aatgactgtc tgactcacca tggtaatttt   40260
tcacaaatta aaaacacatt ttgggttgtg caacagtgtt ctcatctttc caggcaggca   40320
gattatttta atgctgttat acagggaatt gggactctcg gattttcttt tttaaccttt   40380
ttatgccttt cagtagggga agtttccttg aaagttagag agctgcaaat ctctaagtat   40440
caatgtaaag aagccgatga cccaattcgg aaggtggttc aagtgttctg tttgtttaca   40500
aaggcacaga ccacgaccat ggacacaccc agtggaagta accacacccg gtgtgttcct   40560
agaagctcat ctgtgacagt tcaacaagaa cttactattc tagaaaagta ttacacaaag   40620
ttatttaaaa aaatgtctgt acaatcgtta acacggccaa gccaggcctt gggttttgcc   40680
tcttggtgtc cagctgtgct gggaatgcca tgaagaccag cggctggaaa ctgacttggg   40740
catggagaag agactgaggg agagggaggg gacagcacga ctgagcaagg gcacagtgct   40800
ggctgcctca tgggctccag gctccttctg ccaggatgag gaagaggccc cagagcagcg   40860
ttacacagga aatcaaccta tttgctaatc cttttggaaaa acgtttgttt ctggtccaca   40920
aacagaaaat ccaaacagga tggcagctcc ttgtgagggt ggaggggagg gcaccagatt   40980
ctgtgcggct ggaaattcca aggtgctcag aaccaggcgc ctgcacctct ccttatgcca   41040
gaccacaatc ttcaaagagg ccggcagcca tattctcgat ggggaggtgg acaaggccac   41100
cctgggagtt gctttcaatc tgtcctcaca aatcaacaac tccccgccac ctccagagca   41160
ttttctaata gtgtttgttt ttgagacgga atcttgccct gttgcccagg ctggagtgca   41220
atggcacgat cttggctcac tgcaacctcc gcctctgggg ttcaaacaat tctcctgcct   41280
cagcctcctg agtagctgag attacaggca cccaccatca cacccagcta attttttgtat   41340 ttttggtaga cagggtttt catcatgttg gccaggctgg tctcgaactc ctggccttgt   41400
gatccgccat ctgcagcctc ccaaagtgct gggattagag gcctgagcta ccgcagccgg   41460
tcttctatta gtttttgagg aaagcagaaa aaagaaatg gaaacccagg gaaagtcacg   41520
tgacaaaaca tcttcgcagc gcagtgagca cacacctggc ctgtcctcca cacacaggtc   41580
agcggtttta tagaagcggc tgaagcaggt gtagtagccc acgcctatat tctcgacact   41640
acaggaggct gagtgggaag gattgcttga gccgaggagt tcaagaccag cctgggcaac   41700
aaagcgagag cccagctcaa caaaaaaata gccaggcatg gtggcacgtg cctgtggttc   41760
cagccacatg ggaggctgag gtggatcact tgagcccagg aagtcgaggc tgcagtgagc   41820
caagatcatg ccactgtact ccagcctggg tgacagacag agcaagactg tctcaaaaaa   41880 ataaaaggt tacttgtggg ttaaaaagcc tcacttcggt ccatcatcat ggcagacttt   41940
tttgagtagg tagaagttaa tgagtcagaa ttattgctct gtttctgaac gattttatct   42000
tcaggagggg ctattttgt atttcccagg tgagaagcca aatggaaaac cagtgaagtg   42060
accatgggtg ccaaaggcct aaagagcagg caggaaaatg agactcggga ccactggagc   42120
cccatgctgc ctctgacaag ccctggagct ctgggtctca aaggctggct ggcaacaggc   42180
tgcaccgggc atgggaatcc gccggctgcg agattggggg taaagagctc agacatggtc   42240
agaagcctct gcctaacaca cggctccagt agccactcct caggcctcct gcgccctcgg   42300
```

```
gggtgcgtga cacaggagga tgagttgagc tggctggtgg ccccagtgtg ccgtactact    42360
gtcccttggg gagagtggga cagggtgggc gcctgacaca caccacgcgc cccagaaaca    42420
ttcagtgtgg acgtttcctt tttcagcaag gacggcgccc aggtaaacgc cacgtaaccc    42480
aaaccatcaa cactgcagcg tcctgcccaa ggctcacgtg gggaaccgga caggtgctag    42540
atgatgatag aacggtggg ctctgaggga ggacagacag gctcacccca cggggacctc    42600
agaacagcct gcctcatact cagagtccaa aaagaaaag gaacgtacac atctcctccc    42660
aagttaaaca cgagaggttt gtcctcaacc tcagggctgg aaaccaccac aggtaggagg    42720
ctgggcacgg gggctcggcc tgtcatccca gcactgtggg aggtcgggtg ctagaatccc    42780
agcactgtgg gaggccaggc acggggctc acgcctgtaa tcccagcact atgggaagct    42840
gggcgtgggg gctcagcctg taatcccagc actgtaggag gccgggcgcc gtggcgcatg    42900
cctgtaatcc cagcactgtg gatggccgag gcaggcggat cacgaggtta ggagttcgag    42960
accatcctgg ctaacacggt gaaatcccat ctctgttaaa aatacaaata actagctggg    43020
tgtggtggcg ggtgcctgta atcccagcta cttggaaggc tgaggcagga caatagcttg    43080
aacgcgggag gaggaggctg cagtgagctg agatctcacc actcactgca ctccagtttg    43140
ggtgacagag cgagactctg tctcaaaaaa aaaaaaaaa acaagaacat ctcccacaca    43200
ctcacagtgc ctttgtagcc ccagggaaag caatcccta agatcatttg ttgggtgaaa    43260
agggtaccaa gtacacagtg ttaggaccgt gcaaaaaaag ggtgacagga agtacccttt    43320
gcaaactttc cataatgtgt acttaattca ctgctcttat aaaatgaaat taaataaaac    43380
aaaaaaatac tactgaaaaa taattgggca acatgcggtg gctcacgcct gtaatcccag    43440
cactttggga ggccaaggca gacggatcac ctgaggtcgg gagttcgaga ccagcctggc    43500
caagatgatg aaaccctgtc tccactaaaa atacaaaaat tagctgggca tggtggcagg    43560
cacctgtaat cccagcttct cgggagactg aggcaggaaa atgtcttgaa cctgggaggt    43620
ggggttgcag tgagccgaga tcgcgccact gcactccagc ctgggcaaca gcgtgagact    43680
ctggctccaa aaaaaaaaa aaaaaagga aaataattg gctgagtgt ggtggctcat    43740 aattgcagtc ctagcgcttt gggaggccaa ggtgggtgga tcacttgagg ccaggagttc    43800
aagatcagcc tggacaacac agcaaaatcc catctctcaa aaaagtaaa ataaaataaa    43860 ataacaaaa acaaaaatta gcccagcgtg gtggtggaca cctgtagtcc cagctactca    43920
ggaggctgag gcgagaggat cacttgagca gggaggcgga ggttgcagtg agctgagatg    43980
gcaccaccac actccagcct gggtcacaga gcaagactct gtctcaaaaa aaaaaaaaa    44040 gttttttttt tttgaaccac tgctaacaat cactaatgtt cactaaaaca ctaggcttca    44100
ggagcatttg gaataattc ctgaccgcac aaagaaacat gctggtgaga gacagtgacc    44160
aagcccagga gaccaccatg agttccagaa aaagtgagag agagcggcca cttttcctgt    44220
ctcggagata cctcctactc aggacgcagg aagcatgggg cagggcagcg ccatggacaa    44280
ggcgactcgg tgcagggcct gcgggacctg caggtgagag gaagcacaag ctccagctcc    44340
tcagctgtgg aacgctgcgt gcgtggtgca cagctaccag ctcggatggg tatttgagaa    44400
tttaccgcac tgacttggac cagacggaaa gcagagaaga gggagagcta cacctgactg    44460
tccaccattc ccgccagccc caacgtcggc ttttcacttc atgtttgggg acaattacac    44520
ctcctcatga cagatcagaa gtttcagaaa aaaggtccgc tgatttccgc aacagggtat    44580
gaggtggcca gctgctgatg ccagctgcat ggactcctat acttgctggt aacataacct    44640
cattcctttg tatttgccac caaaaagtct ccagtctttt tttttttttt tttttttttg    44700
```

```
agacggagtc tcactctgta gcccaagctg gagtgcagtg gcacaatctc ggctcactgc   44760
aacacccgcc tcccgggctg aagtgattct gatgcctcag cctcccacgc agctgggact   44820
acaggtgcat tcaccaggc ctggctaatt ttttgtgttt tagtaaagac agggttgccc   44880
atgttgccca gggtggtctc gaacccctga gatcaggcaa tctgcctgcc ttgacctcca   44940
gtccacctgg ctagtctcca gtctttaaat tgcacctttg gccgggtgca gtggcttgca   45000
cctgtcatcc cagcactgtg ggaggccgag gcgggcggat cgcctgaggt caggagtttg   45060
agaccagcct ggccaacatg gtgaaacccc gtctccacta aaatacaaa aattagccgg   45120
gcatggtggc acgcgcctgt aatcccagct acttgggagg ctgaggcagg agaatcactt   45180
caacccggga ggcggaggtt gcagtgagcc gagatcaaac caagaaatc cagctctggg   45240
tgacagagca agactctgtt tcgggaaaaa taaaatacat aggcagggcg cggtggctca   45300
cgcctgtaat cccagcactt tgggaggctg aggcgggcag atcacaaggt caggagatcg   45360
agaccatcct ggctaacacg gtgaaaccca gtctctacta aaatacaaa aaaaaattag   45420
ccgggcgtgg tggcggacgc ctgtagtccc agctactcgg gaggcagagg caggagaatg   45480
gcgtgaaccc aggagacgga gcttgcagtg agctgagatg cgctactgc actccagcct   45540
gggcgacaga gcaagactcc atctcaaaaa ataaaataaa atacataaac aaataaattg   45600
cagcttcatt caatctgccc agttacagaa gtggaaagaa gctgaaggat cctccccgtt   45660
tctagagctg caccgcatgg cacaggaagc agtggccaca ggtgtctgtt caagttcaaa   45720
ctgacagcaa tcagcttgaa ttccgaatct ggttcttgtt atattctcca catttcaagg   45780
gctcagaagc cgtatgtggc cagtggctcc tgcactggac agcccagaag agaccattcc   45840
attcctgcag acaaaactag tcgcagcacc ctgctattct agacagaaag cactcaattt   45900
caaaaacctt caaactcaga gacttctagt ggagatttcc ctaaatacct atttcacaca   45960
gtttacggtt tattttacag tttctcattt gtttttttgt tttatttatt ttttttgaga   46020
aggactctcg ctcccatccc ccaggctgga gtgcagtggt gagatctcga ctcactgtaa   46080
cctctggctc ctgggttcaa gtgattctcc tgcctcagcc tcccgagtag ctgggattac   46140
aggtgcccag catcacaccc ggctaatttt tgtattttta gtagagatgg gtttcacca   46200
tgttggccaa gctggtcttg aactactgac ctcaagtgat ccacttgcct tgtcctctca   46260
agtgctggga ttacaggcat gagccactgg gcccggccta tcgtttgcat tcaaacagc   46320
atgggtataa aatagcctag taattacact gcatagccac agtcatcccc gtggaagaga   46380
atcacatgtg tcctttataa аааатасстаg atttctggtc тстттттgтаа асааасстgga   46440
cacactcaac tcttgggaag ttcctctgct cacctgaaag tcaccgggga gатттттсссс   46500
atgagggcgt acgccgtgac gctctgaagg tggaacagga ctccgtctgt cagaagcagc   46560
agcaccacgt cctggttgta gctgaagctc тттсссgстсс tcccgatcac tgggacgtcc   46620
tatgtggcaa асаааагggт actctattgg tttccattt ссаттсастта атсатссасс   46680
асgаасасссс agcgccactc ctgcccagaa actgggtaaa gстgстgссса ctgaggacag   46740
ccctgaaaat gcctcgaggg gacagctgaa ctgtgcactc atccatttc tgttttttgt   46800
ttgtttttat tattttttgc actaattaat tttcaccatg cagatgcaaa tggacaacaa   46860
gcacatgaaa aaggctgaac atcaccatca tcaggaaat gcaacagaaa ccccaatgcg   46920
gggccgggcg tggccagtct ggccaacacg gtaaaacctc gtctctacta aaacataaa   46980
aactaaccag gcatggtggt gggcgcctgt aatcccagct actcaggagg ctgaggcagg   47040
acaatcactt gaacccggag gcggaggttg cagtcagctg agatggcacc actgtacсссс   47100
```

```
agcctgggcg acaagacaga gacttctctg ggctgccaga ggctccggaa gccgggtgcc    47160
tcaggccgtg gcagttccgt cactctccaa cgcctccccc acagacttct ttttgctaaa    47220
tggtatcaag atttctcgt tgttgtcagc aagagagttg gttttctaac atctcatcga     47280
ccatggctgg aggtcaaatc gatgttttaa acttgctgga aataaacggt tcctttcttg    47340
catggctcga tgagcaataa ggttcctctg tgtcattttg tttacgattt ttaggattgc    47400
tttttaaagc cggacacggc ggctgatggc tgtaatccca gcactttagg aggccgaggc    47460
aggaggatca cttgagataa ggagttcagg accagcatgg gcaacacagc gagacccat    47520
ctctatagaa aacacaaaaa tgaggctggg ggtgctcata cacgcactga gggttgaccc    47580
tggtgttctt gccttcttag attcttctgg agctggagat gaactcggac ctcaaggccc    47640
agctcaggga actgattatt acagcagcga gggaaactga agttggtggt ggtgagaaag    47700
ttatcatggg caggtacagc agctcacgcc tggaatccca gcactgtggg gagctgaggc    47760
gggaagatca cgaggtcagg agctcaagac cagcgtggcc aacatggtga accccgtct    47820
ctactaaaaa tacaaaaatt agctgggtgt ggtggcacgt gcctgtaatc ccagctactc    47880
aggggccga agcaggagaa tcgcttgaac ccgggaggca gaggctgcag tgagccaaga    47940
ttgcgccact gcactccagc ctgggcaaca aagcgagact ccatctcaaa aaaaagagg    48000
gccggctgtg gtggctaaca cctgtaatcc cagcactttg ggaggctgag gcgggcggat    48060
caacgaggtc aggagatcga gaccatcctg gctaacacaa tgaaacccag tctctactaa    48120
aaatacaaaa aattagccgg atgtggtggt gggcgcctgt agtcccaact actcaggagg    48180
ctgaagcagg agaatggcga gaacccggga gatggagctt gcagtgagcc gagatcgcac    48240
cactgcactc cagcccgggc gagagagcaa gactccgtct caaaaaaaga aaaaagaaa    48300
aaggccaggc gcaatggctc acgtctgtaa tcccagcact tagggaggcc aaggcgggca    48360
gatcacttga ggtcaggagt tcgagagcag cctggccaac agggtgaaac cctgtctcta    48420
ctaaaataca acagaattag ctgggtgtgg tggcagacag ctgtagtgcc agctacttgg    48480
gagtctgagg caggagaatc gtttgcacct gggaggcaga ggttgcagtg agccaatact    48540
gagccactga actccagcct gggcgacaag gcgacactct gtctcaaaaa aaaaaaaaa    48600
aaagaaagaa agaagaaaa aaaaaaaaa ggaagttatc ataatctttg ttcttcttct     48660
gccactgaaa taattccaga acatccaagt ctggctagta cgtgaattgg agaaaaagtt    48720
cactggtaag tatgtcgtct attgcttaga ggaaaattct gcctaaacca actcaaaaaa    48780
ggtgtacaaa aaataagcaa aagcgtccca ggatccacgc tccgacagct gcgcacgtcg    48840
caatcctcga ggactcggtc ttcccaggtg aaattgtggg caggagaatc cgcgtgaaat    48900
ggacacagca gctcacaagg gttcattcgg acaaagccca gcagaacaac gtggaacgca    48960
aggtccaaac tttttctggt atcgataaga agctcacagc caaggctgtt aattctgaat    49020
ccccagagtt cccagtttca attgttaaga aaaatgacta acgtatactc acagtgaaaa    49080
aacaaaaaga cacacaaaat acaaaaatta gctgggcatg gtggcacatg cctgaggtcc    49140
cagctaccca acaggctgag gtgggaggat tgcctaagcc tgggaggccg aggttgcagt    49200
gagtcgtgac ctcgccactg cactgcagcc tgggcgacag agcaagaccc tgtctcaaaa    49260
acataaaaaa aacaaagaa aaaaacaaa aaaaaccag agttgacttt taggctttga     49320
ttttgttata atcacctaaa cgtgtgtgcg ggtctcaagt gcatgtgggg caagcccaac    49380
cccatcctgg accctcggcc tcctcccgtc cccaaaggca gacagacact tccctcggcc    49440
ttaagatctt gtcgtttctt aaataagcga acacgtgtgc accccacac tccgttcaag     49500
```

```
atgccgcgct ctgtgggcgc ctctgctcct cgctggtttt catgcagcca cactgggtac    49560
gcgacatggg gctgacatgt cactggaaat cgcctgtgag tcattaagag gtgggagagg    49620
caggagcctg ggttgcagct gaggtcaggg gctggggccc aggacaggcc tgtggtggcg    49680
ggtgctgggg aggctgtggg gtgctggcac aggagggccc acggaccagg gccacggcc    49740 gcctgtatgg tgctggccga aggcggcccc cgcccgtcct cttcggatca gtgattggca    49800
cctgcagtaa tcttgcttgc caggaatctg cccagccccc acctgtctcc ccacccagtt    49860
agggccacga gacacaaccc tgccctgacc tccgcatgcc agtgtgagaa cacctggcag    49920
acgccaggct ccaagacacc cccgcacatg tgaccgtgag agaagtgaag gcactgccag    49980
tgtgggcacc actctgagtg gtcctcgcgg cagagcccca tggcaggcag cagagacggg    50040
caccacggat ggaggcctgg gatggtgggg cgcaggcgga ggggtggggc caggggggcc    50100
tcacctgtgt actcccccag aatcatccga gacatgatca ccgtgaagat gggggcggag    50160
ctcttcaccg tctcagcaaa cgaaaccgcc acattttttca ggctgaccaa acccaaaacc    50220
acagttgcaa acctaaaaat gagccaaaag caccatcacc ttagaacgag tctgtctgcc    50280
tgcacccacc gggcaggctc tccaagggc tcgctcgctc ggttggcacg tcggcccctc    50340
tccgcccacc tcctcatcac caacatggtg cctggacccg cttctgtgac gctttaggtc    50400 gagccccag gaaacggcac tgcgtccaat gggaagtgac ttctgccacc ccttgaaaac    50460
gtcccagaga caaggaggca ccctgtcctg agaccaccag cccggaaaga agctgactga    50520
acacacgtgg cagtgagagc cacgaagcca cattcatttg gtgtcctgaa atctggacag    50580
ccctggtgct tttataaagt ctgcactgaa aactcaccag ccagcagagt ccccgctcta    50640
gtaacgagag ggactttaca tttaaagaaa aagagacact caaccaaaac caggagattc    50700
tttacctcat cagacccaca aacagcatcg tcataaggaa gttgggtggg taggaaagcc    50760
gggccttgtg ctgatataaa cagcaaggaa cgagggtttt cacacacccg ataaccgtgg    50820
tggacagcat ctgcaccgca cctgcgggag ggaggggggcc aaagacaaga gggagaatca    50880
cccctcccgt gcctgcagtg ggctccaccc ccggtctccc atcctgacct gggctccccc    50940
ggccctcccg ggtggttgct ggctgctccc tgtggggtgg caggtggccg gcttccaccc    51000
tgcccgagcc gccgcctacc tagcatgctg ggctcgcctc ccagcaggga caggatgtac    51060
ttgttgagga agagcgtgca gaagctgaag aagaaccaca gcgtgaggta gagcagcgcc    51120
cgcgagctcc acacacccaa gtctgactcg atgaccgtgg tctccgtgat ggtgacggtc    51180
agtacgttct catctgtgcc gccgtcgctc ttggcaaaaa caatcttctc acttcggtga    51240
ccaaacagag agccccagct gagaggcgac ctgccttttcg gcttctcttc ggagccagga    51300
accagctctt ccagtgctgg ggttttcacc gaggacgaca tgctgaagcc acagccacga    51360
acgattttac ctccaggctg ggcagcatgg gtcaccgtga ccgccgggg gtggggccgc    51420 agcagggact ccgggcgcca ggaacgaggc caccagggcc tctcccaggc aaagcgtaga    51480
agcagacgct aaaatattaa gaaaaggaaa cacatcaccc gttttgaaca tttaatgtcc    51540
tcaaaggttt caaccaccaa tttaaaatca ctttgaaaat gcaattgggc cgggcacggt    51600
ggctcacacc tgtaatccca gcactttggg aggccgaggc aggtggatca ccttaggtca    51660
ggagttcgag accaccctgg ccaacatgac gaaaccccgt ctctactaaa aatataaaaa    51720
ctagcagggc atggtggccg cgcctgtaa tcccagctac tcgggaggct gaggcagaag    51780
aattgcttga acccaggaga cggaggttgc agtgagccga catgatacca ctgcactcca    51840
gcctcagtga cagagtgaga ctctgtctca agaaaagaaa aaagaaaat gcaatcgttc    51900
```

```
actgtccaaa gattttagc aattgaatcc cgttttctc tgcgcgtgtt ggcggatcct    51960
tgctcttgag agacggtctc ctggcacact tgactgtcgt cctggcagac ctggggctgt   52020
gggtccttca cgccctgcct ggcagctgca ccttctcgat gggctttgtg gctgccgctg   52080
ccgggtgccc aggactaatt ccatgctact ttctttttt ttgagacggg agtctcgctc   52140
tgtcgcctag cctgaagtac agtggcgcga tctcggctca ctgcaagctc cgcctcgcgg   52200
gttctcgcca atctcctgcc tcaggctcct gagtagctgg gactacaggt gcccgtcacc   52260
acgcccggct aattttttgt attttagta gagacggggt ttcacagtgc tagccaggat    52320
gatctcgatc tcctgacctc atgatccgac ctccttggac tcccaaagtg ctgggattac    52380
aggcgtgagc ctccgtgcct ggtcttttat tttttgaga cagagtctct gtcgcccagg    52440
ctggagtgca atggcgcaat ctcagctcac tgcaacctct acctcccggg ttcaagtgat    52500
tctcctgcct cagcctcctg agtagctggg attacaggca cccgccacca tgcccagtga    52560
attttttgtat ttttatttca ttttttagat ggagtttcac tcttgttgcc caggctgcag   52620
tgcaatggca cgatcttggc tcaccacaac ctccgcctcc caggttcaag cgattctcct    52680
gcctcagcct cccaggtagt ggggattaca tgcacgtgcc accaaaccct gctgattttg    52740
tattttttagt agagacgggt tttcgccatg ttggccaggc tggtctcgaa ctcctgacct    52800
cgtgatctgc ccacctcggc ttcccaaagt gctgggattt acaggcatca gccactgtgc   52860
ccagcctccc ttttcttttt tttttttggc tgactcatgg gttagaattc tggattgggc    52920
aaacacataa acattttgta catgacgaga gccagatttc atcatgtgag tgaagcgaga    52980
tgcaaacacg aaaggaagtc cttcaaggca gccttgtagt gaaaaataa aaataaaaat    53040
gaaaaaaga ggctgggcac ggtgactcac gcctgtgatc ccagcacttc gggaggctga    53100
ggtgggcgga tcacaaggtc aggacatcga gatcctcctg ccaacacag tcaaacccca    53160
tttctactac aaaaaattag ccgggcatga tggcgcgtgc ctgtaatccc agctactcag    53220
gaggctgagc caggagaatc gcttgaaccc aggaggcgga ggctgcagtg agcagagatc    53280
gcgccattgc actccagcct gggcggcaga gcgaaactct gtcccagaaa aaataaagc    53340
ttagaaacaa gaggctatgt agtctcgaga tagatccagc cctatgaggc acatgtcaat    53400
cacagaggga aagctatgca cgcacaaagc atgtgtgaat cagagagaaa gctatgcacg   53460
cacgatgagt agaagacaaa cacgtcctgc aaggagacgg aggcgcaggg aggggtggc   53520
agccgtcctc ccaagacatg aggacttcta gttcagtctg agaccttggt gcagggctgg    53580
gcgagtaaac aaatgcaaaa gaataaggac ctcgaggtcg ggcgcggtgg ctcaagcctg    53640
taatcccagc actttgggag gccgaggtgg gcgcatcacg aggtcaggag attgagacca    53700
tcctggctaa cacagtgaaa ccccgtctct accaaaaata caaaaaaatt agctgggcgt    53760
ggtggcgggc acctgtagtc ccagctactc gggacgctga ggctgagaca ggagaatggc    53820
gtgaacccag gaggcggagc tttcagtgag ccaacatcgc gcctttgcac tccaccctgg    53880
gcgactgagc aagaccctct ctcaaaaaaa aaaaaaaaa agcaaaacag aataaacata    53940
cgtaggccag gtgcagtagc tcacgcctgt aatcccagca ctttgggagg cagaggcggg    54000
cgtatcacct gaggtcagga gtttgagacc agccttgcca agatggcgaa atcctactaa    54060
atacaaaaat tagctggaca tggtggtggg tgccagtagt cctaagtaca caggaggctg    54120
aggcacgagg atcgcttgaa cctgggagac ggaggcttta gtaagctgag attgcaccac    54180
tgcactccaa cctgggtgac agagcgagac tgtcttaaaa aaaaaaaaa aaacaaacag    54240
gtctggtgta cgcagaatgg aggcaccacg aattgctgaa gaaggaaact ttattcagtc    54300
```

```
tatgatacca ggacagttgt ccatgctgcc aggcaaaaag aaaaactgga ttctgatctc   54360
attatcagta gacaaacagc gacaattagt aacactgaca cagccctgac tgtgctgctg   54420
gagggtccga agcactctct gcacagcggt gaatccgcac aacagccctc tggggaaggt   54480
gctgttatca cccacgtgag acacacgaag gaaagacacg gcttcgcagc agcagcgtca   54540
tgattcgaac ccaggcggcc tgctcttatg ataaacttaa atgtgtaaaa ctttatgctc   54600
aggaaaatat aagagaatgt cttcctgacc ctttttgggg taggacaata atttctctaa   54660
ccaaacccca aaagcatgac ccattaaaaa aagggtcagg tggactaact tggctaaatg   54720
aagaattctg tttcaccaaa gtacactaca aagtgggcca ggcgcagtgg ctcatgcctg   54780
taatcctagc actttgggag gccaaggtgg gcggatcact tgaggtcggg agctcgagac   54840
cagcctgacc aacatggtga aaccctgttt ctactaaaaa tacaaaaatt aaccaggtgt   54900
ggtggtatgc acctataatc ctggctactt gggaggctga ggcaggagaa ttgcttgaac   54960
ccaggacggg gaggttgcag tgagcccaga ctgcgccgct gcactccagc ctgggcaaca   55020
gggcgagact ctgtcttaag aaaaaaaaag gccagacttg tctcacgcct gtaatcccag   55080
cactttggga ggctgaggtg gcggatcacc cgaggttgga gagttccaga tcagtctgac   55140
caacgtggag aaaccccatc tctactaaaa atacaaaatt agccaggcat ggtggcacat   55200
gcctttaacc ccagctgctc aggaggctga ggcaggagaa tcacttgaac aggggaggca   55260
gaggttgtgg taagccaaga ttgtgccatt gcactccagc ctgggcaaca agagcaaaac   55320
tctgtctcaa aaaaaaaaa gaaaaaaat atatatatat atatacatat acacacacac   55380
acacatacca caaagtgaaa tgaacagcca caacctggca aaagatactt gcaacatgac   55440
aaaggattaa taaccagaaa gtataaagaa ttcctacaaa ccaattagaa aaacaggcaa   55500
aaaaaaaaaa atattggcgg ggcatggtgg ctcatgcttg taatcccagc actttgggag   55560
gccaaggcgg gcagatcacc tgaggtcagg agttcgagac cagcctggcc aacatgatga   55620
aactccgtct ctaccaaaaa tacaaaaatt agccaggcgt ggtggcaggc gcctgtaatc   55680
ccagccacgc aggaggctga ggcagcagaa tcacttgaac ctgggaggcg gaggttgcag   55740
tgagctgaga ctgcgcctgc tccagcctgg gtgacacagc aagactccgt ctcaaaaaga   55800
aaagaaaaaa aaaaaacaaa acaacatatt tcacagagaa gaatttatgt ttttggagaa   55860
ggagtttcgc tcctgtcgcc caggctggag tgcagtggtg agatatcagc tcactgcaac   55920
ctcaacctcc caggttcaag cgattcacag aggacaattt ctaaaaggca aataagaagc   55980
aggaagggtg catgctcctt ctctactgcc ctgtaacagt cattccacac ttaccactc    56040 aaaacaacaa atgcttttga tgttggctcc tgtggggcag caatctgcgg gaagcttagc   56100 caggcaccctc tggcttaagg tccctcctga agctgcagtc acaccatgga ccagggctgt   56160
gacctcatcc gaaggctcaa ctggggctga ggcccacctc tgagctcact caggtggacg   56220
ctggctgggt tcagttcctt gctggctata gtggaaagg gccccacca gtttcttgcc     56280 agcttctcca caggacgccc cacagcctga caggagcttt catccagcaa gctcatcagg   56340
gagtgggaga gagcagccag gacaggagcc caggcctttc tgaacctcat ctcagaagtg   56400
acatccttcc cttctgctgt ctgggcacag ctccccgggt ggagcccgag gactagaagg   56460
aaaagaaaac ttggatttaa aatgggataa agccatagga gctgctcgtc ccaccacagg   56520
aatctcaacg ccgggttact gacaaagcgt cactttgcac ctcgtccaac tgtgcagacc   56580
tctcctagcc aggcccctgc accagaggtt aagaatccgt gccctggtc aggaagtcca    56640 ggtgggttca aacggccagc agggaatttc aggcaaaatg tgtcccaaat cttcaaacca   56700
```

```
cgccccagaa ctcagacctc cccctgggag ttcgtcccaa ggaaaccacc tgcaagaggc   56760
tcaggctgca ggggacactc cgcttccaaa acccggaagc tggagaccac acaagtgccc   56820
aacgccaaag gcaccccgtg gagggacgcc ctgtgccctc ccccgaccag gtgacccgct   56880
gcgccctaca catcttcacc aggaaacatc tgttatcgat gtggacgaag cgcagcctgc   56940
actcccagat ccgctcattt tcgttctgcc ctccgtttta cgattcgcct acactgaaaa   57000
tgcgtgagtg gagtggaaag ccttcctact cctgcctcag cgacccsttc taaaatactg   57060
cctcgtttgg cctgaaaatg tgatttgcag gcttcctgag caaagtagat ttcactccat   57120
taaagaaaaa aaaaagaaa aggcaccgaa cggggctcgg ctgtcgggag ttttgcttta   57180
gttttttgcg tgttttgttt tgtgtttttt tgttgttgtt gttcttttg cggccacgca   57240 caccgcgttc ccaggcttca gggcgtgggg gtcgccgtgg actcccggac gtgaaaacgc   57300
ttaaagccag ctgggaaaac cccaccagcg ttttcgcgc acagcgccag ccataggaaa   57360
ggacccccag gagcgaatcc gggcagggaa acccggacg cccgcacact cagcatcagt   57420
accggcaccc agcacccagc accgagcacc gagcacgcag caccaagcac cgatcaccga   57480
gcagagcacc ccgcacgcag aacccaccga gagcctgatg cagtctccgc cgcaggcata   57540
gcgctaggcc ccggcgcctt cacaacaaag ggacgctggc gggcggggcc taagaggtgc   57600
gcggtggagg ggccgggcgc gaggccgcgg agacagctcg gagctcggca ctggggagtg   57660
gcacagcgct ggcggatcca ggtgggcttc acggggcgcc cgcgggaccg gaaatgacgc   57720
gcagaaccct gcatcgggct cctcgctgcc ccgcgggcgc cgctcctcag tgccccagag   57780
ccacggagcc gggggaaacgc gccgcggccc acaacgcccc cgcggctgcc cgttggttcc   57840
gcccgagccg ttctactcca ggcagacggg aggagaaaca cggcgcgctc agcgtccccct   57900 gccccgttgg ttctgctcgg gcccttccac tgcaggccga cggggtggg aacacgcagt   57960 tttttttttt tttttttta aggtctaggg taacacgggg cttttaagtg cctctccgcg   58020
gccgcctggt ggtccagccc gggccgctgc agtgcagcca cacggggagg gacacggcgc   58080
gccgagtgct ccgggcggcc gcacgttggt tccgcccggg ccgttccact gcaggcagag   58140
ggagaggacg acggtgcgcg tagtgcatcc ccgtggcccg ttggttccgc cggggccgtt   58200
ccactgaagg cagaaggggg gggaaccgtg gccccacccc ccgcggcagc ccgttggttc   58260
cgcccgggct gttccaccag cggcacttca gggcgggatc ggccagtctg tggaggcagc   58320
ggcctctaag ccccggaggg tttactgccc aggtttgggt tccaggaata agaaatccac   58380
tgaataggct taacttagaa gacacaaagg cgcctcctgg cggaagtggc cacgctccgc   58440
ccagcctgag ggaaagctgc tctgacagct gggcccggag ctgcgggggg cggggccgcc   58500
gcgcggggtg aggactcgcc tcaggcgct gattggctgg tggcgcgctc cggggcgggg   58560
ccttcgtatc caggctggcg tcggggctgc cgcgggacat ccggagcaga cacccgcggg   58620
cgcgcctgcg gccccgagga cccccggctc cggagcttcg tcgagcgttt tcctagcgtt   58680
actttcccaa ataattttca ggaatgaagt tacggctaaa gggctcttta gagattactt   58740
ttgggccggg cccggtggct cacgcctgta atctcaacac tttgggaggc cgaggccggc   58800
gcatcacgag gtcaggagct tgagaccagc ctggtatggc caacgtggta aaacgtcgtc   58860
tctactaaaa atacaaaaat tggccgggcg tggtggcggg cgcctgtaat cccagctact   58920
ccggaggctg aggaaggagg atcacctgaa cccgggaggc ggaggttgca gtgagccgag   58980
atggcgccac tgcactccag cctgcgcaca gagtgagact ccgtcaaaaa aaaaaaaaa   59040 ggaagaaaga aaattataaa atgaagtgaa attaacgcag tggagtgcca cctgcctgct   59100
```

```
gcctgagttc actatccaca cggagttcat aaatttgaga gcagtttaca aagtagattc    59160
tcctactttc caggaaaccc agaaatgtct ggtgatttgc ccaacagtct cagctgttgt    59220
ggtcagcagg gccgctgtgg tatccaaatg atttcaaaag cagatttata aaaagtactc    59280 cttgttttt tttgagatgg aatttcgctc tcatcgccca ggttggagtg cagtggcacg    59340
atctcagctc actgcaacct ccgcctccg ggttcaagtg attctcctgc ctcagcctcc    59400
tgagtagctg ggattacaga tgtgtgccct cacgcccagc taattttat attttagta    59460 gagacagggt ttcaccatat tggccaagat gttctccatc tcctgacctt gtgatctgcc    59520
cgcttcagcc tcccaaagtg ctgggattac aggcgtgagc tacccacgc ccggcctta    59580 ttttttttg agacggagtc tcactctgtc gcccaggctg gagtgcagtg gcgcgatctc    59640
ggctcactgc aagctccacc tcccaggttc aagagattct tctgcctcag cctcccgagg    59700
agttgggatc acaggcaccc gccaccatgc ccagctaatt gttttgtatt tttagtagag    59760
acggggtttc accgttgtta gccaggatgc tcttgaactc ctgacctcat gatccaccca    59820
ccttggcctc ccaaagtgct gggattacag gtgtgagcca ccacgcctgg cctctcaaag    59880 ttttatagc aaagccttac atttcatgag gaaccatgca ttttatttta ttttgagat    59940 ggggatctc gctactttgc ccaggctggg ctcaaactca gggctctctg gcctcagcct    60000
cccgagtagc tgggtctgca ggtggctgtc accgtgctgg gcctggggtg tgcgtattaa    60060
tgattttgga atagtgtctg gaagcctgtg tgccttcctc tcttcctctc cccagaagga    60120
cctcccacct cgtcctccca aagtgttggg attacaggtg tgagccacca tgtcccctct    60180
ctttgctatt ttgcctggga ggagtgtatt aataatttta attttaaatt tctttgatta    60240
tgttctagtt tgattattga tcatttactt cttagctatt tatattctt cttgagtcat    60300 cggtttctgc cctttgacaa tttttctgtg aatgttttgt gttgattata tgagctttga    60360
ctgtattgag aacatccacg cattgtatta ttgcaactgt tttcctagtt gagaacatcg    60420
acctgctgta ttattgcaaa tgttttcctg cttgcatgta gtcatttgtt atgcatatta    60480
atgaatttct atccacatga cgtggagtca gttaggaatc agttaggacg ccctcgctgt    60540
gtgggagact gatgggtcca ggcgctgtgc aaaccccgcc tccaaagtgc atccttggct    60600
cactgggacc ttccggggttg tgctgctctt gcttcacagc ctctctgggt ctccctgccg    60660
tctgctgacc tcggggcagg gtctacccag gctgagcggc ccatgggctg tgggattcct    60720
ttcctctgcc ttcaggtcct ggatgatgta gaaggcagga aggaaagcag tcatggctag    60780
ctctgtcctg ccccttcgg ggtccccccc ggcccacagg ctcctccttg tccccagcc    60840 agcctcagtc tgggtctggg ctcccgctgg ggaggagggt gagacctgcc ggcccaaagg    60900
agctgaagtt tcccaagggg cgttgaggac agcaggaag tgtggggtgt gaactgaggc    60960
cccagagaag ggtctgtgcc aaggccccat gggtggggag gaagaaggaa gcgtccccac    61020
ctggagaccc agcctgcagg ccactcggcc acctgcgcag aagtagggga gcagcagccg    61080
ctcatgcccc tgcagtttgt cctcatcagc aggtggggaa actgaggccg gggagttctc    61140
caggccaagg tcactcacgg gcaagttccc gcagcctttg gacctccat acacgtcagg    61200 gccgctcatg ctttcctggg cccttcactg gtttggagga agcttcctgt tgcccagagc    61260
gcactgcctg tctctgagtg tatgtgtctc agtggcgtcc atgtgtattt ttctctgtgt    61320
gtatctgtgt gagtctgtgt gtgtggtgtg tttgtgtctg agtgtgtggt gttagcgtgt    61380
ctcagtggcg tccatgcata ttttctgtg tggtgtgtct gtttgtgtgt gtgtgaatct    61440
acgtgggtgt ttgtccatct ttttgtctgg cctcctgtcc cctctgcaca gagcagctgg    61500
```

```
gtggggatgc tggtcctggg ggcttgtcag caggatgtgg gcgtggggca gccctgggtg   61560
aggcctgagt acaggcccca ggtgcctcct gcacaggggt ggctgagcca gctcctctgt   61620
ggctcccggg tccccaccgc cggtcactgg gcaccacctg tcctggccac ccactcctgc   61680
ccaccctgct ctccgcaggg gcctccttcc tctttcagct gtgcgccctg gttgtggagg   61740
ctcctaagga ggttgtggcc tcggtttacc acctgccttg gctccttggt gttgccagac   61800
cctgaaggca gcccatgccc tggctgagat ccttctgggg cgggatgtgc tggaagcagc   61860
tgaaccacgt ggtgatgtac cagctcctgc tgtccctac atccccagca ccgccagcct   61920
tccctgggct cctccggccg gctcctctac cctgtacccg cccacccctg ctaccacccc   61980
ccaaccagac ttccagctcc aggcagggtc gcagcctcct gggctcccag caggacaggc   62040
ctcacccaga ccccgcagga gccatggac ttgggctggg tctttgggcc tggctgcagc    62100 cccttggac ctgacctgag gagacaccct ggctgtggga ggcagggtgg gggtgccggg    62160
cccagcacag aggtgcccag ggtgcaggct ggcactggcc cggcagggac cgtggatgcc   62220
gccgtttcag gctcgaaaag gtttccatgc cccagagcct gagcccggca gccccgagg    62280 atgtcttggg gactctgtgc tccccaaagc cgagaaggtt aggcttgacc cacagcctct   62340
tccaggccgg ggaggcagag gcgctccagg tcggtagggc ggggcccaca gcccagggtt   62400
tcacgtcccc aaaacggggc agggtgctgg aggcgcaggt gtccacaggg tggtcgtttt   62460
ggtctctcct ggacttgcac gcgtgtagtg cagactggct gccggcaaag ccctgagcca   62520
cattcatctg ggccttgtta ggacaacagg gacggtgcgg ggtggggggg ttgcggggcg   62580
caggaccacg tcagtggagg gagggaggcc gatatcggtg cccaggctgg gcccaggggc   62640
cagcgggtcc tcacctggct tgtggctgcc cctgttaggc agcccggatg gaggggctct   62700
tccagccctg ctggccccgg gaatgcaggg actcaattcc ccctggtctc agtggctctt   62760
ccgggagcaa cacagcctgc ccgagtcgac accacccctc gggtttgagt cccttctgtc   62820 taccccctacc cccgccaggg cactgccccc ttgcccggaa gaggcagcgg caccccccagc  62880 cccttgggga ggatgccctg ccggccccac actcggtgga tgggcatttt ggggctagga   62940
tttaatgggg gtgaccctgc ccgaccccctc tatgttggtt ccacggcgtc agaagaaagc   63000
tgttattaac ccagcttatt ttctacaagt cttgtttatt gaaaggatct gaaaagcgta   63060
ataaggcttt caatgacatt taatacattt tcaagaaatt aatatgaaac attaaaatt    63120 acttcaaaaa tccaaagttt tctagatcat tccatctca cgctgcttta gaggtcagtt    63180
cacaccttct gtgttcagat gagcggctgg aattctgaac actgccgtct tccagcccta   63240
acgctgggcg ctggtccctc tctcctaagc ccacggctgg gcttcccctg tgcccagggt   63300
catggcggac ttcaagccag gccggctgcc cagaatcaca ctcagggttt ttggacgctc   63360
aagtccacag atgctgaggt gcccagacga gggtgagcag ggagacacat gcctcggaga   63420
acgtgcccag gctgggccag gcggctgcgg gaagctcctc acgggcagag gagaacgtct   63480
tgtgccttcc ttatcgatct ccagcagatg agggcaactt cgtgtgcaaa actcagagag   63540
cagttactca aaaaaagac acccgggcag cagtaaccag gacaccaggg tccgaccacg   63600
gcctccacac acctgtgccc gtggaagacg cgggcgccgg ggtaggcagc atccacgtgc   63660
tccacagctg ccggtgctgg gcaggctgga gactcacggg agaggcagga ggagaatcag   63720
cgtgttgagt ccctcgctgt gttagtgtga aaaattctca ttacagttgc aaataaaagg   63780
gatcacgatc actagcccg gaaaccctca tctcccggac catcaggatc gcactgaaca    63840
gaatggtccc ctaatggtcc ctgaggacag cgtcttgcag aacataaatg taaacattga   63900
```

```
atggcagacg actcccttcc ccttgaaatc ttcacaaaag tgtgtacgag aaagtatgta   63960
catcagcact tcagaaagtt taaaagagtc tctaaaaagt atatacagga tttaaactac   64020
cttcctggga gcagaagcta cgtgaggaat gtgtgggtcg ctggcgatgc cagccccctt   64080
cccgctgagt gtcccagact cagtgctggc ctcaagcggg gagggctgga tggcagggga   64140
cgcatccaac cctctccaga aactgagcag aacaaaaccg ccttgccagc cactggcaag   64200
accatgcttt caatggcgcc tccgccaggg gcttccctgc agaagtttta ggggaagagg   64260
tgcaggtcaa ggggaaaagc atggcagctc aaggaaggtt tttggctgag acatttatta   64320
tcaacattga aggacaggtc gagtcattct gactcctctg aatttcaacc gactgatttg   64380
cggaaaaata tcctggcatg gaaattgcgg cagctggagg ccgcgctcca gggacccacc   64440
gcggggtgtc agcaggacag aagcactccc agcccatttc tcacgcttct ttagaaatgc   64500
aaaaaaagtc agacatttta aaaaaacagc tgatctggac aaaaggcaga cccaggctct   64560
aacccagcta cagaaaggaa gtggccgtgc cactgagaca ggcggtcaca gacacacgca   64620
gattggtctg tccccagagg gcgcttggag ggcagcggaa ggattcgggc ctggataggg   64680
gcttgaccta gccctcctcc tcctcctcct cctcctcctc gaagtgggct tgcttcttcc   64740
ggacgttcca atgcaggcac tgggcgaggc tctcaaacca gtcgctcacg gggtcccgca   64800
cacagatgga ggggagcggg tagcatgagg tagtgatgct gatgctggga cgggagagca   64860
gcagcctgag ccagggcttc cagaaaggcc cacccccggc caagaaccct tcctccctcc   64920
ctccctggga atggccggga ctcttttcct gtggggccgg gcagccctc cccgaggcag   64980
gcttgagcag tgccccatgg gtgctgggac agagccatcc caggtcctgg aggggacggt   65040
gcagggaact gacaaactct gccccagggc cctcagggt gaggtccag gaggtgggtg   65100
ggggtgggca gcagtgccag gggggacacc ctcaggcctc tgctggggcc aggcctgcat   65160
gtgccaccgt atgcgacccg ctgcccccag gacgggtgcc ccgactgtga tgctgcaaga   65220
cccagggact caggccctgt ggtgcccag ggacaagct tgtctacag gccaaccgca   65280
agagggcagg cgctgcctgg cccggggagg aggttggcag gcagcgccca gcccggcatg   65340
cagcccacac ctgtctccat ggcggatctc ttgtctcttc cgtccatcaa aggacaccca   65400
tgctgtgttc cttgcttcag gtgacagcat gatctgaggg tcaagcaggg agaggtgtgg   65460
gccccccagct gtggggagga cgcttctagg caccccacccc tgagtgctcg ccagaggtcg   65520
aaggttgggc agctctgacc ctgccttgcg gacggtgcag tgcacgtcct acaggcaccg   65580
gcccagctca gcaccgccag agaccaacaa tggcagaaag cccctcagac ccgggccctg   65640
ggcaccttga tggacagaac tcgggcacca gcaagggaag gcttgcatct gagggggcac   65700
aggatggccc taggatgacg aggccgcgtc tgaggctgga gccagcatgg cagagcgggg   65760
tgctaggtcc cggctttgtg ttgcacgggg tcaaatgact cacaaaccgg aaaaggagtg   65820
tcgttggctc tgaccttcag ctcgacccct gcggggacca cgatgggccg gaaggacagc   65880
gagtgggggc agatgggcgt gatcatgatg ccggcacgt tggggtggat catggaggcc   65940
ccggccgcgg ccgcatacgc cgtgctgccc gtcgggtgg acacgatcac tcctgacagg   66000
gacaggcgca ggcgtcactc ccgcccgagg gacgctcagg gccccaggac agtgctgcgg   66060
gccttaccgt cgcccgtgcac cgtggtgatg aggtgtccgt ccaggtagac atccacattg   66120
gacaggtagg aggaggggcc tctgtcaatc accacctcat tcaggacctg gagggggcgac   66180
agcattgcac actcagggcg ggggatgccg cacggctcgc agacaccctc cgtctcaccc   66240
agccgggctc tccggaaggt cctcatccct gggaccgaag tcgccccacc ctgggcccct   66300
```

```
caccgaggcc gaggcgcctc cactcacctg gtactgcatg gcctgcttcc cgacatccat   66360
gtccaggcct gcagcctgcg agccgttctc acccagccca ttgtgcacgg ccgtcttctt   66420
cccccggagc tccttcacca ccctgacctt cagccgactc cggagaacaa cagctgcgtt   66480
ccctgaggtc cagcaggagt cagagggcat gcatcaggga agtcagtggg gtcaggggcc   66540
ccaccccagg gaggccagtg ggagtcagag ggctctttct tctcccaagt tgacacactt   66600
ctgtgccttt ttcttttat tttgagatgg agtctcactc tgtcacccag gctggaatgc   66660
agtggtgtga tcttggctca ctgcaacctc tgcctcccag gttcaagtga ttctcctgcc   66720
tcagcctccc aagtagctgg aactacgggt gcgcaccacc acgcccagct aattttttgta  66780 ttttttagtag agacggggtt tcaccgtgtt ggccaggatg gtctcatctc ttgacctcgt   66840
gatccgcccg cctcgacctc ccacagtgct gggattacag gcgtgagcca ccgcgcccgg   66900
ccgacacttc tgtgccttct gagagtgaga atcagctcac ttctgcccaa cacacatggc   66960
agcttcaacc tgtgatctgc tgaaacttct cagtgtcagt aaaaggtttg aaccactcaa   67020
gatttagaaa tccctgaatc ttgaaacctt taaatgttgc tccatgcatc attaaatgaa   67080 aataaaccccc ccgcaagcaa gcgagacagc agcgccatga tcagctccc tgtgggctcc   67140 agaacattcc aactcaccct ctatcacctg agtaacttgg gactgaaagt tctcaaagct   67200
gaatggggtc aggaagccca gggagcccag gtggaaggcc atgaccggag ggacgctgcc   67260
ctgtgagccg acggagaggt cactcagtgc ccacgccgtg caccccgca ccacccagct   67320 ttccagcagc acctcaggag ggacccagct ctgtggggac agcaccccga ccctctgcag   67380
gagggactgg ccatgtggac aagcggaggg ggacgtcgca ggccagggtg ggccgggcca   67440
ccagggccaa ggttggtgtg gggagctggt gaggaacaaa ggtggcaggg ctgagcggcc   67500
ccctgggcac ggagggctgg gggagctggc gagggcgggt gggaggcagc cttggggtcg   67560
gagcctcgcg ccccacaggt gctaatgggg agatggggag aaaagcaggg cgggctgcgg   67620
gcatttccgg tgtcaccaac atgcagtggg ccaagggcag agccagggtc ccccacacag   67680
cgtggcccta cagccccagg ggagagctgt gctgctgaga aaccaggaag aggagctcaa   67740
gggaggccca gaggggatgg gccagtaggc gaggtcgttt cccaggaccc accaccctgc   67800
gccactccct gctgtcccag gcgggcgctg gccaccccca gccgtagcac tgtgtccaca   67860
ctgcccctgg ccccaccgtc gcaccccacc gggctgccac catgggcctc agtgctggcc   67920
gctctaggtg actgctctcg tataaagggg tgaaaagcaa tggaagccat gcttgtgagc   67980
ccctcgttac gcagcaccta gactagaacc tggtgtgggt ctggaaatgt cagcgcttca   68040
cctggaaaag cgaggaagcg tacagcagcg tcccgtctcc ccccaggcag atgatgaagt   68100
ctatctgatt ggaaatgtca tcataatcta ggaaacacaa agcaaaacca agaagaggct   68160
gtcacacagt ggcccctctg tggcgcagtg cgcagacacc aatgacaagg gcaacagtgc   68220
cagaagcttc caatggggcg gggaactgtg ctggagaaac caaggacaga gctgctgaca   68280
gcccaccttc tcgaaaggta cagaatttct tcttcactgc cccaaagctt tcatcgctgg   68340
cgatggcagg gtcttctagc actttctttt ccacatacac gatcatgttc tcctggaagc   68400
aaagtgccaa cctgctcatt ccacctgcag accccaccct cctgcaggga ggttcccgac   68460
tcacgggcgc tgtggtcaga gacctggcat cgtggcctgc atgcccgccc cccacgctc   68520 acgctgaaac ttcatcacca acgcgccagg aggaagcagg acctttaaga gatgactggg   68580 cggaggggc tccctctcag gaattgacta aggctgttat ttcaggagtg gctttcctgg   68640
gcgccgcaac ccccacgcct gctcttctga agagaagaca cagcaggaag gcccacgtca   68700
```

```
gatgtggccc cttgatctcg gacttcccgg cctccagggc cacgagccca ccagctcatt  68760
gttggtcacc cagtctggtg cttgccatgg cggcacacac aaacccagac acccggcaga  68820
tccccactca gtccccagtt ccagacaagc agccgttgcc cagcacttga ggtggttccc  68880
atggtctcac ggggcggtga tgtggatgga ggccccccca actccatgtg caccccaggc  68940
ccccttcccc cctgcccgc gtgcctccat gaggtgcgtg cagagctcct tgaacggctg  69000
cagtaggctg gcatctctca tcttcttgat gacaaggacg ctctttgggg acttgttcca  69060
cgtcagccgc tggctcgcgg ggtcctgaat gtgcctttag gggaggagaa aagagttcac  69120
accagctgcg atctccctct tgcggaaaag gtgtatgact tagaaaataa aaaaaaaat  69180
cttaaaaag gtgttttcac ctcccaggga aacgtgctcg gtggccacgg gctcacaggg  69240
cctagggtcg cgccacagag acagggtcag gggtcagtag ggtccggagt gaccacctct  69300
cacctgcttg gccatcaca cgcaggctca ggcccacaac ccccacccgg gcaccacgct  69360
gacccaagtg cacgcaccac agcccttccc agccccggc cacttgcctg cctggctcct  69420
cagtgacgct ggtggggcag aaatgaccac gaaagcccat ggctgggcca ctctttgctt  69480
gatgccctcc tcaggccccc acgaaaaccc aaaccagttg acatggtgac tctgtccca  69540
ggatcctctg cacacagttt ctggccccac gggagcccag gaccctcaa ggacccgctt  69600
ccccccctgc acacagctca ctacctccct gcatgaacgg actttaacct cactcactct  69660
cacagtaaaa atcacaggtt taaaagtccg tggcagccct gacacagcca cccgcgcttt  69720
gctggctctg accccgacca ctgtgccgg tgttctcca caggcagggc ccaccccggt  69780
gggattccca ttaccacgtt agtcacagaa aacatcccag cccagaaccg gaacacaca  69840
ccacggagcc tgctcctgtt cccagaagcc aagggagggc gcagcgggc tggccaccgt  69900
cgtcagcgct caccgcctat cctcagcccc aaaggacaag ttcttatacc accgcgccag  69960
ccagctagtt ccaagttgcc caatcgagaa agctgctgcc tgccatgcct cttcccagca  70020
gtgacttccc caggagtgtg accgtcccac taacacccc agaaccacaa cacagacgcc  70080
gatggcagcc acagggccac agaccttagc ccatcgcttg tgaccttcgg aagctggtca  70140
gcactcaccc tgtgcaggca ttactgggag gcgtggggtc actcatgcca tcccctatga  70200
gctcagcacc tgccgggtca cacatgtggc tcgcgaggta gccctgcct gctgggagcc  70260
ggccagtgtg tccacagcat ccaggccacg cttggcgaac acgcggccgc ccatcggta  70320
tggtcctgac tgtgcgccca cactagaagc ctaagctctt catactcaaa actcaaagca  70380
aaacacaatt gtgatgagac ttggtaaagt tgttgtaaaa gcaactaagt caaaagagct  70440
tcctacactt ataaaaatca aacaaaacaa aacagtttcc tcattggtca catggtcctc  70500
ctgcctaatc ccttctgaaa aaagtcctc agttcagcag caaagaggcc acacttcagc  70560
tccctgctcc taactgagcc gggtgggacc aagccctctg ttcccgtggc ctcagacctg  70620
gccaagtacc cagcctccag cctgccccca gcactgcgcc agccaccgct ctggcccgcg  70680
gaaccggctg ggccccaggg aaggcaccct caggccacag tcaggtggaa gggcgttccc  70740
tgcctcctag cccgctgcgt cactctgctt ggctccggcc caaggcgtg caggtggctc  70800
acggtcctcc ggcctggtca gccagcaaag ccccgccct gcacacggct cccctgctc  70860
tccccgccaa cagtcaccac tgacccagtg gcctggccta cacccattcc agccctgagg  70920
ctcagctgag cccagccaga gccaccagca gcggcgtcgt acaccggccc aggcacccac  70980
cgctgtgtgt gaccacaaac cagcgcctcg acctcttcct gggtcacctg caaagcagga  71040
caccagccct tgcaggcacg cacggctgtg ggtactgcac ggagagggca ggggtggcg  71100
```

```
tgaagcttgc aggcacacac ggctgtgggt actgcacgga gagggcaggg ggtggcgtga    71160
agccagcatg gccacagcct ggcccgcctg gccagctcct actgagactg tctcacacat    71220
gggtggccac gcacactgtg acacacgggc actcacgcac ctccacaaca caggcccacc    71280
aattccctgg acaacaaaac aggaagcggg tgccctcctc accaggcgcc cccacagggt    71340
cttgctctgg actatcaggg aagacggaag ttcagatgca tgggaagccc tgcccctcca    71400
cagcggggat gggaagcggg aggttatgat cccagagaca cagagcccag aggggcgtg    71460 ctcccatggg ggtgccgaga aagctgcatg cccctcaagg ctgccccaca aacccaccgc    71520
ttcctcctgc ggggctgtct ggcctcgggc agctcgggga ccactgagta cgccctggtc    71580
tgagggctga ggcagaacat gcacctgtcc ggtgaccccg ccctggcccg agtgactgac    71640
ggctggtgaa ggcagcagct gagatgcgag tgacaaagga gtggctctgc caggaccagg    71700
aagtgcaggg agggcaccag gcagcggggg agaggcccgg tggggtgcca gggacacagc    71760
aagcacagga tggcgggaca gagccacggc ggggccggga gggcagtgga gcactctggg    71820
tcacccacgt ggctgctgtg cagggaaggg atggtgaggc cgcggcgagt ggtcaggagt    71880
ccacacagcg gagggcagcc gggcaatagt gcagggagc tgcttggata ttttgggatc    71940
aaagtgacag aatctgcaga tggactggat gagggaaagc aaacaggggt cgggcccccc    72000
gcctcaggca tttggcagca gtgacaggtc acagacactc cgggaaccag tggcactgaa    72060
agggctgggc ctcaaaagca caagtgcgag tcacttccat cctaagggc tccgtcagcg    72120 tctggagcag caaggccaac ccccgtcctg cctgggacgc acgctgccgc ggggcccaca    72180 cttttgcagag cagctcctcg gatgactccc ccgtggctcc tgggacctga acttcggtga    72240
cagcccaggg ctggggcctc cgtccctgct gtgcgccccc agcctccatg gcaccggtgc    72300
ctgtcagcaa agggccatgc agtggccgcc cccgtatcac acggccgcat gcgctttct    72360 ggtcaacagt ccccagcagc ctgcgcgctg gaacactcgg cccttccgca tggtcctccc    72420
ttgcagaaag tgaagcatcc atgactccgt gaaggaggag ccctgaaga gagcccgttc    72480 tgcacagagg aagagagccc gttctgcaca gaggcctgag agctgaggca ccagtcccag    72540
aagcaaaggc ttctctgggg aagaggcaat gaggatgtct accaggtgca gaatacgact    72600
ctcagggctg gctgggagct cactttttc tctggagaca gtcttgctct gtcgcccagg    72660
cggaatgcac tttgataatc acagctccct gcaatctcaa cctcccaggt tcaggtgatc    72720
ctcccgcccc agcctccttg gcaactggga ctacaggtgt gtgcaacgat gcctgctaat    72780 ttttgtatttt ttctgagtct gagtcttgct ctgtcgccca ggctggagtg caatggtgcg    72840
atcttcggct tactgcaaca tctgcctccc gggttcaagc agttctctgt ctcagcctcc    72900
caagtagctg ggattatagg cacgcgccac catgcttggc taatttttgt acttttagta    72960
gagatggggt ttcaccatat tggccaggct ggtcttgaac tcctgacctc gtgatccgcc    73020
ccccttggcc tcccaaagtg ctgggattac aggtgtgagc caccgcagct gaccaatttt    73080 tgtgttttt gtagggatgg gctttcacca tgttgcccgg gctggtctca actcctggg    73140 cccaagtgat ctgcctgctt cggactccca cagtgctggg actgcaggtg tgagccactg    73200
cgcccagcct ggattataat tctttacaca taaaacacag atatcagatc gatcactgtt    73260 gcgttttcc catgacacta tgacgggcct ccaggcagaa tgtgttgaca aactgaacca    73320
tcaaatagca aacgcaaccc accccagaat tctcactcac tcttaaagaa acaaaaaggc    73380
agccctgagg atctcatgtg gaagccgcca cacccacggg ctgtgacccg gtctccaggc    73440
cccggctcgc ctgccgtcca cttctctcaaa gccactggaa aagccacagc tggggagccc    73500
```

```
ccgctcggat gcctgcactc agggggttca gggaggacgc ccatgtggct ttttgtttaa   73560
atgacctaaa catgtacttc tcacatgaag tgctagaatc ttcctcaaca cagcgatccc   73620
acaactccac acacatcccg aggactcccc catcccatgg cccccggcac tcacatgatg   73680
gtctaggggt tctctcccctt ccaagaaccc ccgtcctgg ggccccagca ctcacatgat    73740
ggtctggggg ttctgcagca cacaggcctt tggtccaaaa gtggtcaccg gcatggccc    73800
atgaagagag cgtgtcctcc tgtggggaga gggcagtgtc agagccacca gggcctgaaa   73860
ccagacatgc agtgacagac acagatacag aggaggttac acggtaaggc atacatgcaa   73920
tttgaaagat gccaactcca tctgcccagc agccacacaa tagcccttgg aaggttctgc   73980
ccaggtccat ggctgcactg gagcggcacc tgtgaggagc acgcatgccc acgcgccgct   74040
cagatcatga cccaagccgg ggagagcttc agcccaaaca aggaaaatgc cagggccagg   74100
gccagcctgg gatcagaatt cctcagtgtc tccaggaccc ctctctagat ctgcatttgg   74160
gactcaaaac ctgagacaac atctcatctc taaatcgtct agattaaaat tctagcacaa   74220
atgttcactc tgaactcatg tcaataaaaa agacgtaggc cgggcgcagt ggctcacact   74280
tgtaatctca gcacttcagg aggctgaggt gggtggatca cgtgaggtca ggagtttgag   74340
accagcctgg ccaacatggt gaaacccca tccttactaa aaaagaaaa attagccagg    74400
cctggtggcg tgtgcctgca gtccgagcta ctcaggaggc tgaggcaaga gaactgcttg   74460
aacccaggag gtggtggttg cagtgagccg agatcgagcc actgtactcc agcctggctg   74520
aaaaaagtga aactctgtct caaaatgaat gaatgaatga atgaatgaat gaatgaataa   74580
aagacgccag atgaacggct caacaacttt cctagtgatt taaacatggc caggtcacag   74640
ttaaatcacc cagccagggg ctgtggcagc cgcacgcgtc ctggggagaa tgctgtcagg   74700
accgctgtgc tcctcagggt ccagcactga ggctgccctc gtcctaggtg cccgggagcc   74760
tcccagtccc ttcacaaact cagaaaactt gcacacagct ggccaggcaa cggcccaaca   74820
aaatcctcaa gtcccaatgc agaagaacgg ccttccgctg cctcgcaggg ccagacaacc   74880
ccaggagagc cgtggtgccc tgagggctgc tccacaggtg acacaggcgt ggccatcagt   74940
ggtcacggac ttgtttacct cagcctttta aaaattggta agtacaggcc gggtgcagtg   75000
actcacgcct gtaatcccag cactttggga ggccaaggca ggcggatcac gaggcaggag   75060
attgagacca tcctggctaa cacggtgaaa ccctgtctct acacaaaaat acaaaaaatt   75120
agccgggcgt tgtggctcac gcctgtaatc ccagcacttt gggaggctga ggtgggcgga   75180
tcacctcaag tcaggtgttc gagaccagcc tggccaacat ggtgaaatcc catctctact   75240
aaaaatacaa aaattagaca ggcgtggtgg catatgcctg taatcccagc tactcaggag   75300
gctgaggcag gagaatcact tgaactcggg aggcagagct tgcagtgagc ctagatcaca   75360
ccactgcact ccagcctggg cgacagagca agactccatc tcaaaaaaaa aaaaaaaag   75420
aagaagaaaa cgaagtacat tacaaaagaa ttttacttac ttacgaactg aaaagattat   75480
tgcggaaaac aatgtttctc gaagtgggtg ttgggattta atgtttcctt cccaaggaca   75540
ggctatgctt gggcgtattt ggctacctcc tcccccacct cacccctgaag cgcctgtca   75600
ctcactatgg aggcgacctc tgcccagggg ctgctgtcat caggttcaga atgcaacaga   75660
aatggtgcat tatgccaaag aacccacagg aaaaaaaaat aaaacccaa agcaattctg    75720
ttcacgcagt cactgcgctg gggtggcctg gaggtacagg acaacgaccc ccactgacaa   75780
cgaggcaacg aggcatctga gaaaggctga gtggtgacgt ggtgcctgcg ggatgaaggc   75840
agccaccagc gctcgtagcc tcctggctca ggcagcgact ctgtagacag aaaacgtggg   75900
```

```
agtagcctgt ttctccacgg ctgccaccac gtcagaggcg ctacaggctc tcccatctca    75960
ctgggtaaga caacatgctt tctaagacta cttttcacca aaaagccccc cttgcatttg    76020
atagtcgtga tccttgttag gcagcgccgg ctctggcaag cttccaccta aaactcacca    76080
catttaccat caccagaacc gagagcacca tccccaggca ccatcacagc tgtgcttgtg    76140
cggccaccgt catgcaaagc ccggggcgct gttgcccaag cagcattgtg caagggtgag    76200
cgctgtgggc actcttggca caggagggag ccacttgccc aacatgtgag agggctgggc    76260
ccgcccaagg ccacgctcat aactctgcct ccaccagccc tgctcacagt gcagaacccc    76320
ccagccttcg cctctcaaaa caagcagagc caagagggat gtcccctcac accccagtga    76380
cttctgtaga gcaaatgttt ccaggccagg cacagtggct tgcaccggta atcccagcac    76440
tttgggaggc tgagacgggc agatcacctg acgtcagggg ttcaagacca gcctggccaa    76500
catggtgaaa ccccgtctct acaaaaatac aaaaattagc cgggcatggt ggtgcacgcc    76560
tgtaatccca gcttcttggg aggatgaggc aggagaatca cttgaacctg ggaggcggag    76620
gttgcagtga gccaagattg cgccactgca ctccagcttg ggggacagag cgagactcag    76680
tctcaaaaaa aagtttcctc tccaagtgcg cttcagtcta acatcaaggg tcagcgtagg    76740
cgccagttag atggttctgt gctgatacag acagatagag aaacacggtg gcaccctgtg    76800
cctgtgctgg cacctgggaa cgtgcgccag gcaggtgtcc atgggccagg atcccccttc    76860
aagggcacag cttcacctgg gcaaggaccc agcctcacct tccggatgca tcgacgcaga    76920
ctactcagga gaattcttca taatcgtttt aagaaagaat attatgaaat cagacgagaa    76980
aaaaagagg aaccatccct cccagttgta cctgaactcc ttggtgctcc ccagggcggg    77040
cgaggcagac aggctgcgag acttggcccg gccccggatg gggtggttgt aactccaggt    77100
ctcatcgccg tggcaggccg agcagcagta agcagccgcg tctggactca attccttatt    77160
catggtcatt ttttcttgtt ccatttccat tgtcaggaaa tgagaacttc ggtcagaaaa    77220
acactgatgc cttaatttaa taaaataaat aatgtaaata aagtaaataa atatgtatga    77280
aacaataata atttacacat acatatgttc catttcatca aggggaaaaa atggctgaag    77340
tccaatttac caaagtactt tgaaaacaga ctgtttccat tgcaaagata tttaagaact    77400
actctaggtt tttggctggg tgccgtggct cacgcctgtc atcccagcac tttgggaggt    77460
agaggcgggc agatcacttg aggccaggag ttcgaaacca gcctcgcctg accaatatgg    77520
tgaaatcccg tctctactaa aaatacaaaa attagctgtg gtgggcgcct gtagtcctag    77580
ctactcggta gactgaggca ggagaatcgc ttgaacccag gaggtggagg ctgcagtaag    77640
tcgagatcat gccattgcac tccagcctgg gtgactagag tgaaacttca tctcaaaatt    77700
ttttctgtaa aataatatta acaaaaaaaa ttgtttcaaa aagaacaaa atagaaagtc    77760
acactgtgtg gccaggtgtg gtggctcatg cctgtaatcc cagcactttg ggaggctgga    77820
gagaaaggat cagttgaggc caggggttca agaccactct gggcaacaaa gaactcttct    77880
ctagcaaaaa aaaaattagc cgggcatggt agcccatgag cgagaccctg tcttaagaaa    77940
agaaagactc tggccaggtg cggtggctca cctgaggtcg ggagtttgag accagcctga    78000
ccaacatgga gaaaccccca tctctattaa aattacaaaa ttagctgggc gtggttgcgc    78060
atgtctgtaa tccagctac ttgggaggtt gaggcaggag aatcgcttga acccgggaag    78120
cggaggttgt ggtgagctga gattgtgcca ctgcactcca gcctgggcaa caagaacgaa    78180
agaaactccg tctcaaaaaa aaaaaaaaaa aaaaaaaaa aaaaaaaaaa aaagacagg    78240
ctcttttctc gtaaacaata caacacatta atgagagaga agtgtgcaa tttcaaatac    78300
```

```
cctagtccag aaaagctgtc aaataaaatt gaaccagcag atatgttgtg aactccatgc   78360
cttgcatcgt gaattcagcg ccaatgaaat atttaccaaa ctgaccaata ttaagcctca   78420
aagaaaactg gtgaggatag aaaacctcac ccttttttcc ccttttttctt tttctttttt   78480 ttttttttgag acaggatccc acctcagcct tccaagtagc tgggactaca ggagtacagc   78540
accacgtcca gctaatttttt tttcctttgg tagagacagg gtgtcttgct ctgttgccca   78600
ggctggtctt caattcctgg cctcaagtga tcctcccaac tcagcctccc aacacagtgc   78660
taggattata ggcatgagcc accatgcctg gcctagaacc tcatctttttt ttttttgaga   78720 cagagtctca ctctgtcgcc cacgctggag tgcagtggtg tgatcgcagc tcactgcaac   78780
gtctgcttcc cgggttcaag tgattttcct gcttcagcct ccctagcagc tgggactaca   78840
ggcgtgcgcc accacgctca gctaatttttt ttgaatttttt agtagagatg gggtttcacc   78900
atgttggcca ggctggtctc caactcttga cctcaaatga tctgcccgcc tcagcatccc   78960
gaagtgctgg gattacaggc gtaagccacc acgcccagcc tagaacctca tcttctgacc   79020
acaatacaat aaaaccagga agagatagaa acaagaaaa gccctcagcc acttggaagt   79080
ttctgaactt tctcttaagc aacccaggga tcaaagtgaa gatcagaccc aacatctgga   79140
acacccagaa gctggaggtg acataaacag gctgccaggg tcggttcaat cccatcaaag   79200
ctgggtcaca gcccatggga aaccatgaac tgagcattca agccaataaa gccagaaata   79260
gaataaaaca agcttcagaa gaacagaaga ggggccgtgc acagaaacaa taaaaatcac   79320
tcaacagagg ctaaacacac aaaataaagc caaacatacc ttctcattaa agaagataaa   79380
tcttaatgag gacaaggtag attctggcat taaaaaggat aaatgtgaca ttatggactg   79440
aatgtgtcct ccccaaattt atttttttatt tttatttttgt agagacaagg tctctctgtg   79500
ttgcctaggc tggtctcaaa ctcctgggct caggtgatcc tcctgccttg gcttcccaaa   79560
gtgcttggac tataggtgtg agccactcca cccagcaatc cccccaaatt cctacattga   79620
agccctaact tccagtgtgg ctgaatatgg aggtgggcct ctaagaaagg agttaaatgg   79680
gcgcggtggc acacatctgt aatcctaaca ctgtgggagg ctgaggcggg cagatcatct   79740
gaggtcagga gctcaagacc agcctgacca acatagtgaa actctgtccc taaaaaatac   79800
aaaaattagc cgggcgtggt ggcgggcgcc tgtaatccta gctacttggg acgctgaggc   79860
aggagaaatg cttgaaccca ggaggcagag gttgcagtga ccgagattg tgccactgca   79920 ctccagcctg ggccacaaga gcaaaactcc gtctcaaaaa aaaaaaaaa agaaaaaatg   79980 aggtcataag tgtggggtct gatcagacag aatgagcatc cttgtaagaa gagacaccag   80040
gctaggcacg gtggctcact catgtaatcc cagggctttg ggaggctgag gtaagaggat   80100
cacttgaggc caggagttca ggaacagcct gggcaacata gcaggattct gtctctacaa   80160
aacaaaaaca aaacaaaac caaacaaaa acagttggac acagtggtgc atgcctgcag   80220
tcccaggtac ttgaggctc cggcaagagg atcaatgagc ccaggagttt gaggttttgc   80280
agtgaactgt gattgtgctg ttgcactcca gcctaggcaa tagagaccct gtctcaaaaa   80340
caaaacagaa caccagagag ctctctcctc acctctgttc ccaccctcac tgggcacaaa   80400
agtaaagcca tgtggggaca cagagaagat ggccattaca gtgagaaaga gagtctttac   80460
gatgaaccaa attagctggg accctgacct tggactcttg gcctccagag ctctgagaac   80520
aaacattttt gttgtttacc cgccccctgc cccatgcctg tggcactttg ttacagcagc   80580
ctaaataaaa caactaaaat atgtgagatg atggcaaggt gggcagaagg aaagttcagg   80640
aactatggac acaagactgt gggccctatg ctacggtcaa agccaacggg ttctctgaat   80700
```

```
acccaaaagc tggttctctc tctggctgca ttctacaatc accttaggag cttcaaacaa    80760
caccaattcc tacgtgccct ccagactgaa tgatcagaac ctgaaggtac agcccaggca    80820
ccggcacttt aaaagagctc cccagaagat tctaatgttt agcgagaatt gacagtactg    80880
tcccagtggg tcaatatctc cctagcttaa gacataccag gcgggatgtg gtggctcacg    80940
cctgtaatcc cagtgctttg ggagaccaag gtgggcggat cacttcaggc caggagttca    81000
agaccagcct ggccaacatg atgaaaccct gtctcgacta aaagtacagg ctgggtgcgg    81060
tggttcacgc cagtaatccc agcactttgg aaggccgaag cgggcagatc acctgaggtc    81120
agatgtttgt gaccagcctg gccaacatgg cgaaaccccg tctctactaa aaatacaaaa    81180
aacaattagc cgggcgtggt ggtgggcgcc tacactccca gctactcagg aggctgaggc    81240
aggagaatgg cgtgaaccca ggaggcggtg cttgcagcga gccgatatcg cgccatggca    81300
ctccagcttg ggcaacagag cgagactccg tctcaaaaaa aaacaaaaa acaaaaaaca    81360
aactagccgc gtgtggtggc gcgtgcctgt aattccagct gctggagagg gtgaggcatg    81420
agaattcctt gaacctggga ggcagaggct gcagtgagct gagatcgtgc cactgcactc    81480
taacctgggc gacagagcaa gactccatct caaatgaaaa gaaaaaaaaa aaagaaaaa    81540
agacatacca gtgttttatt caaatacatg aaaaattcgg ccagacacgg tggctcacac    81600
ctgtaatccc agcattttgg gaagccgagg tgggtggatc atttgaggtc aggagtttga    81660
gaccagcctg accaacacag tgaaaccctg tctctactaa aaatacaaaa aaagggctgg    81720
gagcagtggc tcttgcctgt aatcccagca ctcaaaacaa aaacaaaaac aaaaacaaaa    81780
acaaaaacaa aaacaaaaaa attagcctgg agtggtggtg ggcacctgta actccagcta    81840
tgcaggaggc tgaggaagga gaacaggaga attgctggaa cctatgaggt ggagggtgca    81900
gtgagccgag atcgcaccac tcactccagc ctgggtgaca gagtgagact ctgcctcaat    81960
aaaaagaaaa aagaaaaaaa gaaaaaaaaa ccatgaaaaa ttcaatgaaa accagaacct    82020
acaaaaacat gtctggtata actactccta ttgaggacta tactagaggc cacagccagt    82080
gcaataacat aagaaaaaaa taaaaggtac agtgacagaa aaggtttggc atgaaatgta    82140
ggtctgttaa acaaaataag aaaaggaaca agtgaagttg tacttgcaga tgacatgaca    82200
tttctatgta gaaaaacaaa taagtgagtt tattagcaag gtttcagaag gcaaattcaa    82260
tacacaaaaa tcgcctgtat ttctatatac tagcaataga caacaggaaa ttgagaccat    82320
cctggctaac atggtgaaac tctgtctcta ctaaaaatac aaaaaattag ccgggcatgg    82380
tggcgggtgc ctgtagtccc agctactcaa gaggctgagg caggagaatg gtgtgaaccc    82440
aggaggcaga gcttgcagtg agcggagatc gcaccactgc accccagcct gggtgacaga    82500
gagagactct gtctcaaaat aataataata ataacaacaa tataatttac agctgggtgt    82560
ggtggctcac gcctgtaatc ccaacactgg gaggccgagg tgggtgggga tcacctgagg    82620
tcaggagttt gtgactagcc tgaccaacat ggtgaaaccc tgtctctact aaatataaaa    82680
aattaggcag gcatggtagc acatgcctgt aatcccagct atttgggagg ctgaggcagg    82740
agaatcactt gaacctgaga ggtggaggtt gcagtaagcc gagattgcac tgcagccttg    82800
gtaacaagag tgagatttca tcttataaaa aaaaaaaaa tatatatata tatatata    82860
cacacacaca cacatatatt attaaaaata tatcttat taaatatat atacatatat    82920
atgatctata atagcattaa aaatataaaa tatgtgggga tatatttggc aaaagacatg    82980
tcagaactgc acactgaaaa ctacaaaata ttgctgacag agatgaaagg aaacctaaat    83040
aaatggagag acataccatg ttcatggatt ggaggactca atattgagat cttagttctc    83100
```

```
atcaaattga tctgcaaatg ttacccaaac acaaccatca aaagccaagc aggcttctct   83160
aaaggaaagg acaagctgat aaaattcaca tgaaaatgta aagtatctag accagctgaa   83220
aaaactttga acaagaacaa acgcgaaggg ctaagttcat gacttgttga aaaactacgg   83280
gaaccagaca gcgtggcagc atcaagacgg acatacacat caaggaaaca ggacggccag   83340
cccaaaggta gacgccacag accctcacac acatgcagtc catgaatttt tgacaggtgc   83400
tgaggtgatt caacatgagg aggatcatct tttcacctaa tagttctgaa caactggaca   83460
gccacgtcta aaagaacgaa gcccaaccac ttcctcatac tacatacaaa tattaactca   83520
gaatggatta tagacctaaa tgtgaggact aaaactatga aactttttag aagaaagcac   83580
tggaaatttt ttttttttg tcttttgtg agacaggatc tcccactgtt gcccaggctg   83640
gagtacagtg gtgtgatctc agctcactgc agcctcaacc ttccaggctc aagcaatcct   83700
cccacttcag cctcccaagt agctgggatt acaggcatgc accaccacac ctggaaattt   83760 ttttttttt ttggtggaga tggggtctcc ctatgttgca caggctggtt tcaaactcct   83820
ggtctcaagt gatcctccca ccttggcctt ccaaagtgtt gggattacag gcgtgagcca   83880
cctcacccag ctggaaaaag tcttagtggt gtttaaaatc ttttatactt aatgaaccc    83940 tgaattttt ttttttttcc tgtttaggc agggtcttac tctgtcccca ggctggagta    84000
cagtgatgta atcatggttc actgtagcct ctacctactg tgctcagaca atcttcccac   84060
ctcagcctcc tgagtaccag ggactacaag catgcaccac catgcctgac taattttgt    84120 attttttgt agagatgagg ttttgccatg ttgcccaggc tgacctcgaa ctcctgggct    84180
caagcaatct ctctgcctca gcatcataat gtgcttggat tacaggcatg agccactgtg   84240
cctagccaaa acactgttaa gaaaattaaa atacagttgg gtgtggtggc ttgtgcctgt   84300
aatcccagca ctttgggagg ccgaggcggg aggatcgctt gagtccagga gttcaagacc   84360
agttctgtgt cttgctagtg gttatataat taatttaaga ggtaacactg catagagcca   84420
tacacacatg taaaactggt gaaacctgaa taaggtctat agtttagtta gcagtatttc   84480
aattccctgg ttttgatatt gtactatgga ggtgtatgga ggtgtaagat gttaacacaa   84540
gggccgggca tggtggctca tgcctgtaat cccagcactt tcggaggcca aggcgggcgg   84600
atcacctgag gtcaggagtt tgagaccagc ctgaccaaca tgcagaaacc gcgtttctac   84660
taaaaataca aaaaatcagc ccggcgtggt ggcgcatgcc tgtaatccca gccactcggg   84720
aggctgaggc aggagaatca cttgaacctg ggaggggag gttgcggtga gctgagatca   84780
cgccattgca ctccagcctg ggcaacaaga gccaaactcc atctcaaaaa aaaaaaaaa   84840 aagatgttaa cacagaggga gctggtgaag ggcacagggg tctctctgta ctattttac    84900 aacttcctat gaattagtct atgattattt tttttttccc cagacgaagt ctcgctcttg   84960
tcccccatgt tggagtgcaa tggcgcaatc ttggctcact gcaacatctg cctccagggt   85020
tcaagcaatt ctcctgcctc agcctcctga gtagctggga ttacaggtgc cgccgccac    85080 acccggctaa ttttttgtatt ttaagtagag atggggtttc accatgttga ccaggttggt   85140
cctcaaactc ctgacctcag gtgatccgcc cgcctcggcc tcccaaagtg ctgggattac   85200
aggtgtgagc caccgcaccc agccaattat ttcaaaataa acagttaata aaggtcagac   85260
acagtggctc acacttgtaa tcccagcact tggaggcc gaagcagggg aatcacctga    85320
agccaggaat tggagaccag cctgggcaac acagcaagac cccgtctcta caaaaacatt   85380
aataaaaaat aaacaaatca aaatcacaaa atgttaaaaa aatgtattta ttactgctac   85440
attacctaga agctctattt tgtgtgtgtg tgtgtgtgtg tgtgtgtgtg tgtgtgtgtg   85500
```

```
tgtgtgtgtg tgtgagagag agagagaaat agagatattg agagactgag aggtagggtc    85560
ttgctctgtc acctaagctg gagtgcagtg gtgcaattac agcttactgc agcctcaatc    85620
tcccaggctt aagggatcct cccatgtagc tgagactaca ggcatgagcc actatgtcca    85680
gctaattttt aaattttttg tagagacagg gtctcgctac cttgaacggg ctgaccttga    85740
actcctgggc tctggtggcc ctcctgtgtt gacctcccaa agcattggga ttacaggcat    85800
gagccactgc acccagccta gaagctctgt tcatatttat ttgcgaagat caatttgatg    85860
actaagcagt aaactaattt ataaaataat attaaatatt aaaaccaact ttaaacaatt    85920
atcttcacct atgtatgtgt gtgtgtgtat atatatacac acacacacac acatatatat    85980
atatttaaca agtatctcca ataccacaac cagtgtattt tttgttttt tgagatggag      86040
cttcgctgat gttgtccagg ctggagtgca gtggcgcgat ctcggctcac cgcaaactct    86100
gcctcccagg ttcaagcaat tctcctgcct cagcttccca gtagctggga actacaggtg    86160
tgcgccacca cgcccagcta attttgtatt tttagtggag acctgcctct taattctcca    86220
acatggaggg gtttctccat gttggtcagg ctggtctcaa actctcaacc tcagatgatc    86280
cgcccgcctt ggcctcccaa agtgctggga ttgcaggcgt cgccaccgcg cacgccacc     86340
attatgcctc ggcctcccac agtgctggga ttacgggcgt ggccactgcg cgcggccacc    86400
attgtgcctc ggcctcccac agtgctggga ttgcaggcgt ggccaccgtg cgcggtcacc    86460
actgtatttt ttgacaaggg tgagtcagga ctgacactta attcatttgt ttgatatatt    86520
aactgcttta aaaggacaca caatgctagc tgcaccaaag tgcattcaaa ttcctcatag    86580
catgaatcta attttaaaaa acctttgtag ggcgggcatg gtggctcacg actgtaatcc    86640
cagcattttg ggaggccgag gcgggcagat cacgacatca ggagttcaac accagcctgg    86700
ccaagatggt gaaactccgt ctctactaaa aatacaaaaa aaattagctg ggcgcggtgg    86760
caggcgcctg tcatcccagc tactcaggag gccgaggcag gagaatcgct tgaacccagg    86820
cggcagaggt tgcagtgagc tgagatcacg ccactgccct ccagcctggg gacagagtg     86880
agactccgcc tcaaagaaaa aaaaaaaatc ctctgtatta ggaagtttta ttagaaaaaa    86940
atactagagc acaataagaa aatattcata acgaacttat acaaagtagc aaggaaaaca    87000
ttaagatgcc aataaataaa tgtgcaaaga acatgaacaa agtcacaca cacacaaata      87060
caaacataat acacgagttc gttcccatgt aagaactcaa tcaatatttg ttgcaagact    87120
aaatgaaaaa ggaaaattta tttagtgaca gaaatgggga acattcaac ctcaaccctg      87180
agtgggaaaa aacttactgc ccactaaatt acccatctca tctcacccg gtaaataatg      87240
cccagtgctg gcatgcacac tggcagtata caaactgaga aagactttct ggaaagtgct    87300
acagccatgt gaccacaggg cttcaccctg tgacctcatt aaacctaagc agattacagg    87360
tctgaagggg gctttcttta gatgtggctc cacctactta ggggcagatg aagaaaacag    87420
gggtctgggc agttctgaat gggaaggcca ggcatcacct ccctcttcag ttgcacaaag    87480
tgtgcgtggc atcctcacat cccatctgcc tcaatttcgc ttttctctg aacacttttc     87540
accatctgtc tgaagcacac acacacattt tattcacttc cccattccca tgcatgaatg    87600
ctaggacctt tgcaattgtg ggccaggaaa gattgcaaat gataagccac cagcacagag    87660
agtagaaatg aaatcctggg gttacaagct aaagcattac tgcacccac ttgtccagaa      87720
cggctgaagc tgggcggtga ctgtcaacag gtatatacgg actagaaagt ggagctgctg    87780
gaggaggccc tgtaccttcc tgccatgaca cagcctcccc ccaagtgctg gcttgtgtg     87840
ctcaacactc cctcttgctg tcatcctacc acacctgcag actggaggta atccagatgc    87900
```

```
aaggccgtcg agtcccgcaa acacccacct gcctcttaat tttccaagtg agacctacat   87960
ttcctcaagc gtgaagctca ataaaatcaa ctattgtttt ccgttttcat cacgagcgcc   88020
actttccccc tatttgttca ccgcctccac tccacaagaa ctgctcttga cttggccaac   88080
tttctgggac accctcacta caaggattta tgagtcaaac aggttttgt gctagcctgg    88140 aaatctaact gctgacagca gttgtttcaa gaagaaaatg ctgttttgga accaaacagc   88200
aggctgccaa ctgaaacaac ataaacccac ctccaagttc aaatgaaaca aacaaacaaa   88260
aagactggtc caagtgaggc aagctgtggt ggctcacacc tgtaatccca gcactttggg   88320
aggccaaggt gggctgatca cgaggtcagg agttcgagac aagcctggcc aacacagtga   88380
aacccgtctc tactaaaaat acaaaaatta gctgagcgtg gtggtgggcg cctgtaatcc   88440
cagctactca ggaggctgag gcaggaaaat cacttgaacc cggagggtgg aggttgcagt   88500
gagccgagat tgtgccactg cactccagcc tgggcaacag agctagactc tgtcttaaaa   88560
aaaaaaaaaa aaaaaaaga ctggtcaaag tggcttacgt ctgtaagatc agcactttgg    88620
gaagtggagg caggaggatc tcttgaggcc aggaggttga actagcctg gacaacacag    88680 tgagactcta tctctacaaa aaatttata aatcagctag gtgtggtggt gcaggcctgt    88740
aatcccagct actcaggagg ctgaggtggg aggatcaatt gagcccagga atttgaggtt   88800
acagtgagct ataatcatgc caccataaac acgcctggag gacagagtga ggccctgttt   88860
ctaacataca cacacatata cacacagaaa catctcgaga ggacacctcc aaatgatgaa   88920
gctattttgt tgggtactgc ggtggcacct gtgattcctc aagtagcttg gaatcagcgt   88980
gctaacacca taaagtggct gcaaaagtcc cagtgaagtc actgctgaga gcaaacaggc   89040
cttacagaga agttccaagg ggacaggaaa tttccagagg cttgagagga caatgttcag   89100
gggaataagt acttgaaggg aattatctaa caaggtgtta aagtaactag cttcttagac   89160
aagatgacat caggaggaaa aaaaaactta ttaaggcaaa catgtcagtt tcaggccaac   89220
taaggctgtc agagagacat ggaacacaag aagagaaagag ttttgaaatg tattcccatc   89280
aagagccaag aataatgaac ttttgaatgt aaaacttagt gtgttccaaa acaagaaagg   89340
aaaaataact tgttactcgg aatcgaagcc aaaaggaatc tcattgcttg gggaggaggg   89400
atgggagggt gggggtggtc cttggcctgg gaaggaaaac tccaccaggc cttcggagct   89460
gggcacgccc tgttcccaca attaagaaaa aaaacgacga cctagagctc aaggccggtg   89520
ctgacatctg acctactgga tggcagccgc ctgtaggaac atcaccatag actattggaa   89580
ttttctggca agtactgggc actaaatcag agatgtgttt ttagagaatt ccatgccaat   89640
actgctgtat agaatctttt attcatactt tcccactagg tttgggcccc tctaagcttt   89700
cacgagtcaa agacccctcc tgcttgctga aaccacccac ggaaggccgg acaccgagga   89760
cctggccgcc caagcagagg cgactgacaa gcgcggtccg ggctggacgg ccccaccttc   89820
cccgcccggg agaccaggc cggacagcgg cctccctcag acccgtcccc aaggccgagc    89880
ctcgccctgg gccgtgctgg tgccccattc gggacggagc ggtggcccgt cagcacttcc   89940
acggcctcct cagcaggcca gatgggcagg gccggcctgg tgtctccccg cctggccgcg   90000
cgctcgcggg cagcgatgac cccaggcagc gggcgacccc aggcggacgg caggccgggt   90060
ctgctcactc accgttcgct gccgcgggcg cctgcggggg cgtctacatg ccggaccgag   90120
cccgcaggcc ccgccgccgc gccgccgcca gccgtcgcta cctggccctt ggcgccctgg   90180
ccgcctgttg cccccatggcc gccggaccc cggcgccggc gccgccgagc agcaatgcgc   90240
cgcgcccgcc cactgcgcag gcgcacccgc cacgcatgcg cgctgccgcg cacgtggggc   90300
```

```
gtcccgcgcg tctgccgggt cccaccggcg ccgggacacc ccgcgcgggc gggaggcggc    90360
gggcgtggcg ggaaagaggc gggcggtggg gaagaggggc gaatcgcggt ggagagcagt    90420
gaccagggag tggaggcggg cagcggggac aggggcgggc gtccgcgact cgggtaggcg    90480
ggggtcggcg ccccgaggag ggcggccccc ggctcccgtc cccactcacc tgccgcgtcc    90540
ggagggcgcc cccgggtccg cccgccacgt ctacgcctag gcgcccccga cattgtgatc    90600
ccagcccggc gtcccgcccc caactcaccg ccaccgcggg cgggacctcc cggaccacgt    90660
gggccggctc aggggagtgc aggtgccccg cgagagctgg ccccgcccgc cgccgcttcc    90720
ctaattaccg ggctgtgaca cggtgtgggc cgagccggat ttgggaaccg aaacttagag    90780
cagctgcggc agcgctgcgc tccctcgggg ctgtccgtcg gggctgggag ggcggccctg    90840
cgcctggggg aaccgcgatc ggcctcacgc ccacctctag cggccaggtg cgccttgcac    90900
gcccacgaac gtcctcagag gtctacgctt gggatcccaa ggctggcagt ggagggagga    90960
cccggtggcc tggggcacct ctaggggac caggagccg tgttttgcgc accccacagg    91020
ctggaggact cggggagttg ggggaggagg ccaaagccac aggagcggac tttgtagtgt    91080
ttgttggaac tgcgggtccc acccagcccg cacttgctga actggtggct gctcatcagc    91140
gccttcaggc ctcaaatatc ccaataatgt gccctatacc cagttctcag ctctcgagtc    91200
actgtcaggt aaactggcaa tgcacgacca gctgctctaa cctgctggtc ccccaggtgc    91260
cagacattgt tttgtttttc tgagatagtg tctcattcgt cccccaggcc ggagtccagt    91320
ggcgggctca cggctcactg cagccttgac ctctcaggtg caagcgatcc ttccacttca    91380
gcttccctag tagttgggac tacaagtagg tcccgccaca ctcgactact tcattcatat    91440
atatatatat ttgtgtgtgt gtgtgtgtgt gtgtgtagag atgaggtttt accattttgc    91500
ccaggctggg tctcaaactt cacccgcctc ggcctcccaa agtactagga ttataggcgt    91560
aagccactgc acctgcccca gccattgttt tctgaggttc agtccctgtc tatactttct    91620
gtgtgatcac ctggcccagg gtcggtgtgg acctgagtcc tctgcagccc ttccccacac    91680 ccgcataccct gctctctggt caggactcct gggacttgaa tccagagaca cggaacacgg    91740
cctggccaag tcttcctgaa aaacacagct cttcagttca ggaccacagt gaagtacagg    91800
gcaccaaggg tgactggaaa gggaagcaag gatcatgaga acttggggga tttcttaagc    91860
tctgtaactt ctcccggggt tattttgcaa acccaactgt ttcaaagtga ccaccagcca    91920
cacccacaga agcggccttg agctgcccag ttcttttttct ttggcggggg gagaggggggc    91980 ggataagatc attaacataa taatgcgtga gctgagtttt tgcatatgat cattagcata    92040
ataatgcttg atctagatgg cgcacccaca agccaggcac tgagccaggc ctcagtagaa    92100
tcttctagag tggaggcagt caactgcttc tgcagaggca accagtgact gtcgtgggcc    92160
ccaggtcaca cagcaggtgc ccttcgcgtg tcccgctgtg tagggagctc cagcagctgc    92220
cccgtctgtg gcatgaaaac cctttgtcta ccctgggcct gggcactgcc tgcaggagag    92280
cttccctgtt tcagagatga gaaaacaaaa ccagggctgt ggtttccttc agctgacagg    92340
ttgtgcaatt tctcagggca ggccccggat atgaccttga agattcaggg gccaagatct    92400
cacacccaca cctcacccca ggcctggcca gcaataacta agaccaaagc tgggaaggct    92460
ccttagggca cccagaatgg tccaagaggc agctttgctt gggctgagac caaagggaag    92520
agatgttccc gcagcaggaa cagaagggtc cagggctatc atgggggctt ctgccagatg    92580
gtgcacagga agaggctctg ccttcaaggg attgggggtc aggaaaggcc ccctcctgcc    92640
tgaccaggcc ccagggatgg ggcagcagtg ggtggcatcc cctgccctga ccttcctcag    92700
```

```
cccagggct gccattgctc aaggtggcag tggactcttc acataatttc gcattgtttt    92760
ttgtattctt taaggatggc tcccatgttg tttacttcag aaccccaaaa acctggaccc   92820
atcctcttct gggggtcagc agggatgggg agggtggagg gagaaggggg aacggaggcc   92880
atgagggatg gagcaggatg gggtgcactg gggtacaggt tgctcctggg gaggctgagg   92940
agagagggaa gttggcttca ggtggcctgg ctccagtaaa ctgggtgaac gaagtctgcc   93000
cagaacccac aagggtaagt ggcctggagc ctggggaaag gatgactggg aaggactgag   93060
gctcccagtg aaggacatca gtatggcagg ctatctggtc atctcatcca gcctccagcc   93120
agcacccggc acaggccctg cccaggctga agccaggat  aggggcgtct gcaggggcca   93180
gtgtctggat ctgctcacat gacagtcttc tgtttggcct ggtttggggc gaggggcaac   93240
ctctttccca ggatgccagc catgtgcagg gcatactgag gattcaacag tggaaaccaa   93300
agtccatcag gtgttcacct tctagtgggg cagacgggca agaagcagaa ttggtggggg   93360
caggcagggg ttggggtaca gttttgacca aggtacccag ggacaagtgt ttctctctca   93420
ggcagaggca gcagcaagga ccaggaccct gaagtggtga gagcctagag tgggcgggga   93480
tcatcaacag taaccacctg gcaggactgg gactccctgt gtcctcacaa gatccttacc   93540
aagcagccta gtataagacg aagtctcgct ctgtagctca ggctggagtg tagtggcatg   93600
atctcagctc actgcaagct ccgcctcccg ggttcaagcc attctcctgc ctcagcctcc   93660
agagctggag ttacaggcgc acaccactga acccggctca ttttttgtat tttagcaga   93720 gacgggtttt catcatgttg gccaggctgg tcttgaactc ctgatctcag gtaatccatc   93780
cacctcggcc tcccaaagtg ctgggattac aggcgtgagc cacagcgccc ggccacagcc   93840
tggtacgttt attgtccaca tttttcacgc gggggccaga ggcacagaga ggccaagtaa   93900
cttgctcaag gtcacccagc gaggaaaggg agctgggggg tgggggtagg ggacagggcg   93960
aggccagaga gtagtgggag gggccgaggc ggccttttcc gggagcgctc ggttcccggc   94020
cggcccttct attggcccca gtcactcagg ctcccaggtc cggctcgggg gggagcgggg   94080
ggccgcgcca ggccgctgaa gtgtccccgt ttcgcgtggg cagagcgcgc ctccccacgc   94140
atcctgctga gggccagcct ctgctaggtg cgtgacacgg aggggacaga acggaaacct   94200
tgtcctgctc aagtgtggac gtgcgtgcca cgtgctagag taaaattgag gtggggaacc   94260
tccatccctg ggacatggag cacaggggcg acccgcgcc  gcttggtcaa aggaggtccg   94320
aggccctgca ggaacagccc acagccggag cgagctgcag gtcactccac tgcctgtgtc   94380
cacctgcgac aggtgcgccc gcgcaagcgg ggcgagcca  ggtgacccgg acacaggaag   94440
cgcgccaggg gccccacac  cgcggagctg ctggcgacaa agggcgctgc tcctgcatag   94500
gccaggctaa tgcaatctac aaactagatt tctgtgccta cagtttgaaa atgattgcag   94560
ttcactcagc cagtgtggaa ttatcctcct cttttccacac tgccttagtc agtgccgctg   94620
tccaagtgca cgttgttggc gcccgttttc atttcctgtt ttgctaagaa agtggggcag   94680
tggcctccat gcccgccaag ggacaggcag gccgccccag ggagggggtcc ccctcagctc   94740 tggctcttcc aggccaaagc caaggggaag gggcaccaga gggtcccagg tcccacatgc   94800
cagctccctc agtctgcggg gtgccaggct aggacacaga agccaacagg aatccccaaa   94860
gggaggaagt ggagtcgggg gtgtggcagc cgtgctgaga tgctcggcct ttatttactc   94920
tgggcaggga ccaagatagg ccactgcagg ccggcaccct gcctcccggc tgctggagcc   94980
cctccctccc aggaactgcc agccaggaaa gagcctcagg tactctctgc atttaatttt   95040 taatttttttt tttcttttga cgcctccaag acaagttcaa ctctctagtg attttaagtg   95100
```

```
gggttttgt aagacagctg gcagggttag ggcttgtgaa gaacttgcat gtctatgaag    95160
aactgattta tttcagggaa aagtggggga tgacgaagcc aggcgagccc accccgttca    95220
gcctgccaat cacacccact tcagcagcct aaaacagcac caggtcaccc caccagggag    95280
acaacgccat agtgtcactt gcagtgctgg cagatgggca cccttggtgg cgtcagaaac    95340
acacccagca ccttgcctgg agcagggcgg ctgggccctg ctccgtgaat cccaagtgcc    95400
ctatgggagc ctctccggcc agggactgcc agcctagagg aggggctgct gggttctctg    95460
gtgcccaggg gaggaggggg cctacaggta ctttctgctg agagccttct tcacttacta    95520
ggaaaaagtt tggctgggtg cggtggctcg gcctgtaatc ccagcacttt gggaggctga    95580
ggagggcgga tgacaaggtc aggagatgga gaccatcctg gctaagatgg tgaaaccccg    95640
tctctactaa aaatacaaaa attagccggg tgtggtggtg ggcacctgta gacccagcta    95700
ctcggaaggt tgagccagga gaatggcgtg aacccaggag gcagagcttg cagtgagccg    95760
agatcgcgcc actgcactcc agcctgggca agagcgagac tccatctcaa aaacaacaa    95820 caaattagcc gggcatctgg gccaggcgcg gtggctcaca cctgtaaccc cagcactttg    95880
ggaggctgat gtgggtggat cacaaggtca ggagatcgag accatcctgg caaacatggt    95940
gaaaccctgt ctctactaaa aatacaaaaa attagctggg catggtagca ggcgcctgta    96000
atcccagcta cttaggaggc tgaggcagga gaatcgcttg aacctgggag gtggaggttg    96060
cagtgagctg agatcgcacc attgcactcc agcctgggca aaaagagcg aaactccgtc    96120 tcaaaaaaaa aaaaaaaaaa aaattagcgg ggcgtcgtgg tacgtgcctg taatcccagc    96180
tacttgggag gctgaggcag gagaatcact tgaacccaga aggcagaagt tgcagtgagc    96240
tgagatagcg ccactgcact ccagcctggg ccacagagcg agactccaca tcaagggaga    96300 aaaaaaaaa aagttccagc tgctggagcc atgggaatta aaaaattact tttttttttt    96360
ttttgagagg cagtcttgct ctctcaccca ggctggagtg cagtggtgcg atcttggctc    96420
actgcaaact ccgccttccc gggttcatgc cattctcctg cctcagcctc cagagtagct    96480
gtgattacag gcgtgtgcca ccatgcccag ctaattttgt attgcctatt taagatttta    96540
aaaaatcacc agtttggaaa gcagggaagt ggatggttct ggagcctagg agcggctatt    96600
tgggacacac acagccatgg ttttccacac taccatggcc agtgctcatt ttttcttac    96660 tagatgcagt tctttatatt cagaccaaga ggaacactca gttcagtccc aaggaaagct    96720
agtctctgga gtaacatcct cagacattct aagggaggga aatggcagag gagaaaggca    96780
aggcagccgc ctgtggagac tcccacggtg ctgtgggcaa ggcctatgcc tgggaggggg    96840
tctgggcgat ggcaggtgga cctccctgct ctgctggcct gtgaggtgga gcttcccagg    96900
aacccctccg aggagccaat gcgccactca tggattctgt gacgtggtgg cggccatggc    96960
accgcctggc atgagcaggc ccgtcagacc tcacagcaac agggacagct tagggaagcg    97020
ggcgcgttgc aaactggaag tggacccgta ataatcacc acaccaaagt ccctcatgtc    97080
aaactgcttt attacatctt aaataacagt acagtttaat atagtatcta tcttgcatcc    97140
agcttccttg cagtacactg actttaaaat taaatacaaa aggtgaaaag gggtaagggt    97200
gcagagagct ctacagagtt gttggacgga aagagaaaga aggggtttca tttgtattct    97260 cttttgccaga tccaggccta ccgcaaggtc acagcacagt tttgtataga atgttgcaga    97320
aaacaggatg gagaagccac tactgctgct atgaaggagt cgggggggcg gggcgggggg    97380
tcccacagaa cctgctttcc aaacgctgct gctgaacact ggccttgaaa tgaacaccag    97440
gacaatctgt gtgtgatggg aatgagccac ctcagatgtg gagggccctg aagaatccat    97500
```

```
ataggagggc aggctcttca ctccctctcc ctccctctct ctccctcccc accctcagaa   97560
tccaacagca gtcgtttgca acagaacttt tttttttta aagaaataaa gaaaacagtg   97620
acttatcccg ctacccaagc gtgtagagcc gcgcgctgta ctgcttccga tatgtgccac   97680
agagcagcaa cgagaagtgg acagagccgc aatggttaca actgtaagag gttatttctt   97740
aaaagaaaaa gaacacctaa ggactgagtc ccatatgcac ttttgagcat ttctacagca   97800
tgcgattcta agagtaaacc cacccaatat ggcaaacaat caaaattttt aaaatttaac   97860
ttagaaagtc tgagatcatt attttcaaaa cattgatttg tacattgttt catacacaaa   97920
taattgactg actatccaag cacaggacag gcatctctct tgaaaacaga ggttcctcct   97980
agttgggggt ggggtagtgt taggctatta taaacttccc tccaacttca caaggaaacc   98040
caaagtgaga ttaaaaactc aactgagaag atagacagga tgggtcagga ggaacatggg   98100
gctggatctg agctcacttt tcagcaaagg tgaaggattc tctgatcacg catttgagac   98160
cgtccccgca tgtgcttggc cccatggctt ctgaacatgt tcttttctat gccacgtttg   98220
tgtgcaacaa tgatctgtga catcagacag aaaattaaaa accagggact gaatttacat   98280
cattgacaac atcagagagg ctgccctaga ctctctggtt ttgattaact gttgaacaca   98340
aaggaataca ttttaaaaag gaaatatgaa tgcttccaaa atcttgctac aaacatgact   98400
gaaatttgga cacgatgacc agatgaacaa agccctcagc atgttttgca tgaatgccac   98460
aaaacagggt cactggtcta aaattcaaat acactggtgg aaaagtgtgt ctgtctgaca   98520
attacactca agtttacctt ctggttaaca ttttttattat atatttcctt ttaaaattca   98580
ttcaagacaa aaagaaaac aaagacgatg gccccggaag gaatgcacaa tttgttttag   98640
tttacagcac agagatcttt ctctcaatgg gaattgtgct cttggtttca gcaataagtg   98700
aaggaaaaaa gatcttgccc ttttgaagtt ctgaggggag gtgtagggtg tccacgttag   98760
tacggttgga taggatatgc tctcatggta acgcgtccaa gttggaatgg tcttccagtc   98820
tccatggcat ccacatgctg ttttaaacag agtttaaaga aatgtgaaaa gaggcagaga   98880
atctaagtgc agacgcacag ccaggtcact gctcttccca tcactgcatg agtgtctgca   98940
gctgagggca cgtgacttca gctttctgta aacgtttccc acaacacaat tccaaatcaa   99000
tgctacatca acatttatct agaaaccgtt aatgacaact tcaaatgttc tatgagaaac   99060
acgcacagtt ctcctcagag aagggcattt gggctgctgc attacctact ggcgttagtt   99120
ccagatcttg aggaagctat cccaggaccc tgtcgccaca gccatgccat cgtcagtcac   99180
gcccaggcag ctgacgcggt tgtcatgccc agccaagaca cctgggagca acaacagca    99240 gaatcacacc aaagcccaga ggcatcgatc tcacctgtgt gccatgttgt gacgaggacg   99300
gatggtgcat ctctcatggg acaagaccca gagtctccca cggccaggaa gggagggaaa   99360
gttgcatcca cgtggggaat taacctgcag catatggcca gccttgttaa aattcaaaga   99420
cacgcacaca cacgcaatcg ataaatccag agccctgc attgacttct cagcactcac    99480
ttataaaact aaaaaaaga agcaaaggcc actatcaaaa aaatcaaaac tatcatcaga   99540
cgcagtggct taggcctgta atcccagcac gttggaaggc cgaggcaggc agatcatgag   99600
gtcaggactt tgagaccagc ctggccaata tggtgaaacc ccatttctac taaaaataca   99660
aaaaccagca gggcgtggtg gtgcgggccg tagtcccagc tactcaggag ctagggtag    99720 gagaatcatt ggaacccagg aggtggagct tgcagtgagc caagatcgtg ccagtgctct   99780
ccagcctggg cgacagagcg agactccatc tcaaaaaaaa aaaaaaaaa tcaaaaccgc    99840 cccaatctca aagcaatctg taacacagga gcttagaggc atgagccgtt tttcctttgt   99900
```

```
ctgtgatccc tagagcccag cacaaggcac agaacacagg agtagcgatg gtggctgaga    99960
ccactggcac tgcactgtca ctgtcatgtg atgaggggc cttctgtcaa cactcccaat   100020
aaccttggct tggatcatca ccagccagaa gctccacttc ctcccagggg gatccgaagg   100080
cccatttcag ccaccctcct ccacctcctg cagccaccac acagctgagt acagggccg    100140 gcgtgtgctc tgccaaggcc tgggctggct tccaccgccc ttcaacagca ctgtgactgt   100200
gagacttggc tggaaatggc tccactctgg tcccccagg ctgggagaa aaagaaatgt    100260 gtttaaccag gaggtgggag tggcacccat ccggaagcag gaagcccgg taagggccaa    100320 gacctggagc catgctccct tctgtcctcc caggtactga acaaatgaa tctaagtctg    100380 taagtgtcaa cagttctcaa attcaaatgc ccaaatgacc attttagta aggaagtctc    100440 atcttttgta cacctggcaa taacacgctt gcctttgata tgttaactgt aacggcaccc    100500
agaggtgtcc ctgcatggaa ctcctccccc tgaagcagag ttcagagggg aaagcacggg    100560
gctgggccct ggagcctgca cagctgaccc tctcctgccc actgactctc ccagagccc    100620 tccccgacgc atgtgggaag atctgctggt actcctcgga gtccacttgc ctggagggtc    100680
agagctgggc catcagtttg cgactgtcac tcctgctacg ccatgccaca gtcccaccga    100740
tactaaaaca ctgcagctta tgcaaccact ctgtgtttgc tctaaagata ccacgtaaat    100800
gtccacaaga cacagaaagg ccccatggcc acgtacctgc ccggtcggct ttgagtgcat    100860
cccagacgtt gcagttgaag tcgtcgtacc cagcaaggag gaggcgcccg ctcttggaga    100920
aggagacaga ggtgatcccg cagatgatgt tgtcatggga gtaagtcatg agctcctggt    100980
cagcacgaag gtcaaacagc ctgcaggtgg cgtcgtctga gccagtggca aatgcattgc    101040
catttggaaa gaactggaaa gagaaagcaa atcaagacat catgtaaacg ctcagaaaga    101100
aacattggga atatggattg ctcaatggta gggctgcaga gaacacagca ggcaaagacc    101160
agcaagactg tgctctggta agaacagagg gctgggccgg gtgcggtggc tcatgcctgt    101220
aatcccagca ctttgggagg ctgacgcggg tggatcacct gagatgggga gtttgagacc    101280
agcctgacca acatagagaa accccatcta tactaaaaat acaaaattag ctgggcgtgg    101340
cggcgtgcgc ctgtaatccc agctactcaa gaggctgaag caggagaact gcttgaaacc    101400
gggaggcggc ggaggctgcg gtgagccaag attgcaccat tgcacccag cctgggcaac    101460 aagagcaaaa ctccgtctca aaaaaaaaa aaaagggtg gggggatggg ggaggaacta    101520
caggggactg ggatgggagg ggatttgcac tggggaggca cacaaacact gtgatcttgg    101580
acactgtgat tactgtcccc aaagagtaga atttattcca aaggatagtg agaaagtagt    101640
catcactgac aggtgtgcat gttgctgtag ctgccagcca tcagggctaa tctcatggag    101700
gaaggaggga agcgggctga ccaaggctgt ggtcaggact gcagcagagc tctgtccaac    101760
caacagatac atccttctaa gtctcctcac aaggccaggg gctggaaaca ctgcctagcc    101820
atccgcgtgc taaagaggag ggcaggttcc ctggttagct gtgcccctga ccagtaaggc    101880
tctgtaacca ctggtggcct gagttatctt actgtctttc ccctccagga tcccaaccac    101940
tgctcagctg tagaggtggg aacgggact ggcatacaac ccctgtgag tatctgtgag    102000 acaagtggtc aacacagaga agttcccat cgggagtttt ctgtatcccc atctgtacat    102060
gaggttgtat aaggatcaga aaggagaaca tctaatccag aaaagtttaa aatttagcaa    102120
tctgaacggc tagcagagac ggcagaggac ccgacccac acctccaccc agactcacgc    102180
aaatggcatt gatgtcagac tcgtggccag tgaaggtctg ccggcacatg ccttctcgca    102240
catcccagag tttggctgaa gcatcacaag caccagagac gaacagtctg gtgtcaggag    102300
```

```
caagagaaag gctcatgaca tctccagtgt gtccggtaaa cgtggtcgtc tgctggccgg   102360
tctcgatgtc ccacagggca ctggagcagg agcgaatgac aagggggacat cagccttaac   102420 ttcttgggtg gctagtcatg tgacagacaa tctgtccttc aaaccaccca gggccacagt   102480
gagcctctgc actgttactt taaaaacgta aattgtttaa agacaaattt aaatgtaata   102540
caactttgga agggaaacaa agcaaagcaa gcaaaattat acagagatga gcacagggcc   102600
tgggcttcag aatgacggga tcgctacctc aactcaaatg ccagcaaaca gggagctggg   102660
ggcacttttc aagcagcacc actgaggctg tgccccctct ttggtcatgg atgggcatgg   102720 aagggggtggc aggaagctac gtggaggccc tggatggcgg aggggacgcg actctatctg   102780
tggctgctcc ctctgtgccc tcccttggcc tcccctccac agggtctcag aaaaggcagg   102840
caggagaagg ccaatgccag gtaaacaaat ggctcacagc aattctgagg tcctcctgcc   102900 cttcctgga atcacaaaca ggagagcagc tgagttctca gtgatcacac ctggtatttt   102960
tttttttttt ttgagaccga atttcactct tgttgcccag gctggagtgc aatggcgcga   103020
tcttggctca ccacaacctc cgcctcccga gttcaagcga ttctcctgcc tcagcctctc   103080
cagtagctgg gattacaggc atgcgccacc atgcccggct aattttgttt gtattttag    103140 tagagacggg gtttctccat attggtcaga ctggtctcga actcctgacc tcaggtgatc   103200
cgcccgcctc ggcctcccaa agtgctggga ttacaggcat gagccaccgc gcccggccat   103260
acctggtatt ctatcacatt tctgcttaac aagctgtcaa aggtgagac gctgacagag    103320 ccctgcacag agcagaagcc tggctcaggt gtaaggacag ctgtgagggc cacacgccca   103380
ccaacatact attctcctgt gcctcgaccc atggaaggca acaccagaga gcactgtccg   103440
ttcatgtcag cctcagagga aagcctggct gggcctggca atgcaaatcc aatcagccaa   103500
tctcaacaga cactgcacag ggagcctcct ctctagggcc tgagggactg actgcagaag   103560
ggaagcaaga tacgtaaaag agtctgaaaa aaatgattaa tgaacagaag cacttaaaaa   103620
atatcttcta ataaataaag tcttctcaag attgacaatc taggtgacaa atcttttgta   103680
aatctatgaa atttatacaa cgaggacacc ttataatacc acagatgctt gctgacaag    103740 ttggttaagg gcccatgtct cggtgaaccc caccaactgc gtgactaggg gtctgtgccc   103800
tgggctgggc acagctcctg ccaccaaatc atgcctcaga agaccagaaa acccacatg    103860 gccagctgaa gtctaaaatg actctcataa aataactatc tggacattta atttagtact   103920
ttgatgccac aaatgaaaaa attctagcat ttaagtgggc ttccgtttac ctgtaaggtg   103980
aaaacactaa aaatgaagtc tgatggaatc acttgaattg tgacgtctgt tattttagt    104040 ctgtgctcat tgttcacaat gacatgatgc tatcagaaag ggacaatcaa aaccccaccct  104100 actcccacct atcatcacct aaggaggtac aaatatatag aggggaaaaa aaagaagagc   104160
aggtactttg agcctgattg tagttaaaat atctatgttg gccaggcatg ggggctcaca   104220
cctgtaatcc cagcactttc agaggctgac gcaggcagat cacgaggtca acggataaga   104280
gaccatcctg gccaacgtgg tgaaatcccg tctctactga aaatacaaaa attagctggg   104340
tgtggtggcg cacacctgta gttcccagct actcggagg ctgagagggg agaattgctt    104400
gaatctggga ggcagaggtt gcaatgagcc gagatcacgc cactccactc tagcctggag   104460
acagagagag actctatctc aaaaaaaaaa aaaaaagaa aaaatgtgt attttagttc      104520 tcagctgctg aaaattaaac tttgtaaatt tattagaagt ataatgaggc taggcacgga   104580
ggctcacgcc tgtaatccca gcactttggg aggccgaggt gggcaggtca cctgaggtca   104640
ggagttcagg accagcctgg ccaatgtggt gaaacctggt ctctactaaa aatacaaaaa   104700
```

```
ttagtcaggc gtggtggcgg gcacctgtaa tcccagctat tcaggaggat gaggcaggag 104760
aatcatttaa acccggcagg cagatgtcgc agagccaaga ttgagccatt gtactccagc 104820
ctgggtgaca agaacaaaac tccatctcaa aaaaaaaaaa agtataatga attcacacat 104880
tgctactatg tgtttaaat cttaaggcca cttaaattac agatggccta atattatgtc 104940
aagaaccta tttcctccat gttcacagag gaatgtgcca ggggctgtgg gttctcaagg 105000
cactgcctgc cccgggtcag gtacttacca cgtggtgtct ccagagctgg tgacgatctg 105060
attgtcatcc aggaatcggc agcaggacag gtaacctggc aaagaacagg cctaagtgat 105120
gagctgaatc cagcaggcct tgcacccagc ctcatacata gagaaacaca ttggcccggt 105180
ggaagctcta cgtctaaggt aagaccagca ccatgctagt gaccttttat tcccatctgt 105240
gcacacagca gaaggtccac acgcactgct ggtgagggtg agagcctggc caggcaggac 105300
agcacgtccc acagagaccc acagctccgt gatggggca gaagcagaaa ccacacccat 105360
gaaacataca catctttcat ctgctttact gtttgaccca tcaaaggctg gggatccctc 105420
gtctatttac tcattcaggg cacgctgact ccagtgccca ggaagcagcc ttaaccagac 105480
agacacctcc tgctctccta cagcccacgc tcagcaggga cagagaatga gaatcactga 105540
aagaggacat cagaaaggga gtgctagggg aaggaagagg acaaagtagg ggcctcacaa 105600
gatggaagcc aggagaggag ggaggacgag agtagactca gagaaggagg atccaaacag 105660
agggcccagc cagggcagga ggcggcgagg ccacagggtc agggtggcaa gggcctgcag 105720
gtcatggaag ggataacgaa ggcaacagga acgcggcatg gcagcaacac tgcagacacg 105780
ggggtgctcg tgaatatgtg tgggtgggtt tgttttcttg gggacagtgg ctgtgacacc 105840
cacatcagcg tgggcacaat tctgtgtctc tgagtattcc cacccactcc cactgggaag 105900
gaagcatcag aggcgagagc aggacacacc aagatgcccc gtcctaaaca acttccaaaa 105960
tgaggaaaag caacaacaaa aaatcagtcc gcaatatcca cacatgatga ctggtctcta 106020
ctaaaaatac aaaaattaag cgtggtggcg ggcacctgta atcccagcta ctcaggaggg 106080
tgaggcagga gaatcatttg aacccggcag ttcaagttgt taatgacttc tgttgaccat 106140
tatttctttt gtacattgat cacagttctg gtatttactg tggaactaaa agcatagggt 106200
caacaaacca gttagtgtgt gcccaggatt ggtgacagac tggccctaat ctgaagattc 106260
aggggttcca gtggcactgg tgattcttgg gatacctgtt tagatttgag tgtttactga 106320
aaagccttcc ccccaactac accccaggga gtcatgcgac actgcgtgaa tcagcaaaca 106380
acaaaaataa aatgcaccaa aagaagaaac ccactgggg tttaatgtag aaagtgtaag 106440
attacagaga aaacaaagca tttatttaac aaacattatt atcactattt tttgagacag 106500
agtctcgtgc tgtcgccagg ctggagtgca gtgatgtgat ctcggctcac cgcaacctcc 106560
acctcccagg tcaagcgatt ctcctgcctc agcctcccaa gtagctggga ctacaggtgc 106620
acgccaccac acacagctaa ttttgtatt tttagtagag atggggtttc accatgttgg 106680
tcaggatggt cttgatctct tgaccttgtg atccacccac ctcggcttcc caaagtgcta 106740
ggattacagg cgtgagccac catgcctggc caacaaacat tattaaactg gctctgcagg 106800
aagaaaaata tgcatagatg acagagctca aaatattaac tacgtgccta cgaaagtatg 106860
cgtggtcaaa tacttcctgg aggccacacc acagggacac tagggaccac aaaggtgaac 106920
ccaagtccag ctcagaggag gatagccctg catacctggc gcccctgta gtgccctgca 106980
gcttgctgtc gtgcccgca gctcactgtc atgctcccgg gtctccaccc gagccctcct 107040
ccactggctt cctggttcac actcacccctt gcttcaggga agcaccccca ccccgtcaga 107100
```

```
tgcccatcca gaccaggcca ccgagccttg tagcacttag cctgtttgaa tgtgagcaca    107160
gaagggcagg aaagaagagt catggagacc tcagcacagc ctgcatctca cacagggac     107220 caggcggagg cactcccaag tttactgcat gaaagaatca tgaccttggc tggacgcggt    107280
ggctcatgac tgtaatccca gcacttgggg aggctgaggt caggagtttg agaccagcct    107340
ggccaacatg gtgaaacccc gtctctacta aaatataaaa aattagccag ctgtggtggt    107400
gggtgctggg tctgtaatcc cagctactcg agaggctgag gcaggagaat cgcttgaacc    107460
caggaggcag aggttgcagt gagccgagtt cacagcggtg cactccagcc tgggcaacag    107520
agtgagactc tgcctcaaaa aaacaaaaaa catgacctca taggtctcaa agatgacctc    107580
tctgtcccac cctgtgcagg ctgtagtgaa gctacacaga atccatcagc ttcttactcc    107640
aagaaccaga gactgaaccc taaaatcaca gctctcaagc gctgataaaa tgatgtggac    107700
aagcatcagc tgacaggaac tatgaaggac aaggggaatg accgaatgta taagccacac    107760
atggcccctg acttacaatt ttgtgacttt atgatggttt gaaagacaca cgcatttaat    107820
aggaaaacca tgctccaagt acccatacaa ctattctgtg ttttcatttt caggagtgtc    107880
caataattta catgagatgt tcaactttt cttataagat atgtattatg ttagatggtt      107940
ctgcccaacc agaggccact ctaagtgtct gtgcatgttc aggttggggg gtgaggtgtg    108000
tccagtgcgg ctggagagca ggatgggtgg tgcaatgccc agggtgcaag catactccat    108060
gaggcccagt ctgtgaacag agaccaggtc taaccccttc ttccaggaaa gcctcgtagg    108120
gccttctggc caagaggcca cgagtggtga agactgcaga ctctgaaatc agaaatacct    108180
gggctccact gtcagcatgg cagctgagga agagtgaaaa ttcctctaag ttcttttaga    108240
agtcccagcc tccccatgta actggggaac tgatgggagg agcagagctg tctgtgcaca    108300
taagaagttc tcagtaaatg gagacagtta ctatttctgt tattattgaa tttgaacaaa    108360
ttccctgggt atgtgtgggg ggacacttca ggtgaaaaca cgcccctcct ccctggtgc      108420 gggggcctgt gctgccaccc tctggaagcc tgcagagggg cagggaaaac agaccctgaa    108480
caaaagtgtg cacccagtga ggaggtgcaa gggcacaaag gtggcaccaa gtgcctcaag    108540
gagaggctga aacgcggcct ggggacctcg cagtggtctg gtcatatagg cagtgggtgt    108600
gaagggctgt cctgtgtctc atagggacca ctggctatag gacaaggct gttaaagtcc       108660 aggagagagg gggtggcttg aagagaggca cggcagagag tggaagcgta ggagaaagat    108720
gggctcctgg gcatgtggtg tcagcagagg tgcctcaagg atagagtgag tccagagtct    108780
agaaaggagc agatcaccag gctctgggaa gagcacagca tgggtgcaca cactgctcta    108840
cccagcatgg ctgccgaccc aaagacagca aagccaagaa ggacacacaa gcgtggccag    108900
atgcagccct gtgaggaaac ttacccaaga acgggacgat gggcttgaga aaccatccat    108960
ctacaaggat ggcgtttgct gcagcaatgt ttataataaa ttgtgggaaa ctgtgaactg    109020
cctaaatgtc tcacaatagg aacaaattag tgcaccacac catgaaactc tctacagctc    109080
ctgagttaca gaacgacagt ataatactat agttatataa tactgtataa tactactgca    109140
taactattgt ataatactgt atttctggat ggaattatag ggtctcccaa cataaaagat    109200
gatgattcaa agttcctttc caaaattcct ttttttttt gagatggagt ctcgctctgc      109260
cacccaggct ggagtgcagt ggtgcggcct ctgctcactg caacctccgc caccccggtt    109320
cagcacttct cctgcttcag cctcccaagt agctgggact acaggcacct gccaccacat    109380
ccagctaatt tttgtatttt tagtagagat ggggttttgc catgttggca ggctggtctt    109440
gcactcctaa catcaggtga tccacctgcc tcagcctccc aaagtgctgg gattataggc    109500
```

```
atgagccacc gcgcccagcc ccctttccaa aatttctaca atgaacacac tttgaaaggt  109560
ttagttctcc tacctgcacc ctggagaaca tccctgttgg gagcaggggc aaggagaccc  109620
cacccaaggg aggcgcacag gacacactga aaggcaggcg ggcaaatgcc aagaagtcag  109680
ccatgaccac gcccagtccc tcactagtcc tcctccgaca ggtggtttca ggagcacctg  109740
tgccgcccca ggatcggctc aaggagcaa aaacaagacc gtgctggcga gggacaggct  109800
cagcctagac ctggagggaa aggtgcccag ccctgcaccg aggcatgcac ttggagcaga  109860
gaggtgtttt cttcaagttc agtaagaagg aaaatgaaag agatgaggaa gtaacttgaa  109920
gatgtgaaag tgaggctcag aggggttcac agaggagtgc ccgggcacca tgagtgcctc  109980
catgatggtg tgaggctgtg aggcccacca gtgcagccaa gatactgggg ctggtaacag  110040
tgagcctcaa gcagacatcc cagtcaccag ctgcccctgtt gtggctcctg aagcagggtt  110100
tacggggaga caacatatat cccttctgt gtccaagctt gtgaggcctg tcagaaaaaa  110160
atccgctatt ttcatgaata tagaaaatgt tctgcttctc actatatgaa gacaccgtgc  110220
ctaaaaatgc caagttttgg ccaccacagt gggctctgtc actgacagct gtgcacgctg  110280
tatcatgaag gccttaggct ggacttctga tcaatgctta tgtatctgta gccatcttga  110340
tcagaatgat ccaggcaagg gccgccgtgt ctccactgcc cgagaggtat gcaaagaaca  110400
aagctctaag agcaagcgtt gagtctccct gcattggccc ttagggatct gctttgataa  110460
aaatctgaga ctggatcaga gggctggaaa taagcttttt ttggagacgg agtttcgctc  110520
ttgttgccca ggctggagtg tagtggagcg atctcagctc actgcaacct tgcctgctgg  110580
gttcaagtga ttctcctgcc tcaggatc                                    110608

<210> SEQ ID NO 4
<211> LENGTH: 59
<212> TYPE: DNA
<213> ORGANISM: Homo sapiens

<400> SEQUENCE: 4
ctaactaaaa taattgagta aaactcatag gtcaaggggg aattctaatt aagtgaaat       59

<210> SEQ ID NO 5
<211> LENGTH: 56
<212> TYPE: DNA
<213> ORGANISM: Homo sapiens

<400> SEQUENCE: 5
ctaaataaca tacttttaga taacccatag gtcaagaag aagtcaaaag tgaaat           56

<210> SEQ ID NO 6
<211> LENGTH: 27
<212> TYPE: DNA
<213> ORGANISM: Homo sapiens

<400> SEQUENCE: 6
taaaaatgac ttgcaagaga atggtaa                                          27

<210> SEQ ID NO 7
<211> LENGTH: 27
<212> TYPE: DNA
<213> ORGANISM: Homo sapiens

<400> SEQUENCE: 7 taaaagtat ttagaaccaa atgaaaa                                           27

<210> SEQ ID NO 8
```

```
<211> LENGTH: 60
<212> TYPE: DNA
<213> ORGANISM: Homo sapiens

<400> SEQUENCE: 8
taactaaaat aattgagtaa aactcatagg tcaaagggga attctaatta agtgaaatta    60

<210> SEQ ID NO 9
<211> LENGTH: 55
<212> TYPE: DNA
<213> ORGANISM: Homo sapiens

<400> SEQUENCE: 9
taagtaatat aagtaaataa tccataggtc aaagaggaaa ttttatggga aatta         55

<210> SEQ ID NO 10
<211> LENGTH: 25
<212> TYPE: DNA
<213> ORGANISM: Homo sapiens

<400> SEQUENCE: 10
aaaatgactt gcaagagaat ggtaa                                          25

<210> SEQ ID NO 11
<211> LENGTH: 26
<212> TYPE: DNA
<213> ORGANISM: Homo sapiens

<400> SEQUENCE: 11
aaaacatgtt ttgaactgaa tgaaaa                                         26
```